(12) United States Patent
Boyden et al.

(10) Patent No.: US 7,738,627 B2
(45) Date of Patent: Jun. 15, 2010

(54) GEOMETRIC X-RAY FLUORESCENCE VISUALIZER, IMAGER, OR INFORMATION PROVIDER

(75) Inventors: Edward S. Boyden, Cambridge, MA (US); Roderick A. Hyde, Redmond, WA (US); Muriel Y. Ishikawa, Livermore, CA (US); Edward K. Y. Jung, Bellevue, WA (US); Eric C. Leuthardt, St. Louis, MO (US); Robert W. Lord, Seattle, WA (US); Nathan P. Myhrvold, Medina, WA (US); Dennis J. Rivet, Portsmouth, VA (US); Michael A. Smith, Phoenix, AZ (US); Clarence T. Tegreene, Bellevue, WA (US); Thomas A. Weaver, San Mateo, CA (US); Charles Whitmer, North Bend, WA (US); Lowell L. Wood, Jr., Bellevue, WA (US); Victoria Y. H. Wood, Livermore, CA (US)

(73) Assignee: The Invention Science Fund I, LLC

( * ) Notice: Subject to any disclaimer, the term of this patent is extended or adjusted under 35 U.S.C. 154(b) by 391 days.

(21) Appl. No.: 11/906,156

(22) Filed: Sep. 28, 2007

(65) Prior Publication Data
US 2009/0086895 A1    Apr. 2, 2009

(51) Int. Cl.
*G01N 23/223* (2006.01)
(52) U.S. Cl. ........................................... 378/44
(58) Field of Classification Search ............... 378/4–27, 378/37, 55, 62, 64, 98.8, 98.9, 98.12, 44–50
See application file for complete search history.

(56) References Cited

U.S. PATENT DOCUMENTS

| 5,105,452 | A | 4/1992 | McInerney |
| 5,274,688 | A | 12/1993 | Grodzins |
| 5,293,415 | A | 3/1994 | Hartley et al. |
| 5,481,109 | A | 1/1996 | Ninomiya et al. |
| 5,595,636 | A | 1/1997 | Franzen |
| 5,832,054 | A | 11/1998 | Kuwabara |
| 6,052,431 | A | 4/2000 | Onoguchi et al. |

(Continued)

OTHER PUBLICATIONS

Carr-Brion, Ken; "On-Line X-Ray Fluorescence Analysis: Theoretical Background"; X-Ray Analysers in Process Control; London and New York; Elsevier Applied Science; 1989; pp. 6-37.

*Primary Examiner*—Courtney Thomas

(57) ABSTRACT

One aspect relates to determining a location of an at least one X-ray fluorescing event occurring within an at least some matter of at least a portion of an individual, wherein the determining the location of the at least one X-ray fluorescing event is based at least in part on determining a relative angle at which an at least one applied high energy photon and/or particle is being applied to the at least some matter of the at least the portion of the individual, a relative position from which an at least one applied high energy photon and/or particle is being applied to the at least some matter of the at least the portion of the individual, a detected location of an at least one induced fluorescing X-ray photon fluoresced during the at least one X-ray fluorescing event, and a received angle at which the at least one induced fluorescing X-ray photon is received.

69 Claims, 30 Drawing Sheets

U.S. PATENT DOCUMENTS

| | | |
|---|---|---|
| 6,115,452 A | 9/2000 | Marrs |
| 6,477,227 B1 | 11/2002 | Kaiser et al. |
| 6,697,453 B1 | 2/2004 | Mueller et al. |
| 6,754,304 B1 | 6/2004 | Kumakhov |
| 6,788,760 B1 | 9/2004 | Janik et al. |
| 6,801,595 B2 | 10/2004 | Grodzins et al. |
| 6,856,827 B2 | 2/2005 | Seeley et al. |
| 7,092,485 B2 | 8/2006 | Kravis |
| 7,183,547 B2 | 2/2007 | Yun et al. |
| 7,330,531 B1 | 2/2008 | Karellas |
| 7,342,996 B2 | 3/2008 | Kumakhov |
| 7,409,037 B2 | 8/2008 | Puusaari et al. |
| 7,430,273 B2 | 9/2008 | Yellepeddi |
| 7,440,542 B2 | 10/2008 | Baumann et al. |
| 7,583,781 B2 | 9/2009 | Wakai et al. |
| 7,623,625 B2 | 11/2009 | Boyden et al. |
| 7,627,085 B2 | 12/2009 | Boyden et al. |
| 2005/0031078 A1 | 2/2005 | Kumakhov |
| 2006/0291623 A1 | 12/2006 | Smith et al. |
| 2007/0064864 A1 | 3/2007 | Wakai et al. |
| 2007/0189449 A1 | 8/2007 | Baumann et al. |
| 2007/0201610 A1 | 8/2007 | Adachi et al. |
| 2007/0253908 A1 | 11/2007 | Rice et al. |
| 2008/0008292 A1 | 1/2008 | Krmar et al. |
| 2008/0073539 A1 | 3/2008 | Vija et al. |
| 2008/0253511 A1 | 10/2008 | Boyden et al. |
| 2008/0253513 A1 | 10/2008 | Boyden et al. |
| 2008/0253520 A1 | 10/2008 | Boyden et al. |
| 2008/0253521 A1 | 10/2008 | Boyden et al. |
| 2008/0253522 A1 | 10/2008 | Boyden et al. |
| 2008/0253523 A1 | 10/2008 | Boyden et al. |
| 2008/0253524 A1 | 10/2008 | Boyden et al. |
| 2009/0086902 A1 | 4/2009 | Boyden et al. |
| 2009/0086903 A1 | 4/2009 | Boyden et al. |
| 2009/0296887 A1 | 12/2009 | Boyden et al. | induced X-ray fluorescing photon 122 (emitted at arbitrary angle)

4600 → determining a location of an at least one X-ray fluorescing event occurring within an at least some matter of at least a portion of an individual, wherein the determining the location of the the at least one X-ray fluorescing event is based at least in part on determining a relative angle at which an at least one applied high energy photon and/or particle is being applied to the at least some matter of the at least the portion of the individual, a relative position from which an at least one applied high energy photon and/or particle is being applied to the at least some matter of the at least the portion of the individual, a detected location of an at least one induced fluorescing X-ray photon fluoresced during the at least one X-ray fluorescing event, and a received angle at which the at least one induced fluorescing X-ray photon is received 4602

FIG. 51

4800 → inducing at least one induced X-ray fluorescing photon within an at least some matter of an at least a portion of an at least one individual responsive to a single input energy event based at least partially on an at least some input energy being applied to the at least some matter of the at least the portion of the at least one individual 4802

X-ray fluorescence visualizing, imaging, or information providing within the at least some matter of the at least the portion of the at least one individual responsive to the inducing at least one induced X-ray fluorescing photon 4808

FIG. 52

GEOMETRIC X-RAY FLUORESCENCE VISUALIZER, IMAGER, OR INFORMATION PROVIDER

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

1. For purposes of the USPTO extra-statutory requirements, the present application constitutes a continuation-in-part of U.S. patent application Ser. No. 11/906,161, entitled "X-Ray Fluorescence Visualizer, Imager, or Information Provider", naming Edward S. Boyden, Roderick A. Hyde, Muriel Y. Ishikawa, Edward K. Y. Jung, Eric C. Leuthardt, Robert W. Lord, Nathan P. Myhrvold, Dennis J. Rivet, Michael A. Smith, Clarence T. Tegreene, Thomas A. Weaver, Charles Whitmer, Lowell L. Wood, Jr. and Victoria Y. H. Wood, as inventors, filed Sep. 28, 2007, which is currently co-pending, or is an application of which a currently co-pending application is entitled to the benefit of the filing date.

2. For purposes of the USPTO extra-statutory requirements, the present application constitutes a continuation-in-part of U.S. patent application Ser. No. 11/906,142, entitled "Combining X-Ray Fluorescence Visualizer, Imager, or Information Provider", naming Edward S. Boyden, Roderick A. Hyde, Muriel Y. Ishikawa, Edward K. Y. Jung, Eric C. Leuthardt, Robert W. Lord, Nathan P. Myhrvold, Dennis J. Rivet, Michael A. Smith, Clarence T. Tegreene, Thomas A. Weaver, Charles Whitmer, Lowell L. Wood, Jr. and Victoria Y. H. Wood, as inventors, filed Sep. 28, 2007, which is currently co-pending, or is an application of which a currently co-pending application is entitled to the benefit of the filing date.

3. For purposes of the USPTO extra-statutory requirements, the present application constitutes a continuation-in-part of U.S. patent application Ser. No. 11/906,144, entitled "Portable Aspects For X-Ray Fluorescence Visualizer, Imager, or Information Provider", naming Edward S. Boyden, Glenn B. Foster, Roderick A. Hyde, Muriel Y. Ishikawa, Edward K. Y. Jung, Eric C. Leuthardt, Robert W. Lord, Nathan P. Myhrvold, Dennis J. Rivet, Michael A. Smith, Clarence T. Tegreene, Thomas A. Weaver, Charles Whitmer, Lowell L. Wood, Jr. and Victoria Y. H. Wood, as inventors, filed Sep. 28, 2007, which is currently co-pending, or is an application of which a currently co-pending application is entitled to the benefit of the filing date.

4. For purposes of the USPTO extra-statutory requirements, the present application constitutes a continuation-in-part of U.S. patent application Ser. No. 11/906,169, entitled "Tool Based X-Ray Fluorescence Visualizing, Imaging, or Information Providing", naming Edward S. Boyden, Roderick A. Hyde, Muriel Y. Ishikawa, Edward K. Y. Jung, Eric C. Leuthardt, Robert W. Lord, Nathan P. Myhrvold, Dennis J. Rivet, Michael A. Smith, Clarence T. Tegreene, Thomas A. Weaver, Charles Whitmer, Lowell L. Wood, Jr. and Victoria Y. H. Wood, as inventors, filed Sep. 28, 2007, which is currently co-pending, or is an application of which a currently co-pending application is entitled to the benefit of the filing date.

5. For purposes of the USPTO extra-statutory requirements, the present application constitutes a continuation-in-part of U.S. patent application Ser. No. 11/906,096, entitled "Repositioning X-Ray Fluorescence Visualizer, Imager, or Information Provider", naming Edward S. Boyden, Roderick A. Hyde, Muriel Y. Ishikawa, Edward K. Y. Jung, Eric C. Leuthardt, Robert W. Lord, Nathan P. Myhrvold, Dennis J. Rivet, Michael A. Smith, Clarence T. Tegreene, Thomas A. Weaver, Charles Whitmer, Lowell L. Wood, Jr. and Victoria Y. H. Wood, as inventors, filed Sep. 28, 2007, which is currently co-pending, or is an application of which a currently co-pending application is entitled to the benefit of the filing date.

6. For purposes of the USPTO extra-statutory requirements, the present application constitutes a continuation-in-part of U.S. patent application Ser. No. 11/906,150, entitled "Time of Flight Aspects For X-Ray Fluorescence Visualizer, Imager, or Information Provider", naming Edward S. Boyden, Roderick A. Hyde, Muriel Y. Ishikawa, Edward K. Y. Jung, Eric C. Leuthardt, Robert W. Lord, Nathan P. Myhrvold, Dennis J. Rivet, Michael A. Smith, Clarence T. Tegreene, Thomas A. Weaver, Charles Whitmer, Lowell L. Wood, Jr. and Victoria Y. H. Wood, as inventors, filed Sep. 28, 2007, which is currently co-pending, or is an application of which a currently co-pending application is entitled to the benefit of the filing date.

7. For purposes of the USPTO extra-statutory requirements, the present application constitutes a continuation-in-part of U.S. patent application Ser. No. 11/906,151, entitled "X-Ray Fluorescence Visualizing, Imaging, or Information Providing of Chemicals, Compounds, or Biological Materials", naming Edward S. Boyden, Roderick A. Hyde, Muriel Y. Ishikawa, Edward K. Y. Jung, Eric C. Leuthardt, Robert W. Lord, Nathan P. Myhrvold, Dennis J. Rivet, Michael A. Smith, Clarence T. Tegreene, Thomas A. Weaver, Charles Whitmer, Lowell L. Wood, Jr. and Victoria Y. H. Wood, as inventors, filed Sep. 28, 2007, which is currently co-pending, or is an application of which a currently co-pending application is entitled to the benefit of the filing date.

8. For purposes of the USPTO extra-statutory requirements, the present application constitutes a continuation-in-part of U.S. patent application Ser. No. 11/906,172, entitled "Selective Elemental Color Providing For X-Ray Fluorescence Visualization, Imaging, or Information Providing," naming Edward S. Boyden, Roderick A. Hyde, Muriel Y. Ishikawa, Edward K. Y. Jung, Eric C. Leuthardt, Robert W. Lord, Nathan P. Myhrvold, Dennis J. Rivet, Michael A. Smith, Clarence T. Tegreene, Thomas A. Weaver, Charles Whitmer, Lowell L. Wood, Jr. and Victoria Y. H. Wood, as inventors, filed Sep. 28, 2007, which is currently co-pending, or is an application of which a currently co-pending application is entitled to the benefit of the filing date.

9. For purposes of the USPTO extra-statutory requirements, the present application constitutes a continuation-in-part of U.S. patent application Ser. No. 11/906,154, entitled "Scintillator Aspects For X-Ray Fluorescence Visualizer, Imager, or Information Provider", naming Edward S. Boyden, Roderick A. Hyde, Muriel Y. Ishikawa, Edward K. Y. Jung, Eric C. Leuthardt, Robert W. Lord, Nathan P. Myhrvold, Dennis J. Rivet, Michael A. Smith, Clarence T. Tegreene, Thomas A. Weaver, Charles Whitmer, Lowell L. Wood, Jr. and Victoria Y. H. Wood, as inventors, filed Sep. 28, 2007, which is currently co-pending, or is an application of which a currently co-pending application is entitled to the benefit of the filing date.

10. For purposes of the USPTO extra-statutory requirements, the present application constitutes a continuation-in-part of U.S. patent application Ser. No. 11/906,135, entitled "Proximity-Based X-Ray Fluorescence Visualizer, Imager, or Information Provider", naming Edward S. Boyden, Roderick A. Hyde, Muriel Y. Ishikawa, Edward K. Y. Jung, Eric C. Leuthardt, Robert W. Lord, Nathan P. Myhrvold, Dennis J. Rivet, Michael A. Smith, Clarence T. Tegreene, Thomas A. Weaver, Charles Whitmer, Lowell L. Wood, Jr. and Victoria Y. H. Wood, as inventors, filed Sep. 28, 2007, which is currently co-pending, or is an application of which a currently co-pending application is entitled to the benefit of the filing date.

11. For purposes of the USPTO extra-statutory requirements, the present application constitutes a continuation-in-part of U.S. patent application Ser. No. 11/906,155, entitled "Personal Transportable X-Ray Fluorescence Visualizing, Imaging, And/Or Information Providing", naming Edward S. Boyden, Roderick A. Hyde, Muriel Y. Ishikawa, Edward K. Y. Jung, Eric C. Leuthardt, Robert W. Lord, Nathan P. Myhrvold, Dennis J. Rivet, Michael A. Smith, Clarence T. Tegreene, Thomas A. Weaver, Charles Whitmer, Lowell L. Wood, Jr. and Victoria Y. H. Wood, as inventors, filed Sep. 28, 2007, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

TECHNICAL FIELD

Certain aspects of this disclosure can relate to, but are not limited to, a variety of embodiment of a variety of embodiments of an X-ray fluorescence visualizing, imaging, or information providing, and associated mechanisms and/or techniques.

BRIEF DESCRIPTION OF THE FIGURES

FIG. 51 is a flow chart of an embodiment of a X-ray fluorescence visualizing, imaging, of information providing technique as combined with a tool operation, as can be performed by certain embodiments of the X-ray fluorescence visualizer, imager, or information provider of FIGS. 1 and 2, and other locations through this disclosure; and FIG. 52 is a flow chart of an embodiment of a X-ray fluorescence visualizing, imaging, of information providing technique as combined with a tool operation, as can be performed by certain embodiments of the X-ray fluorescence visualizer, imager, or information provider of FIGS. 1 and 2, and other locations through this disclosure.

DETAILED DESCRIPTION

Figure 1:
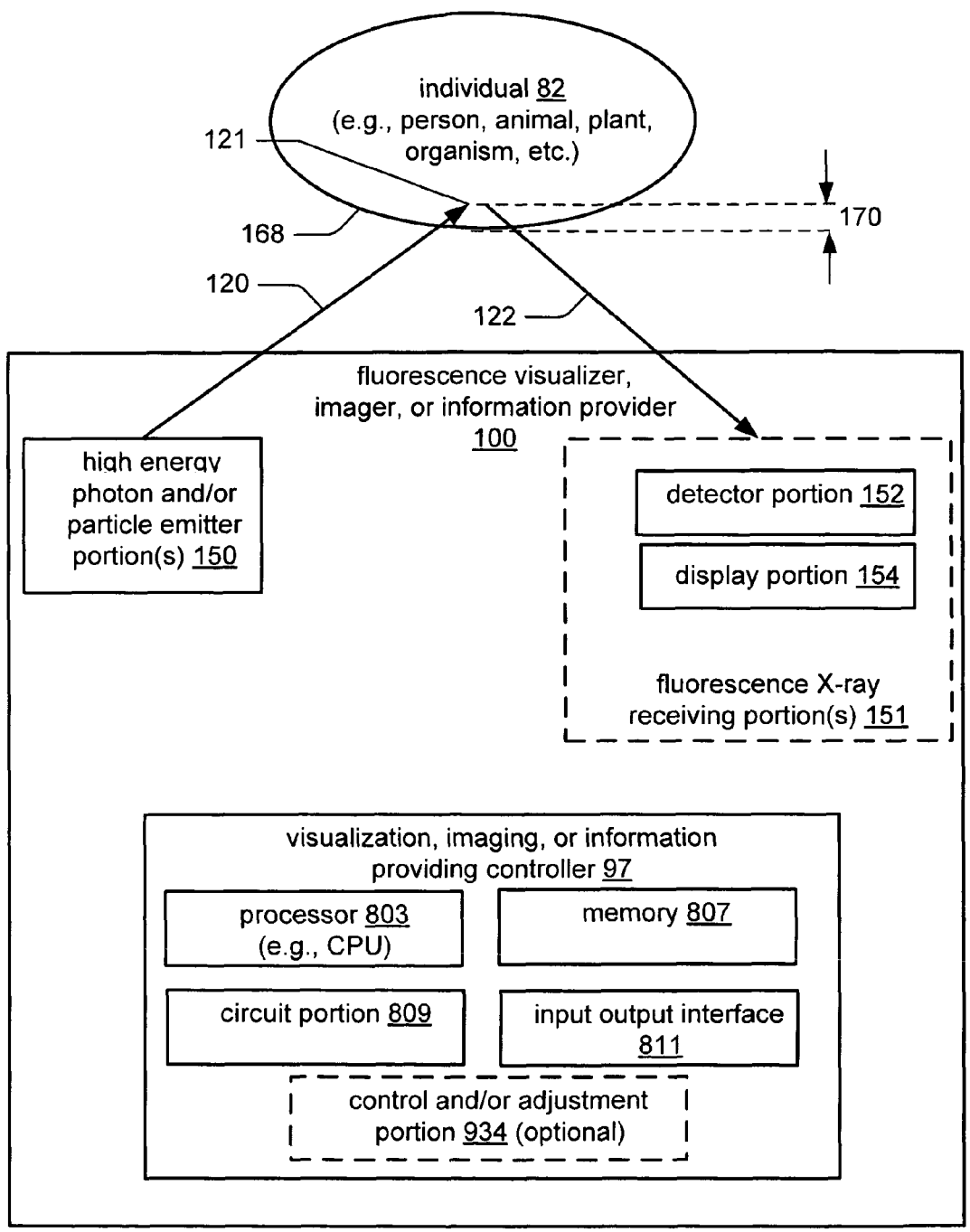
FIG. 1 is a block diagram of one embodiment of an X-ray fluorescence visualizer, imager, or information provider.

At least certain portions of the text of this disclosure (including claims, detailed description, and/or drawings as set forth herein) can support various different claim groupings and/or various different applications. Although, for sake of convenience and understanding, the detailed description can include section headings that generally track various different concepts associated with claims or general concepts contained therein, and the detailed description is not intended to limit the scope of the invention as set forth by each particular claim. It is to be understood that support for the various applications or portions thereof thereby, can appear throughout the text and/or drawings at one or more locations, irrespective of the section headings.

1. Certain Embodiments of an X-Ray Fluorescence Visualizer, Imager, or Information Provider This disclosure pertains to a number of applications, a variety of embodiments, as well as associated techniques, pertaining to different embodiments of an X-ray fluorescence visualizer, imager, or information provider 100, certain embodiments are as described in block form with respect to FIG. 1 or 2 which are as described in this disclosure, can X-ray fluorescence visualize, image, and/or provide information pertaining to a variety of matter of at least a portion of an individual. Certain embodiments of the X-ray fluorescence visualizer, imager, or information provider 100 can be configured to X-ray fluorescence visualize, image, or provide information based upon at least some X-rays being fluoresced from the matter of the at least the portion of the individual by passing through to or within the at least one X-ray fluorescence range to at least one prescribed substantial X-ray fluorescence depth 170, as described with respect to FIGS. 1 to 12, as well as at other locations through this disclosure. Certain embodiments of the X-ray fluorescence visualizer, imager, or information provider 100 can rely at least partially on X-ray fluorescence, since X-rays can be configured to travel through a variety of matter of the individual such as tissue, bones or portions thereof, blood, blood components, bodily fluids, implants or inserts, etc. Certain embodiments of the X-ray fluorescence range and/or the prescribed substantial X-ray fluorescence depth can be arbitrarily thin or thick, depending on such factors as the configuration of the X-ray fluorescence visualizer, imager, or information provider 100, desired visualizing, imaging, or information providing quality, imaging speed, expense, imaging volume or area, dimensions, etc.

Certain embodiments of the X-ray fluorescence visualizer, imager, or information provider 100 can be configured to visualize, image, or provide information based at least partially on one or both of the material density and/or the elemental composition of the matter of the at least the portion of the individual. For example, certain embodiments of the X-ray fluorescence visualizer, imager, or information provider 100 can be configured to visualize, image, or provide information based at least partially on the element composition (e.g. for each chemical element) included in or contained within the matter typically directly such as without the addition of an X-ray fluorescence enhancing additive, a taggant, or a contrast agent, etc. Such X-ray fluorescence enhancing additives, taggants, or contrast agents, etc. can be applied using pills, medications, intravenously, suppositories, or by using other known application techniques.

Within this disclosure, the element composition can include, but is not limited to, the composition of the element(s), the chemical(s), the compound(s), implants, and/or the biological materials, etc. included in or contained within the at least some matter of the at least the portion of the individual. As such, certain embodiments of the X-ray fluorescence visualizer, imager, or information provider 100 can be configured to visualize, image, or provide information (or improve such operations) based at least partially on the chemical, compound (e.g. chemical mixture or compound), and/or biological material included in or contained within the matter typically directly such as with the addition of the X-ray fluorescence enhancing additive, taggant, or contrast agent, etc.

Certain embodiments of the X-ray fluorescence visualizer, imager, or information provider 100 can also visualize, image, or provide information based at least partially on elements, chemicals, compounds, and/or biological material by, for example, adding X-ray fluorescence enhancing additives, taggants, or contrast agents, etc. to the portion of the individual being visualized, imaged, or information provided that can be reacted to or received by that particular chemical or element, and thereupon visualizing, imaging, or providing information according to that chemical, element, and/or biological material. As such, within this disclosure, the visualizing, imaging, or providing information based at least partially on an element can, depending on context, relate to visualizing, imaging, or providing information according to an element, compound, or chemical, biological material, or a combination of, either directly or at least partially based on an addition of an X-ray fluorescence enhancing additive, taggant, or contrast agent, etc. which when combined with the matter of the at least the portion of the individual can indicate or improve the X-ray fluorescence visualizing, imaging, or information providing of the matter.

By allowing X-ray fluorescence visualizing, imaging, or information providing relative to particular elements, compounds, or chemicals, and/or biological material, certain individuals such as human medical patients can perform screening for one or more elements, compounds, chemicals, and/or biological material, or a combination thereof. Such X-ray fluorescence visualizing, imaging, or providing information that may be based at least partially on the density, element, chemical, or compound, and/or biological material included in or contained within the matter may add a richness. For example, the presence, or excessive amount, of certain elements, chemicals, compounds, and/or biological material within a particular matter of the at least the portion of the individual could be detected as a particular color, text, symbol, or other known technique such as is generally known in display or graphical user interface (GUI) techniques. As such, certain chemicals, compounds, elements, and/or biological material that may be indicative of certain illnesses, infections, sicknesses, injuries, poisoning, etc. can be readily scanned, diagnosed, image to, visualized, and/or analyzed. It may be possible for certain embodiments of the X-ray fluorescence visualizer, imager, or information provider 100 to detect an elemental signature of the matter of the at least the portion of the individual, and as such act as a type of spectrometer.

By configuring certain embodiments of the X-ray fluorescence visualizer, imager, or information provider 100 to be relatively low power, relatively inexpensive to purchase or operate, or relatively portable, and/or such devices may be a particularly suitable to relatively poor or remote portions of the world. Additionally, certain embodiments of the X-ray fluorescence visualizer, imager, or information provider 100 may allow more modern medical imaging or visualizing techniques to be applied to the population of considerable portions of the world, and/or be used for such applications than up to this time the population may not have had suitable X-ray fluorescence visualizing, imaging, or information providing. Certain embodiments of the X-ray fluorescence visualizer, imager, or information provider 100 could therefore be utilized in particularly rural, remote, or poorer regions to thereby improve the available visualizing, imaging, or information providing, and therefore the general medical care as described in this disclosure. In addition, the increased affordability of the certain embodiments of the X-ray fluorescence visualizer, imager, or information provider 100 could allow a number of these devices to be used that could each be suitably configured for its particular application, such as cancer treatment or scanning, association with surgical tools, element composition screening, surgical uses such as searching for gunshot or explosive wounds, etc. Such aspects as reduced expense, limited dosage exposure to X-rays or other electromagnetic radiation, devoted application, potential simplicity of operation or configuration, etc. as described in this disclosure could make the use of certain embodiments of the X-ray fluorescence visualizer, imager, or information provider 100 particularly useful and desirable, in general.

Certain embodiments of the X-ray fluorescence visualizer, imager, or information provider 100 can be configured to perform combined X-ray fluorescence visualizing, imaging, or information providing of some combination of elements or additives thereto such as X-ray fluorescence enhancing additives, taggant, or contrast agents, etc. (that may, e.g., enhance or provide X-ray visualizing, imaging, or information providing of elements, chemicals, compounds, and/or biological material, etc) such as themselves as may be color coded. For example, certain embodiments of the X-ray fluorescence visualizer, imager, or information provider 100 can be configured to visualize or image calcium as white, oxygen as blue, and iron as red. The resulting images including matter including or containing some distribution iron, calcium, and iron can then be compiled such that the various mixtures create more color combinations or color mixes such as, for example, oranges, greens, purple, etc. Such combined colors may be easily detectable of readable by a human or a machine image color-reading or certain other image processing device. Consider that conventional CAT scans and conventional MRI typically yield a "black and white" or some level of grayscale display or images. Certain embodiments of the X-ray fluorescence visualizer, imager, or information provider 100 could be truly polychromatic, thereby enhancing the richness of the X-ray fluorescence visualizing, imaging, or information providing, and in result allowing for more robust evaluation of a given matter such as tissue. The various colors could represent, for example, topography of the matter, elements of concern to be scanned, etc.

Certain embodiments of the X-ray fluorescence visualizer, imager, or information provider 100 can be configured to X-ray fluorescence visualize, image, or provide information relating to an elemental, chemical, and/or biological material make-up in the body, particularly with the use of X-ray fluorescence enhancing additives, taggants, or contrast agents, etc. For example, a drug, pill, suppository, injection, or other applier/injector could apply the additive, taggant, etc. to be applied to a patient, and the additive, taggant, etc. could be associated at the molecular level with X-ray fluorescence enhancing additives, taggants, or contrast agents, etc. The particular X-ray fluorescence enhancing additives, taggants, or contrast agents, etc. could be selected as to be harmless to the individual, but include an element that is easily detected by the X-ray fluorescence visualizer, imager, or information provider 100. The concentration or location of the drugs in matter of the person (individual) could be monitored on a one-time or repetitive manner. This could lead to effective research on drug dosing techniques, effectiveness, regimen, time for the drug to diminish, particular concentrations of drugs in matter of the particular regions of the body, and other such aspects.

Within this disclosure, the term "individual" can, depending on context, pertain to a person, animal, plant, organism, of whom at least a portion thereof is being imaged and/or examined by the X-ray fluorescence visualizer, imager, or information provider 100. The term "user" can, depending on context, pertain to those persons using and/or operating certain embodiments of the X-ray fluorescence visualizer, imager, or information provider 100, such as, but not limited to: doctors, physicians, dentists, veterinarians, researchers, assistants, technicians, researchers, persons performing medical forensics and/or autopsies, users, and/or other persons, assistants to, derivatives from, etc. who can view or utilize the X-ray fluorescence visualized, imaged, or information provided portion of the individual using certain embodiments of the X-ray fluorescence visualizer, imager, or information provider 100.

Within this disclosure, the term "user" can also include, in addition to the human users as described above: computers, automated systems, controllers, robotic devices, other devices etc. As such, certain users can be used to automate X-ray fluorescence visualization, imaging, providing information, inspection, or analyzing of certain depth image information as output by certain embodiments of the X-ray fluorescence visualizer, imager, or information provider 100 using such X-ray fluorescence visualizing, imaging, or information providing techniques as described in this disclosure. Consider, for example, that certain depth image information can be more readily utilized or processed by computers based on computer-generated vision, machine based imaging, machine vision, machine-based devices, etc. to X-ray fluorescence visualize determine, X-ray fluorescence visualize image, process, and/or provide X-ray fluorescence information. Certain embodiments of the X-ray fluorescence visualizer, imager, or information provider 100 can be configured to alert medical surgeons, dentists, etc. when a tool (particularly one that can harm the patient such as certain cutting tools, certain lasers, certain tissue removing devices, etc.) that is being used is proximate of certain elements, which may be used to indicate a sensitive area. For example, the element iron may be used to determine or indicate the presence of blood vessels, aortas, certain organs, etc. due to its existence in hemoglobin (a component of blood). As such, certain embodiments of the X-ray fluorescence visualizer, imager, or information provider 100 that are being associated with surgical tools might be configured or adapted to quantitatively determine or interpret the relative depth, distance to, or proximity of certain blood vessels, nerves, etc. Certain embodiments of such X-ray fluorescence visualization, imaging, or information providing may be particularly effective in the vicinity of relatively homogenous matter as compared with inconsistent material.

This disclosure describes a variety of embodiments of X-ray fluorescence visualizing, imaging, or information providing to a variety of prescribed depths. For instance, certain embodiments of the X-ray fluorescence visualizer, imager, or information provider 100 can X-ray fluorescence visualize, image, or provide information down to a prescribed depth such that any elements, chemicals, or compounds that are being particularly scanned for that are within that depth from the surface (e.g., iron for hemoglobin, or certain elements characteristic of particular types of cancer or tissue, etc.) should be indicated. While such scans within a range of depths may lack the clarity of scans limited to a relatively thin depth, certain embodiments of the X-ray fluorescence visualizer, imager, or information provider 100, such techniques for scanning for particular elements, as described in this disclosure, can be effectively performed and reliably indicated even through a prescribed depth range of matter. Such surface scans through a prescribed depth can be from outside the individual, or at least partially internal to the individual such as via a surgical opening, a naturally occurring opening, or a minimally invasive opening such as for a scope-type device that may or may not be associated with a tool.

By comparison, certain embodiments of the X-ray fluorescence visualizer, imager, or information provider 100 can X-ray fluorescence visualize, image, or provide information can X-ray fluorescence visualize, image, or provide information at within a prescribed depth range. For instance, it may be desired to determine what is in some matter of the at least the portion of the individual at some prescribed depth from a surface (at least partially internal or at least partially external) from a tool being used. Such range of prescribed depths being X-ray fluorescence visualized, imaged, or information provided can, in certain embodiments of the X-ray fluorescence visualizer, imager, or information provider 100, be controlled or altered as desired by the user, or alternately under control of a controller, computer, hardware and/or software component, etc. as described in this disclosure.

This disclosure describes certain embodiments of the X-ray fluorescence visualizing, imaging, or information providing relative to particular elements, compounds, chemicals, and/or biological material a number of times. Many or all elements can be visualized, imaged, or have information provided based particularly on elements (with or without X-ray fluorescence enhancing additives, taggants, or contrast agents, etc.) provided there is little interference with the elements being visualized, imaged, or have information provided with the elements of the background. A sizable percentage of the elements, chemicals, compounds, and/or biological material can be visualized, imaged, or have information provided with X-ray fluorescence enhancing additives, taggants, or contrast agents, etc. provided there is little interference with the X-ray fluorescence enhancing additives, taggants, or contrast agents, etc. being visualized, imaged, or have information provided and the elements, chemicals, compounds, biological material, X-ray fluorescence enhancing additives, taggants, or contrast agents, etc. of the background.

Certain embodiments of the X-ray fluorescence visualizer, imager, or information provider 100 can be configured to X-ray fluorescence visualize, image, or provide information of or through matter of the at least the portion of the individual in a manner as to view certain medically relevant, surgically relevant, or other image-interesting locations. Certain embodiments of the medically relevant information may include, but are not limited to, the location of at least a portion of the X-ray fluorescence visualizer, imager, or information provider 100 (or an associated device such as a tool). For example, the proximity of the X-ray fluorescence visualizer, imager, or information provider 100 to a tool such as a blood vessel, nerve, bone, etc. can be indicated.

Such proximity can be used to locate a desired location as well, for example assuming that the blood vessel, nerve, bone, etc. is being searched for as being medically relevant or interesting. Certain embodiments of the medically relevant information may include, but are not limited to, a matter perfusion such as tissue perfusion. For example, certain actions by a surgeon, doctor, individual, etc. can alter blood flow to a critical region. For example applying a clip to an aneurysm may change flow dynamics which can compromise flow to a distal portion of tissue.

Certain embodiments of the medically relevant information may include, but are not limited to, a modification of a tissue function. For example, could a medical or surgical procedure or operation be putting too much pressure, kinking, or otherwise distort matter such as tissue. Such tissue function aspects could lead to a physical, chemical, or functional alteration of the tissue or organ in question. An example would be if a doctor was using a retractor on a portion of the heart, and the pressure was causing a decrement in the ejection fraction or the electrical conductance.

Certain embodiments of the medically relevant information may include, but are not limited to, a modification of the composition of the tissue or other matter such as a somehow be reflected in the X-ray fluorescence visualizing, imaging, or information providing. Such modification of the tissue composition may be similar to the modification of a tissue function as described above, but instead the instrument manipulation effects the tissue oxygenation or $CO_2$ retention.

Within this disclosure, the term "matter aberration" can, depending upon context, relate to the matter composition (e.g., element composition) of the surrounding region that can be used to distinguish from the surrounding matter based on the matter composition or other X-ray fluorescence visualizing, imaging, or information providing characteristics. Within this disclosure, including the appended claims, the terms "imaging", "visualization", "probing", and/or "information providing" that at least partially rely on X-ray fluorescence can, depending context, be considered as being included individually or in combination within the inclusive term "X-ray fluorescence visualization, imaging, or information providing". As such, it is envisioned that there are a variety of embodiments of the X-ray fluorescence visualizer, imager, or information provider 100 that are intended to be protected by the scope of the claims of this disclosure.

There are a variety of elements that can be used to enhance or provide X-ray fluorescence visualizing, imaging, or information provider by certain embodiments of the X-ray fluorescence visualizer, imager, or information provider 100. Certain embodiments of the X-ray fluorescence visualizer, imager, or information provider 100 can be configured to visualize, image, or provide information based at least in part on titanium or other implant elements, etc. Such titanium-based visualizing, imaging, or information providing may be particularly useful considering that it is a common metal used as implants within humans due to such characteristics as long wear, and resistance to corrosive effects, within the body. Certain embodiments of the X-ray fluorescence visualizer, imager, or information provider 100 can therefore visualize, image, or provide information on the titanium in a manner that would be distinct or could be differentiated from the calcium-based element of bones, while providing density-based information about both the titanium and/or the calcium in certain embodiments. For example, an orthopedic surgeon could potentially better visualize, image, or provide information following surgery inputting a screw into a bone, inserting a spinal construct, etc. Such titanium-based implants could also be X-ray fluorescence visualize, imaged, or have provided information following the implant, such as subsequent to surgery, on a routine checkup basis, etc. Certain embodiments of the X-ray fluorescence visualizer, imager, or information provider 100 can also enhance the X-ray fluorescence visualizing, imaging, or information providing of or at the junction between implant, screws, constructs, etc. and tissue associated therewith. In this manner, the operation, association with the matter, or integrity of the implant, screws, constructs, etc. can be visualized, imaged, or have information provided in manner that might provide suitable information, etc., to allow for limiting invasive surgery, etc.

Certain embodiments of the X-ray fluorescence visualizer, imager, or information provider 100 can also visualize, image, or provide information of the matter of the least portion of the individual based at least partially on copper contained within the body. Copper represents the third most common metal element in the human body. Such visualizing, imaging, or information providing based on copper in the matter of the least portion individual could be a useful indicator of inflammation of the matter of the individual, and notably certain abscesses could be detected using certain embodiments of the X-ray fluorescence visualizer, imager, or information provider 100. Consider that the reason that puss is green is, in part, due to the high copper content of the puss.

For example, puss in neutrophils (that have copper based enzymes) can be used to produce free radicals to combat infections.

Certain embodiments of the X-ray fluorescence visualizer, imager, or information provider 100 can visualize, image, or provide information relating to various elements to diagnoses and variety of diseases. For example, aberrant copper and iron deposition can be detected as a result of specific diseases to such organs as the kidneys, brain, eyes (such as Wilson's disease whose symptoms may include increased density of copper in the eyes), heart, liver, and brain (e.g., the basal ganglion). As such, since certain embodiments of the X-ray fluorescence visualizer, imager, or information provider 100 can be configured to richly visualize, richly image, or provide relatively detailed information of a variety of diseases, conditions, disorders, infections, etc. based at least partially on elements, chemicals, compounds, and/or biological material present in the matter, as well as elemental density, chemical density, compound density, and/or biological material density.

Certain embodiments of the X-ray fluorescence visualizer, imager, or information provider 100 can improve visualizing, imaging, or information providing of matter within at least a portion (e.g., having a high concentration of an element) of individual by ensuring the background contains relatively little of the element being used for visualizing, imaging, or information providing. For example, such elements of the matter can be selected that are unlikely to be present in the normal or background matter. Alternatively, X-ray fluorescence enhancing additives, taggants, or contrast agents, etc. can be applied to the matter that can bind to desired elements, chemicals, compounds, and/or biological materials to be visualized, imaged, or information provided, and may thereupon be used to enhance or provide the visualizing, imaging, of information providing, and such X-ray fluorescence enhancing additives, taggants, or contrast agents, etc. and could be selected to have limited presence in the background or other matter of the at least the portion of the individual. Alternately, certain signal processing techniques may be used to filter out or limit the distortive or interfering effects by similar or interfering elements in the background matter. For example, those regions of the matter having a sufficient concentration or density of the element(s) being used for the X-ray fluorescence visualizing, imaging, or information providing could be displayed or provided, while those regions having a lower concentration or density might be filtered out, etc. such as by using certain image processing and/or filtering techniques.

Certain aspects of X-ray fluorescence could be utilized to enhance visualizing, imaging, or information providing, as described in this disclosure. For example, certain embodiments of the X-ray fluorescence visualizer, imager, or information provider 100 can image based at least partially on elements (or with the use of X-ray fluorescence enhancing additives, taggants, or contrast agents, etc. can image for elements, chemicals, compounds, and/or biological materials) or densities thereof within particular targets such as the at least one target atom or fluorophore 121. Such matter aberrations as melanomas, cancers, abscess, arterial plaque, blood impurities, implants, inserts, etc. could be differentiated from surrounding matter based on the composition of the elements, chemicals, compounds, and/or biological materials (using, e.g., X-ray fluorescence enhancing additives, taggants, or contrast agents, etc.) using certain embodiments of the X-ray fluorescence visualizer, imager, or information provider 100. Such matter aberrations can cause fluorescing of certain of the target atom or fluorophore 121 such as with tissue, teeth, bones, and/or junctions of different type matter, etc. Certain embodiments of the X-ray fluorescence visualizer, imager, or information provider 100 can be multi-modal, such as to be able to X-ray visualize, image, or provide information relating to elements, chemicals, compounds, and/or biological materials such as chloride. Chloride, for example, may be X-ray fluorescence visualized, imaged, or information provided in manner that may be used to detect and/or indicate brain actuation or brain inhibition.

Certain implant, man-made devices, etc. may be identified with a presence of numbers, text, etc., using certain embodiments of the X-ray fluorescence visualizer, imager, or information provider 100. For instance, certain implants or other man-made devices might be identified such as being physically coated with or coupled to a bar code-type device that is associated with an implant (e.g., pacemakers, skeletal implants, etc.) that may be used to identify the device. Certain embodiments of the X-ray fluorescence visualizer, imager, or information provider 100 could be used to read the bar-code, text, type, numerals, or other such information based on the elements that the bar-code, text, type, numerals, or other such information is printed or formed with. Certain implants, for example, may include, e.g., a bar-code or other technique that might be X-ray detectable, optical detectable, encoder detectable, etc.

There can be a variety of configurations of the X-ray fluorescence visualizer, imager, or information provider 100 depending at least in part on configuration, that as described herein are intended to be illustrative in nature but not limiting in scope. Certain embodiments of the X-ray fluorescence visualizer, imager, or information provider 100 can therefore be configured to X-ray fluorescence visualize, image, and/or provide information at least partially by employing a nearly monochromatic illuminating X-ray "pencil" radiation, flooding radiation, fan-radiation, scanning radiation, or other ones of the at least one high energy photon and/or particle emitter portion(s) 150. For example, certain embodiments of the X-ray fluorescence visualizer, imager, or information provider 100 can be configured to apply a fan, flooding, scanning, or other type of the at least one applied high energy photon and/or particle 120 from the high energy photon and/or particle emitter portion(s) 150 to a relatively large area of matter (such as a relatively large portion of a person); whereupon the X-ray fluorescence receiving portion(s) 151 can create an X-ray fluorescence visualization, image, or provided information that can be used to detect the at least one induced X-ray fluorescing photon 122 being emitted by a relatively small area (e.g., within an internal organ such as a heart or brain, as may be positioned using a catheter or other device) containing the target atom or fluorophore 121.

With certain embodiments of the X-ray fluorescence visualizer, imager, or information provider 100, it may be desired to X-ray fluorescence visualize, image, or provide information of at least some matter of at least the portion of the individual that is particularly close, or proximate to, the at least one X-ray fluorescence receiving portion(s) 151 (that may operate regardless of the position of the at least one high energy photon and/or particle emitter portion(s) 150. Such configurations can operate based at least partially on the frequency of the at least one induced X-ray fluorescing photon 122, and therefore how far the at least one induced X-ray fluorescing photon 122 can travel through the at least some matter of at least the portion of the individual. For example, certain embodiments of the at least one applied high energy photon and/or particle 120 can be selected to be of a frequency to travel for relatively extensive distances through the at least some matter of at least the portion of the individual, such as with a flooding beam, pencil-beam, or fan-beam, or other embodiment. It is important that the at least one applied high energy photon and/or particle 120 be selected (e.g., having suitably high frequency) to travel to the at least some matter of at least the portion of the individual being X-ray fluorescent visualized, imaged, or information provided.

There can be a variety of configurations of the X-ray fluorescence visualizer, imager, or information provider 100 in which the respective at least one high energy photon and/or particle emitter portion(s) 150 and/or the at least one X-ray fluorescence receiving portion(s) 151 can respectively pass the at least one applied high energy photon and/or particle 120 and/or receive the at least one induced X-ray fluorescing photon 122 for various prescribed distances through the at least some matter of the at least a portion of the individual. Such prescribed distance of the respective at least one applied high energy photon and/or particle 120 and/or at least one induced X-ray fluorescing photon 122 can vary depending upon the respective energy levels (e.g., characterized by frequencies). In certain instances, it might be desired to pass the at least one applied high energy photon and/or particle 120 for relatively short distances through the matter, such as to pass for a considerable distance and thereby allow illumination of matter at an X-ray fluorescence location relatively shallowly into the individual, such as to illuminate a surface region of the individual. By comparison, in certain instances, it might be desired to pass the at least one applied high energy photon and/or particle 120 for relatively long distances through the matter, such as to pass for a considerable distance and thereby allow illumination of matter at the X-ray fluorescence location relatively deeply into the individual, such as to illuminate a relatively deep region of the individual. By comparison, in certain instances, it might be desired to receive the at least one induced X-ray fluorescing photon 122 from relatively short distances through the matter, such as to pass for a considerable distance and thereby allow X-ray fluorescence visualizing, imaging, or information providing of matter at an X-ray fluorescence location relatively shallowly into the individual. By comparison, in certain instances, it might be desired to receive the at least one induced X-ray fluorescing photon 122 from relatively long distances through the matter, such as to pass for a considerable distance and thereby allow X-ray fluorescence visualizing, imaging, or information providing of matter at the X-ray fluorescence location relatively deeply into the individual.

Such selection of the percentage of the at least one applied high energy photon and/or particle 120 and/or the at least one induced X-ray fluorescing photon 122 travels for relatively short or longer distances through the matter of the individual may depend on the energy of the at least one applied high energy photon and/or particle 120 or the at least one induced X-ray fluorescing photon 122. Typically, a large percentage of X-rays can travel for a considerable distance through matter, as evidenced by conventional transmissive X-rays that can often pass through the tissues, organs, or other matter of large portions of humans. With X-rays of lower energy levels than those used in conventional X-rays, the distance traveled may be considerably reduced, and a larger percentage of the X-rays can be absorbed.

By the process of X-ray fluorescence as described in this disclosure with respect to FIGS. 3, 4a, 4b, 4c, and other locations in this disclosure, the frequency of each of the at least one applied high energy photon and/or particle 120 that X-ray fluorescingly interfaces with the at least one target atom or fluorophore 121 will cause a reduction in the energy level (and a corresponding decrease in the frequency) as the at least one induced X-ray fluorescing photon 122 is being generated such as can be quantified as the characteristic energy drop which characteristically differs for each element (or chemicals, compounds, and/or biological materials that have received X-ray fluorescence enhancing additives, taggants, or contrast agents, etc.) undergoing X-ray fluorescence visualizing, imaging, or information providing as described in this disclosure.

It may be desirable to configure the frequency of the induced X-ray fluorescing photon 122 that undergoes X-ray fluorescence from the at least some matter of the at least the portion of the individual (at the X-ray fluorescing event) to be of such a frequency as to be largely absorbed or attenuated by the at least some matter of the at least the portion of the individual prior to traveling for an extensive distance through the at least some matter of the at least the portion of the individual. As such, the at least one induced X-ray fluorescing photon 122 that travels through the at least some matter of the at least the portion of the individual that is received by the at least one X-ray fluorescence receiving portion(s) 151 largely results from an X-ray fluorescing event proximate to (e.g., physically nearby) the at least one X-ray fluorescence receiving portion(s) 151. As such, certain embodiments of the X-ray fluorescence visualizer, imager, or information provider 100 can be configured such that the at least one X-ray fluorescence receiving portion(s) 151 substantially receive the at least one induced X-ray fluorescing photon 122 from only physically proximate X-ray fluorescence event based on attenuation of the at least one induced X-ray fluorescing photon 122 travelling through the at least some matter of the at least the portion of the individual.

There can be a considerable variety of embodiments of the X-ray fluorescence visualizer, imager, or information provider 100 that rely, at least partially, on the absorbance, attenuation, or other such process of the at least one induced X-ray fluorescing photon 122 within relatively short distances through at least some matter of the individual, in combination with the relative transmission or non-attenuation of the at least one applied high energy photon and/or particle 120 for relatively long distances through at least some matter of the individual such as described with respect to FIGS. 5 to 12, and at other locations through the disclosure. For instance, certain embodiments of the X-ray fluorescence visualizer, imager, or information provider 100 can be configured such that the at least one high energy photon and/or particle emitter portion(s) 150 largely "floods" such that the at least one applied high energy photon and/or particle 120 can travel through a portion of the individual. Certain embodiments of the at least one X-ray fluorescence receiving portion(s) 151 can thereupon be positioned proximate the X-ray fluorescing event(s) undergoing X-ray fluorescence visualizing, imaging, or information providing in the flooded portions of the at least some matter of the at least the portion of the individual. Such flooding techniques can rely in certain embodiments on proximity of the X-ray fluorescence receiving portion(s) 151 to the at least some matter of the at least the portion of the individual undergoing the X-ray fluorescence event(s), depending upon attenuation of much of the induced X-ray fluorescing photon 122 that travels for greater distances that within the proximate region.

Such "proximate" embodiments of the X-ray fluorescence visualizer, imager, or information provider 100 can be configured such that the at least one X-ray fluorescence receiving portion(s) 151 can be provided on a scope, catheter, tool, or other device within a localized region. Such techniques can provide localized X-ray fluorescence visualizing, imaging, or information providing within a relatively small region such as an organ, tissue, or other matter. For example, certain embodiments of the X-ray fluorescence visualizer, imager, or information provider 100 can be positioned as a tool, catheter, scope, etc. at a desired location within the heart, brain, liver, intestine, wounded abdomen, etc., and a larger region can undergo flooding by the at least one applied high energy photon and/or particle 120. Certain proximity-based embodiments of the X-ray fluorescence receiving portion(s) 151 can image on a real-time or other basis of such critical organs as hearts, brains, livers, etc. (including the fluid passage thereto).

By comparison, certain "flooding" embodiments of the X-ray fluorescence visualizer, imager, or information provider 100 can be utilized with pulse-type applied high energy photon and/or particle 120, and thereupon undergo X-ray fluorescence, visualizing, or information providing based at least partially on time of flight calculations as described in this disclosure. Such computed time of flight duration can, depending on context, vary depending on the distance traveled of the at least one applied high energy photon and/or particle 120, the duration of resulting X-ray fluorescing of the X-ray fluorescing event (which in many instances with X-ray fluorescence can be comparatively neglected since it is relatively brief), and the distance traveled of the at least one induced X-ray fluorescing photon 122.

A number of embodiments of the X-ray fluorescence visualizer, imager, or information provider 100 can rely on non-flooding techniques of the applied high energy photon and/or particle 120, such as application of pencil-beam, angle-beam, fan-beam, or other embodiments of the applied high energy photon and/or particle 120. For example, certain tools, probes, scopes, catheters, etc. can include both the at least one high energy photon and/or particle emitter portion(s) 150 and the at least one X-ray fluorescence receiving portion(s) 151. As such, certain embodiments of the X-ray fluorescence receiving portion(s) 151 can be configured to operationally interface with the high energy photon and/or particle emitter portion(s) 150 such that the receiving technique of the former is consistent with the later, and vice versa. For example, if the high energy photon and/or particle emitter portion(s) 150 is configured to generate the applied high energy photon and/or particle 120 that is undergoing a scanning operation, then the X-ray fluorescence receiving portion(s) 151 should be configured to receive the induced X-ray fluorescing photon 122 based on receiving the scanned operation. Alternately, if the high energy photon and/or particle emitter portion(s) 150 is configured to generate the applied high energy photon and/or particle 120 that is undergoing a flooding operation, then the X-ray fluorescence receiving portion(s) 151 should be configured to receive the induced X-ray fluorescing photon 122, which can operate based at least partially on receiving the flooding operation, or other such operation.

Such techniques could be used to provide highly precise imaging, visualizing, or information providing that may be configured to operate in a static, fixed picture, video, real time, and/or other such mode. Certain embodiments of the X-ray fluorescence visualizer, imager, or information provider 100 could thereby be configured to X-ray fluorescence visualize, image, or provide information relative to blood, lymph, or other fluid flowing through, or contained in, an organ such as the heart, brain, liver, etc., such as may be at least partially based on elements, chemicals, compounds, and/or biological materials contained therein.

Blood, lymph, explosives, bullets, tissue, wounds, infections, and a variety of other types of matter can be X-ray fluorescence visualized, imaged, or information provided based at least partially on the elements, chemicals, compounds, and/or biological materials either making up, contained within, or associated with the at least some matter of the at least the portion of the individual. Certain other exemplary embodiments of the X-ray fluorescence visualizer, imager, or information provider 100 can be configured to apply a desired or suitable side or shape of the at least one applied high energy photon and/or particle 120 and/or the at least one induced X-ray fluorescing photon 122. A three-dimensional bullet-wound path or explosive-injury pattern could be X-ray fluorescence visualized, imaged, or information provided using certain embodiments of the X-ray fluorescence visualizer, imager, or information provider 100 based at least partially on the elements, chemicals, compounds, and/or biological materials in the matter or otherwise associated therewith.

Certain medical diagnosis using conventional imaging techniques can be time-consuming, difficult, and require considerable skill and interpretation. For example, certain doctors specializing in cancer, blood disorders, etc. might review output from a conventional MRI, CT scan, etc. for considerable duration to consider whether an aberration and tissue, lung, bone, etc. should be of concern or is indicative that further treatment may be useful or necessary, etc. One challenge with certain types of conventional imagers, visualizers, or information providers is that while some matter might appear in the same shape as a matter aberration, there is often little indication as to the elements, chemicals, compounds, and/or biological materials making up the particular matter aberration. Since certain embodiments of the X-ray fluorescence visualizer, imager, or information provider 100 can be configured to provide an elemental, chemical, compound, and/or biological material indication of the matter (of the normal matter aberration such as the tissue aberration), such elemental, compound, chemical, or biological material analysis can be used to make the determination, diagnosis, or analysis of a particular matter aberration (having particular element characteristics) more or less likely.

As such, certain embodiments of the X-ray fluorescence visualizer, imager, or information provider 100 can provide for simplifying visual review of the X-ray fluorescence visualizing, imaging, or information providing such that the doctor (or other user) could target specific elements associated with certain illnesses, cancers, abscesses, heart conditions, infections, injuries, conditions, etc. such targeted elements, etc. can be imaged or visualized as a distinct or identifiable color or pattern. Certain embodiments of the X-ray fluorescence visualizer, imager, or information provider 100 can more finely differentiate matter, such as tissue, blood, bones, inserts, etc.

The quality of the visualizing, imaging, or information as provided by certain embodiments of the X-ray fluorescence visualizer, imager, or information provider 100 that may be based at least partially on the density of the elements, chemicals, compounds, and/or biological materials, included in or contained within the matter may thus likely be "richer", more polychromatic, or more "robust", and/or perhaps "more" detailed that a variety of conventional imagers that operate based on density of the matter being imaged, such as with conventional CT scans or MRIs. The increased richness of certain embodiments of the X-ray fluorescence visualizer, imager, or information provider 100 may, depending on context, result from the visualizing, imaging, or providing information that can be distinguished based at least partially on the elements, chemicals, compounds, and/or biological materials in or within the matter, matter aberration, and/or matter irregularity. Such increased richness of the visualizing, imaging, or providing information can at least partially result from differentiation of different elements, chemicals, compounds, and/or biological materials such as by providing different colors, textures, text, etc., as an indication of the distinct matter. For instance, certain embodiments of the X-ray fluorescence visualizer, imager, or information provider 100 that are configured to scan for cancer may indicate any elements, chemicals, compounds, and/or biological materials indicative of a higher probability of cancer by a distinct color, shape, cross-hatching, and/or associated text. It is also preferred that certain embodiments of the X-ray fluorescence visualizer, imager, or information provider 100 provide an indication as to element, chemical, compound, and/or biological material density, as well as element, compound, chemical, and/or biological material presence.

Within this disclosure, certain embodiments of the visualizing, imaging, or providing information can be applied as to include, but is not limited to, confocal X-ray fluorescence microscopy such as may be used to look at an at least partially internal matter of at least a portion of the individual. For instance certain embodiments of the X-ray fluorescence visualizer, imager, or information provider 100 can be attached to a portion such as a tip of a scope device (e.g., an endoscope) to provide a fiber confocal X-ray fluorescence microscopy, depending on the achievable resolution. Certain embodiments of the X-ray fluorescence visualizer, imager, or information provider 100 can use such image processing techniques as filtering, magnification, image combining, image subtraction, convolution, etc. to achieve the desired level of magnification.

Certain embodiments of the X-ray fluorescence visualizer, imager, or information provider 100 can provide for visualizing, imaging, or information providing of a richness or quality of information relating to elements, chemicals, compounds, and/or biological materials that may be suitable to limit the use of biopsies for living individuals, or autopsies for deceased individuals. As such, instead of using such procedures as invasive biopsies or autopsies, in certain instances, certain embodiments of the X-ray fluorescence visualizer, imager, or information provider 100 can be used to obtain, provide, or display similar information as such procedures relating to the contents of the at least some matter of the at least the portion of the individual. Since the X-ray fluorescence visualizing, imaging, or information providing can be performed quicker and less expensively than biopsies (and some times without as much doctor or surgeon interaction), certain embodiments of the X-ray fluorescence visualizer, imager, or information provider 100 can provide a very real cost, time, and patient danger savings as compared to such procedures as certain biopsies or autopsies. Additionally, certain embodiments of the X-ray fluorescence visualizer, imager, or information provider 100 can allow for scanner a wider volume of matter than is typically possible with conventional imagers such as MRI or CAT scans that can be used in biopsies or autopsies.

Certain embodiments of the X-ray fluorescence visualizer, imager, or information provider 100 can likely provide considerable cost savings, time savings, or danger for the individual (e.g., patient), the user (e.g., doctor, surgeon, dentist, researcher, etc.), as well as the government or insurance company (e.g., medicare, etc.) paying for the visualizing, imaging, or information providing procedure. As an example of time savings and reliability by using certain embodiments of the X-ray fluorescence visualizer, imager, or information provider 100, a large number of moles on a persons back can be scanned for those that may be indicative of a melanoma. Those moles associated with or indicative of a melanoma might, for example, be relatively easily detectable due to the presence of an indicative element often present in such cancers as melanomas, as described in the disclosure.

Certain embodiments of the X-ray fluorescence visualizer, imager, or information provider 100 can be configured to be relatively small, perhaps low power, and perhaps inexpensive, as compared to certain conventional imaging systems such as MRIs, CT scans, etc. This low power aspect relies on the at least one high energy photon and/or particle emitter portion(s) 150 being configured to apply sufficient X-rays to cause the matter of the individual to fluoresce, instead of requiring the X-rays to transmit through the portion of the individual as with transmissive X-ray mechanisms. Certain MRI systems, for example, are so expensive that certain hospitals and/or cities can economically justify only one (or a low number) that has to be expensively applied to a variety of applications. Certain embodiments of the X-ray fluorescence visualizer, imager, or information provider 100 can be relatively inexpensive to operate as compared with certain conventional imagers, and as such can be applied inexpensively to a variety of applications at a variety of different or multiple locations.

As such, certain conventional imaging modalities such as MRI may be sufficiently expensive as to limit their use to only certain important applications. In addition, certain conventional tomographic devices are sufficiently expensive and time consuming as to limit their use to only particularly serious or important applications. By configuring certain embodiments of the X-ray fluorescence visualizer, imager, or information provider 100 to be smaller, less expensive, less time consuming, etc., they can be used more frequently and for more applications. For example, certain doctor offices or hospital exam rooms used for specific applications such as screening for cancer, heart condition, abscesses, brain condition, etc. can utilize certain specialized embodiments of the X-ray fluorescence visualizer, imager, or information provider 100 that may be configured for its particular use, as well as relatively inexpensive and easy to operate.

Another nearby operating room, patient room, doctor's office, dental office, veterinarian, etc. can include another X-ray fluorescence visualizer, imager, or information provider 100 that may be configured for a different purpose, for example. Those in life-threatening conditions, operating rooms, or intensive care, for example, may benefit from a more recent updated or continuous, or substantially real-time progression of certain embodiments of the X-ray fluorescence visualizer, imager, or information provider 100 that may be suitably devoted to a particular application. It is likely that certain embodiments of the X-ray fluorescence visualizer, imager, or information provider 100 may be configured relatively smaller than many conventional imagers to require considerably less space in doctors offices, medical examination rooms, hospitals, veterinarians, dentists, researchers, etc. Due to such factors as expense, large size, high complexity, considerable operating duration, etc.

Certain embodiments of the X-ray fluorescence visualizer, imager, or information provider 100 may, by comparison, be quite adaptive, relatively inexpensive, and re-configurable as desired. By configuring certain embodiments of the X-ray fluorescence visualizer, imager, or information provider 100 to be relatively low power, relatively inexpensive to purchase or operate, or relatively portable, such devices can gain access to considerable portions of the world than up to this time the population has not had access to desirable or appropriate imaging techniques. Certain embodiments of the X-ray fluorescence visualizer, imager, or information provider 100 could therefore be utilized in particularly rural, remote, or poorer regions to thereby improve the available visualizing, imaging, or information providing, and therefore provide for considerable improved medical care as described in this disclosure.

Certain embodiments of the X-ray fluorescence visualizer, imager, or information provider 100 can X-ray fluorescence visualize, image, or provide information through a variety of information providing depths 170 which may be as applied through a variety of thicknesses into the at least one matter of the at least the portion of the individual, depending at least partially on configuration and/or operation. For example, certain embodiments of the X-ray fluorescence visualizer, imager, or information provider 100 can X-ray fluorescence visualize, image, or provide information pertaining through to one or more prescribed substantial X-ray fluorescence depths into varied portions of the at least a portion of an individual. Examples of such individuals that can be X-ray fluorescence visualized, imaged, or have information provided thereabout can include, but are not limited to: humans, animals, organism, and/or plants, combinations thereof, or a portion thereof. As such, a major or minor body portion of an animal or person, a leaf, a stem, or another portion of a plant, an organism or portion thereof, etc. represent examples of individuals that may be visualized, imaged, or information provided Certain embodiments of the at least one X-ray fluorescence visualizer, imager, or information provider 100 can include, but is not limited to, an at least one high energy photon and/or particle emitter portion(s) 150, an at least one X-ray fluorescence receiving portion(s) 151, and/or optionally an at least one X-ray fluorescence visualization, imaging, or information providing controller 97. The at least one high energy photon and/or particle emitter portion(s) 150 can be, depending on context, configured to emit at least one applied high energy photon and/or particle 120 into and/or through matter of the at least portion of the individual 82 that can raise the energy level of the target atom or fluorophore 121 of the matter. With the energy level of the target atom or fluorophore 121 in a raised state, it can thereby emit at least one induced X-ray fluorescing photon 122 (in a somewhat random direction since it is likely to be emitted in any direction as likely) as described with respect to FIG. 3 or 4c, in accordance with the general principles of X-ray fluorescence as described below. The energy level of which the target atom or fluorophore 121 release may thereby correspond to the chemical, atomic, element, and/or biological material structure of target atom or fluorophore. The at least one X-ray fluorescence receiving portion(s) 151 can thereby, depending on context, be configured to receive high energy photons and/or particles that have been received from the matter (e.g., tissue, bones, etc.) of the at least portion of the individual 82. Certain embodiments of the at least one high energy photon and/or particle emitter portion(s) 150 can be situated within, outside of, or at least partially internal relative to the at least a portion of the individual 82. Certain embodiments of the at least one X-ray fluorescence receiving portion(s) 151 can be situated within, outside of, or at least partially internal relative to the at least a portion of the individual 82.

Figure 2:
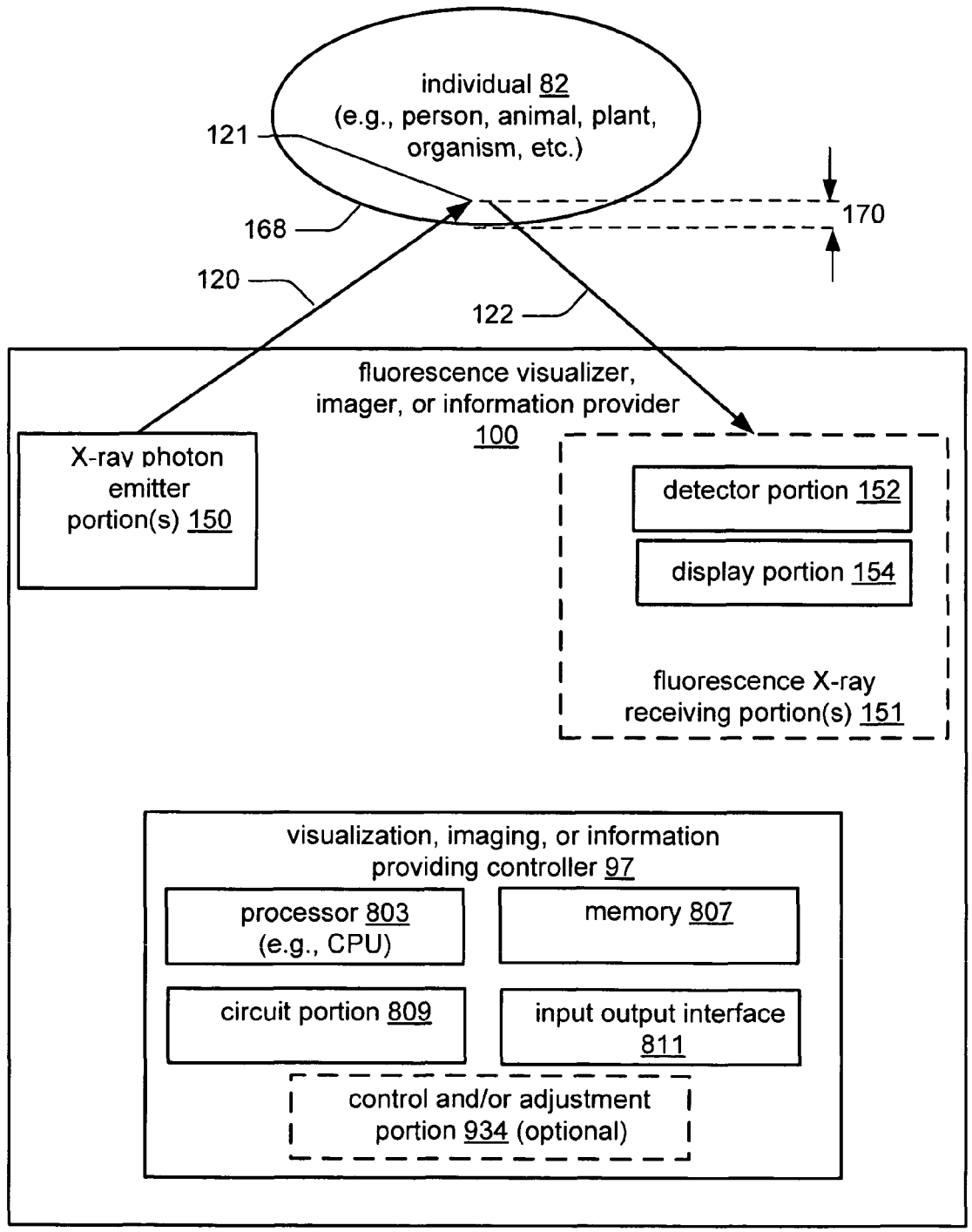
FIG. 2 is a diagram of the X-ray fluorescence visualizer, imager, or information provider including certain embodiments of a high energy photon and/or particle emitter portion.

Within this disclosure, the term "high energy" can, depending on context, be applied to a variety of the applied high energy photon and/or particle 120 can include, but is not limited to, X-rays, gamma rays, particles such as electrons, protons, neutrons, etc. as described in this disclosure. FIGS. 1 and 2 differ in that the high energy photon and/or particle emitter portion 150 of FIG. 1 is described as the X-ray photon emitter portion of FIG. 2. Certain embodiments of the X-ray fluorescence visualizer, imager, or information provider 100 can X-ray fluorescence visualize, image, or provide information operate, for example, at a relatively high energy. Certain embodiments of the X-ray fluorescence visualizer, imager, or information provider 100 are configured such that at least some of the induced X-ray fluorescing photon 122 are within the range of the particular electromagnetic radiation. Within this disclosure, certain embodiments of the high-energy of the applied high energy photon and/or particle 120 can, depending upon context or embodiment, be considered as being alternatively: greater than or equal to 1 KVolt, greater than or equal to 10 Kvolts (both of which may generate photons characterized as X-rays), and/or greater than or equal to 100 KVolt (also which may generate photons characterized as gamma rays). The use of such high energy frequencies of the at least one applied high energy photon and/or particle 120 and/or the at least one induced X-ray fluorescing photon 122 may be particularly suitable using certain embodiments of the X-ray fluorescence visualizer, imager, or information provider 100 to provide X-ray fluorescence depth visualization, depth imaging, and/or depth information providing for a considerable or controllable depth into and/or through the matter of the at least the portion of the individual that may be based at least partially on the density of the elements, chemicals, compounds, and/or biological materials included in or contained within the matter.

There are a variety of applications for certain embodiments of the X-ray fluorescence visualizer, imager, or information provider 100, certain illustrative aspects are described. A variety of such aspects are intended to be illustrative in nature but not limiting in scope, as to describe the variety of the embodiments. Certain embodiments of the X-ray fluorescence visualizer, imager, or information provider 100 could be used in combination (such as in various configurations) with other visualizing, imaging, or information providing modality, such as conventional MRI, CT scans, etc.

Certain embodiments of the X-ray fluorescence visualizer, imager, or information provider 100 can be configured to provide very good resolution and/or magnification, such as with the confocal X-ray fluorescence microscopy techniques as described herein. Certain embodiments of the X-ray fluorescence visualizer, imager, or information provider 100 can be configured with sufficient resolution and/or magnification to provide an analysis of a genetic state of the individual, etc. The genetic state of the individual may be used, for example, to provide non-invasive biopsy for DNA imaging.

Certain embodiments of the X-ray fluorescence visualizer, imager, or information provider 100 can provide for X-ray radiographic analysis (without necessarily relying on protons as with certain conventional imagers or magnetic fields as with certain conventional MRI). Certain embodiments of the X-ray fluorescence visualizer, imager, or information provider 100 can provide for dynamic imaging such as with use of signal propagation as to provide an anatomic physiology or functional physiology of the matter of the at least the portion of the individual. For example, the tissue, plaque, muscle, fat, blood flowing through, or other matter of the heart could be imaged on a repetitive manner such as by detecting a rate of calcium flux (or certain other elemental aspects. Additionally, the flow of blood through the heart, kidneys, brain, or other organ, muscle, aorta, etc. can be visualized, imaged, or provided information based at least partially on iron (i.e., hemoglobin) or other suitable elements, chemicals, compounds, and/or biological materials.

Certain embodiments of the X-ray fluorescence visualizer, imager, or information provider 100 can provide for early detection of strokes. For example, portion of tissue of the heart that is non-oxygenated, or oxygenated but not detected may be visualized, imaged, or have information provided based at least partially on the level (density) of oxygen. Certain embodiments of the X-ray fluorescence visualizer, imager, or information provider 100 can monitor the certain tissue oxygen levels to determine whether there is an increased likelihood of heart attack, or stroke. Ischemia, which relates to reduction of blood supply to the heart (as well as other heart diseases) may be monitored considering blood supplies as well as level of oxygen in the blood using certain embodiments of the X-ray fluorescence visualizer, imager, or information provider 100. As such, certain embodiments of the X-ray fluorescence visualizer, imager, or information provider 100 can consider the oxygen state of the blood, etc. Certain results from the X-ray fluorescence visualization, imaging, or providing information may be indicative of stroke, heart attack, or other circulatory problem that may be based at least partially on the density of the elements, chemicals, compounds, and/or biological materials included in or contained within the matter (e.g., oxygenated tissue).

Certain embodiments of the X-ray fluorescence visualizer, imager, or information provider 100 can be applied to a variety of applications such as biopsies, autopsies, anesthesia, drug or nutrition monitoring, etc. based at least partially on element composition in the blood, tissue, or other matter. Such monitoring of certain element composition levels can be performed when a person or animal is unconscious or anesthetized, such as during an operation, surgery, an accident, during transport to a hospital, etc.; as well as when the person or animal is conscious such as during a routine exam, being scanned for a condition, etc. Certain embodiments of the X-ray fluorescence visualizer, imager, or information provider 100 can be configured to provide relatively low radiation emission, such as to limit the radiation dosage applied to the individual. One example of such monitoring could include the ability to detect such element composition as fluorine or fluorine-based chemicals, compounds, or biological matter in anesthetized patients (e.g., using haloflorane). This may provide a non-invasive and effective way for the X-ray fluorescence visualizer, imager, or information provider 100 to detect levels or locations of inhaled anesthetic, as well as visualize, image, or provide information relating to inhaled anesthetic relative to the individual such as a human particularly in certain matter of the at least a portion of the individual that may be based at least partially on the density of the elements, chemicals, compounds, and/or biological materials included in or contained within the matter.

Certain embodiments of the X-ray fluorescence visualizer, imager, or information provider 100 could be used to detect certain poisons, medications, elements, foods, etc. based at least partially on their element composition. For example, certain poisons, medications, elements, foods, etc. that include elements (e.g., lead), or are traced with, certain X-ray fluorescence enhancing additives, taggants, or contrast agents, etc. can be used to provide the element composition can be X-ray fluorescence visualized, imaged, or provide information based at least partially on the element composition provided that the element composition being used for the X-ray fluorescence visualizing, imaging, or information providing does not interfere with the background. Certain embodiments of the X-ray fluorescence enhancing additives, taggants, or contrast agents, etc. can be used in those instances where there might be interference between the background and certain elements, chemicals, compounds, and/or biological materials. In the instance of poisons, the locations of the particularly high concentrations of the poisons could be monitored to determine where the affects of the poisoning may be most adverse. As such, certain embodiments of the X-ray fluorescence visualizer, imager, or information provider 100 could be utilized in such fields as autopsies, biopsies, poisoning, nutrition, medication, etc. based on the element composition through the body of the individual (e.g., person) based on use of certain embodiments of the X-ray fluorescence visualizer, imager, or information provider 100.

Certain embodiments of the X-ray fluorescence visualizer, imager, or information provider 100 can be configured for operation using an addition of contrast agent, such as via a probe that may be considered as one embodiment of a tool as described in this disclosure. Such contrast agent may allow for improved X-ray fluorescence visualizing, imaging, or information providing based on certain elements, as well as allowing or improving X-ray fluorescence visualizing, imaging, or information providing based on certain elements, chemicals, compounds, and/or biological materials such as may have receptors to absorb or maintain the contrast agents. This may amount to addition of fluorescing element such as can be received by a particular elements, chemicals, compounds, and/or biological materials, or alternately enhancement of existing fluorescing element. Certain matter of the individual may be monitored using the X-ray fluorescence visualizing, imaging, or information providing techniques for a varied rate of contrast flux, for example.

Certain embodiments of the X-ray fluorescence visualizer, imager, or information provider 100 can be configured to provide possible user interface including creating color coding, gray scale, analyzed data, and other techniques such as may provide for multiple elemental imaging sequences be viewable in a way that aids diagnosis and/or anatomic evaluation. Such techniques may have the effect of increasing the richness of the X-ray fluorescence visualizing, imaging, or information providing such as by allowing element, chemical, compound, and/or biological material aspects to be reviewed or monitored and/or more easily considered.

Certain embodiments of the X-ray fluorescence visualizer, imager, or information provider 100 can be configured to monitor for glutamate receptors. Glutamate is a neurotransmitter in nerve cells that binds to all glutamate receptors located on neuron membranes, and is an example of a transmembrane receptor. Glutamate is a common neurotransmitter in the body, and exists in much of the nervous tissue in humans. Glutamate, when it binds, allows calcium to pass through. Magnesium is an example of an element which may participate in the glutamate/glutamate receptor interaction. With ligand receptor binding, the magnesium can be removed from the ion channel allowing calcium to influx into the cell. As such, the magnesium, for example, can be traced using certain embodiments of the X-ray fluorescence visualizer, imager, or information provider 100, such as to determine a region of the brain undergoing certain (e.g., toxic) functions.

Such embodiments of visualizing, imaging, or information providing based at least partially on elements as described in this disclosure are intended to be illustrative in nature, but not limiting in scope. It is likely that there will be a large variety of elements, chemicals, compounds, and/or biological materials they can be used for visualizing, imaging, or providing information that may be based at least partially on the density of the elements, chemicals, compounds, and/or biological materials included in or contained within the matter, as described in this disclosure.

Certain embodiments of the X-ray fluorescence visualization, imaging, and/or information providing can operate at least partially at the high energy level (e.g., corresponding to frequency or wavelength) of the high energy photon and/or particle to depth visualize, image, or provide information for a considerable prescribed substantial X-ray fluorescence depth into the individual 82. Conventional transmissive X-rays are generally understood as being capable of being capable of passing for considerable distances through tissue, bones, bodily fluids, or other matter of individuals such as persons, animals, etc. As such, certain embodiments of the high energy photons and/or particles, as emitted by the at least one high energy photon and/or particle emitter portion(s) 150, can pass for a considerable prescribed substantial X-ray fluorescence depth through a variety of tissue or matter of the at least the portion of the individual 82 to a prescribed substantial X-ray fluorescence depth that may be based at least partially on the density, elements, chemicals, compounds, and/or biological materials included in or contained within the matter. Certain embodiments of the X-ray fluorescence visualizer, imager, or information provider 100 may thereupon be used to indicate a presence or absence of an element in the matter of the at least a portion of the individual, since each of the target atom or fluorophore 121 fluoresces at its characteristic frequency. The amount of the prescribed substantial X-ray fluorescence depth may be based at least partially on the energy level, matter, and characteristics of the emitted at least one applied high energy photon and/or particle 120 and/or the at least one induced X-ray fluorescing photon 122 that may be based at least partially on the density, elements, chemicals, compounds, and/or biological materials included in or contained within the matter.

Some energy may be lost as the at least one applied high energy photon and/or particle 120 is converted into the at least one induced X-ray fluorescing photon 122 by the fluorescing event occurring within the at least one target atom or fluorophore 121. Within this disclosure, the frequency or energy level of the at least one applied high energy photon and/or particle 120 may be selected such that the at least one induced X-ray fluorescing photon 122 may be emitted within the X-ray fluorescence range during X-ray fluorescence.

Certain embodiments of the X-ray fluorescence visualizer, imager, or information provider 100 can map the matter of the at least the portion of the individual based at least partially on the element concentration in the matter, or the densities of the elements. Such mapping can be provided for a single element, or for a number of elements (e.g., each element may be mapped using a different color or combinational color, etc.). As such, the operators of certain embodiments of the X-ray fluorescence visualizer, imager, or information provider 100 can select a particular color associated with an element, or combination of elements, chemicals, compounds, and/or biological materials, etc. during screening of the at least portion of the individual for that element, or combination of elements, chemicals, compounds, and/or biological materials, etc.

Certain embodiments of the at least one X-ray fluorescence receiving portion(s) 150 of FIG. 1 can thereby include an X-ray version as described with respect to FIG. 2. This follows since certain frequencies or energy levels of the applied high energy photon and/or particle 120 can produce certain of the induced X-ray fluorescing photon 122 upon fluorescing of the at least one target atom or fluorophore 121. Certain embodiments of the X-ray fluorescence visualizer, imager, or information provider 100 may be configured to sense the location, concentration, shape, severity, or other aspects of certain elements within the at least a portion of the individual. Such X-ray fluorescence visualizing, imaging, or information providing based at least partially on concentration of particular elements may be particularly useful in those instances where the existence of the certain elements within the individual may indicate a particular sickness, injury, cancer, abscess, infection, illness, bodily condition (e.g., heart, liver, bone, etc.). Such locating can be at least partially utilized in, or associated with, the X-ray fluorescence visualizing, imaging, or information providing, based at least partially on characteristics and/or configurations of the matter, tissue, bodily fluids, bones, skeletal portions, etc.

The X-ray fluorescence visualization, imaging, or information providing may result, in certain embodiments, in an application or travel of either the at least one applied high energy photon and/or particle 120 and/or induced X-ray fluorescing photon 122 through at least some matter or across at least one surface delineating the matter. Such X-ray fluorescence high energy (e.g., X-ray, gamma ray, photon, particle, etc.) can X-ray fluorescence at one or more fluorescing event within an at least one X-ray fluorescence range to at least one prescribed substantial X-ray fluorescence depth. Certain embodiments of the X-ray fluorescence visualizer, imager, or information provider 100 can X-ray fluorescence visualize, image, and/or provide information within a region or volume extending between at least two prescribed substantial X-ray fluorescence depths 170. As such, certain regions and/or volumes can be spaced an X-ray fluorescence range of prescribed substantial X-ray fluorescence depths or distances from a surface 168 of the at least the portion of the at least a portion of the individual. The region or volume of the individual 82 that is being X-ray fluorescence visualized, imaged, or have information provided can be of some selected and/or controllable thickness, which when made arbitrarily thinner may be considered as approaching a two-dimensional substantially homogeneous surface.

Depending upon the configuration or usage of the X-ray fluorescence visualizer, imager, or information provider 100, it may be desired to have the regions for photons and/or particles pass through the individual 82 either along the at least one applied high energy photon and/or particle 120 to cause the matter of the individual 82 to fluoresce, or alternatively the at least one induced X-ray fluorescing photon 122 that is emitted from the at least a portion of the individual 82 upon X-ray fluorescence. Certain embodiments of the X-ray fluorescence visualizer, imager, or information provider 100 can vary from precise application of the applied high energy photon and/or particle 120 relative to a relatively concentrated portion of the individual 82 extending to flooding the individual, or portion thereof, with the applied high energy photon and/or particle 120.

Certain of the "X-ray fluorescence range" to the "prescribed substantial X-ray fluorescence depth", as described in this disclosure, may be visualized, image, or provide information at least partially based on determining the characteristic frequency through to the at least one X-ray fluorescence range to at least one prescribed substantial X-ray fluorescence depth (or alternately the at least one substantially X-ray fluorescence range at or between at least one prescribed substantial X-ray fluorescence depth(s)). The at least one X-ray fluorescence range to at least one prescribed substantial X-ray fluorescence depth may, depending upon context, pertain to the X-ray fluorescence range within the region of the matter of the at least the portion of the individual that is undergoing X-ray fluorescence visualization, imaging, or information providing.

The at least one X-ray fluorescence range to at least one prescribed substantial X-ray fluorescence depth may, depending upon context, pertain to the region of the matter of the at least portion of the individual to which the at least one applied high-energy photon or particles are being applied substantially down to the prescribed substantial X-ray fluorescence depth (as well as a potential variety of the X-ray fluorescence ranges of the prescribed substantial X-ray fluorescence depth).

Certain of the at least one applied high-energy photon or particles can alter their applied energy level, such as to travel to a variety of prescribed substantial X-ray fluorescence depths into the matter of the at least the portion of the individual. Certain of the at least one applied high-energy photon or particles can continue to pass to beyond the prescribed substantial X-ray fluorescence depth (but this number may be relatively small or at least distinguishable such as to allow their effects to be filtered out or otherwise limited). The at least one applied high-energy photon or particles that continue to pass beyond the prescribed substantial X-ray fluorescence depth may thereupon, following fluorescing interaction or fluorescing event with the atoms of the matter of the at least the portion of the individual, cause the atoms of the matter to fluoresce, and thereupon generate fluorescing photons at depths greater than the prescribed substantial X-ray fluorescence depth. The X-ray fluorescence visualized, imaged, or information provided matter of the at least the portion of the individual can dimensionally vary considerably in different embodiments of the X-ray fluorescence visualizer, imager, or information provider 100, as well as in different individuals, or portions thereof. For instance, such X-ray fluorescence ranges of the prescribed substantial X-ray fluorescence depths can vary from an infinitesimal dimension, through a few to hundreds of microns, to a considerable or entire distance through such individuals as humans, animals, plants, and/or organisms. The particular prescribed substantial X-ray fluorescence depth can depend on such factors as the configuration, type, use, fluorescing tendency, matter being X-ray fluorescence visualized or imaged, matter including elements being X-ray fluorescence visualized or imaged, and/or or matter being imaged; as well as the type, power, directionality, and/or other characteristic of the X-ray fluorescence visualizer, imager, or information provider 100.

The potential quality, resolution, potential applications, and/or accuracy, of X-ray fluorescence visualization, imaging, or information providing can vary, in different embodiments, based at least partially on variations of, e.g.: configurations, designs, and/or numbers of probes included in the at least one high energy photon and/or particle emitter portion(s) 150 and/or the at least one X-ray fluorescence receiving portion(s) 151. Resolution of certain embodiments of the X-ray fluorescence visualizer, imager, or information provider 100 can, in certain embodiments, to be down to 1 mm or even for, which is similar to certain conventional MRI. The variation of the quality, resolution, potential applications, and/or accuracy, of X-ray fluorescence visualization, imaging, or information providing can further continue to sophisticated imaging systems allowing for detailed X-ray fluorescence visualization, imaging, or information providing.

Within this disclosure, certain embodiments of the at least one X-ray fluorescence receiving portion(s) 151 could be applied from an at least partially internal location to the individual, applied from an at least partially external location to the individual, configured as a complete unit, and/or configured as a number of combined units at least some of which may interact together.

Certain embodiments of the at least one high energy photon and/or particle emitter portion(s) 150 and/or the at least one X-ray fluorescence receiving portion(s) 151 can be configured as unitary devices, distinct units of devices, combined units of devices, discrete units of devices, arrays of distinct devices, and/or alternately as arrays of composite devices. Such varied, complex, or other devices made using such processes as semiconductor processing, very large scale integration (VLSI), ultra large scale integration (ULSI), and/or other known semiconductor or other manufacturing processes. The X-ray fluorescence depth visualization, imaging, or information processing associated with the at least one high energy photon and/or particle emitter portion(s) 150 and/or at least one X-ray fluorescence receiving portion(s) 151 should be selected to be suitable for operation of the particular device(s), as well as the potential user input.

The associated X-ray fluorescence visualizing, imaging, information providing, and/or processing devices and/or associated techniques can therefore be designed, used, processed, and/or scaled based, at least in part, on the sophistication and complexity of the X-ray fluorescence visualizer, imager, or information provider 100. Certain embodiments of X-ray fluorescence visualization, imaging, or information providing can be performed by a variety of either at least partially internal embodiments, and/or at least partially external embodiments. Certain embodiments of the X-ray fluorescence visualizer, imager, or information provider 100, as described in the disclosure, can be at least partially generalized to, and generally at least partially operate according to, the disclosure as described with respect to the block diagrams of FIGS. 1 and/or 2.

Certain types of X-ray fluorescence visualization, imaging, or information providing that may be able to operate its certain X-ray fluorescence ranges to prescribed substantial X-ray fluorescence depth, resolutions, colors, characteristic frequencies, etc. to can be configured to perform certain activities are types of diagnosis better, similar to, or worse than others. This disclosure describes a number of embodiments of the X-ray fluorescence visualizer, imager, or information provider 100 that may each be configured for X-ray fluorescence visualization, imaging, or information providing such as may be suited to detect particular illnesses, injuries, infections, cancers, tumors, bone conditions, abscesses, teeth, implants, etc. in either a devoted or multi-purpose manner. Certain embodiments of the X-ray fluorescence visualizer, imager, or information provider 100 may be relatively inexpensive to purchase and/or operate as compared with certain conventional tomographic imagers due to potential simplicity in design, relatively lower power systems, etc. As such, certain embodiments of the X-ray fluorescence visualizer, imager, or information provider 100 might be used for varied operations (such as in a vehicle), or alternately a number of the X-ray fluorescence visualizer, imager, or information provider 100 can be configured for devoted applications, instead of a single relatively expensive conventional imager may have to be used for many applications due to its expense and size (e.g., MRIs). As such, each devoted embodiment of the X-ray fluorescence visualizer, imager, or information provider 100 can be configured in the used only a fourth particular task, and may not have to be reconfigured for multiple tasks possibly making the overall operation simpler and limiting the likelihood of confusion.

Figure 3:
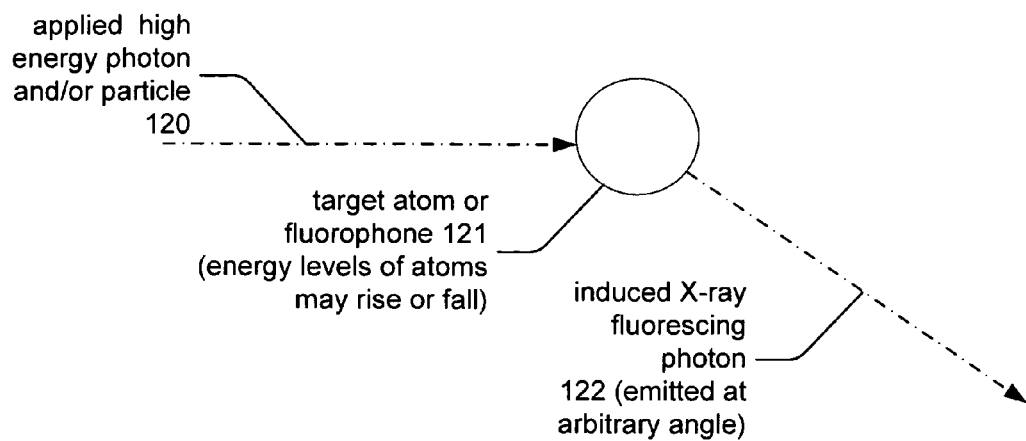
FIG. 3 is a diagram of an X-ray photon undergoing a fluorescing event, such as can be performed by certain embodiments of the X-ray fluorescence visualizer, imager, or information provider.

The FIG. 1 or 2 embodiment of the X-ray fluorescence visualizer, imager, or information provider 100, shown in block diagram format, can be applied to a variety of configurations, operating X-ray frequencies or energies, etc. as well as applications, etc. FIG. 3 shows, for example, a diagram of a fluorescing event associated with an X-ray photon of the at least one applied high energy photon and/or particle 120 contacting a target atom and/or fluorophore 121. The target atom and/or fluorophore 121 may be included as at least a portion of the "matter" of the individual as described in this disclosure that can be X-ray fluorescence visualized, imaged, or information provided based at least partially on elemental composition (or with the use of X-ray fluorescence enhancing additives, taggants, or contrast agents, etc. can image for composition of elements, chemicals, compounds, and/or biological materials) or densities thereof within. After the at least one applied high energy photon and/or particle 120 contacts at least a portion of the target atom and/or fluorophore 121, then an at least one induced X-ray fluorescing photon 122 can be generated/emitted (usually in a somewhat random direction) from the target atom and/or fluorophore 121. Within this disclosure, the term "fluorophore" can, depending upon context, pertain to atoms, particles, etc. that are capable of undergoing a fluorescing event, or X-ray fluorescence. Such elements or atoms that can undergo X-ray fluorescence can be in their natural state and/or may include the X-ray fluorescence enhancing additives, taggants, or contrast agents, etc. to enhance the X-ray fluorescence visualizing, imaging, or information providing. The at least one applied high energy photon and/or particle 120 may generally lose energy during its transition to generate the at least one induced X-ray fluorescing photon 122 during the fluorescing event. Such loss of energy may at least partially result from heat and transition of displaced atoms between the various valence bands within the target atom and/or fluorophore 121 (included as at least a portion of the "matter" of the individual as described in this disclosure). Such fluorescing of the target atom and/or fluorophore 121 during the fluorescing event often results in loss of energy therein.

The X-ray fluorescence energy level can be used to derive the energy transfer based on the equations included in this disclosure, and as described with respect to FIG. 3. Certain embodiments of the X-ray fluorescence X-ray fluorescence visualizing, imaging, or information providing can be derived based at least partially on a combination of: a) the initial trajectory (direction and energy level of the atom) of the at least one applied high energy photon and/or particle 120 such as may be emitted by the at least one high energy photon and/or particle emitter portion(s) 150 of FIG. 1 or 2 in which the detected fluorescing position which the at least one induced X-ray fluorescing photon 122 can be received at the at least one X-ray fluorescence receiving portion(s) 151 of FIG. 1 or 2, for example, and c) the detected angle of the at least one induced X-ray fluorescing photon 122 being received as may be detected by certain embodiments of the at least one X-ray fluorescence receiving portion(s) 151.

Certain embodiments of the X-ray fluorescence visualizer, imager, or information provider 100 can be used to visualize, image, or provide information relating to nerve condition, muscle, etc. as may be used to indicate nerve conduction or muscle extension/retraction. Such nerve conduction or muscle extension/retraction may be visualized, imaged, or have information provided at least partially as a result of detection of sodium, potassium, calcium, or other such element such as may be used to indicate nerve conduction or muscle contraction\expansion. It may be possible to use certain embodiments of the X-ray fluorescence visualizer, imager, or information provider 100 to more easily detect, analyze, and even perhaps treat Alzheimer's disease, or other neurological or spinal disease or condition that may be based at least partially on the densities, elements, chemicals, compounds, and/or biological materials, included in or contained within the matter as more elements, chemicals, compounds, and/or biological materials, etc. are understood to be used to detect or scan for their presence. Certain embodiments of the X-ray fluorescence visualizer, imager, or information provider 100 can be multi-modal, such as to be able to detect elements, chemicals, compounds, and/or biological materials like, or that include, chloride (e.g., chlorine). Chloride may be used to detect brain actuation or brain inhibition in humans or animals.

Certain embodiments of the X-ray fluorescence visualizer, imager, or information provider 100 may, depending on context, be used to X-ray fluorescence visualize, image, or provide information relating to such aspects as elements, infections, additives, differentiable symptoms, etc. associated with the flu, bronchitis, common cold, etc.

Those induced X-ray fluorescing photons 122 emitted from identical elements of the at least some matter of the at least the portion of the individual (e.g., the target atom) should have similar or identical characteristic energy levels of the at least one induced X-ray fluorescing photons 122, as may be referred to the characteristic energy for that particular element. As such, certain embodiments of the X-ray fluorescence visualizer, imager, or information provider 100 can operate to detect the presence or absence of certain elements in the volume by filtering (such as by using a notch filter) those X-ray fluorescing photons 122 being applied to the at least one X-ray fluorescence receiving portion(s) 151, which typically fall within a particular energy level/frequency corresponding to the characteristic energy of the elements (or chemicals, compounds, and/or biological materials) indicative of the presence of elements and their particular location or density. As such, an entire individual, or a portion thereof, could be scanned for particular elements, chemicals, compounds, and/or biological materials using certain embodiments of the X-ray fluorescence visualizer, imager, or information provider 100 that may be based at least partially on the densities of the elements (or chemicals, compounds, and/or biological materials) included in or contained within the matter.

As such, the characteristic energy as produced by certain photon that have undergone X-ray fluorescence generally corresponds to the energy loss resulting at least partially from the fluorescing event, and the characteristic energy should be similar or identical for fluorescing events occurring from the same element. For example, certain electrons of certain elements (such as iodine or calcium) may produce by X-ray fluorescence at least one induced X-ray fluorescing photon 122 having identical energies, and therefore frequencies when their electrons return to their relaxed state, which corresponds to the characteristic energy level or characteristic wavelength of the at least one induced X-ray fluorescing photon 122. The X-ray fluorescing position of the X-ray fluorescing event generating the at least one induced X-ray fluorescing photon 122 can be determined based at least partially on the X-ray fluorescence equations, photonic equations, Stokes equations, energy equations, etc. as described herein, as well as geometric equations. By compiling a large number of X-ray fluorescence angles and positions of the received at least one induced X-ray fluorescing photon 122 of fluorescing events, and is obtained by one or more of the at least one X-ray fluorescence receiving portion(s) 151, an image can be derived having a continuously improving image quality with an increasing number of detection of fluorescing events.

X-ray fluorescence, as described with respect to FIGS. 3, 4a, 4b, and 4c, may be considered to be a type of luminescence, in which susceptible molecules emit X-ray photons from electronically excited states. X-ray fluorescence can result from at least one applied high energy photon and/or particle 120 being applied either from within the optical, X-ray, infrared, ultraviolet, gamma or certain other spectra. For the purpose of this disclosure, though, the emitted induced X-ray fluorescing photon 122 may, depending on context, be considered to be within the X-ray spectra. Certain aspects of this disclosure may, depending on context, be particularly directed to high energy photons or particles, such as the X-ray, gamma, or other spectra that are particularly applicable to penetrate into the matter of the individual 82, and are therefore useful for X-ray fluorescence visualizing, imaging, or information providing.

Figure 4A:
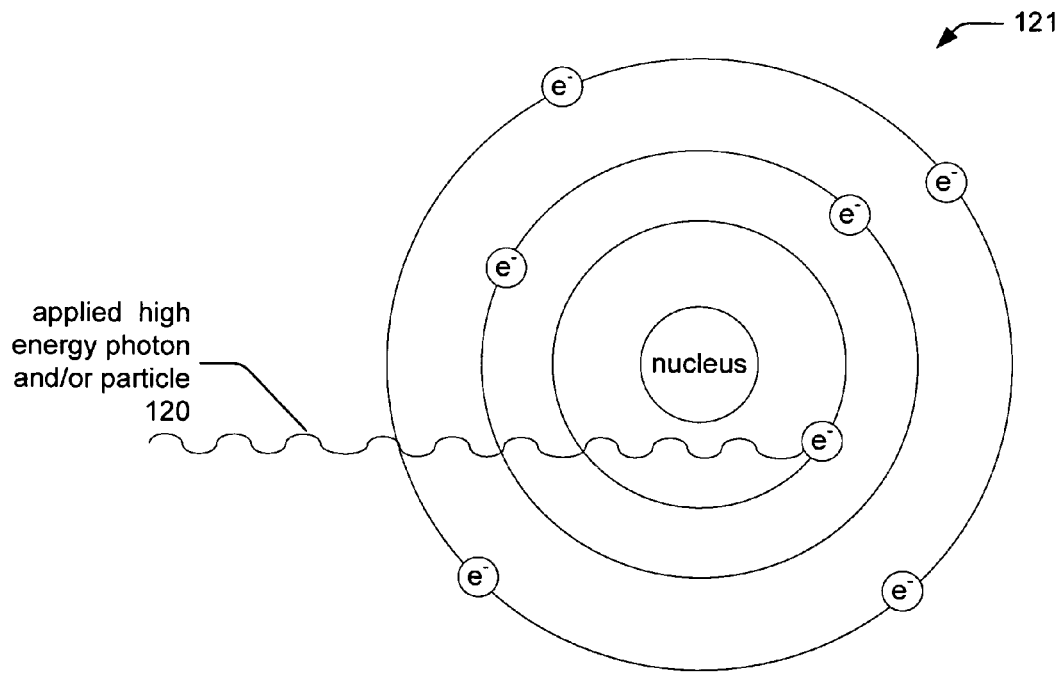
FIGS. 4a, 4b, and 4c is a series diagram of an embodiment of an X-ray fluorescence atomic interaction showing a fluorescing event.
Figure 4B:
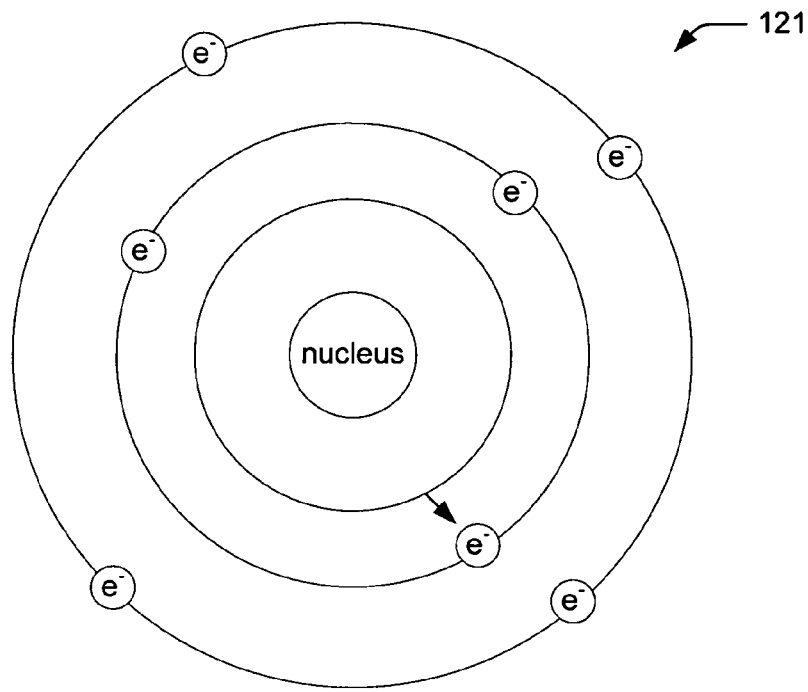
Figure 4C:
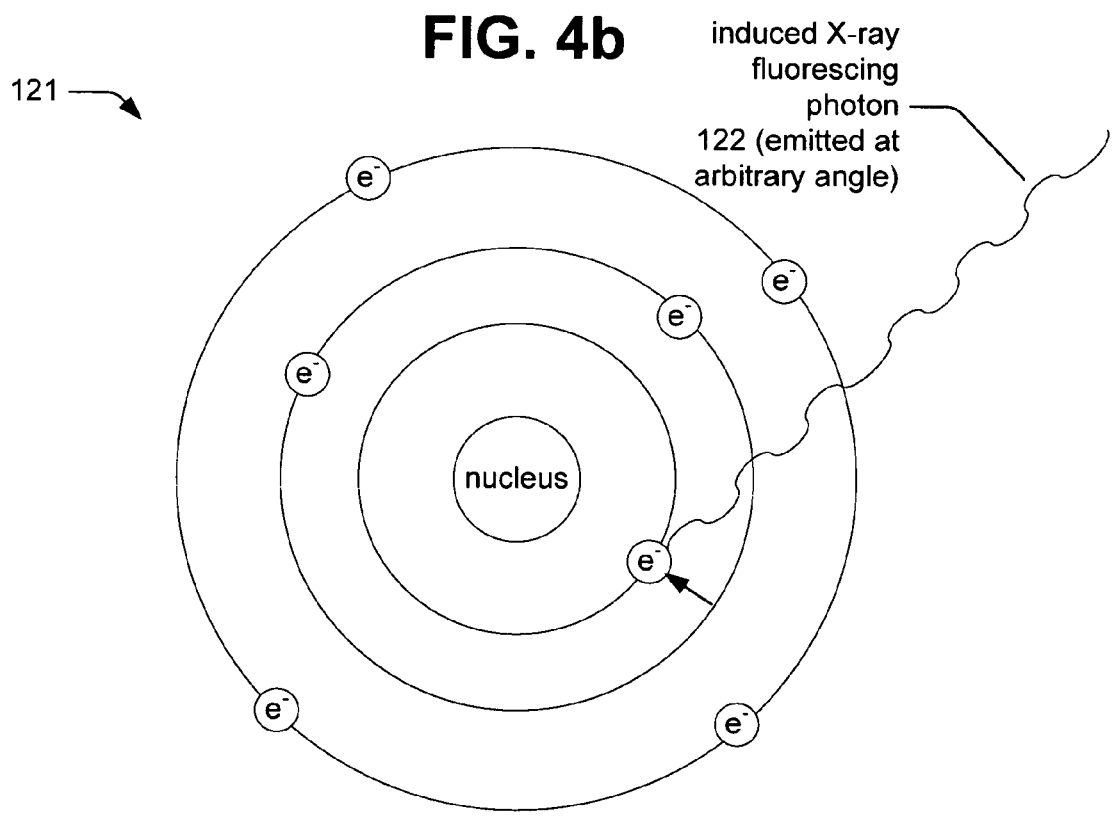

X-ray fluorescence may be established using a variety of mechanisms, but within this disclosure X-ray fluorescence can, depending upon context such as described with respect to FIG. 4a, may relate to a high energy photon or particle in the form of the at least one applied high energy photon and/or particle 120 being applied to the target element, thereby raising the energy level of at least one of the electrons of the target elements to a higher energy state and as described with respect to FIG. 4b. Thereupon, the electron whose energy state is raised returns to the normal state, and the high energy photon in the form of the at least one induced X-ray fluorescing photon 122 can be emitted as described with respect to FIG. 4c. The characteristic energy, and associated wavelength, of the induced X-ray fluorescing photon 122 as described with respect to FIG. 4c may be characterized according to the at least one element included in high energy photon, and may be characterized according to the characteristic energy level. As such, the term "X-ray fluorescence" may, depending on context, relate to an X-ray phenomenon in which the molecular absorption of a photon triggers the emission of another photon with a longer wavelength (i.e., lower frequency or lower photonic energy level) such as comparing the energy of the at least one applied high energy photon and/or particle 120 of FIG. 4a with respect to the energy of the at least one induced X-ray fluorescing photon 122 as described with respect to FIG. 4c. The energy difference between the absorbed and emitted photons may result in the production of molecular vibrations and/or heat. Usually the absorbed photon is in the X-ray fluorescence range, gamma-ray range, or other suitable range (e.g., particle range) and the emitted light is in the X-ray fluorescence range, but this depends on the absorbance curve and Stokes shift of the particular target atom or fluorophore 121. X-ray fluorescence can thereby occur when a molecule relaxes to its ground state after the electrons of the target atom or fluorophore 121 is electronically excited as described with respect to FIGS. 3, 4a, 4b, and 4c.

There are a variety of aspects of certain embodiments of the X-ray fluorescence that may be utilized by certain embodiments of the X-ray fluorescence visualizer, imager, or information provider 100. Stokes shift, for example, may be considered as the difference, e.g., measured in wavelength or frequency, between positions of the band maxima of the absorption and luminescence spectra (or X-ray fluorescence) of the same electronic transition of the electron of the target atom or fluorophore 121. When the target atom or fluorophore 121 absorbs photons, such as by absorbing the applied high energy photon and/or particle 120, the electron of the at least one target atom or fluorophore 121 can enter an excited electronic state. The Stokes shift occurs because, and may be characterized by, the electrons of the target atom or fluorophore 121 while in its excited state losing a small amount of the absorbed energy before re-releasing the rest of the energy. Such re-releasing of the energy may cause production of the at least one induced X-ray fluorescing photon 122 at least partially using X-ray fluorescence, and may be referred to as Stokes X-ray fluorescence. The energy associated with the Stokes shift is often lost as thermal energy. Stokes X-ray fluorescence may be considered to represents the reemission of longer wavelength (lower frequency) photons (energy) by the target atom or fluorophore 121 that has absorbed photons of shorter wavelengths (higher frequency).

Both absorption and radiation (emission) of energy are unique characteristics of the particular target atom or fluorophore 121 during the X-ray fluorescence process. Certain embodiments of the applied high energy photon and/or particle 120 can be absorbed by the target atom or fluorophore 121, which causes electrons of the target atom or fluorophore 121 to become excited to a higher electronic state. The electrons of the target atom or fluorophore 121 can remain in the excited state for some duration then, assuming all of the excess energy is not lost by collisions with other molecules, the electron of the target atom or fluorophore 121 can thereupon return to the ground state. Energy can be emitted during this return to the ground state in the form of a generation of the at least one induced X-ray fluorescing photon 122. The at least one induced X-ray fluorescing photon 122 emitted by the target atom or fluorophore 121 typically has a longer wavelength than its corresponding applied high energy photon and/or particle 120 absorbed by the target atom or fluorophore 121, due largely to limited characteristic energy drop/loss by the target atom or fluorophore 121 (which occurs during emission of the at least one induced X-ray fluorescing photon 122). The characteristic energy drop may be consistent (e.g., characteristic) for each element.

Certain embodiments of the X-ray fluorescence visualizer, imager, or information provider 100 can thereby utilize mechanisms that can include, but may not be limited to, the at least one high energy photon and/or particle emitter portion(s) 150 as well as the at least one X-ray fluorescence receiving portion(s) 151. Certain embodiments of the at least one X-ray fluorescence receiving portion(s) 151 can X-ray fluorescence visualize, image, and/or provide information such as which can thereupon be analyzed, displayed, computed, and/or processed, etc. Certain embodiments of the at least one X-ray fluorescence receiving portion(s) 151 can include, but is not limited to, at least one detector portion 152 and/or the at least one display portion 154. Certain embodiments of the X-ray fluorescence visualizer, imager, or information provider may allow the X-ray fluorescence visualization, image, or information provided to be captured, processed, filtered, and/or combined, etc. based at least partially on such imaging or processing techniques as: deconvolution, transform (e.g., integral transform, inverse Fourier transform, inverse FFT, etc.), image subtraction, weighted subtraction, functional subtraction, weighted subtraction, functional subtraction, inverse integral transform, subtractive inverse integral transform, inverse functional transform, and subtractive inverse functional transform, or other such processes or computations, and other known image processing or other processing algorithms. Such X-ray fluorescence visualization, imaging, or information providing may occur either on a one time, multiple times, repetitive, continuous, or other such basis, perhaps in an as-programmed, user controlled, as-desired, or other suitable manner.

Within this disclosure, deconvolution techniques (such as can utilize processing, image processing, computation, image combination, and/or other similar techniques) can be used to limit or reduce the obscuring effect(s) of depth of matter, tissue, X-ray opaque matter, noise, etc. as applied to cloud desired images, etc. As such, deconvolution can be used to clarify the X-ray fluorescence visualization(s), image(s), and/or provided information. Deconvolution techniques and technologies are well established and understood, and have been in use in certain technological areas since prior to World War II. Deconvolution is conventionally used in image processing, signal processing, and other computer-based imaging techniques. Certain embodiments of the X-ray fluorescence visualizer, imager, or information provider 100 can utilize deconvolution, transforms, and other distortion diminishing techniques. Such techniques can limit the amount of distortion, as well as enhance, X-ray fluorescence visualizing quality, imaging quality, and/or information quality enhancing techniques may be used for limiting distortive effects resulting at least partially from, for example: X-ray opaque matter, obscuring matter, signal noise, etc. such as to identify or X-ray fluorescence visualize aircraft hidden in clouds, limit signals and/or images in noisy backgrounds, medical imaging, etc. Other such distortion-limiting image processing techniques may be applied, where appropriate, in a manner as would be obvious to one skilled in the art.

The "matter" of the human or animal individuals (such as by including fluorophores can undergo fluorescing as described in this disclosure) that can be X-ray fluorescence visualize to, image, or information provided, or alternatively can provided background to the X-ray fluorescence, visualizing, imaging, or information providing can, depending upon context include, but is not limited to: tissue, flesh, muscle, fluorophores (naturally existing and/or enhanced), optically opaque tissue, organ(s), bone(s), bone part(s), hair, bone fragment(s), implant(s), fat, blood vessel(s), blood capillary(s), skin, teeth, epidermis, dermis, brain, tumors, cysts, contrast agents such as iodinated contrast agents, gadolinium, certain fluid(s), blood or blood component(s), CSF, irritant, IV fluids, water, aqueous solutions, implant materials such as ceramic, steel, titanium, nitinol, etc. Plant and organism embodiments can include such matter (naturally occurring or man-made or applied) that can be imaged, X-ray fluorescence visualized, or have information provided depending at least partially on the structure and/or location being imaged as a portion of, and/or associated with, the plant or organism. As such, certain matter or fluorophores can be naturally-occurring, while others may utilize application of the X-ray fluorescence enhancing additives, taggants, or contrast agents, etc. to enhance or provide the differentiation of matter aberration for the X-ray fluorescence visualizing, imaging, or information providing.

Certain embodiments of the X-ray fluorescence visualizer, imager, or information provider 100 can achieve relatively high resolution of their X-ray fluorescence depth visualizations, images, and/or information provided. As such, certain embodiments of the X-ray fluorescence visualizer, imager, or information provider 100 can be configured such that the matter of the at least the portion of the individual can be inclusively imaged as at least a portion of the individual 82. Certain embodiments of the X-ray fluorescence visualizer, imager, or information provider 100 can X-ray fluorescence depth visualization, image, and/or provide information relating to a considerable number of distinct types of matter as compared with, for example, certain conventional X-ray techniques.

Certain embodiments of the X-ray fluorescence visualizer, imager, or information provider 100 can thereby X-ray fluorescence visualize, image, and/or provide information relating to such matter of the at least the portion of the individual as such tissue as flesh, tissue, muscle, fat, fluid (blood, lymph, spinal fluid, etc.) in a controllable and/or adjustable manner. In this manner, an initial X-ray fluorescence depth visualizing, imaging, or information providing can be performed of a region, and upon locating areas of interest, the X-ray fluorescence visualization, imaging, or information providing can be filtered, processed, analyzed, compared, transformed, adjusted, magnified, angled, etc. as described in this disclosure to X-ray fluorescence visualize, image, and/or provide information relating to desired regions. Such fluorescing visualizing, imaging, or information providing techniques, that may be similar to those in common usage and conventional imaging systems, are intended be within the scope of the present disclosure.

Certain embodiments of the X-ray fluorescence visualizer, imager, or information provider 100 can be used to X-ray fluorescence visualize, image, and/or provide information relating to the spine of humans or animals, such as may be particularly useful with certain spinal surgeons, doctors, chiropractors, etc. Such X-ray fluorescence depth visualizing, imaging, or information providing of the human or animal spine (as well as associated plates, pins, blood vessels, muscles, etc.) can be performed prior to, during, and/or following surgery; and can provide imaging, X-ray fluorescence visualizing, or provide information of appropriate or desired quality depending on the desired purpose, equipment, condition, or application. Such X-ray fluorescence visualization, imaging, or information providing following surgery can be provided at one or more suitable angles, such as to illustrate interaction with plates, pins, constructs, etc. relative to the spine, associated nerves, bones, and associated pins, constructs, etc. Those embodiments of the X-ray fluorescence visualizer, imager, or information provider 100 that are configured to image the matter, spine, bones, tissue, implants, etc. should be configured based on the desired depth imaging, X-ray fluorescence depth visualizing, and/or examination, and may be adjusted and/or controlled, perhaps on a near real time basis, or another basis.

Figure 43:
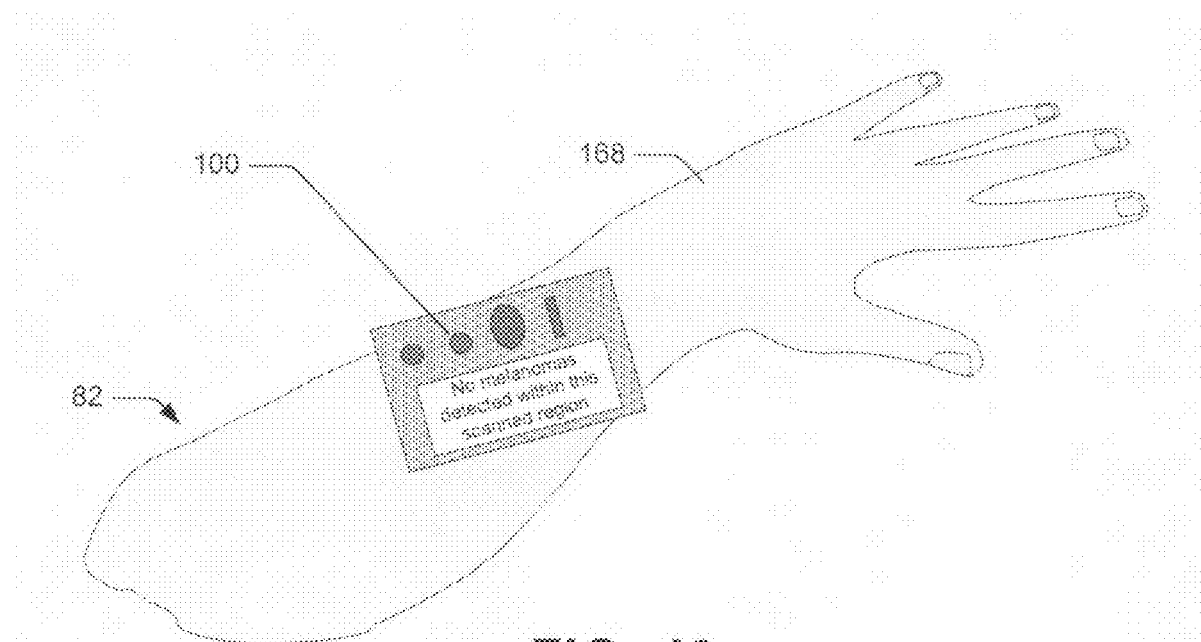
FIG. 43 shows another embodiment of the X-ray fluorescence receiving assembly that is configured to output information.

Certain embodiments of the X-ray fluorescence visualizer, imager, or information provider 100, as described with respect to many of the figures and at other locations through this disclosure, primarily pertain to devices that can display X-ray fluorescence visualizations and/or images over various embodiments of the at least one X-ray fluorescence receiving portion(s) 151. By comparison, certain embodiments of the X-ray fluorescence visualizer, imager, or information provider 100, such as illustratively described with respect to FIG. 43 and at other locations through this disclosure, can pertain to displays that can provide information in such form as text, analysis, data, graphs, data computations, or other processed information, or a combination or modification thereof, etc. More particularly, FIG. 43 illustrates a non-limiting example of the X-ray fluorescence visualizer, imager, or information provider 100 that can provide information, text, data, etc. in other non-image or non-visualization form. Depending on the application of the particular embodiment of the X-ray fluorescence visualizer, imager, or information provider 100, such information, text, data, etc. can include such derived sentences as "the patient's tooth has no cavities", "the flow through the patients artery is some number of gallons per minute", "this cow is free of mad cow disease", etc. that may be based at least partially on at least one particular densities, elements, chemicals, compounds, and/or biological materials, included in or contained within the matter that can be X-ray fluorescence visualized, imaged, or information provided. The various embodiments of the X-ray fluorescence visualizer, imager, or information provider 100, as described in this disclosure, can also include a graphical user interface, buttons, switches, or other mechanism to allow a user or individual to provide input as to the X-ray fluorescence visualization, imaging, or information providing as desired, suitable, and/or designed. Certain embodiments of the X-ray fluorescence visualizing, imaging, or information providing such information can be relatively computationally simplified as compared with the conventional imagers, such as MRIs, CAT scans, etc. Also, certain embodiments of the X-ray source can be specialized by "scanning" or other imaging, information providing, or visualizing technique for a particular elements, chemicals, compounds, and/or biological materials as described in this disclosure, such as may be utilized by relatively unskilled users or operators. As such, within this disclosure, each of the terms "X-ray fluorescence visualize", "image", or "provide information" is, depending on context, intended to be inclusive of each of these terms.

Certain embodiments of the X-ray fluorescence visualizer, imager, or information provider 100 can be configured for a variety of particular applications. The user of certain embodiments of the X-ray fluorescence visualizer, imager, or information provider 100 may select a particular aspect such as quality, refresh rate, real-time aspects, resolution, color, etc. based on the particular task at hand. For example, a doctor examining a patient's external skin may obtain one or more X-ray fluorescence visualizations, images, or provided information, or may treat certain surface aberrations using certain embodiments of the X-ray fluorescence visualizer, imager, or information provider 100. Also, a surgeon or other user who is using certain embodiments of the X-ray fluorescence visualizer, imager, or information provider 100 that may be attached, integrated, or otherwise secured to a surgical tool. Examples of certain embodiments of surgical tools that may utilize certain embodiments of the X-ray fluorescence visualizer, imager, or information provider 100 may be used in examples of such procedures as cutting, separating, ablating, deforming, processing, tactile feedback providing, adding material, removing material, or otherwise handling matter such as tissue, bone, fluid, blood, etc.

Certain embodiments of the X-ray fluorescence visualizer, imager, or information provider 100 may be satisfied with various quality X-ray fluorescence depth visualizations or images that can vary from detailed or excellent images to relatively sketchy images of X-ray fluorescence visualizations. Detailed images, for example, can provide a representation of the matter of the at least the portion of the individual. In certain instances, relatively sketchy X-ray fluorescence visualizations or provided information (which can still include information about elemental composition, density, etc.) adequate to indicate a relative position of a desired X-ray fluorescence visualized item such as a blood vessel, bone, portion, nerve, construct, etc., such as can be used to enhance locating or avoidance during use of such illustrative but not limiting tools such as scalpels, cutters, gamma knives, laser cutters, tactile feedback providers, ablators, scopes, Bovie electrocautery devices, material adding tools, material removing tools, etc. As such, certain embodiments of the X-ray fluorescence visualizer, imager, or information provider 100 can be configured to provide for textual output of the provided information (likely based on some image or other processing or analysis) of that matter of the at least the portion of the individual. Certain embodiments of the X-ray fluorescence visualizer, imager, or information provider 100 can be provided at a refresh rate sufficient rate to operate as desired, or operate a tool in combination as desired without contacting blood vessels, nerves, or other matter to be protected within the individual, for example. As such, certain embodiments of the X-ray fluorescence visualizer, imager, or information provider 100 can be associated with a variety of tools; and can be used to assist in X-ray fluorescence visualizing or information providing during such tool actions as, but not limited to: deforming, separating, distorting, guiding, cutting, avoiding, and other such actions as can be performed by a variety of the tools.

Certain embodiments of the X-ray fluorescence visualizer, imager, or information provider 100 can be configured to visualize, image, or provide information based at least partially on the elements, chemicals, compounds, and/or biological materials including the at least one target atom or fluorophore 121. As such, at least portions or the entirety of the individual (e.g., portion of a human, animal, plant, or organism) can be scanned for elements, chemicals, compounds, and/or biological materials using a variety of techniques as described in this disclosure. Consider that certain elements, chemicals, compounds, and/or biological materials can be indicative of illnesses, infections, injuries, or conditions (e.g., cancer, heart disease, gangrene, Alzheimers disease, abscesses, gun-shot wounds, explosions, etc.). As such, certain embodiments of the X-ray fluorescence visualizer, imager, or information provider 100 can be configured such that areas or portions of the individual that likely have a condition, infections, illness, injuries, etc. can be detected particularly in those instances where the elements, chemicals, compounds, and/or biological materials is relatively sparse in the background being visualized, imaged, or having information provided. For instance, assume that iodine, iron (e.g., in hemoglobin), calcium, or some other elements, chemicals, compounds, and/or biological materials is indicative of some medical condition, and the elements, chemicals, compounds, and/or biological materials are not located in appreciable concentration in the background being visualized, imaged, or information provided. As such, certain embodiments of the X-ray fluorescence visualizer, imager, or information provider 100 can utilize processors or filters, etc. (e.g., notch filters), etc. to limit the X-rays being received at the at least one X-ray fluorescence receiving portion(s) 151 that can indicate the characteristic frequency of a particular elements, chemicals, compounds, and/or biological materials for which the at least the portion of the individual is being visualized, imaged, or information provided. Certain of the at least one target atom or fluorophore 121 can receive a X-ray fluorescence enhancing additives, taggants, or contrast agents, etc. such as to improve the visualizing, imaging, or information providing by certain embodiments of the X-ray fluorescence visualizer, imager, or information provider 100. Consider that certain embodiments of the X-ray fluorescence visualizer, imager, or information provider 100 can be configured to visualize, image, or provide information relative to bone structure, teeth structure, junctions between teeth and/or bones with tissue, etc. based on the elements, chemicals, compounds, and/or biological materials in the portion being imaged (assuming that relatively little of the elements, chemicals, compounds, and/or biological materials are in the background or field of view).

As such, to enhance visualizing, imaging, or information providing based at least partially relative to elements, chemicals, compounds, and/or biological materials, the background or general area being visualized, imaged, or information provided should be considered as to their concentration of those elements, chemicals, compounds, and/or biological materials. For instance, assuming that certain embodiments of the X-ray fluorescence visualizer, imager, or information provider 100 were being used to visualize, image, or provide information based on iron/hemoglobin (e.g., blood), then such visualizing, imaging, or information providing can be enhanced if there is little other iron in the background matter of the individual being imaged.

Additionally, filtering and/or image processing techniques (which may represent adapted versions of those currently in use) may be utilized to limit at least some of the potentially interfering aspects of elements, chemicals, compounds, and/or biological materials in the background where the elements, chemicals, compounds, and/or biological materials are being visualized, imaged, or information provided. For example, certain filtering, notch filtering, Markov filter, adaptive filtering or processing, or other such filtering or processing techniques may be utilized to limit the effect of background elements, chemicals, compounds, and/or biological materials that are being visualized, imaged, or provided information.

Certain embodiments of tools that can be associated with, or operatively coupled to, certain embodiments of the X-ray fluorescence visualizer, imager, or information provider 100 can provide tactile feedback to a user. Such tactile feedback providing tool can be used particularly in combination with certain embodiments of the X-ray fluorescence visualizer, imager, or information provider 100, such as to allow the user to perform such tactile feedback operations as "feeling" and/or "touching" (or at least receiving information corresponding to feeling or touching) the various regions of the individual for treatment or examination purposes, even if only remotely while similarly observing the region. The use of tactile feedback mechanisms is generally understood by those skilled in the robotics, automation, surgical, and other such arts or technical areas. Certain orthopedic surgeons, etc., who are interested in general positions of such particular matter as bones, organs, etc. may be satisfied with X-ray fluorescence depth visualizations and/or images that have limited resolution or image quality. As such, certain embodiments of the tactile feedback provider may be considered as "tools" within certain meanings and/or certain contexts as applied within this disclosure. Additionally, certain users may select to use certain scintillator or other fluoroscope embodiments of the X-ray fluorescence visualizer, imager, or information provider 100 that may be based at least partially on the density, elements, chemicals, compounds, and/or biological materials included in or contained within the matter, as described in this disclosure.

Certain embodiments of the X-ray fluorescence visualizer, imager, or information provider 100 may be configured to operate in association with at least one tool portion relative to, for example, at least some matter of the at least the portion of the individual. The particular component and/or configuration selected may depend, at least in part, on the application of the X-ray fluorescence visualizer, imager, or information provider 100 and/or the associated tool. For instance, certain embodiments of the X-ray fluorescence visualizer, imager, or information provider 100 can be associated with a particular tool, including but not limited to: an at least one cutting tool, an at least one scalpel, an at least one laser cutter, an at least one tactile feedback provider, an at least one ablator, an at least one scope, an at least one Bovie electrocautery device, an at least one material adding tool, an at least one material removing tool, etc. such as to allow a user to search, image, or X-ray fluorescence visualize within a particular region for a specific elements, chemicals, compounds, and/or biological materials, etc. as a tool-based process is being performed. Such imaging, X-ray fluorescence visualization, or information providing may be used relative to the location of blood vessels, cancer, tumors, organs, infections, injuries, abscesses, etc. Alternately, certain embodiments of the X-ray fluorescence visualizer, imager, or information provider 100 can be configured to detect, X-ray fluorescence visualize, image, and/or provide information relative to an area of potential interest, such as a field of surgical operation, within the at least the portion of the individual in which at least the at least the portion of the individual.

A user may desire to use certain embodiments of the X-ray fluorescence visualizer, imager, or information provider 100 to image, X-ray fluorescence visualize, image, and/or provide information at a considerable depth into matter such as tissue, and/or obtain X-ray fluorescence depth visualizations or images that may have a high resolution or quality. Certain X-ray fluorescence visualizations or images that can be produced by certain embodiments of the X-ray fluorescence visualizer, imager, or information provider 100 may be of similar quality of such conventional imaging as, for example, MRI, CAT Scans, PET scans, etc. Certain embodiments of the X-ray fluorescence visualizer, imager, or information provider 100 can be performed relatively quickly as compared with conventional imaging modalities, such as in certain instances to be applied on a near-real time basis. The user may thereupon select to use certain embodiments of the X-ray fluorescence visualizer, imager, or information provider 100 that rely upon consider image processing to achieve suitable and/or desired X-ray fluorescence visualization, imaging, or information providing quality, as described in this disclosure. As such, the user can select one or more suitable embodiments of the X-ray fluorescence visualizer, imager, or information provider based, at least in part, on the particular task at hand.

Certain embodiments of the X-ray fluorescence visualizer, imager, or information provider 100 can be applied from a variety of embodiments of mechanisms that can be configured to provide X-ray fluorescence visualization, imaging, or information providing structures, including depending on context, but not limited to: platforms, tables, hand-held, endoscopes, attached to or integrated within a tool, etc. Within this disclosure, the description of the particular X-ray fluorescence visualization, imaging, or information providing structure being used is intended to be illustrative in nature but not limiting in scope. As such, it is intended that a description of an embodiment of the X-ray fluorescence visualizer, imager, or information provider 100 being applied to a particular X-ray fluorescence visualization, imaging, or information providing structure may be applied to a variety of X-ray fluorescence visualization, imaging, or information providing structures, depending on context.

Certain embodiments of the X-ray fluorescence visualizer, imager, or information provider 100 can utilize directionality of travel of the at least one induced X-ray fluorescing photon 122 as received at the at least one X-ray fluorescence receiving portion(s) 151, which may be utilized to determine a location of the fluorescing events. Following determination of the directionality of travel of the high-energy photons, certain embodiments of the X-ray fluorescence visualizer, imager, or information provider 100 may determine a location of and/or determine the amount of energy following X-ray fluorescence interaction with the electrons and/or particles of the matter to raise the energy state of the atom, wherein the relaxation of the energy state can be detected by such detectors as may be included in the at least one X-ray fluorescence receiving portion(s) 151. Such devices as collimators, filters, polarizers, may be utilized to limit travel of certain of the at least one induced X-ray fluorescing photon 122 that are being applied to certain detector portions 152 and/or the at least one induced X-ray fluorescing photon 122 that are being received by the at least one X-ray fluorescence receiving portion(s) 151 to those traveling within particular directions. The energy level variation (which is likely a loss as a result of heat generation principles) of the at least one applied high energy photon and/or particle 120 that, upon contacting the target atom or fluorophore 121, may cause the target atom or fluorophore to approach its excited state. When in a sufficiently high excited state, certain embodiments of the target atoms or fluorophores 121 within the at least some matter of the at least the portion of the matter of the individual may likely undergo the fluorescing event, releasing the at least one induced X-ray fluorescing photon 122.

Certain embodiments of the X-ray fluorescence visualization, imaging, or information providing can be performed using a variety of mechanisms and involving a variety of techniques. Determination of the depth within matter of the at least the at least the portion of the individual that is being X-ray fluorescence visualized, imaged, and/or information provided, can be at least partially derived involving analytical determination, computation as well as numerical calculation such as can be performed by computers and/or controllers; or alternately can involve experimentation or analysis. Certain aspects of X-ray fluorescence visualization, imaging, or information providing can be based on such factors as each particular matter being X-ray fluorescence visualized, imaged, or information provided, the energy level and/or frequency of the at least one applied high energy photon and/or particle 120 and/or at least one induced X-ray fluorescing photon 122, and/or other such factors. Certain versions of such X-ray fluorescence visualization, imaging, or information providing that may rely at least partially on tomography, or other similar mechanism, such as may result from generating a series of X-ray fluorescence visualizing, imaging, or information providing X-ray fluorescence visualizing, imaging, or information providing slices, etc. Each X-ray fluorescence visualizing, imaging, or information providing slice being relatively thin can help to enhance quality or consistency (e.g., homogeneity) of the X-ray fluorescence visualizing, imaging, or image providing such as which may be enhanced across certain X-ray fluorescence visualizing, imaging, or information providing slices, such that by utilizing analysis, comparison, our processing of the information or data between the different X-ray fluorescence visualizing, imaging, or image providing slices.

Certain techniques associated with the X-ray fluorescence visualizer, imager, or information provider 100 may be similar to those that provide X-ray fluorescence visualizing, imaging, or information providing slices such as with conventional tomography imaging techniques. Certain embodiments of the X-ray fluorescence visualizing, imaging, or information providing slices can be arranged in a variety of shapes including, but not limited to, in a straight, curved, complex, or some other desired or suitable or desired shape. Combining a number of the X-ray fluorescence visualizing, imaging, or information providing slices, which may be considered as a three dimensional region of X-ray fluorescence visualizing, imaging, or information provider having a limited thickness that can be imaged by the X-ray fluorescence visualizer, imager, or information provider 100, can produce a thicker image or X-ray fluorescence visualization of the particular matter and with a non-combined X-ray fluorescence visualizing, imaging, or information providing slices. This disclosure initially describes a variety of techniques for such X-ray fluorescence visualization, imaging, or information providing.

Consistency of the matter being X-ray fluorescence visualized as imaged across the thickness can thereby improve imaging quality, especially in the direction parallel to a direction at which the X-ray fluorescence visualization, imaging, or image providing be being performed. For instance, such visualizing, imaging, or information providing may be taken substantially through the thickness of the X-ray fluorescence visualizing, imaging, or information providing axis X-ray fluorescence visualizing, imaging, or information providing slice, or at some angle relative thereto. Similarly, imaging quality may diminish in certain embodiments of the X-ray fluorescence visualizer, imager, or information provider 100 as the matter becomes more non-heterogeneous or dissimilar across the thickness of the imaging X-ray fluorescence visualizing, imaging, or information providing slice, and therefore less consistent. Such X-ray fluorescence visualization, imaging, or information providing may be taken in a straight, curved, complex, or some other desired or suitable or desired contour or shape.

Certain embodiments of X-ray fluorescence visualization, imaging, or information providing can be used to X-ray fluorescence visualize, image, or provide information within the at least one X-ray fluorescence range to the at least one prescribed substantial X-ray fluorescence depth (e.g., from a surface, or alternately spaced from the surface). The actual or maximum X-ray fluorescence range to the at least one prescribed substantial X-ray fluorescence depth being X-ray fluorescence visualized, imaged, or information provided may vary between different embodiments, and may be based on particulars of the X-ray fluorescence high energy (e.g., X-ray, gamma ray, photon, particle, etc.) X-ray fluorescence depth visualizing, imaging, or information providing and/or the matter undergoing X-ray fluorescence depth visualizing, imaging, or information providing. Certain processor characteristics and operations of the X-ray fluorescence visualization, imaging, or information providing controller 97 can be used to select, filter, and/or determine the level, characteristic frequency, or other such parameters of the X-ray fluorescence range and/or the prescribed substantial X-ray fluorescence depth. Some of the at least one applied high energy photon and/or particle 120 can X-ray fluorescence to provide the fluorescing event wherein the X-ray fluorescence photon or particle (e.g., X-ray or gamma ray) may X-ray fluorescence at a depth greater than the at least one X-ray fluorescence range to the at least one prescribed substantial X-ray fluorescence depth that may be based at least partially on the densities, elements, chemicals, compounds, and/or biological materials, included in or contained within the matter.

Based on the energy level of the at least one applied high energy photon and/or particle 120, the number of the at least one applied high energy photon and/or particle 120 with the fluorescing event occurring at the X-ray fluorescence range of X-ray fluorescence visualizing, imaging, or information providing depths greater than the set X-ray fluorescence range to the set prescribed substantial X-ray fluorescence depth can, for certain X-ray fluorescence visualization, imaging, or image providing, be assumed to be ignored either computationally, be effectively filtered out, be limited by certain weighting techniques, be removed using image processing techniques; or even accepted by some device. Certain X-ray fluorescence visualizations, images, or provided information can be provided even by ignoring a limited percentage of relatively deep X-ray fluorescence. Certain embodiments of the X-ray fluorescence visualizer, imager, or information provider 100 can be configured to limit the effects of the at least one applied high energy photon and/or particle 120 that are returning from the fluorescing event occurring through greater depths than the at least one X-ray fluorescence range to the at least one prescribed substantial X-ray fluorescence depth 170. Additionally, certain of the X-ray fluorescence depth visualizing, imaging, or information providing effects of the at least one applied high energy photon and/or particle 120 can X-ray fluorescence at the X-ray fluorescence range of the prescribed substantial X-ray fluorescence depths greater than some prescribed level. Additionally, at least some of the distorting effects can be either ignored, filtered, and/or otherwise limited using image processing techniques, deconvolution, and/or other techniques.

Another embodiment of X-ray fluorescence visualization, imaging, or information providing can control or adjust the X-ray fluorescence depth visualizing, imaging, or information providing at least partially by increasing, such as by ramping up, the energy of the at least one applied high energy photon and/or particle 120. By changing the energy level or frequency of the at least one applied high energy photon and/or particle 120, the effective prescribed X-ray fluorescence range or the prescribed substantial X-ray fluorescence depth into the matter of the at least the portion of the individual can in certain instances be modified (e.g., increased or decreased) and/or controlled. As such, the energy level and/or frequency of at least some of the at least one applied high energy photon and/or particle 120 that are being used to X-ray fluorescence visualize, image, and/or provide information can be tuned as to effect variation in the prescribed substantial X-ray fluorescence depth of the X-ray fluorescence visualization, imaging, or information providing process. Such image data different depths can be computationally combined (e.g., subtracted) using image processing, weighing, or other techniques to determine the X-ray fluorescence visualizing, imaging, or information providing between the two (adjusted) energy levels.

The variety of embodiments of the X-ray fluorescence visualizer, imager, or information provider 100 may be configured, used, and/or operated differently from each other or in different forms, and may be expected to provide different results, visualizations, images, or information. Certain computer based embodiments, (or even human-vision embodiments) of the X-ray fluorescence visualizer, imager, or information provider 100 can be configured in home-test form, emergency form, task-specific form, relatively low power form, or even in a form that can be used without the assistance of a skilled user or another user. As such, within this disclosure, in certain instances, particularly with certain simplified or devoted embodiments of the X-ray fluorescence visualizer, imager, or information provider 100, certain embodiments of the term "user" can also include the individual, the individual's family or friend's thereof, and/or care providers for the individual who can assist in operating certain embodiments of the X-ray fluorescence visualizer, imager, or information provider for the individual. Certain such home-test embodiments of the X-ray fluorescence visualizer, imager, or information provider might preferably be used for one, or a few, devoted purposes such as, but not limited to: mammograms, cancer or tumor screening, blood flow, injury, infection, tissue aberrations, drug or poison concentrations through various portions of the body, possible bone break or tissue tear, etc., as described in this disclosure and/or discernible from this disclosure.

By allowing certain embodiments of the X-ray fluorescence visualizer, imager, or information provider 100 to utilize automation, computerized systems, etc., it is likely that certain elements that are indicative of a condition (e.g., cancer, high risk of stroke or heart attack, abscesses, injuries, infections, etc.) could be automatically reviewed even in those instances that the individual or patient is not being visualized, imaged, or information provided for that particular purpose. For example, consider the where a human patient is visiting a doctor for a regular check-up. A relatively quick and non-invasive scan can be performed over at least a portion of the body by the X-ray fluorescence visualizer, imager, or information provider 100, and particular elements indicative of a health risk can be automatically considered, such as a build-up of plaque in the arteries, malignancies, poor blood or other bodily fluid circulation, etc.

Certain computer-based or machine based embodiments of the X-ray fluorescence visualizer, imager, or information provider may prove quite effective at X-ray fluorescence visualizing, imaging, information providing, or otherwise analyzing through particular X-ray opaque matter (perhaps at least partially utilizing deconvolution, transforms, filtering, or other such processing techniques to limit the obscuring effects). Certain embodiments of the X-ray fluorescence visualizer, imager, or information provider 100 can be configured to operate at a suitable frequency as to be particularly X-ray fluorescence particular target elements (such as calcium, iodine, or other elements) which may be particularly correlated to a particular condition of the individual (e.g., cancer, hardening of arteries, dead or unhealthy matter, infections, injuries, abscesses, etc.). Such techniques may accomplish such tasks as determining existence and/or depths of cancer, tumors, bones, abscesses, or other matter within the individual, and may thereby limit, reduce, or double-check the human scanning over large regions of the individual has be performed. The location of certain portions of bones, tissue, inserts, implants, etc. that are undergoing X-ray fluorescence, visualizing, or information providing could be adjusted using certain embodiments of the X-ray fluorescence visualizer, imager, or information provider 100.

Certain based embodiments of the X-ray fluorescence visualizer, imager, or information provider 100 (some of which may rely at least partially on computer vision) can be configured to model certain matter aberrations within the at least the portion of the individual perhaps using, or without, deconvolution, transform, or other such techniques. Certain embodiments of the X-ray fluorescence visualizer, imager, or information provider may prove superior to others in determining extent, dimensions, degrees, etc. of certain aberrations, such as melanomas, tumors, cancers, abscesses, bone growth, infections, injuries, etc., the X-ray fluorescence high energy (e.g., X-ray, gamma ray, photon, particle, etc.) by using mapping techniques such as are commonly used in tomography, MRI, and other conventional imaging techniques.

Within this disclosure, X-ray fluorescence visualization, imaging, or information providing can, depending on context, pertain to X-ray fluorescence depth visualizing, imaging, or information providing of a volume of matter that can have an arbitrary thickness depending on the desired X-ray fluorescence visualization, imaging, or information providing application, but may be considered to be three dimensional. The three dimensional volume (having some thickness) being X-ray fluorescence visualized, imaged, or information provided can be at least partially separated from an internal or external surface such as external skin or membrane, internal lumen, etc. that is being imaged through. Certain embodiments of the X-ray fluorescence visualizer, imager, or information provider 100 can be positioned at regions adjacent the surface 168 to provide some location that can be used to relatively position to X-ray fluorescence visualize, image, and/or provide information relating to portions of the individual. The surface 168 of the individual can provide some location at which certain embodiments of the X-ray fluorescence visualizer, imager, or information provider 100 can be angled, moved, or otherwise displaced or positioned to enhance the X-ray fluorescence visualization, imaging, or information providing. As such, in certain instances, proximate or adjacent the surface can provide a good location from which to X-ray fluorescence visualize, image, or provide information.

As described with respect to FIGS. 1 and 2, as well as at other locations in this disclosure, certain embodiments of the X-ray fluorescence visualizer, imager, or information provider 100 can include, but are not limited to, at least one high energy photon and/or particle emitter portion(s) 150 (which may comprise an at least one X-ray photon emitter portion as described with respect to FIG. 2) and/or at least one X-ray fluorescence receiving portion(s) 151. Certain embodiments of the at least one high energy photon and/or particle emitter portion(s) 150 can be configured to emit or direct at least some the at least one applied high energy photon and/or particle 120 toward the at least the portion of the individual 82. Certain embodiments of the at least one high energy photon and/or particle emitter portion(s) 150 can be adjustable, adjustably filterable, adjustably weighable, and/or controllable such as to be able to respectively control and/or adjust generation and/or direction of the at least one applied high energy photon and/or particle 120 being applied to the at least some matter of the at least the portion of the individual. At least some of the at least one applied high energy photon and/or particle 120 may thereupon X-ray fluorescence within the fluorescing event to form the X-ray fluorescence high energy (e.g., X-ray, gamma ray, photon, particle, etc.), which can thereupon be received by the at least one X-ray fluorescence receiving portion(s) 151. Certain embodiments of the at least one high energy photon and/or particle emitter portion(s) 150 can be used to adjust or control the at least one X-ray fluorescence visualizing, imaging, or information providing within the at least one X-ray fluorescence range to the at least one prescribed substantial X-ray fluorescence depth of certain embodiments of the X-ray fluorescence visualizer, imager, or information provider 100. Within this disclosure, the at least one applied high energy photon and/or particle 120 or the at least one induced X-ray fluorescing photon 122 can include (e.g., comprise) a number of X-ray photons whose characteristic energy level and/or frequency can dictate the characteristics of the X-ray radiation.

Certain embodiments of the at least one X-ray fluorescence receiving portion(s) 151 can be configured to detect at least some at least one induced X-ray fluorescing photon 122 undergoing X-ray fluorescence from the at least the portion of the individual 82. Certain embodiments of the at least one X-ray fluorescence receiving portion(s) 151 can operate based, at least in part, by receiving at least one induced X-ray fluorescing photon 122 from a first X-ray fluorescence visualizer, imager, or information provider 100 X-ray fluorescence of fluorescing events from the at least one applied high energy photon and/or particle 120 that were generated by a different X-ray fluorescence visualizer, imager, or information provider 100. Certain embodiments of the at least one X-ray fluorescence receiving portion(s) 151 are controllable and/or adjustable such as to be able to respectively control and/or adjust the characteristics of the at least one induced X-ray fluorescing photon 122 that can be detected. Certain embodiments of the at least one X-ray fluorescence receiving portion(s) 151 can include, but is not limited to, each, or any combination of the at least one detector portion 152 and/or the at least one display portion 154.

The operation of certain embodiments of the at least one high energy photon and/or particle emitter portion(s) 150 and/or the at least one X-ray fluorescence receiving portion(s) 151 may be at least partially controlled or adjusted utilizing at least partially by the X-ray fluorescence visualization, imaging, or information providing controller 97, as described in this disclosure (although certain embodiments utilize relatively little or no control and/or adjustment). Certain embodiments of the at least one X-ray fluorescence receiving portion(s) 151 can X-ray fluorescence visualize, image, and/or provide information relating to the at least the portion of the individual 82 based, at least in part, on detecting the matter of the at least one induced X-ray fluorescing photon 122 X-ray fluorescenced from the at least the portion of the individual.

The potential variety of X-ray fluorescence visualization, imaging, or information providing, as described in this disclosure, can indicate the variety of potential embodiments of the X-ray fluorescence visualizer, imager, or information provider 100 that can vary in complexity from relatively simple probes to relatively complex systems. More complex systems can include arrays of a considerable number of the at least one high energy photon and/or particle emitter portion(s) 150 and/or a considerable number of the at least one X-ray fluorescence receiving portion(s) 151. Certain embodiments of the at least one X-ray fluorescence receiving portion(s) 151 can be used to determine a location of fluorescing events based at least partially on the at least one applied high energy photon and/or particle 120 energy level and/or trajectory of the at least one applied high energy photon and/or particle 120, as well as the location and trajectory (as can be determined by a polarizer, collimator, etc.) of the at least one induced X-ray fluorescing photon 122. In neutron, X-ray and gamma ray optics, a collimator may be considered a device that filters a stream of rays so that only those traveling parallel to a specified direction may be largely allowed to pass through the device while those of different directions may be deflected, reflected, absorbed, or otherwise limited from passing. Certain embodiments of the X-ray fluorescence visualizer, imager, or information provider 100 can, depending on context, be fabricated using a range of devices, systems, or fabrication techniques ranging from distinct components to semiconductor processing, and may involve suitable image processing, hardware, and/or software, etc. to perform suitable image deconvolution, transforms, filtering, modulation, etc.

Figure 5:
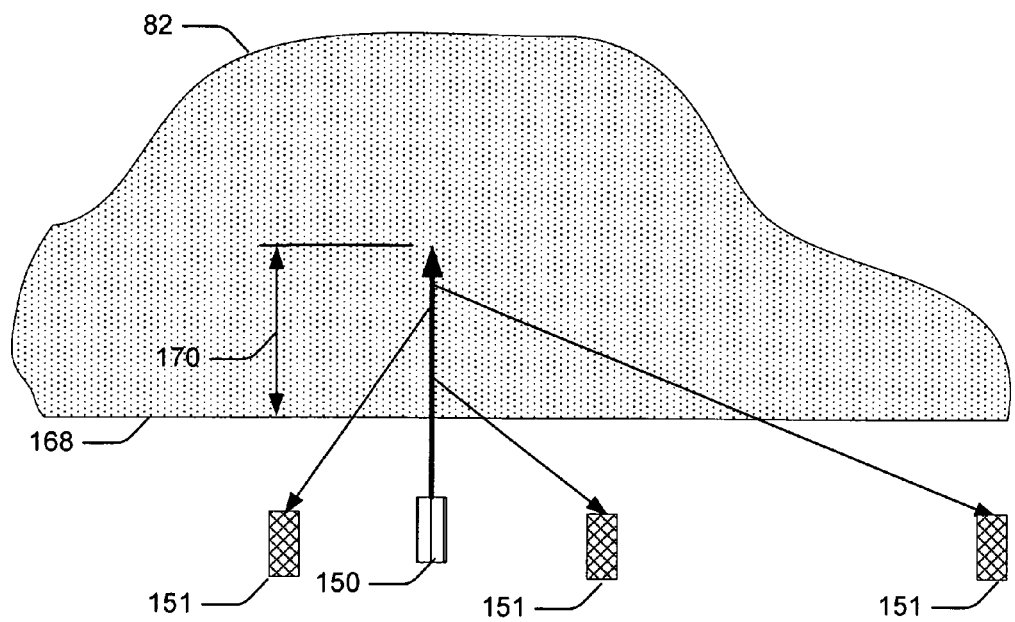
FIG. 5 is a diagram of an embodiment of the X-ray fluorescence visualizer, imager, or information provider.

There are a variety of embodiments of the X-ray fluorescence visualizer, imager, or information provider 100 that are within the intended scope by the present disclosure. FIG. 5 illustrates an embodiment of the X-ray fluorescence visualizer, imager, or information provider 100 being configured to have at least one high energy photon and/or particle emitter portion(s) 150, as well as one or more of the at least one X-ray fluorescence receiving portion(s) 151. Certain embodiments of the at least one X-ray fluorescence receiving portion(s) 151 may make use of suitable X-ray detection such as may utilize depth subtraction or combination, time of flight, geometric determination of location of a fluorescing event, and/or scintillator (and/or fluoroscope) aspects, or other techniques as described in this disclosure. Certain embodiments of the X-ray fluorescence visualizer, imager, or information provider 100 can operate with the at least one high energy photon and/or particle emitter portion(s) 150 emitting the at least one applied high energy photon and/or particle 120.

Certain embodiments of the X-ray fluorescence visualizer, imager, or information provider 100 can operate along a specific direction or prescribed substantial X-ray fluorescence depth into the at least some matter of the at least the portion of the individual that can X-ray fluorescence upon the fluorescing events within the matter of the at least the portion of the individual. Certain scintillator or other embodiments of the X-ray fluorescence visualizer, imager, or information provider 100 can utilize convolution or deconvolution, one or more transforms and/or inverse transforms, and/or other techniques to increase imaging quality of X-ray fluorescence visualizing, imaging, or information providing, etc. through X-ray opaque or other matter. Certain embodiments of the X-ray fluorescence visualizer, imager, or information provider 100 can provide an image deconvolution operation that can clarify between multiple ones of the at least one induced X-ray fluorescing photons and/or particles 122 (e.g., X-ray or gamma ray) traveling to the at least one X-ray fluorescence receiving portion(s) 151 from a number of separated, but closely aligned, fluorescing events.

A number of X-ray photons can be expected to X-ray fluorescence within the at least one X-ray fluorescence range to the at least one prescribed substantial X-ray fluorescence depth at least partially from the X-ray fluorescence high energy (e.g., X-ray, gamma ray, photon, particle, etc.). The particulars of the at least one X-ray fluorescence range to the at least one prescribed substantial X-ray fluorescence depth may correspond, at least in part, on the energy level of the X-ray photons (which corresponds to the frequency of the at least one applied high energy photon and/or particle 120). As such, a larger percentage of X-ray photons that have more energy may travel deeper into matter of similar characteristics than those X-ray photons having less energy. As such, the electromagnetic radiation including X-rays of certain relative lower frequencies (e.g., higher energy) may generally be expected to penetrate deeper, proportionately, through certain matter than X-rays with relatively higher frequencies. It might be desirable to simplify the structure and/or action of at least certain of the embodiments or applications of the X-ray fluorescence visualizer, imager, or information provider 100. Simplification of design, construction, etc. might be desirable for such purposes as to reduce expenses, simplifying image processing or system computations, focusing on X-ray fluorescence depth visualizing a single or a few aberrations. Being able to detect matter aberrations at least partially based on the elements, chemicals, compounds, and/or biological materials of the matter might therefore be particularly useful for such applications as melanomas, tumors, cancers, abscesses, tissue edges, blood pools, blood vessels, liquids, organ edges, tissue matter change delineations, etc.

Certain of such embodiments of the X-ray fluorescence visualizer, imager, or information provider 100 can be configured to image a particular material, elements, chemicals, compounds, biological materials, fluid, fluid flow, solid, or other detectable aspect. For instance, certain of these embodiments of the X-ray fluorescence visualizer, imager, or information provider 100 can be attached to a probe, tool, cutter, tactile feedback provider, laser device, Bovie electrocautery, separator, X-ray fluorescence visualizer, imager, etc.

Certain tool-based embodiments of the X-ray fluorescence visualizer, imager, or information provider 100 could be placed on the end of a probe or scope that is inserted into the body for a variety of purposes. For example, as a probe or other tool passes through tissue (e.g., brain, heart, or other organ or even flesh, muscle, etc.) an alarm that could include audio, video, or other media, etc. can be set off such as can be used to notify the user that the probe is coming into close proximity to a blood vessel, organ, bone, or other sensitive location.

Certain embodiments of the X-ray fluorescence visualizer, imager, or information provider 100 could be attached to or integrated within a tool such as a drill (e.g., certain embodiments of such drills could be used, for example, to penetrate the pedicle of the spine, tooth by a dentist, etc.). Certain tool-based or associated embodiments of the X-ray fluorescence visualizer, imager, or information provider 100 could be configured to notify the user if the drill tip, etc. is too close to adjacent vital or sensitive structures such as a nerve root, spinal canal, blood conduits, artery, or nerve root, etc. As such, certain embodiments of the X-ray fluorescence visualizer, imager, or information provider 100 may be configured to act as surgeons eyes within tissue or other obscuring matter such as tissue or other matter to limit potential injury or even death of the individual, or make surgeons or other doctors or dentists job easier and/or more effective.

Certain embodiments of the X-ray fluorescence visualizer, imager, or information provider 100 could be attached to an electrocautery instrument or other tool that will terminate current flow or provide some other limiting technique to cease effective operation of the tool/instrument when the instrument is passing relatively proximate to a definable danger zone or other undesirable area, such as a blood vessel, nerve, vital organ structure, etc. Certain embodiments of the X-ray fluorescence visualizer, imager, or information provider 100 that is associated with a tool could also include an override mechanism such that surgeons could provide an operation (e.g., cutting, repairing, etc.) based on overriding such ceasing of the tool operation based on proximity. There are instances where doctors, surgeons, etc. may want to operate within a sensitive area such as with an operational override, but it is important to provide an operational warning beforehand to limit unintended and/or undesired interference with sensitive regions.

Certain tool-based embodiments of the X-ray fluorescence visualizer, imager, or information provider 100 could be configured to make certain medical techniques, operations, or procedures perhaps easier, perhaps improved, perhaps more easily visualized or imaged, X-ray fluorescence visualization, perhaps with quicker feedback or response, and/or that might be safer. Certain surgeons operating in a manner to avoid blood vessels, nerves, etc. (while often necessary to keep their patient healthy and/or alive) can be slow and/or laborious in certain circumstances, and can considerably extend the duration, extent, and risk of operations, procedure, examinations, etc. The presence of blood vessels, nerves, etc. in locations where surgeons may not clearly see via their tools due to a skewing of the visualizing, imaging, or information providing through matter, tissue, bones, etc., can also result in additional risks to the patients (e.g., individuals). Surgeons attempting to operate too quickly or when they are tired, confused, inexperienced in a particular procedure or portion of the anatomy, etc. can risk the increased possibility of injury, or even death, to their patients by contacting, severing, or rupturing their blood vessels, nerves, brain tissue, or other organ and/or sensitive matter. Allowing a surgeon to detect such sensitive areas as blood vessels, nerves, spinal portions, sensitive tissue, etc. can thereby be utilized in an attempt to operate in, or around, the sensitive area or region without contacting are entering the sensitive matter or region. Such allowing surgeons to effectively determine relative locations of tools, portions of the X-ray fluorescence visualizer, imager, or information provider 100, etc. to sensitive matter or regions could therefore be expected to increase the rate at which surgeons might safely be able to operate while safely negotiating past the sensitive matters or regions within the individual while limiting the number of undesired contact with such sensitive, but detectable, matter of the at least the portion of the individual. This increase in safe operating rate might be expected to allow the surgeons to be more alert (by limiting fatigue) while increasing the rate at which they can safely and accurately operate, and thereby limiting or reducing the expected associated expenses.

If more than one of the at least one high energy photon and/or particle emitter portion(s) 150 are operating, then there should be some mechanism to limit confusion between the at least one applied high energy photon and/or particle 120 provided by each high energy photon and/or particle emitter portion(s) as detected by certain embodiments of the at least one X-ray fluorescence receiving portion(s) 151. Such differentiation or combination of X-ray fluorescence high energy (e.g., X-ray, gamma ray, photon, particle, etc.) at each at least one X-ray fluorescence receiving portion(s) 151 between the at least one applied high energy photon and/or particle 120 being generated by each of the at least one X-ray fluorescence receiving portion(s) 151 can rely on such techniques as described in this disclosure as, for example: altering the transmission time, coding of the carrier signal, differentiating signal weightings, geographically situating each fluorescing event to distinguish there between, shifting frequency of the at least one applied high energy photon and/or particle 120 between the different ones of the at least one applied high energy photon and/or particle 120, altering the energy levels of the photons altering the pulse durations of the at least one applied high energy photon and/or particle 120, etc. as described in this disclosure.

Certain embodiments of the X-ray fluorescence visualizer, imager, or information provider 100 can thereby be configured to differentiate at least certain ones of the at least one applied high energy photon and/or particle 120, and/or the directing at least certain ones of the at least one applied high energy photon and/or particle 120 in a different direction along non-interfering directions and sets of potential fluorescing events, such that the X-ray fluorescence high energy (e.g., X-ray, gamma ray, photon, particle, etc.) that are returning from different fluorescing events can be distinguished from each other each other. Additionally, certain polarizers, filters, weighting techniques, louvers, or other mechanical, microelectrode mechanical systems (MEMS), electronics, electrical, electromechanical, computer-based, or other such systems as described, for example, as the filter, polarizer, geometric limiter, angle polarizer, or variant thereof with respect to FIGS. 5 to 12, or other locations in this disclosure, could be utilized. Such techniques similar to deconvolution, inverse transforms, time division multiplexing, frequency division multiplexing, code division multiplexing, etc. (which are known to those skilled in the communications arts) can also be utilized to distinguish between, or clarify, different the at least one applied high energy photon and/or particle 120 being received by different ones of the at least one high energy photon and/or particle emitter portion(s) 150, and thereby limit interference at the at least one X-ray fluorescence receiving portion(s) 151 between multiple ones of the X-ray fluorescence high energy (e.g., X-ray, gamma ray, photon, particle, etc.) X-ray fluorescence from different fluorescing events.

Figure 6:
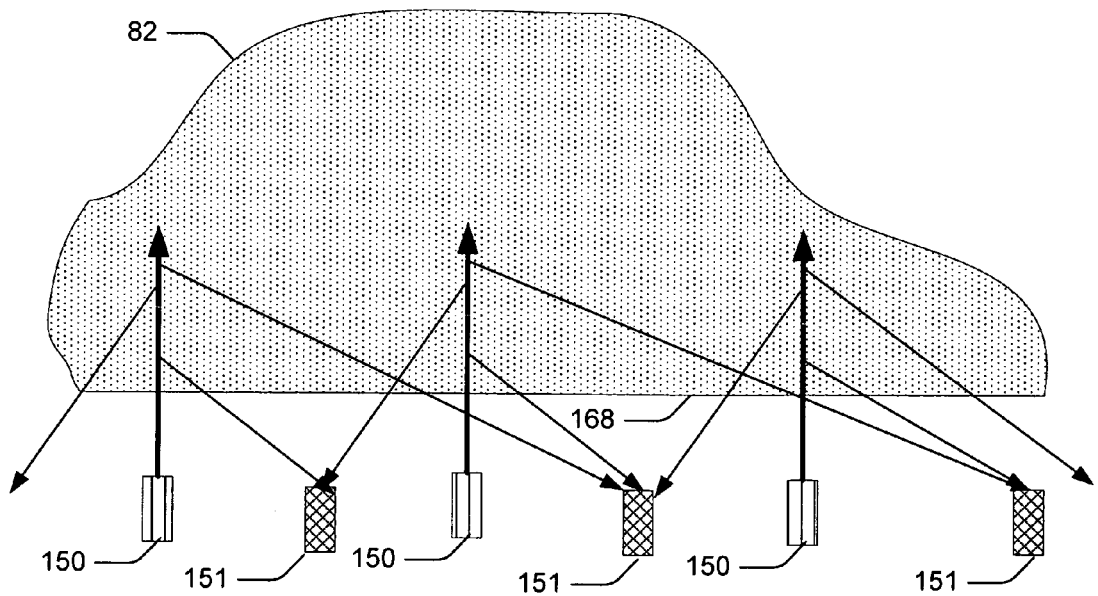
FIG. 6 is a diagram of another embodiment of the X-ray fluorescence visualizer, imager, or information provider.

FIG. 6 illustrates another embodiment of the X-ray fluorescence visualizer, imager, or information provider 100 that can be configured with the at least one high energy photon and/or particle emitter portion(s) 150, as well as one or more of the at least one X-ray fluorescence receiving portion(s) 151 (similar to as described with regards to FIG. 5 to that illustrates only one high energy photon and/or particle emitter portion). Multiple ones of the at least one high energy photon and/or particle emitter portion(s) 150 may, or may not be, arranged in a desirable associated relative configuration, such as at least one array, conforming to the matter, etc. Certain embodiments of the at least one high energy photon and/or particle emitter portion(s) 150 can be configured to emit the at least one applied high energy photon and/or particle 120 (as well as the at least one induced X-ray fluorescing photon 122) in a manner that can be differentiated from other ones (as well as other at least one induced X-ray fluorescing photon 122) based at least partially on deconvolution, transforms, time multiplexing, frequency multiplexing, code division multiplexing, directing of a variety of devices that can emit X-ray radiation in a variety of patterns such as pencil radiation, fan radiation, etc. to a desired location, and/or other such fluorescing event differentiating techniques, use of collimators, lenses, filters, etc. For example, certain embodiments of the at least one high energy photon and/or particle emitter portion(s) 150 can emit their the at least one applied high energy photon and/or particle 120 at different deconvolution or transform characteristics at different times, having different frequencies, with different weightings, or based on different coding algorithms such as is generally understood with a variety of multiplexing techniques.

Certain such embodiments of the X-ray fluorescence visualizer, imager, or information provider 100 may be utilized as a X-ray fluorescence visualizer having limited resolution; and may provide especially useful in conjunction with a tool as to provide X-ray fluorescence visualization, imaging, or information providing for blood vessel and other sensitive area avoidance, as well as cancer, abscesses, infections, or other matter aberration detection to X-ray fluorescence visualization, imaging, or information providing as described in this disclosure. Abscesses or infections are highly dangerous, and may be quite difficult, dangerous, or expensive to detect with any reasonable certainty. Certain embodiments of the X-ray fluorescence visualizer, imager, or information provider 100 may be able to scan for regions of abscesses, infections, etc. that may be based at least partially on the density, elements, chemicals, compounds, and/or biological materials included in or contained within the matter indicative of the abscess, infection, etc.

Certain embodiments of the at least one X-ray fluorescence receiving portion(s) 151 can include a variety of detectors that can include, but are not limited to, a streak camera, a pixelated streak camera, an avalanche detector, a CCD device, or other device that can detect the presence, energy level, and/or condition of X-ray fluorescence high energy (e.g., X-ray, gamma ray, photon, particle, etc.), preferably at a suitable rate to provide the desired resolution. Certain embodiments of the streak camera and/or the pixelated streak camera might be configured to act quite quickly, and can function in the low or fractional picosecond range, such as may be particularly useful for time of flight calculations or other similarly precise or suitable applications.

Certain embodiments of X-ray fluorescence visualizer, imager, or information provider 100 can include one or more collimated (e.g., "pencil", "fan", or other) radiation of the at least one applied high energy photon and/or particle 120, as illustrated in FIG. 5 or 6. Certain embodiments of the high energy photon or particle radiations 120 can scan the at least the portion of the individual in two directions while the at least one X-ray fluorescence receiving portion(s) 151 can measure the X-ray fluorescences resulting from the interactions of the high energy photons and/or particles (e.g., X-rays) with the bodily tissues. A variety of X-ray fluorescence depth visualizing and/or imaging information, particular to a given 3-D voxel within the display of the at least one X-ray fluorescence receiving portion(s) 151, can be derived using the two-dimensionally scanned X-ray radiation, which can be detected in several ways as described herein.

Certain embodiments of the X-ray fluorescence visualizer, imager, or information provider 100 can utilize time-resolved detection of the at least one induced X-ray fluorescing photon 122. Here, the time-of-return, $\Delta t$, of each X-ray fluorescence high energy (e.g., X-ray, gamma ray, photon, particle, etc.) from a fluorescing event corresponding uniquely to a position, x, along the illuminating collimated X-ray radiation, such that:

$$x = A * \Delta t + B \quad (1)$$

where A and B are proportionality constants that may be determined by the relative location of the illuminating X-ray radiation and the X-ray detector, as described in this disclosure. There can be a sufficient temporal pause (or other time, spatial, or coding technique understood by those skilled in multiplexing) between illumination by the at least one applied high energy photon and/or particle 120 of the at least one high energy photon and/or particle emitter portion(s) 150 at specific 2-D ray angles to limit fluorescing signal confusion between the at least one induced X-ray fluorescing photon 122 as received at the at least one X-ray fluorescence receiving portion(s) 151. Conventional and modified computation and processing techniques, based on triangulation of the at least one induced X-ray fluorescing photon 122, can result in more precise or higher quality X-ray fluorescence visualizing, imaging, or information providing. If determined to be significant, the effects of one or more elements present in the background of certain field of views (as to not interfere with the desired effects of the at least one induced X-ray fluorescing photon 122) can be reduced by adding energy discrimination to the detector, since each fluorescing event results in a reduction in energy levels of the photon or particle during the conversion from the at least one applied high energy photon and/or particle 120 to the at least one X-ray fluorescing photon and/or particle 122. For example, energy of the at least one applied high energy photon and/or particle 120 lost by the moving X-ray photon particle during collisions with other moving particles such as target atoms forming the matter of the at least the portion of the individual, that can be described based on X-ray fluorescence equations, heat, as well as other geometric or other equations, as described in this disclosure or elsewhere but generally known.

By scanning the body repeatedly using certain embodiments of the X-ray fluorescence visualizer, imager, or information provider 100 in one, two, or three (e.g., orthogonal) directions, but at varying energies so that the radiation penetrates progressively more or less deeply so fluorescing events can occur up to a progressively respectively deeper, or shallower, prescribed substantial X-ray fluorescence depth. Thereupon, a model (which may be three or two dimensional) of the subcutaneous bodily structures can be progressively combined and/or refined by comparing it to the time-integrated models. As such, certain embodiments of the at least one induced X-ray fluorescing photon 122 can be obtained from each illuminating particle radiation angle and then performing a de-convolution similar to those used in conventional tomography imaging. In addition to helping provide depth discrimination, such progressive illumination at different energies can reveal differences in the absorption and/or X-ray fluorescence characteristics of various fluorescing events occurring in particular matter. The value of the X-ray fluorescence characteristics of the X-ray fluorescing event can be an enhanced or diminished, in certain instances, by adding contrast agent, etc., such as to increase the contrast of the resulting image. In certain instances, the energy level of the at least one applied high energy photon and/or particle 120 can be increased, decreased, controlled, ramped, and/or otherwise altered (preferably in a gradual and/or predictable manner as described elsewhere in this disclosure, such that changes in the energy level will have little effect on imaging distortion) such as to allow adjustability or control of the X-ray fluorescence visualizing, imaging, or information providing by certain embodiments of the X-ray fluorescence visualizer, imager, or information provider 100.

Certain embodiments of the X-ray fluorescence visualizer, imager, or information provider 100 can therefore be configured to X-ray fluorescence visualize, image, and/or provide information at least partially by employing a nearly monochromatic illuminating X-ray "pencil" radiation, flooding radiation, fan-radiation, scanning radiation, or other ones of the at least one high energy photon and/or particle emitter portion(s) 150. The location of the fluorescing events along one or more of the radiation of the at least one applied high energy photon and/or particle 120 (in which, in certain instances, multiple ones thereof can be intersected to increase the intensity) where the X-ray photon of the X-ray fluorescence can be determined or detected based on the value of its characteristic energy level (as may be partially indicated by its wavelength, $\Delta\lambda$). For the usual case of the fluorescing events for each once-high energy photon, the change in wavelength of the X-ray photon upon X-ray fluorescence is given by the Planck's Law. Planck's Law may be characterized as the energy of electromagnetic waves is contained in an indivisible quanta that may be radiated or absorbed as a whole. The magnitude of the energy of the electromagnetic waves is proportional to the frequency and/or wavelength.

Planck's law (which may be modeled using physics as electromagnetic radiation of a black body) describes the spectral radiance of electromagnetic radiation at all wavelengths from a black body at temperature T. As a function of frequency $\nu$, Planck's law is written as:

$$I(\nu, T) = \frac{2h\nu^3}{c^2} \frac{1}{e^{\frac{h\nu}{kT}} - 1} \quad (2)$$

Planck's law may be written as a function of wavelength $\lambda$:

$$I(\lambda, T) = \frac{2hc^3}{\lambda^5} \frac{1}{e^{\frac{hc}{\lambda kT}} - 1} \quad (3)$$

The functions of equations (2) and (3) have different units. Equations (2) is given in is radiance per unit frequency, while equations (3) is given in radiance per unit wavelength. Hence, the quantities $I(\nu,T)$ and $I(\lambda,T)$ are not equivalent to each other, but correspond to each other. To derive one from the other, they cannot simply be set equal to each other. However, equations (2) and (3) may be related through:

$$I(\nu,T)d\nu = I(\lambda,T)d\lambda \quad (4)$$

In which, I is the spectral radiance or energy per unit time per unit surface area per unit solid angle per unit frequency or wavelength (as specified). Also, $\nu$ is the frequency of the high energy photon (e.g., X-ray). Additionally, $\lambda$ is the wavelength of each of the at least one applied high energy photon and/or particle 120. T is the temperature of the black body encompassing the high energy photon. Also, h=Planck's Constant, in Joule's per second. Additionally, c is the speed of light. Additionally, e is the base of the natural logarithm, 2.718281 . . . . Finally, k=Boltzmann's constant.

The X-ray fluorescence processes of the at least one target atom or fluorophore 121 may be viewed as being governed by three events: excitation, vibrational relaxation, and emission, as described in this disclosure. The excitation process of the at least one target atom or fluorophore 121 can be characterized as:

$$S_0 + h\nu \rightarrow S_1, \quad (5)$$

in which $h\nu$ is a generic term for photon energy where: h=Planck's constant and $\nu$=frequency of photons (e.g., often within the X-ray or gamma frequencies), and the state $S_0$ is the ground state of the at least one target atom or fluorophore 121. The specific frequencies of exciting and emitted photons may be dependent on the particular system. The emission process can be characterized as:

$$S_1 \rightarrow S_0 + h\nu, \tag{6}$$

where $S_1$ is the first (electronically) excited state of the at least one target atom or fluorophore 121. A molecule such as may include the at least one target atom or fluorophore 121 may be at one time configured in its excited state, $S_1$, and can thereupon relax by various pathways. The at least one target atom or fluorophore 121 can undergo 'non-radiative relaxation' in which the excitation energy is dissipated as heat (vibrations). Excited ones of the at least one target atom or fluorophore 121 can also relax via conversion to a state which may subsequently relax via phosphorescence or by a secondary non-radiative relaxation step. Relaxation of the at least one target atom or fluorophore 121 in its $S_1$ state can also occur through interaction with a second molecule through X-ray fluorescence quenching. Certain of the target atoms and/or fluorophores 121 that are excited through application of X-ray photons can transfer energy to a second one of the target atom and/or fluorophore 121, which is converted to its excited state and can then fluoresce.

The X-ray fluorescence quantum yield gives the efficiency of the X-ray fluorescence process. The X-ray fluorescence quantum yield may be viewed, depending on context, as the ratio of the number of photons emitted to the number of photons absorbed.

$$\Phi = \frac{\# \text{ photons emitted}}{\# \text{ photons absorbed}} \tag{7}$$

The maximum X-ray fluorescence quantum yield is 1, indicating every photon absorbed results in a photon emitted. Another way to define the quantum yield of X-ray fluorescence, is by the rates excited state decay:

$$\Phi = \frac{k_f}{\Sigma_i k_i} \tag{8}$$

where $k_f$ is the rate of spontaneous emission of radiation of the at least one target atom or fluorophore 121; and $\Sigma_i k_i$ is the sum of all rates of excited state decay of the at least one target atom or fluorophore 121. Other rates of excited state decay of the at least one target atom or fluorophore 121 by mechanisms other than photon emission and are therefore often considered as "non-radiative rates". X-ray fluorescence quantum yield may be measured by comparison to a standard with known quantum yield. The X-ray fluorescence lifetime refers to the time the molecule stays in its excited state before emitting a photon. X-ray fluorescence typically follows the first-order kinetics equation:

$$[S_1] = [S_1]_0 e^{-t/\tau}, \tag{9}$$

where $[S_1]$ is the remaining concentration of the at least one target atom or fluorophore 121 in their excited state molecules at time t, and $[S_1]_0$ is the initial concentration after excitation. Equations (9) represents an instance of exponential decay of the of the at least one target atom or fluorophore 121. The lifetime of the at least one target atom or fluorophore 121 is related to the rates of excited state decay as:

$$\tau = \frac{1}{\Sigma_i k_i}. \tag{10}$$

Thus, equations (10) is similar to a first-order reaction in which the first-order rate constant may be considered as the sum of all of the rates (a parallel kinetic model). Thus, the lifetime may be related to the facility of the relaxation pathway. If the rate of spontaneous emission, or other rates, are relatively fast, and the lifetime is inversely short (for commonly used X-ray fluorescence compounds typical excited state decay times for X-ray fluorescence compounds that emit photons with energies from the X-rays range. The X-ray fluorescence lifetime is an important parameter for practical applications of X-ray fluorescence such as X-ray fluorescence resonance energy transfer.

If necessary, time resolution, directional resolution, deconvolution, or other such image combination techniques can be added to at least certain of the approaches, as described in this disclosure, to assist in suppressing background noise, interfering signals, or other distorted affects from the at least one induced X-ray fluorescing photon 122 being emitted from fluorescing events. Such image combination techniques can include, but are not limited to, image subtraction, image differentiation, image transformation, deconvolution, weighted subtraction, functional subtraction, and group including inverse integral transform, subtractive inverse integral transform, inverse functional transform, and subtractive inverse functional transform, or other image processing techniques.

A number of embodiments of the X-ray fluorescence visualizer, imager, or information provider 100 are described, which can be configured to determine the location of X-ray fluorescence at least partially based on a geometric determination of a location of the at least one fluorescing event. Such geometric determination of a location of the at least one fluorescing event may provide information representative of some characteristics of the X-ray fluorescence high energy (e.g., X-ray, gamma ray, photon, particle, etc.) being received at the at least one X-ray fluorescence receiving portion(s) 151. FIGS. 5 to 12 illustrate a number of the X-ray fluorescence visualizer, imager, or information provider 100 can be used in combination for geometric determination of a location of the at least one fluorescing event using trigonometry or geometric techniques.

The FIGS. 5 to 12 embodiments of the X-ray fluorescence visualizer, imager, or information provider 100 may be configured with the at least one high energy photon and/or particle emitter portion(s) 150, the at least one X-ray fluorescence receiving portion(s) 151, and an at least one receiver X-ray fluorescence angular limiting portion 172 and/or 192. Certain embodiments of the at least one receiver X-ray fluorescence angular limiting portion 172 and/or 192 can be configured to include geometric angular X-ray limiting elements 172 and/or 192 as described with respect to FIGS. 7 to 12 that can limit passage of the at least one induced X-ray fluorescing photon 122 that passes to the X-ray fluorescence receiving portion(s) 151 to a particular angle. For instance, the embodiment of the at least one receiver X-ray fluorescence angular limiting portion 172 and/or 192 may include angular limiting elements 172 and/or 192 that can be angled at a relatively high angle $\theta_1$ to pass to the X-ray fluorescence receiving portion(s) 151 (as compared with the angular limiting elements 172 and/or 192 that are angled at a relatively shallow angle $\theta_2$ as described with respect to FIG. 8). Examples of angular limiting elements 172 and/or 192 that may be used in certain embodiments of the at least one receiver X-ray fluorescence angular limiting portion 172 and/or 192 as described with respect to FIGS. 7 to 12, or at other locations through the disclosure can include, but are not limited to, mechanical louvres elements, polarizers, X-ray filters, certain MEMs X-ray passage limiting elements, piezoelectric elements, angular collimators, beamformers, etc. In addition, certain embodiments of the at least one receiver X-ray fluorescence angular limiting portion 172 and/or 192 can be angled or controlled, as to provide similar control and/or angling of the associated angular limiting elements 172 and/or 192.

Figure 9:
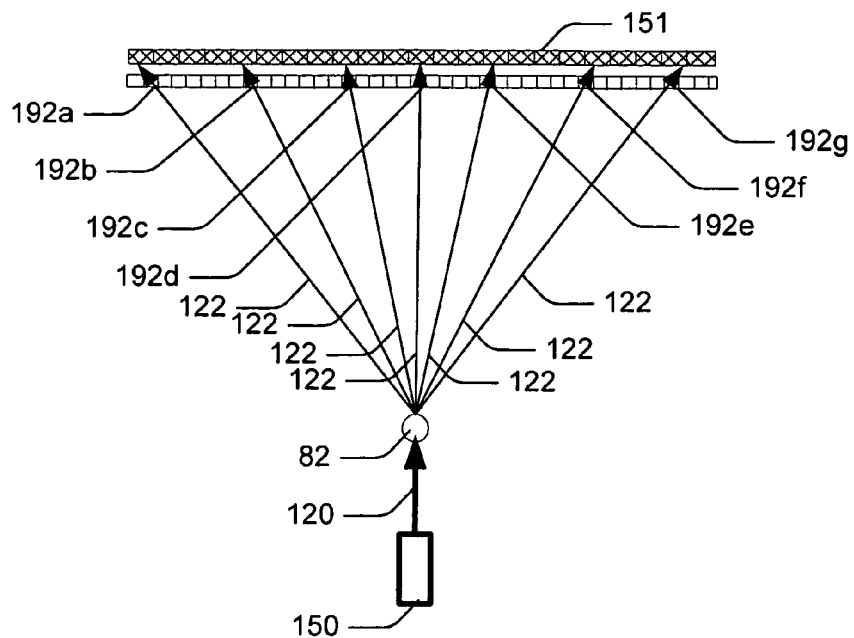
FIG. 9 is a view of the X-ray fluorescence visualizer, imager, or information provider of FIG. 8 as taken along section lines 9-9.
Figure 10:
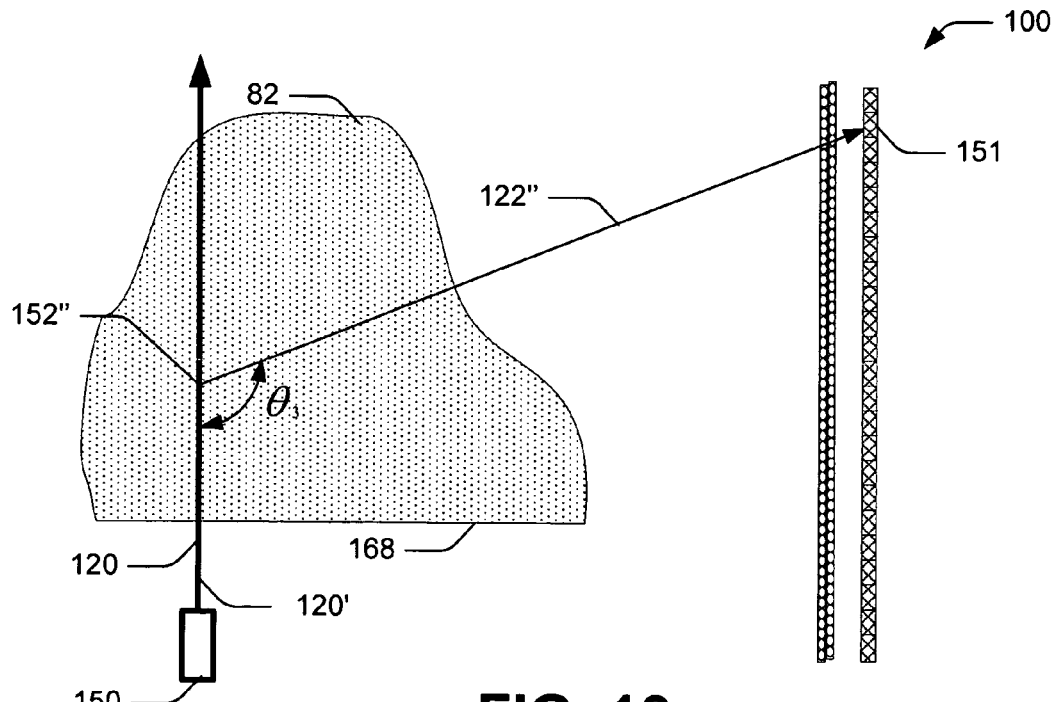
FIG. 10 is a diagram of another embodiment of the X-ray fluorescence visualizer, imager, or information provider including a scanning shield portion.

FIG. 10 shows another embodiment of two or more receiver X-ray fluorescence angular limiting portions 172 and/or 192 that interact (e.g., can be moved vertically as shown in the figure relative to each other) to limit passage of those induced X-ray fluorescing photon 122 that passes to the X-ray fluorescence receiving portion(s) 151 to a particular angle. Each of the two or more receiver X-ray fluorescence angular limiting portions 172 and/or 192 can independently allow for X-rays to pass through a variety of angles, however, by being positioned in close proximity with each other, X-rays are limited to pass only at particular angle(s) $\theta_3$. Certain embodiments of the angular limiting elements of the two or more receiver X-ray fluorescence angular limiting portions 172 and/or 192 as described with respect to FIG. 10 may include, but are not limited to, slit collimators, etc. Certain embodiments of the X-ray fluorescence visualizer, imager, or information provider 100 can be configured to allow relative motion between the two or more receiver X-ray fluorescence angular limiting portions 172 and/or 192 in such as manner as to allow relative adjustment and/or control of the angle(s) $\theta_3$ which the two or more receiver X-ray fluorescence angular limiting portions 172 and/or 192 can allow light to pass, as indicated by the arrows in FIG. 10. The various embodiments of the at least one receiver X-ray fluorescence angular limiting portion and/or the angular limiting elements as described with respect to FIGS. 5 to 12 are intended to be illustrative in nature but not limiting in scope, and may include those known devices that allow particular X-ray photons, etc. to pass as limited within particular angle(s).

Certain embodiments of the at least one X-ray fluorescence receiving portion(s) 151 can be configured with at least one high energy photon and/or particle emitter portion(s) 150, as well as the at least one X-ray fluorescence receiving portion(s) 151. The at least one high energy photon and/or particle emitter portion(s) 150, as described with respect to FIGS. 5 to 12 as well as other locations in this disclosure, can be configured to provide a variety of X-rays including, but not limited to those, arranged from pencil radiation emitter, a fan emitter, a flooding emitter, or other emitter that can controllably direct the at least one applied high energy photon and/or particle 120 as desired or designed in a particular path or direction and/or we associated X-ray photons having a particular energy level. For example, if there are a number of the at least one high energy photon and/or particle emitter portion(s) 150, then each one may be configured or designed to emit the X-rays along a controllable direction, time, angle, depth, etc. such as to not interfere with others.

Certain embodiments of the X-ray fluorescence visualizer, imager, or information provider 100 can be configured and/or designed such that the at least one applied high energy photon and/or particle 120 of FIGS. 5 to 12 can be directed along a path, that extends substantially continuously in a prescribed direction. While FIGS. 5 to 12 illustrate the at least one applied high energy photon and/or particle 120 having a trajectory at some angle across the surface into the matter of the at least the portion of the individual. Some other trajectory angle can be provided with the surface as well, and still comply with fluorescing equations as described in this disclosure, such as with respect to FIG. 3 and at other locations. At least one X-ray fluorescence receiving portions 151 (illustrated respectively in FIGS. 5 to 12 as an array of receiving assemblies) can be configured to receive X-rays directed at an angle, and thereby receive only photons traveling substantially in a direction substantially corresponding to the angle, relative to the at least one applied high energy photon and/or particle 120. The at least one X-ray fluorescence receiving portion(s) 151 can thereby be configured to receive a variety of the at least one induced X-ray fluorescing photon 122 that can travel along a number of paths 122', 122", etc. that X-ray fluorescence at a variety of illustrative locations 152', 152", etc. which can be somewhat limited for allowing only electromagnetic radiation (e.g., X-rays, etc.) from within a prescribed range of angles to pass.

Figure 7:
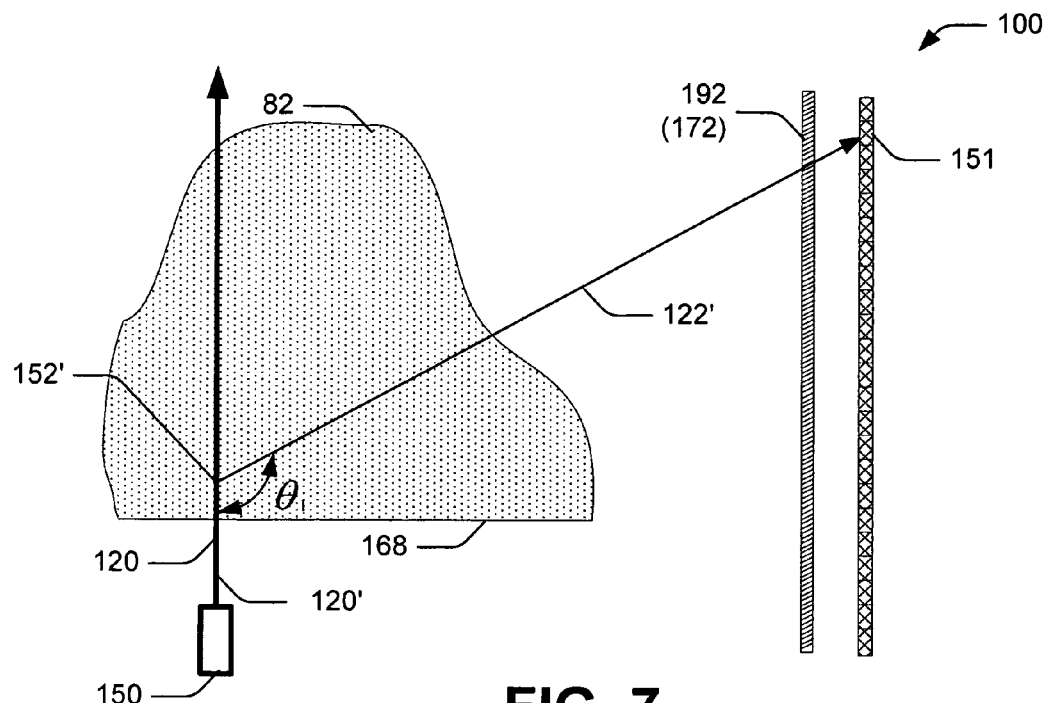
FIG. 7 is a diagram of yet another embodiment of the X-ray fluorescence visualizer, imager, or information provider.

As such, FIG. 7 illustrates that the at least one induced X-ray fluorescing photon traveling along path 122', that is within a range of angles as indicted by $\theta_1$, will pass through the filter, polarizer, geometric limiter, or angle polarizer 192. Additionally, FIG. 8 indicates that the at least one induced X-ray fluorescing photon 122 traveling along path 122" that is within a range of angles as indicted by $\theta_2$ will pass through the at least one filter, polarizer, geometric limiter, or angle polarizer 192. As such, photons that have fluoresced at a specific angle from a fluorescing event situated along the path of the at least one applied high energy photon and/or particle 120 will be allowed to pass through the at least one filter, polarizer, geometric limiter, or angle polarizer 192. The location of each fluorescing events 152', 152" can be situated along the path of the at least one applied high energy photon and/or particle 120, can be determined based, at least in part, on X-ray fluorescence angle, $\theta_1$ and $\theta_2$, etc. of the at least one induced X-ray fluorescing photon 122 that can travel along path(s) 122' of FIG. 7 and path(s) 122" of FIG. 8 being received at the at least one X-ray fluorescence receiving portion(s) 151, such as which can be limited to operating at only certain angles, such as by using a collimator 172 that may be configured as the at least one filter, polarizer, geometric limiter, or angle polarizer 192.

FIG. 9 indicates that two or more of the filter, polarizer, geometric limiter, or angle polarizer 192 can be arranged across an array of the at least one X-ray fluorescence receiving portion(s) 151 to allow detection of X-rays traveling at various angles. For instance, multiple angle polarizers 192a, 192b, 192c, 192d, 192e, 192f, 192g, and/or 192h can be arranged across the at least one X-ray fluorescence receiving portion(s) 151, each of which may be set at a different or the same angle to thereby act as an individual collimator 172. While certain of the multiple angle polarizers 192a, 192b, 192c, 192d, 192e, 192f, 192g, and/or 192h are illustrated relative to FIG. 9 as being spread over an area, it is to be understood that the multiple angle polarizers can be made of many various configurations and/or dimensions. Certain embodiments of the multiple angle polarizers 192a, 192b, 192c, 192d, 192e, 192f, 192g, and/or 192h can be fabricated to be quite small using a variety of semiconductor processing techniques, etc. Certain of the multiple angle polarizers 192a, 192b, 192c, 192d, 192e, 192f, 192g, and/or 192h may thereby allow the at least one induced X-ray fluorescing photon 122 to pass to the at least one X-ray fluorescence receiving portion(s) 151 that is traveling at different trajectory angles.

Certain embodiments of the slit collimator 172 can be arranged with a variety of members that are relatively moveable, such as to control the direction received. Other X-ray receiving mechanisms as polarizers, filters, processors, software, etc. could be used as certain embodiments of the slit collimator 172. Various embodiments of various computations, certain ones as described in this disclosure, can be used to locate the position of the fluorescing events 152', 152", etc., as described with respect to FIGS. 7 to 12, can be derived based at least in part on deconvolution, transforms, etc. to provide geometric X-ray fluorescence visualization, imaging, or information providing techniques, etc. A number of one, two, or three-dimensional arrays of the at least one X-ray fluorescence receiving portion(s) 151 can be arranged to about the at least one applied high energy photon and/or particle 120, in a manner to enhance the determination of the position of the fluorescing events 152', 152". Such determination can be based at least in part on the location of the multiple received arrays of the at least one X-ray fluorescence receiving portion(s) 151.

The embodiment of the at least one X-ray fluorescence receiving portion(s) 151, as described with respect to FIGS. 7 to 12 can be used to derive at least one position of the fluorescing event 152 in which the at least one applied high energy photon and/or particle 120 fluoresces such as by contact, or traveling close to: atoms, electrons, neutrons, or other such matter. The embodiment of the at least one high energy photon and/or particle emitter portion(s) 150 as described with respect to FIG. 11 can be similar, or identical, to those embodiments as described with respect to FIG. 1 or 2, as well as other locations in this disclosure. Certain embodiments of the at least one X-ray fluorescence receiving portion(s) 151, as described with respect to FIG. C11, can include a slit collimator 172 or other such device that can limit the angle at which X-ray fluorescence high energy (e.g., X-ray, gamma ray, photon, particle, etc.) can reach the at least one X-ray fluorescence receiving portion(s) 151. Certain embodiments of the collimator can also be configured as a lens, filter, collimator, or other device that can be used to limit passage of the X-ray fluorescence high energy (e.g., X-ray, gamma ray, photon, particle, etc.) to the at least one X-ray fluorescence receiving portion(s) 151 to only within a range of degrees, etc. Certain embodiments of the slit collimator, lens, filter, etc. could be provided between the path of the at least one applied high energy photon and/or particle 120' and the at least one X-ray fluorescence receiving portion(s) 151. Those X-ray fluorescence high energy (e.g., X-ray, gamma ray, photon, particle, etc.) being applied from the position of the fluorescing event of the at least one X-ray fluorescence receiving portion(s) 151 may only be detected if flowing in a direction substantially aligned with the slits of the slit collimator. The structure and use of slit collimators, lenses, filters, etc. are generally understood by those skilled in the X-ray, optics, electromagnetics, and other similar areas; and will not be further described in this disclosure. Alternate types of collimators, lenses, filters, etc. that can limit the passage of the X-ray fluorescence high energy (e.g., X-ray, gamma ray, photon, particle, etc.) to those within an angular range such as to detect fluorescing events within that angular range may also be utilized. The angular orientation of the slit collimator can be angled, such as to change the angle of the at least one induced X-ray fluorescing photon 122 being received.

Figure 11:
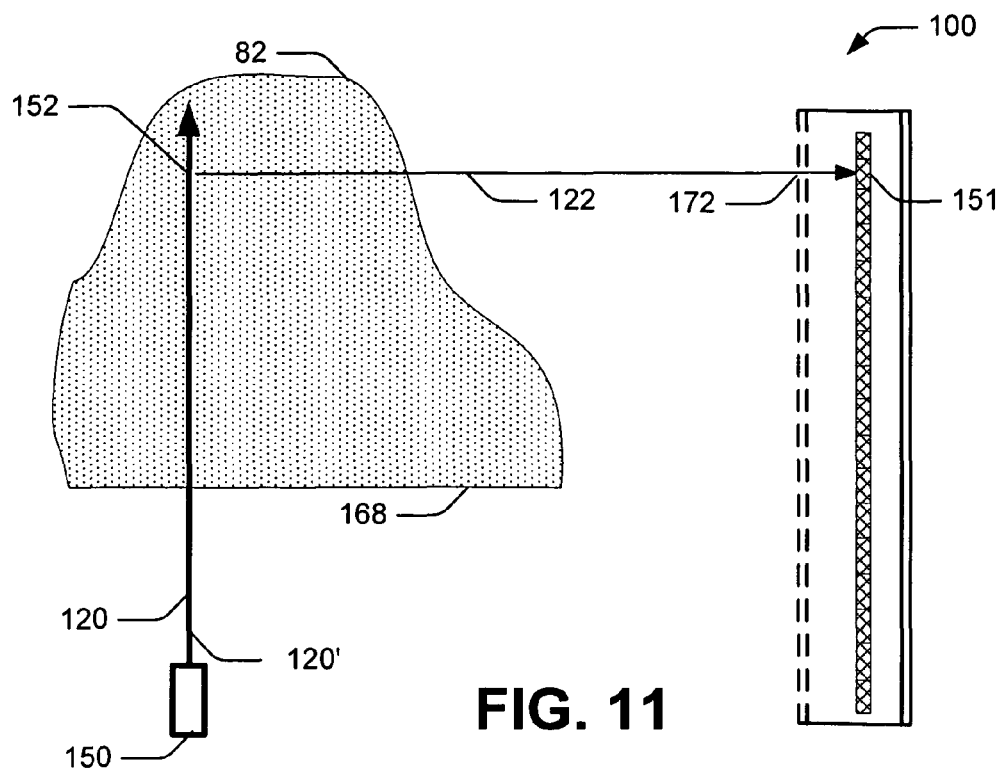
FIG. 11 is a diagram of another embodiment of the X-ray fluorescence visualizer, imager, or information provider including a collimator.

One slit is shown in the slit collimator 172 as illustrated in FIG. 11. One or more of the slits of the slit collimator 172 can be arranged, such as to be aligned to allow passage of the at least one induced X-ray fluorescing photon 122 at certain angles relative to a particular element of the at least one X-ray fluorescence receiving portion(s) 151. While a single slit collimator is described with respect to FIG. 11, it is to be understood that multiple slit collimators can be respectively associated with at least one unit of the at least one X-ray fluorescence receiving portion(s) 151. In addition, utilizing one or more of a variety of technologies that are generally understood, the X-ray fluorescence high energy (e.g., X-ray, gamma ray, photon, particle, etc.) can be steered, beam-formed, or otherwise directed in a manner as desired or appropriate. By using the embodiment of the at least one X-ray fluorescence receiving portion(s) 151 as described with respect to FIG. 11, location of one or more fluorescing events occurring along one more the at least one applied high energy photon and/or particle 120 can be determined.

Figure 12:
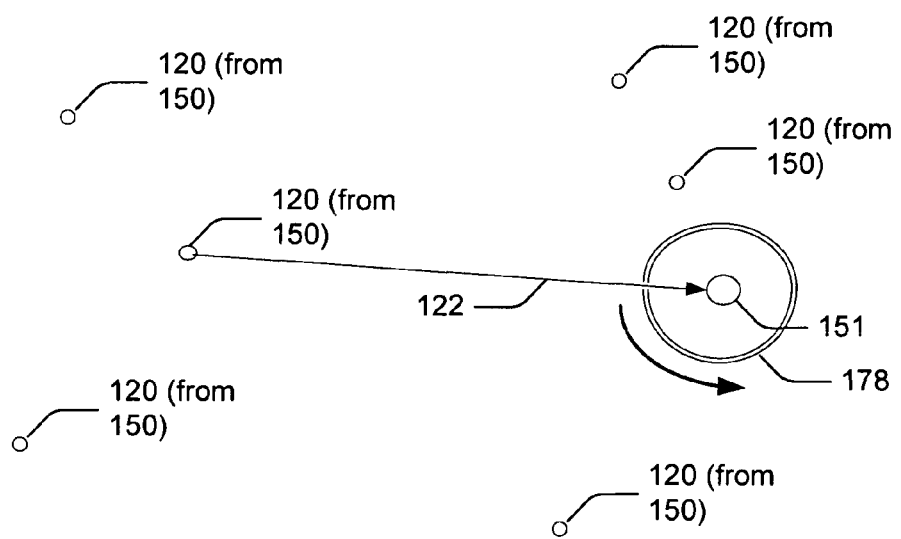
FIG. 12 is a diagram of another embodiment of the X-ray fluorescence visualizer, imager, or information provider including a scanning shield portion.

Certain embodiments of the X-ray fluorescence visualizer, imager, or information provider 100, as described with respect to FIG. 12, can be configured such that the at least one X-ray fluorescence receiving portion(s) 151 can be steered or directed in a plane perpendicular to that of the which the X-ray fluorescence receiving assembly can sense the position of the fluorescing event. For example, the paths of the at least one applied high energy photon and/or particle 120, as shown in FIGS. 3, 5-11, etc. the path of the at least one applied high energy photon and/or particle 120 may at least partially extend substantially within the plane of the paper in those figures. Certain ones of the fluorescing event detection, imaging, X-ray fluorescence visualizing, and/or information providing mechanisms, as described above, may utilize such exemplary mechanisms to determine the position of the fluorescing event as: subtraction or combination, deconvolution, transforms, time of flight, X-ray fluorescence angle, loss of energy level of the X-ray fluorescence X-ray photons, geometric X-ray fluorescence computation, collimator, other derivatives, etc., and other locations through this disclosure. Each at least one X-ray fluorescence receiving portion(s) 151, as described with respect to FIG. 10, can include a scanning shield portion 178, which can be configured to limit photons (e.g., X-rays or gamma ray wavelengths) passing to that within certain angular ranges. More specifically, provided that there are an array, or a number of, the at least one applied high energy photon and/or particle 120, then the scanning shield portion 178 can limit passage of only one or a number of the at least one applied high energy photon and/or particle 120 at any one time period. Certain embodiments of the scanning shield portion 178 and/or the at least one high energy photon and/or particle emitter portion(s) 150 can be dynamic, such as being positionable at controllable angles and/or rotatable such as may provide for positionable control and/or scan; or alternately limit passage of only one or certain of the at least one applied high energy photon and/or particle 120 continuously if the scanning shield portion 178 and the at least one high energy photon and/or particle emitter portion (s) 150 are fixed or static.

As such, certain embodiments of the at least one slit collimator 172, as described with respect to FIG. 11, can be viewed as limiting the angle(s) from horizontal of the at least one induced X-ray fluorescing photon 122 fluorescing from the at least one applied high energy photon and/or particle 120, and passing to the at least one X-ray fluorescence receiving portion(s) 151 (e.g., in a directional substantially parallel to an axial direction of the at least one applied high energy photon and/or particle 120 as illustrated, or at another orientation). By comparison, certain embodiments of the scanning shield portion 178, as described with respect to FIG. C12, can be viewed as limiting the angle (within the plane of the paper) at which the at least one induced X-ray fluorescing photon 122 which X-ray fluorescence from the at least one applied high energy photon and/or particle 120, and passing to the at least one X-ray fluorescence receiving portion(s) 151, in a directional substantially perpendicular to an axial direction of the at least one applied high energy photon and/or particle 120. Both the scanning shield portion 178 as described with respect to FIG. 12, and the slit collimator 172 as described with respect to FIG. 11, can thereby be viewed as embodiments of collimators, since they both limit passage of the X-ray fluorescence high energy (e.g., X-ray, gamma ray, photon, particle, etc.) from fluorescing events that are situated within an angular range to the at least one X-ray fluorescence receiving portion(s) 151. In addition, the material forming the housing material (as compared to the slits which may be air, or some X-ray transmissive material) of the scanning shield portion 178 and the slit collimator 172 should limit passage of X-rays there through, such as to limit screened X-rays from being applied to the at least one X-ray fluorescence receiving portion(s) 151.

Within this disclosure, both the scanning shield portion 178 and the slit collimator 172 are intended to be illustrative in nature, but not limiting in scope. Certain processes as performed by either the scanning shield portion 178 and/or the slit collimator 172 could also be configured as a lens, a filter, a beamformer, or other electromagnetic, mechanical, electronic, or X-ray type mechanism, etc. As such, certain embodiments of the scanning shield portion 178 could limit passage of the X-ray fluorescence high energy (e.g., X-ray, gamma ray, photon, particle, etc.) being applied to the at least one X-ray fluorescence receiving portion(s) 151 to within a range of angles, etc.

A number of filters, collimators, angular polarizers, and/or other devices can thereby be configured to limit passage of at least one induced X-ray fluorescing photon 122 that enter the X-ray fluorescence receiving portion(s) 151 to within particular angles, from particular directions, etc. It is thereby envisioned that collimators, filters, and other such devices can limit the angle of the applied high energy photon and/or particle 120 that are being applied to the at least the portion of the individual 82 to within particular angular ranges.

It is generally understood that with certain electromagnetic, optical, and/or X-ray technologies, certain operations can be performed utilizing two or more devices and/or their associated technique(s). Such devices, or techniques, may be viewed as equivalents, each of which is able to perform a similar function, operation, or technique. As such, certain embodiments of the collimator 172, scanning shield portion 178, etc. can be performed either by the device as described herein, or other generally known electromagnetic, optical, or X-ray equivalent devices and/or modifications thereof. Such generally equivalent devices are known by those skilled in the art can be utilized, and are intended to remain within the scope of the present disclosure.

This disclosure thereby illustrates a number of exemplary mechanisms (and associated techniques of certain embodiments of the at least one X-ray fluorescence receiving portion(s) 151) which can geometrically, computationally, or otherwise derive position of the fluorescing events within some matter. Such deriving the positions of the fluorescing events can be based at least in part on characteristics of at least some at least one induced X-ray fluorescing photon 122 (while assuming a static or predictable at least one applied high energy photon).

Figure 15:
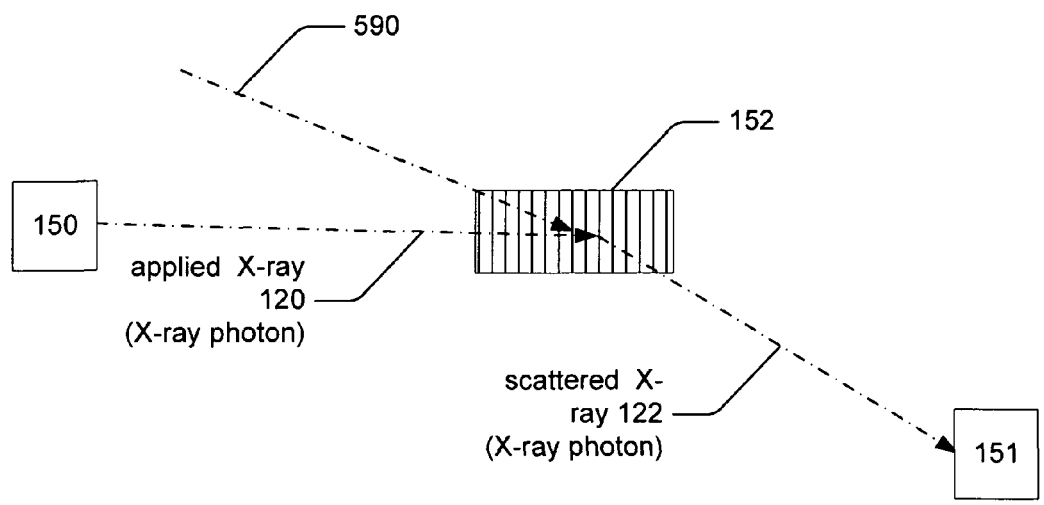
FIG. 15 is a diagram of another embodiment of the X-ray fluorescence visualizer, imager, or information provider in which another electromagnetic radiation is applied to the at least one applied high energy photon.
Figure 16:
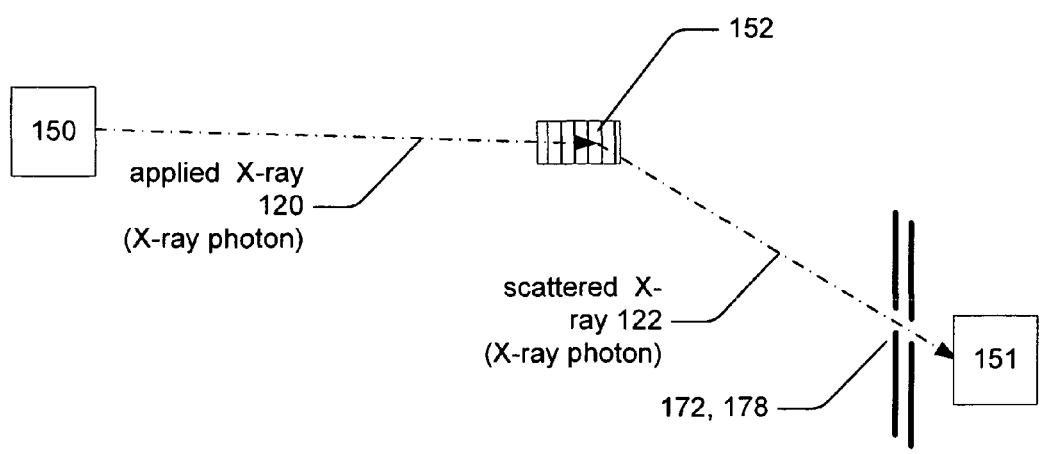
FIG. 16 is a diagram of another embodiment of the X-ray fluorescence visualizer, imager, or information provider including a collimator or scanning shield portion.

FIGS. 15 and/or 16 illustrate an embodiment of the X-ray fluorescence visualizer, imager, or information provider 100 that can be used, for example, in spatially confined imaging utilizing the output from the fluorescing event 152. Certain embodiments of the at least one X-ray fluorescence receiving portion(s) 151 are X-ray associated with a collimator 172 or 178, as described with respect to FIG. 11 or 12, or at other locations, in this disclosure. As such, certain embodiments of the at least one X-ray fluorescence receiving portion(s) 151 will only be able to detect X-ray fluorescence high energy (e.g., X-ray, gamma ray, photon, particle, etc.) X-ray fluorescence from fluorescing events 152 may occur within a spatially confined region. As such, certain embodiments of the at least one high energy photon and/or particle emitter portion(s) 150 can be configured as pencil radiation, fan radiation, flooding radiation, or as having other radiation configurations. However, each the at least one applied high energy photon and/or particle 120 provided by the at least one high energy photon and/or particle emitter portion(s) 150 could be directed within the spatially confined imaging region (of the fluorescing event) such as to illuminate that region sufficiently such that the X-ray fluorescence high energy (e.g., X-ray, gamma ray, photon, particle, etc.) can be detected by the associated at least one X-ray fluorescence receiving portion(s) 151.

Figure 8:
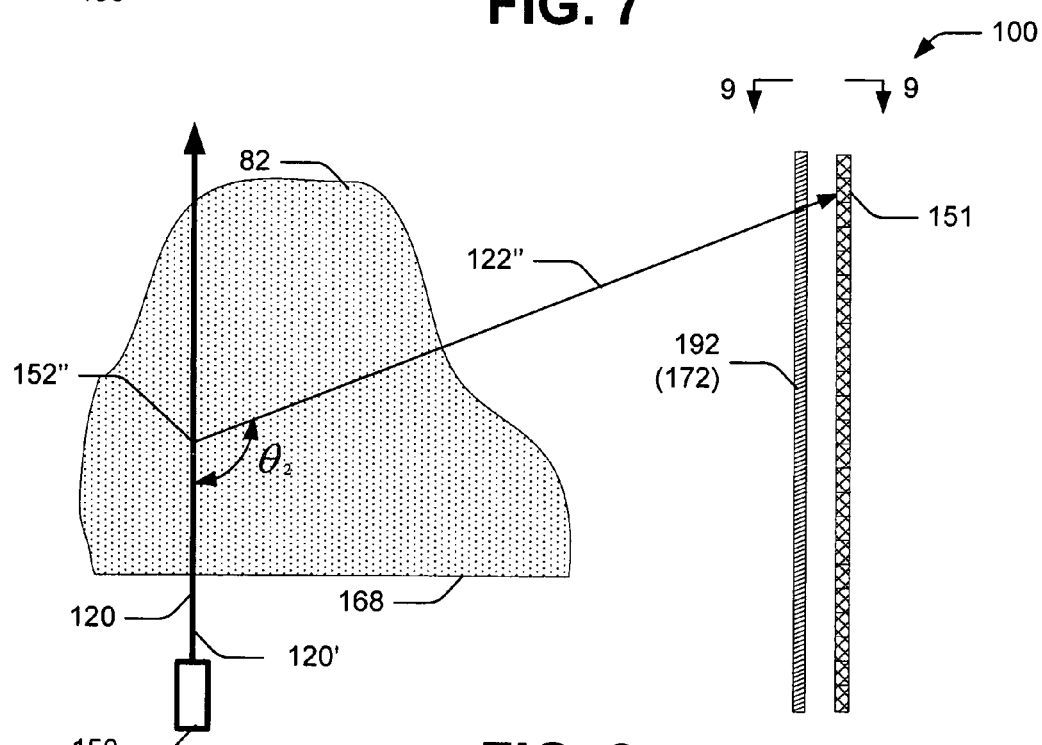
FIG. 8 is a diagram of another embodiment of the X-ray fluorescence visualizer, imager, or information provider including a collimator.

For the combination of any of the at least one high energy photon and/or particle emitter portion(s) 150 and any of the at least one X-ray fluorescence receiving portion(s) 151 as described in this disclosure, a variety of X-ray fluorescence high energy (e.g., X-ray, gamma ray, photon, particle, etc.), at least one applied high energy photon, matter, and other parameters can be determined that can be stored in a database, etc., and thereupon be used to derive the location of the position of the fluorescing events 152', and/or 152", etc. along the at least one applied high energy photon and/or particle 120 along path 120' as described with respect to FIGS. 7, 8, 9, and/or 12 utilizing known geometric, material, X-ray, and other techniques and/or calculations. Since certain of the at least one applied high energy photon and/or particle 120 can be applied intermittently at certain ones of the position of the fluorescing events 152', 152", etc.; the X-ray fluorescence visualization, imaging, or information providing parameters at the various positions of the fluorescing events can be intermittently obtained. As the at least one applied high energy photon and/or particle 120 X-ray fluorescence at each position of the fluorescing event based on X-ray fluorescence, the X-ray fluorescence visualization, imaging, or information providing parameters of each position of the fluorescing event 152', and/or 152", such as can be used to image there from, and can be determined.

Certain X-ray fluorescence visualization, imaging, or information providing techniques can rely on generation of image information or X-ray fluorescence visualization information that can represent data or other form of information. Such data, text, information, etc. can be stored or maintained in a database storage, processed using understood image processing techniques, etc., such as described with respect to certain embodiments of the X-ray fluorescence visualization, imaging, or information providing controller 97 as described with respect to FIGS. 1 and 2, as well as other locations through this disclosure.

Certain embodiments of the X-ray fluorescence visualizer, imager, or information provider 100 can X-ray fluorescence visualize, image, and/or provide information at least partially by making 2-D or 3-D scans from different "vantage points" (which for example receives the at least one induced X-ray fluorescing photon 122 outside the body), detecting the time-integrated X-ray return signal from each 2-D or 3-D X-ray/vantage-point combination. A variety of 2-D or 3-D scans can be combined, as may be the case with a variety of tomography-like reconstructions of such as depth-related 3-D structures that may be taken at a number of angles, as described with respect to FIGS. 17a, 17b, and 18. Such tomographic-type reconstructions can differentiate matter based, at least partially, on the element composition (and/or chemical composition, compound composition, or biological material composition with the addition of X-ray fluorescence enhancing additives, taggants, or contrast agents, etc.) of the at least some matter of the at least the portion of the individual.

Figure 17A:
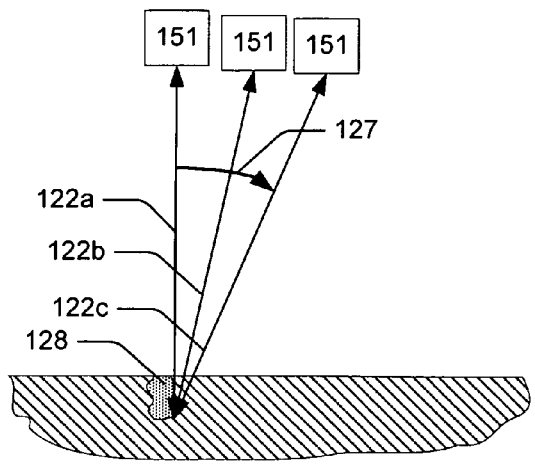
FIGS. 17a and 17b are a diagram illustrating motion of certain embodiments of the X-ray fluorescence visualizer, imager, or information provider such as may occur during certain types of volumetric X-ray fluorescence visualization, imaging, or information providing.
Figure 17B:
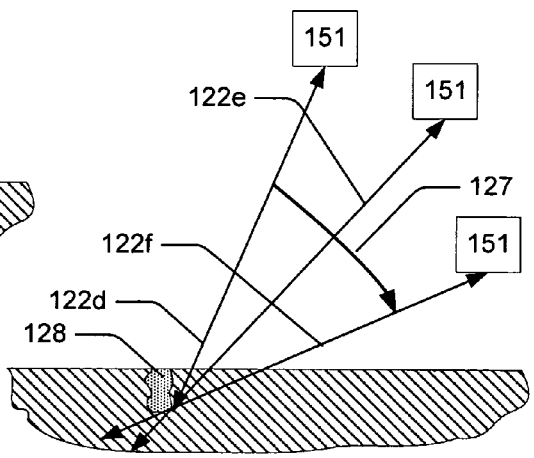

FIGS. 17a and 17b illustrate a number of vantage views by the at least one X-ray fluorescence receiving portion(s) 151 of one embodiment of the X-ray fluorescence visualizer, imager, or information provider 100, which can be displaced to adjust and/or control an imaging perspective by which the angle of the at least one induced X-ray fluorescing photon 122 changes from the various paths 122a, 122b, 122c. The displacement of the at least one X-ray fluorescence receiving portion(s) 151 is as indicated by an arrow 127, can be used to image the portion of the individual. During the X-ray fluorescence visualization, imaging, and/or information providing, as described with respect to FIG. 17a, a variety of image information (similar in certain ways to conventional tomographic imaging or volumetric imaging techniques) can be derived. However, there can also be a considerable amount of information that can be determined based upon the X-ray fluorescence of the at least one applied high energy photon and/or particle 120 from a certain direction, or a limited range of directions. For example, a depth of the tissue aberration (or other tomography-type feature) 128 is largely uncertain during the X-ray fluorescence visualization, imaging, or information providing as described with respect to FIG. 17a as a result of the relative direction in which the at least one X-ray fluorescence receiving portion(s) 151 receives the X-ray fluorescence high energy (e.g., X-ray, gamma ray, photon, particle, etc.). Such depth-information of matter aberrations can be provided or enhanced using certain embodiments of the X-ray fluorescence visualizer, imager, or information provider 100 considering element composition (and/or chemical composition, compound composition, or biological material composition with the addition of X-ray fluorescence enhancing additives, taggants, or contrast agents, etc.) of the at least some matter of the at least the portion of the individual.

As the angle of the X-ray fluorescence high energy (e.g., X-ray, gamma ray, photon, particle, etc.) continues to increases through an angle, as described with respect to FIG. 17b as along paths 122d, 122e, and 122f, the depth determination or extent of the feature 128 (using volumetric, tomographic, or other such techniques) can be modified as the angle of the X-ray fluorescence high energy (e.g., X-ray, gamma ray, photon, particle, etc.) continued to change (in this instance increases). As such, the prescribed substantial X-ray fluorescence depth can be more readily and accurately determined based at least partially on the angle of the X-ray fluorescence high energy (e.g., X-ray, gamma ray, photon, particle, etc.) increasing its angle from a normal to a surface being X-ray fluorescence visualized, imaged, or information provided. Such fluorescence X-ray visualizing, imaging, or information providing may be based at least partially on the density, elements, chemicals, compounds, and/or biological materials included in or contained within the matter. Such dimensions, extents, etc. of the features can be determined to more fully and accurately map the X-ray fluorescence visualization, image, or provided information relative to the matter of the at least a portion of the individual, such as: tissue, tissue aberrations, organs, edge features, bones, constructs, inserts, bony portions, fluid or blood vessels, reservoirs, pooling, etc. that may be based at least partially on the density, elements, chemicals, compounds, and/or biological materials, included in or contained within the matter. Such blood pooling may be useful is considering certain injuries, certain infections, explosion injuries, gunshot wounds, etc.

While the imaging perspective described with respect to FIGS. 17a and 17b can be used to adjust or control the angle of the X-ray fluorescence high energy (e.g., X-ray, gamma ray, photon, particle, etc.) relative to matter of the least to portion of the individual, there can be a variety of other imaging perspectives that can be similarly adjusted, controlled, and/or otherwise utilized. For instance, the at least the portion of the individual could be moved relative to the at least one applied high energy photon and/or particle 120 and/or the X-ray fluorescence high energy (e.g., X-ray, gamma ray, photon, particle, etc.). As the field of view of the X-ray fluorescence visualization, imaging, or information provided is zoomed, focused, filtered, transformed, or otherwise modified to provide other "new" or "modified" (e.g., and/or adjusted or controlled) information, such new or modified information can be added to the enhanced model, X-ray fluorescence visualization, image, or information; such new or modified information can be compared with the original information to improve or alter accuracy or detail of the X-ray fluorescence visualization, image, or information. The techniques used for adjustment and/or control of the X-ray fluorescence visualization, imaging, or information providing, certain ones of which are described relative to FIGS. 47 through 50 as described in this disclosure, can be used to improve a quality of X-ray fluorescence visualization, imaging, or information provided based on a variety of vantage points, and can be utilized for tomography or volumetric-type imaging.

Certain embodiments of the X-ray fluorescence visualizer, imager, or information provider 100 can thereby be configured to provide tomography X-ray fluorescence visualization, imaging, or information providing. The tomography provided would be expected to be similar to the tomography provided by other imaging modalities such as CAT scans, PET scans, and MRI, with the exception that certain embodiments of the X-ray fluorescence visualizer, imager, or information provider would image matter to the prescribed substantial X-ray fluorescence depth. Other embodiments of the X-ray fluorescence visualizer, imager, or information provider 100, by comparison, would be expected to image through the matter of the at least some matter of the at least the portion of the individual that may be based at least partially on the density, elements, chemicals, compounds, and/or biological materials, included in or contained within the matter. Additionally, the embodiments of the X-ray fluorescence visualizer, imager, or information provider 100 can generally utilize X-ray fluorescence, as compared to transmissive X-rays as with CAT scans, transmissive positrons as with PET scans, and magnetic fields as with MRI. Each visualizing, imaging, or information providing modality might therefore be expected to X-ray fluorescence visualize, image, of provide information somewhat differently with potentially different output (such as with or without the use of additives, contrast agents, etc.) that may be based at least partially on the density, elements, chemicals, compounds, and/or biological materials included in or contained within the matter.

Figure 18:
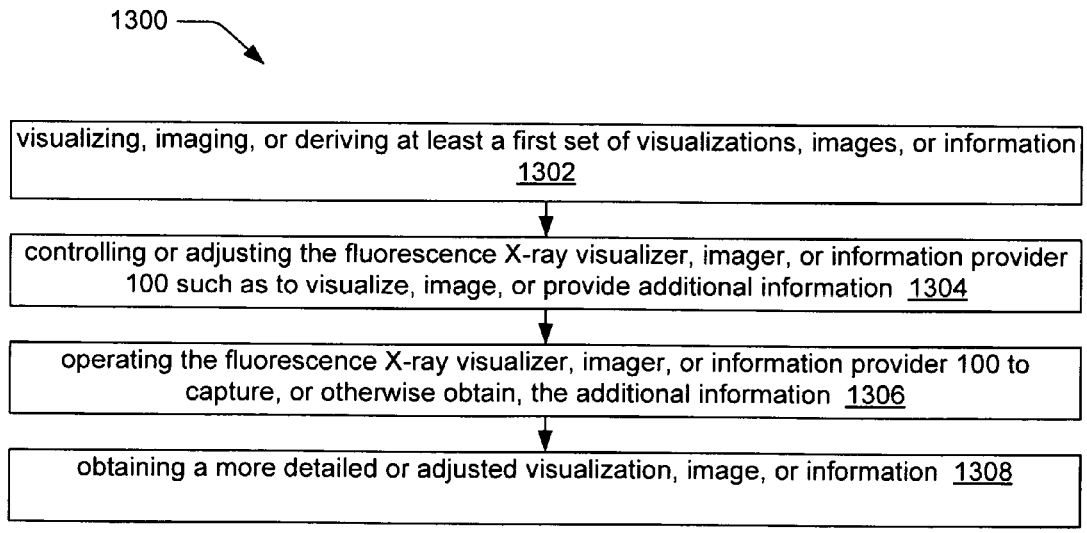
FIG. 18 shows a flow chart of one embodiment of X-ray fluorescence visualization, imaging, or information providing, such as may occur using certain embodiments of the X-ray fluorescence visualizer, imager, or information provider as described with respect to FIGS. 17a and 17b.

FIG. 18 show a flowchart 1300 of one embodiment of the X-ray fluorescence visualizer, imager, or information provider 100 that can be configured to provide X-ray fluorescence visualization, image, or information in a manner that includes illustrative, but not limiting, processes 1302, 1304, 1306, and/or 1308. Process 1302 can include, but is not limited to, X-ray fluorescence visualizing, imaging, or information providing, and thereby deriving at least a first set of X-ray fluorescence visualizations, images, or information. For example, certain X-ray fluorescence visualization, image, or provided information (e.g., relatively crude or more refined in various embodiments) can be obtained using certain embodiments of the X-ray fluorescence visualizer, imager, or information provider 100 as described in this disclosure. Process 1304 can include, but is not limited to, controlling or adjusting the X-ray fluorescence visualizer, imager, or information provider 100 such as to X-ray fluorescence visualize, image, or obtain "varied" or "additional" information. Certain of the at least one high energy photon and/or particle emitter portion(s) 150 can be controlled or adjusted to vary the angle or other aspect by which the at least one applied high energy photon and/or particle 120 is applied to and/or received from the at least the portion of the individual being visualized, imaged, or information provided. Process 1306 can include, but is not limited to, operating the X-ray fluorescence visualizer, imager, or information provider 100 to capture, or otherwise obtain, the new information, such as to allow imaging from a modified angle or vantage point. Process 1308 can include, but is not limited to, obtaining a more detailed or final X-ray fluorescence visualization, image, or information such as by geometrically, tomographically or volumetrically integrating the additional information. As such, viewing certain regions from different perspectives, such as to limit unknowns and uncertainties in the X-ray fluorescence visualization, imaging, or provided information as the tomographic-type embodiments of the X-ray fluorescence visualizer, imager, or information provider 100 change some aspect (e.g., energy level, direction, X-ray fluorescence range, prescribed substantial X-ray fluorescence depth, etc) in a manner as to improve the quality of the X-ray fluorescence visualizing, imaging, or information providing.

Certain scintillation, time of flight, energy loss, and image combination type embodiments of the X-ray fluorescence visualizer, imager, or information provider 100 can generally provide their quality X-ray fluorescence visualization, image, or provided information based on processing of each interaction of the at least one high energy photon and/or particle emitter portion(s) 150 and its associated at least one X-ray fluorescence receiving portion(s) 151. By comparison, certain tomographic or volumetric embodiments of the X-ray fluorescence visualizer, imager, or information provider 100 can have a considerable number of unknowns following each interaction of the at least one high energy photon and/or particle emitter portion(s) 150 and its associated at least one X-ray fluorescence receiving portion(s) 151, wherein such unknowns are generally reduced or limited using tomographic or volumetric techniques, in a similar manner as with conventional tomography, as generally understood in the medical imaging technologies. Such scintillators can produce at least one induced X-ray fluorescing photon 122 that can allow certain embodiments of the X-ray fluorescence visualization, image, or provided information to be viewed directly by a user (such as a doctor, veterinarian, medical assistant, the individual, etc.), or alternately the at least one induced X-ray fluorescing photon 122 may undergo processing, filtering, etc. that can enhance or transform the at least one induced X-ray fluorescing photon 122 to make the X-ray fluorescence visualization, image, or provided information visible or enhanced to the user.

Certain tomography or volumetric aspects of certain embodiments (or output) of the X-ray fluorescence visualizer, imager, or information provider 100 can therefore be quite similar in processing characteristics to those of conventional tomography imagers, such as conventional CAT scans, conventional PET scans, etc. (such that they can result from generating a number of two-dimensional X-ray fluorescence visualizing, imaging, or information providing slices). The X-ray fluorescence visualizing, imaging, or information providing slices are often, but not necessarily, planar. The X-ray fluorescence visualizing, imaging, or information providing slices can thereupon be combined to allow information of any three-dimensional volumetric and/or tomographic image in a similar manner as with conventional CAT scans, MRIs, etc. Depending upon the desired configuration, a variety of shapes, X-ray fluorescence, or other configurations of X-ray fluorescence visualizing, imaging, or information providing slices can be generated. Within this disclosure, volumetric imaging may, depending upon context, be considered as including tomography. A description of conventional tomography or volumetric imaging devices, etc., such as may be utilized for conventional medical X-ray imaging or information providing, are described, for example, in "The Essential Physics of Medical Imaging, Second Edition", J. T. Bushburg, et al., Lippincott Williams and Wilkins, 2002 (incorporated by reference herein in its entirety). Such conventional tomography devices are commercially available and is, as such, not described in greater detail.

Certain embodiments of the X-ray fluorescence visualizer, imager, or information provider 100 may rely upon the adjustment and/or control to affect imaging of new matter of new directions, locations, positions, energy levels, etc. that may be based at least partially on the density, elements, chemicals, compounds, and/or biological materials included in or contained within the matter. Such adjustment or control may be useful for tomography-type X-ray fluorescence visualization, imaging, or information providing that may be based at least partially on the density, elements, chemicals, compounds, and/or biological materials included in or contained within the matter. Certain embodiments of the deconvolution and/or tomography processes necessary to perform such operations may be, in certain aspects, computationally similar to those used in normal X-ray CT scans. However, with the X-ray fluorescence visualizer, imager, or information provider 100, X-ray fluorescence X-rays instead of transmitted X-rays, etc. may be detected (instead of the X-rays being transmitted through the individual as is the case with conventional CT scans as compared with X-rays undergoing X-ray fluorescence as described in this disclosure).

Certain embodiments of the X-ray fluorescence visualizer, imager, or information provider 100 can X-ray fluorescence visualize, image, and/or provide information at least partially by use of an angle-collimated X-ray detector such that the intersection of the illuminating radiation and detector sensitivity direction can define an operational 3-D voxel as described with respect to FIGS. 7 to 12, and other locations. Such angle-collimated X-ray detectors can be used to derive X-ray fluorescence visualization, imaging, or information providing information in the at least one X-ray fluorescence receiving portion(s) 151. Certain embodiments of the X-ray fluorescence visualizer, imager, or information provider 100 can X-ray fluorescence visualize, image, and/or provide information at least partially by combinations of the embodiments described elsewhere in this disclosure, that allows X-ray fluorescence visualization, imaging, or information providing at higher resolution and/or higher contrast information from the subcutaneous bodily structures.

Figure 19:
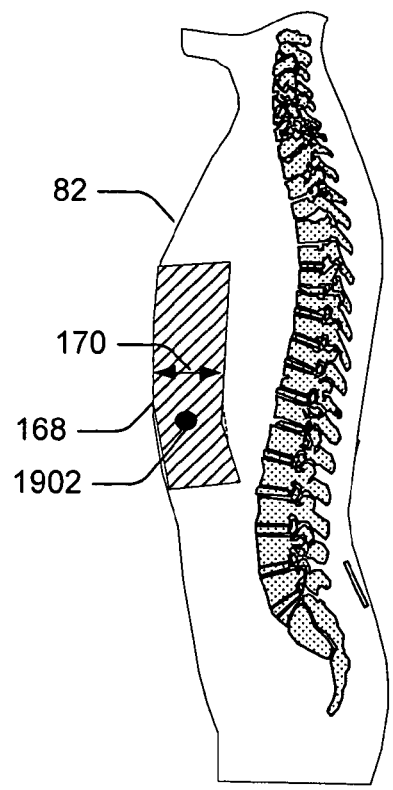
FIG. 19 is a diagram of an embodiment of the X-ray fluorescence visualizer, imager, or information provider configured to X-ray fluorescence visualize, image, and/or provide information from at least a surface of an individual.

Certain embodiments of the X-ray fluorescence visualizer, imager, or information provider 100 can control the prescribed substantial X-ray fluorescence depth to which it can image based, at least in part, on photons energy level of the at least one applied high energy photon and/or particle 120 as applied to the matter of the at least the portion of the individual. The greater the energy level of the photons of the at least one applied high energy photon and/or particle 120 (and correspondingly the lesser the frequency of the photons of the at least one applied high energy photon and/or particle 120), generally the greater depth a larger percentage of the at least one applied high energy photon and/or particle 120 can travel into the matter of the at least the portion of the individual, undergo X-ray fluorescence, and return to effect X-ray fluorescence visualization, imaging, or information providing. As such, generally, a larger number of, or percentage of, X-ray photons having greater energy levels (and therefore correspondingly lower frequencies) can generally X-ray fluorescence visualize, image, and/or information provide down to a greater at least one X-ray fluorescence range to the at least one prescribed substantial X-ray fluorescence depth than X-ray photons having a generally lower energy level (and correspondingly higher frequencies). This generalization assumes consistency of such factors as angle or position of the at least one applied high energy photon and/or particle 120, materials being imaged, etc. Certain embodiments of the X-ray fluorescence visualizer, imager, or information provider 100, as described in this disclosure with respect to FIG. 19, can facilitate X-ray fluorescence visualization, imaging, or information providing of a region of the fluorescing events extending from at least a surface 168. A matter aberration 360 can be X-ray fluorescence visualized, imaged, or information provided such as can be provided or enhanced based at least partially on the elemental composition (or chemical composition, compound composition, or the biological material composition with the use of X-ray fluorescence enhancing additives, taggants, or contrast agents, etc.).

These embodiments of the X-ray fluorescence visualizer, imager, or information provider 100 might be particularly useful for X-ray fluorescence visualization, imaging, or information providing for the at least the portion of the individual near the surface 168 of the individual (the surface may be underneath and at least partially internal surface or at least partially external surface). For example, certain embodiments of the X-ray fluorescence visualizer, imager, or information provider 100, that can image from a surface to within the at least one X-ray fluorescence range to the at least one prescribed substantial X-ray fluorescence depth, may be suitable for such X-ray fluorescence visualization, imaging, or information providing even without complex image processing that may be based at least partially on the density, elements, chemicals, compounds, and/or biological materials included in or contained within the matter. Such prescribed substantial X-ray fluorescence depths may not interfere with each other provided a relatively homogeneous material across the X-ray fluorescence range. By comparison, certain embodiments of the X-ray fluorescence visualizer, imager, or information provider 100 can X-ray fluorescence visualize, image, or information provide one and relatively non-homogeneous material across the at least one X-ray fluorescence range provided suitable processing capability.

Certain embodiments of the X-ray fluorescence visualizer, imager, or information provider 100 can X-ray fluorescence visualize, image, or provide information relating to at least partially internal and/or at least partially external matter of the at least the portion of the individual utilizing a variety of X-ray fluorescence visualization, imaging, or information providing techniques. Such X-ray fluorescence visualization, imaging, or information providing can be configured to provide for, for example: examinations, testing of cancer, sicknesses, injuries, tissue aberrations, abscesses, infections, etc. (such cancers and/or tumors can include, but are not limited to, breast cancer, lung cancer, prostate cancer, bladder cancer, cervical cancer, etc.); as well as both internal or external X-ray fluorescence visualizing, imaging, or information providing aberrations of certain matter of the at least the portion of the individual (such as tissue, bone, dental, etc. or a combination); X-ray fluorescence visualization, imaging, or information providing lumen matter and matter examinations; X-ray fluorescence visualization, imaging, or information providing edges, discontinuities, or matter inconsistencies or aberrations of organs, tissue, or other matter; X-ray fluorescence visualization, imaging, or information allowing a variety of heart examination and/or treatments, heart valve structure, operation examination and/or treatments, brain examination and/or treatment, lung examination, liver examination, other organ, matter, or tissue examination and/or treatments etc. Within this disclosure, the term "depth" X-ray fluorescence visualizing, imaging, or information providing can include, but is not limited to, X-ray fluorescence depth visualizing, imaging, or information providing through at least one volume of matter situated beneath the surface 168 of the at least the portion of the individual, perhaps including imaging through the surface 168 of the at least the portion of the individual.

Certain embodiments of the X-ray fluorescence visualizer, imager, or information provider 100 can be configured to detect specific elements, or sets, combinations, alloys, and/or mixtures of specific elements that may be based at least partially on the elements, chemicals, compounds, and/or biological materials included in or contained within the matter. Such detection may, e.g., be used to obtain signatures of pathological state or tissue identity. Such techniques may be used for screening persons for specific illnesses, infections, conditions, injuries, exposures, etc. While iron, titanium, magnesium, calcium, and other elements are mentioned in this disclosure as examples of elements that may be included in matter which can be used to enhance X-ray fluorescence visualizations, imaging, and/or information providing; it may also be desirable or useful to detect other elements or sets of elements. Depending on context, X-ray fluorescence signatures of tissue (which may be considered to be one embodiment of X-ray fluorescence visualization, imaging, or information providing information), may be very helpful for a variety of diagnosis or examination purposes, for example.

Zinc is another example of an element, which could be detected by certain embodiments of the X-ray fluorescence visualizer, imager, or information provider 100. Zinc can be used as a naturally-occurring indicator of certain types of pathological brain tissue. For example, the elevated presence of zinc in the brain can be used to identify epileptic areas in the hippocampus (in the medial temporal lobe of the brain). As such, certain embodiments of the X-ray fluorescence visualizer, imager, or information provider 100 can be configured to detect particular elements, matter, combinations of matter, materials, metal, alloys, fluids, bones, etc., and as such may be particularly useful for X-ray fluorescence visualization, imaging, or information providing for certain applications. Certain embodiments of the X-ray fluorescence visualizer, imager, or information provider 100 can be controllable and/or adjustable such as to allow setting or adjusting for particular X-ray fluorescence visualization, imaging, or information providing applications.

Certain embodiments of such X-ray fluorescence visualization, imaging, or information providing from the surface 168 may be performed from within the at least one X-ray fluorescence range to the at least one prescribed substantial X-ray fluorescence depth that may be based at least partially on the density, elements, chemicals, compounds, and/or biological materials included in or contained within the matter. Certain of the X-ray fluorescences returning to the at least one X-ray fluorescence receiving portion(s) 151, that X-ray fluorescence at fluorescing events from matter from different ones of the at least one X-ray fluorescence range to the at least one prescribed substantial X-ray fluorescence depth, may overlap and potentially interfere with X-ray fluorescence high energy (e.g., X-ray, gamma ray, photon, particle, etc.) that have a contributed X-rays from different fluorescing events. Such clarification between interfering X-ray fluorescence high energy (e.g., X-ray, gamma ray, photon, particle, etc.) resulting from different fluorescing events at different prescribed substantial X-ray fluorescence depths, and/or positions, etc., can limit confusion among image information obtained from different fluorescing events at varying prescribed substantial X-ray fluorescence depths.

Assuming a relatively narrow X-ray fluorescence range to the at least one prescribed substantial X-ray fluorescence depth based at least partially on X-ray fluorescence from fluorescing events. The overlap of X-ray fluorescence from different depths can be considered as originating from a single one of the at least one X-ray fluorescence range to the at least one X-ray fluorescence visualizing, imaging, or information providing depth, assuming the material is substantially homogenous across the X-ray fluorescence range of the prescribed substantial X-ray fluorescence depths. The overlapped X-rays can thereupon be processed or treated as originating from the same location. For example, X-ray fluorescence visualization, imaging, or information providing of the skin, and/or some other relatively homogeneous matter, of a person may appear consistent, even if the X-ray fluorescences X-ray fluorescence from within the at least one X-ray fluorescence range to the at least one prescribed substantial X-ray fluorescence depth.

Certain embodiments of the X-ray fluorescence visualizer, imager, or information provider 100 can be configured to X-ray fluorescence visualize, image, or provide information based at least partially on X-ray fluorescence high energy (e.g., X-ray, gamma ray, photon, particle, etc.) X-ray fluorescence the slightly overlapped prescribed substantial X-ray fluorescence depths of fluorescing events, and can thereby reduce quality or uniformity of imaging or X-ray fluorescence visualization. For example, consider the X-ray fluorescence could be expected to be X-ray fluorescence, down to similar prescribed substantial X-ray fluorescence depths, within similar type matter within the person, assuming substantially homogeneous or consistent matter down through the prescribed substantial X-ray fluorescence depth. Certain types of X-ray fluorescence visualization, imaging, or information providing can be performed as scanning, such as to screen for, or detect, aberrations of the matter (e.g., skin) such as cancers, lesions, abscesses, infections, tumors, moles, cuts, abrasions, etc. Certain embodiments of the X-ray fluorescence receiving assembly, which can be used to X-ray fluorescence visualize, image, or provide information relating to a considerable variety of matter, such as regents made up of relatively thin matter that are selected to increase the homogeneity of the region. By selecting or using the relatively thin image region, the matter's homogeneity thereby generally increases in a manner that can provide improved X-ray fluorescence visualization, imaging, or information providing.

By using relatively thin image regions, which are therefore likely to be more homogeneous than thicker regions; certain embodiments of the X-ray fluorescence visualizer, imager, or information provider 100 may utilize such devices as scintillators (and/or fluoroscopes, certain of which can also include scintillators) which can directly convert X-ray fluorescence high energy (e.g., X-ray, gamma ray, photon, particle, etc.) into viewable and/or visible light, as described in this disclosure. Within this disclosure, "viewable" light can, depending on context, be intended to include, but is not limited to, visible light such as is recognized as being viewable by most sighted humans, as well as at least certain infra-red and ultra-violet light. Certain embodiments of the X-ray fluorescence visualizer, imager, or information provider 100 can utilize certain of the at least one X-ray fluorescence receiving portion(s) 151 including scintillators, examination with further processing capabilities which can image process, or otherwise process, the output of the scintillator prior to being displayed to the user. As such, the output of the scintillator may be included as input to, for example, a processor performing image processing or other such technique. The output can thereupon be applied to the user as visualizing, imaging, or providing information. Additionally, certain embodiments of the X-ray fluorescence visualizer, imager, or information provider 100 can operate including a such later or similar device that as input to a processor such as an image processor, the output may not be displayed to the user, but instead can be stored such as data in a database, applied to some detection system or sensing system, or alternatively utilized in some non-display are non-visualizing fashion.

Within this disclosure, such conversion of X-ray photons by scintillators into viewable and/or visible light that may be viewed (directly or by subsequent processing) by certain users directly. By comparison, certain embodiments of the at least one X-ray fluorescence receiving portion(s) 151 may include a photodiode or other photodetector operably associated with the output of the scintillator (not shown, and considered as a portion of the scintillator) which can output to certain portions of the X-ray fluorescence receiving assembly. As such, certain scintillator-based embodiments of the X-ray fluorescence visualizer, imager, or information provider 100 can provide viewable and/or visible light directly to a user, or alternately output viewable and/or visible light that can be further analyzed, amplified, filtered, or otherwise processed such that could be viewed by the user following the multiple steps such as by a machine, machine-based processor, optical processing device, etc. Certain scintillators, for example, could be operably coupled to photodiodes, whose outputs can thereupon be further analyzed.

Certain scintillator embodiments of the X-ray fluorescence visualizer, imager, or information provider 100 being applied to certain relatively thin organisms, plants, etc. may also X-ray fluorescence visualize, image, or provide information about the thickness of at least some matter of the at least certain portions of the individual using such techniques. Certain such scintillator (and/or fluoroscope) embodiments of the X-ray fluorescence visualizer, imager, or information provider 100 may be operationally simpler, and therefore involve relatively little processing as compared with other X-ray fluorescence visualization, imaging, or information providing techniques by other (more processor-complex) embodiments of the X-ray fluorescence visualizer, imager, or information provider 100. The scintillator embodiments of the X-ray fluorescence visualizer, imager, or information provider 100 can create images based, at least in part, on the at least one induced X-ray fluorescing photon 122 received by the at least one X-ray fluorescence receiving portion(s) 151; since the X-ray fluorescences being produced by the former are being converted directly into viewable or visible light using scintillators (and/or fluoroscope-based technology).

Figure 20:
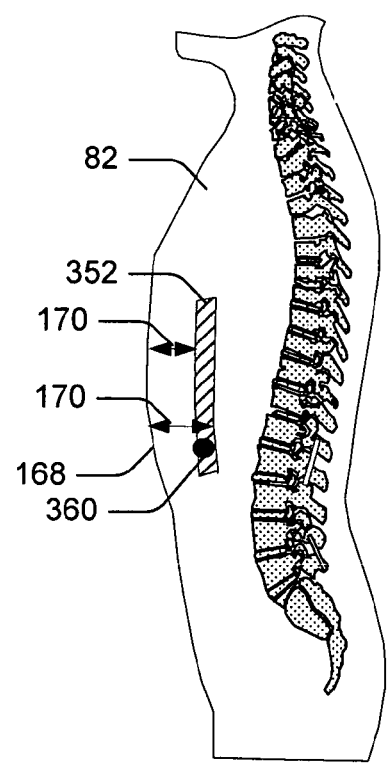
FIG. 20 is a diagram of an embodiment of the X-ray fluorescence visualizer, imager, or information provider configured to X-ray fluorescence visualize, image, and/or provide information within a volume from a first prescribed substantial X-ray fluorescence depth to a second prescribed substantial X-ray fluorescence depth.
Figure 21:
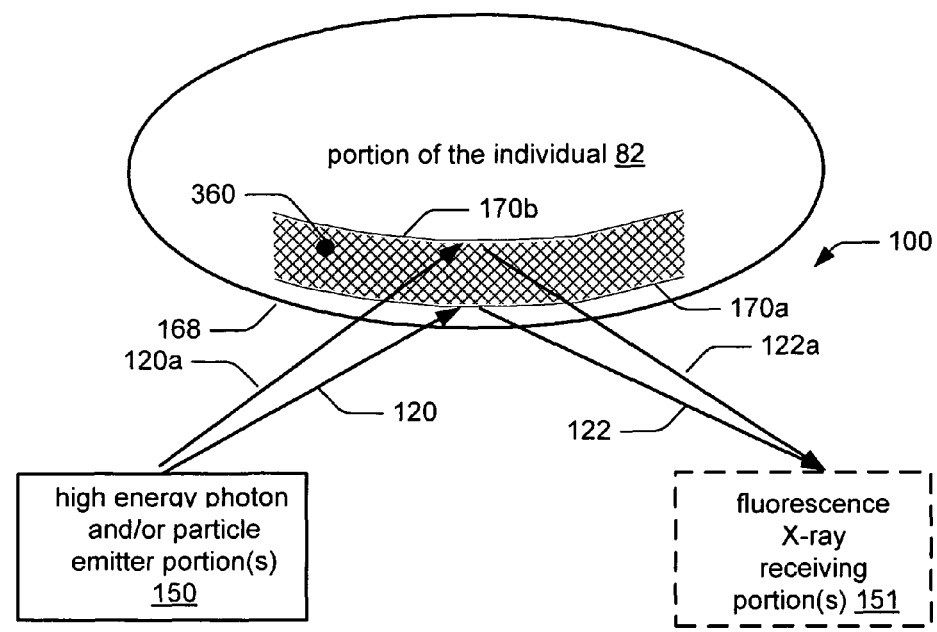
FIG. 21 shows another embodiment of the X-ray fluorescence visualizer, imager, or information provider.
Figure 22:
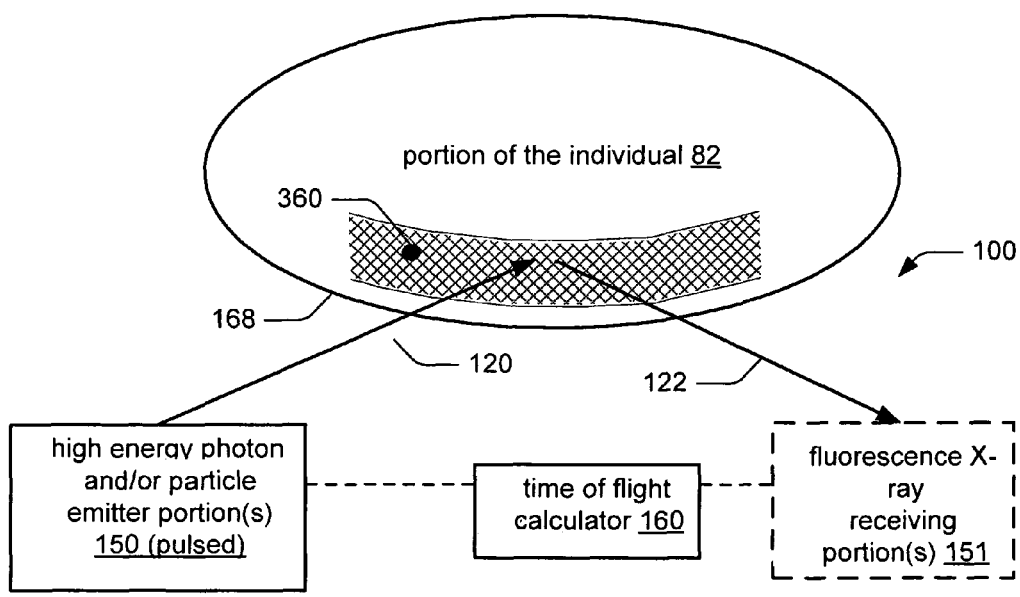
FIG. 22 shows yet another embodiment of the X-ray fluorescence visualizer, imager, or information provider.

Certain embodiments of the X-ray fluorescence visualizer, imager, or information provider 100, as described in this disclosure with respect to FIG. 20, 21, or 22, can facilitate X-ray fluorescence visualization, imaging, or information providing between a first one of the at least one X-ray fluorescence range to the first one of the at least one prescribed substantial X-ray fluorescence depth from the surface 168. Such X-ray fluorescence visualizing, imaging, or providing information can occur either from an internal or external surface of the portion of the individual (or the first one of the at least one X-ray fluorescence range to the first one of the at least one prescribed substantial X-ray fluorescence depth from the surface 168) to a second one of the at least one X-ray fluorescence range to a second one of the at least one prescribed substantial X-ray fluorescence depth from the surface. The matter aberration 360 can be X-ray fluorescence visualized, imaged, or information provided such as can be provided or enhanced based at least partially on the elemental composition (or chemical composition, compound composition, or biological material composition with the use of X-ray fluorescence enhancing additives, taggants, or contrast agents, etc.).

Certain of such X-ray fluorescence visualization, imaging, or information providing techniques can be obtained at least partially by combination (e.g., image differentiation, image subtraction, image transformation, deconvolution, weighted subtraction, functional subtraction, and group including inverse integral transform, subtractive inverse integral transform, inverse functional transform, and subtractive inverse functional transform, time of flight calculation, or other such computation or image processing techniques). With such combination of images, etc., multiple X-ray fluorescence depth visualizations or images can be obtained, in the form of X-ray fluorescence depth visualization or image information, from X-ray fluorescence visualization, imaging, or information providing from the surface 168 down to multiple different prescribed substantial X-ray fluorescence depths 169, 170, thereby imaging through a depth 172.

Certain occurrences of the X-ray fluorescence depth visualizations, images, and/or provided information can thereupon be obtained from the shallower X-ray fluorescence depth visualizations, images, and/or provided information value using image combining (such as by using image subtraction, image differentiation, image transformation, deconvolution, weighted subtraction, functional subtraction, and group including inverse integral transform, subtractive inverse integral transform, inverse functional transform, and subtractive inverse functional transform, or other such image processing or computational techniques), from between multiple X-ray fluorescence depth visualizations, images, and/or provided information values. To depth-image a relatively thick portion of the individual (e.g., a X-ray fluorescence visualizing, imaging, or information providing slice that is thicker than can be depth imaged by itself with desired resolution, image quality, etc.), a number of relatively thin image X-ray fluorescence visualizing, imaging, or information providing slices can be imaged, and the number of images can thereupon be added, summed, or otherwise combined using a variety of appropriate image processing techniques.

As described in this disclosure, the X-ray fluorescence visualization, imaging, or information providing of X-ray fluorescence visualizing, imaging, or information providing slices can be performed by successive image combination, by which the information, data, value, etc. of the shallower image can be combined, subtracted, or otherwise transformed out from that of the thicker image for each successive X-ray fluorescence visualizing, imaging, or information providing slice, to obtain image information of the particular X-ray fluorescence visualizing, imaging, or information providing slice.

Such techniques can also be utilized by certain image combining processes (e.g., image subtraction, image differentiation, image transformation, deconvolution, weighted subtraction, functional subtraction, and group including inverse integral transform, subtractive inverse integral transform, inverse functional transform, and subtractive inverse functional transform, time of flight techniques; scintillator or fluoroscope techniques, or other X-ray fluorescence-based techniques). Certain image combining techniques may be particularly useful when attempting to visualize, image, or provide information relating to a particular region such as with imaging slices were visualizing slices that may be separate from the at least one high energy photon and/or particle emitter portion(s) 150 and/or the at least one X-ray fluorescence receiving portion(s) 151, such as by using image subtraction, etc. The X-ray fluorescence visualizing, imaging, or information providing slices can at least partially involve combining relatively thick portions of the individual, and can thereupon be digitally, analog, or otherwise combined using combining image processing techniques, and can be clarified such as to limit distorting aspects such as opaque X-ray matter, noise, etc, such as involving deconvolution, transforms, etc. Certain of the X-ray fluorescence visualizations, images, and/or information can be maintained to form a model, which can be relied on for X-ray fluorescence visualization, imaging, or information providing purposes. Alternately, a two-dimensional X-ray fluorescence visualizing, imaging, or information providing slice having some thickness and either a substantially planar or curvilinear surface (simple curve, complex curve, or other) can be X-ray fluorescence visualized, imaged, or have information provided within the at least the portion of the individual at a location nearby, or away from, the surface of the at least the portion of the individual. For example, certain examples of X-ray fluorescence visualization, imaging, or providing information can occur with the at least one emitter being positioned adjacent the skin, as can be applied internally such as can be applied within lumens, etc.

Alternately, time of the flight computations can be used to derive X-ray fluorescence visualization, imaging, or information providing information, as described in this disclosure. Certain embodiments of the X-ray fluorescence visualizer, imager, or information provider 100 can X-ray fluorescence visualize or image a volume or portion extending between two of the at least one X-ray fluorescence ranges from the surface 168 can utilize time of flight computations (such as described with respect to FIG. 22). Certain time of flight computations can operate at least partially by determining a total distance from the at least one high energy photon and/or particle emitter portion(s) 150, to the particular fluorescing event of the at least the portion of the individual, and thereupon continue to the at least one X-ray fluorescence receiving portion(s) 151. Such distance can be determined, for example, by measuring the duration for X-rays to travel that distance. The distance can thereby be determined at least partially based on the combined temporal duration (time) of the travel by the at least one applied high energy photon and/or particle 120 and/or the at least one induced X-ray fluorescing photon 122. Certain embodiments of the X-ray fluorescence visualizer, imager, or information provider 100 of FIG. 22 can include a time of flight calculator 160 (which can be included in the X-ray fluorescence visualization, imaging, or information providing controller 97 of FIG. 1 or 2), which can derive the time of flight duration(s), and thereupon compute the total time of flight distance(s).

Certain embodiments of time of flight computation such as can utilize the time of flight calculator 160, as described with respect to FIG. 22, can involve generation of relatively brief pulses of the at least one applied high energy photon and/or particle 120 (e.g., X-ray photon radiation), which are directed by the at least one high energy photon and/or particle emitter portion(s) 150 towards the imaged region of the at least the portion of the individual. Thereupon, the X-rays forming the pulses or bursts of the at least one applied high energy photon and/or particle 120 can be X-ray fluorescence within the matter of the at least the portion of the individual at the fluorescing event, such as can be detected by the at least one X-ray fluorescence receiving portion(s) 151 following X-ray fluorescence of the brief pulse (also considered a form of time modulation). Time of flight calculations can be derived based, at least partially, on the time required for the at least one applied high energy photon and/or particle 120 to travel to and X-ray fluorescence at the fluorescing event (within the matter of the at least the portion of the individual), and thereupon have the X-ray fluorescence high energy (e.g., X-ray, gamma ray, photon, particle, etc.) travel to the at least one X-ray fluorescence receiving portion(s) 151. Considering the total distance between the point of X-ray fluorescence at the fluorescing event and the X-ray fluorescence receiving assembly, and thereupon the angle of X-ray fluorescence and fluorescing event through which the X-rays travel through the at least the portion of the individual. The location of the fluorescing event within the matter of the at least a portion of the individual can thereupon be determined relying on calculations based on the speed of X-rays, their direction traveled (as determined by limiting the passage of the X-ray fluorescence photons to only those traveling within a prescribed range of degrees at within a prescribed region), and thereupon their distance traveled. The speed of X-rays and gamma rays, for example, correspond to the speed to light.

The combined distance from the at least one high energy photon and/or particle emitter portion(s) 150, to the location of the fluorescing event, and thereupon to the at least one X-ray fluorescence receiving portion(s) 151, can thereby be used to derive the at least one X-ray fluorescence range to the at least one prescribed substantial X-ray fluorescence depth at least partially using time of flight calculations. With time of flight calculations, precision in the detected timing and measured distance is important in accurately determining the location of X-ray fluorescence within the matter. Therefore, certain embodiments of the detector portions of the X-ray fluorescence receiving assembly and/or high energy photon and/or particle emitter portions, as described with respect to FIG. 22, could have at least low picosecond range detection operational duration to provide suitable accuracy. Such picosecond range detection operational duration to provide suitable accuracy can be performed using, for example, certain streak cameras, pixelated streak cameras, an avalanche detector, CCD, or other detector embodiments of the at least one X-ray fluorescence receiving portion(s) 151. Other embodiments of the detector portions could operate with considerably longer signal detection duration rate while perhaps accepting reduced quality or resolution in X-ray fluorescence visualization, imaging, or information providing.

Certain embodiments of the X-ray fluorescence visualizer, imager, or information provider 100 can utilize a variety of controllers, computers, etc. (considered as a portion of the X-ray fluorescence visualization, imaging, or information providing controller 97) as certain users such as to provide a variety of automation and/or enhanced reliably of operation or analysis. As such, with certain embodiments of the X-ray fluorescence visualizer, imager, or information provider 100, a variety of human or automated users can X-ray fluorescence visualize, image, and/or provide information relating to the subsurface of the at least the portion of the individual 82 at certain typically controllable prescribed substantial X-ray fluorescence depths. The mechanism for X-ray fluorescence are generally understood by those skilled with X-ray technology, and will not be described in greater detail except where suited to this particular disclosure.

With individuals such as humans and/or animals, for example, the external surface 168 can include such surfaces as skin, mucous membranes, and other such external surfaces etc. Certain individuals such as plants or organisms (living in the environment such as outside, living in humans, animals, plants, or other organisms, and/or human-designed or human created) can have at least one external surface 168 that may come in contact with the external environment from which much of the potential X-ray fluorescence visualization, imaging, or information providing could be performed. Examples of the external surface may include the outer layer of a leaf, a trunk, a stalk, a fruit, a root portion, a vegetables, etc. It may not be necessary, in those embodiments of the X-ray fluorescence visualizer, imager, or information provider 100, that are applied within the matter of the individual (such as via incision, or other breach of the surface), to X-ray fluorescence visualize, image, and/or provide information at least partially through the surface.

Certain individuals, such as organisms, plants, or portions thereof, can be X-ray fluorescence visualized, imaged, or have information provided using certain embodiments of the X-ray fluorescence visualizer, imager, or information provider 100 for such purposes as to determine health, internal structure, insect infestation, contamination, illness, etc. Certain types of individuals such as fruits, roots, or vegetables as produced by plants can be X-ray fluorescence visualized, imaged, or have information provided using certain embodiments of the X-ray fluorescence visualizer, imager, or information provider 100 as to determine freshness of the item, suitability of the item, insect infestation, disease, contamination, inconsistency from desired state, etc. A store or market (which may commercially sell certain meats, vegetables, fruits, plants, etc., for example) may utilize certain embodiments of the X-ray fluorescence visualizer, imager, or information provider 100 such as to X-ray fluorescence visualize, image, and/or provide information relating to at least a portion of the individual to determine their health, condition, etc. Such determination of the condition can be applied either prior to purchase, following storage for some duration, or prior to selling, etc. In this manner, certain embodiments of the X-ray fluorescence visualizer, imager, or information provider 100 can be configured to visualize, image, or provide information relating to animals that are living, deceased, autopsied, or being prepared or maintained for food or consumption, etc. Such X-ray fluorescence visualization, imaging, or information providing of animals, plants, organisms, roots, etc. can be based, at least in part, and changing X-ray fluorescence characteristics as or to guard against the matter rotting, disintegrating, melting, distorting, aging, or otherwise changing.

With such individuals as humans and/or animals, the term "internal" can pertain to those locations accessible through normally open openings (e.g., mouth, ears, nose, various lumens, blood vessels, urethra, anal, etc.) and/or normally closed openings, such as may be accessed via an incision as described in this disclosure. The interior of such individuals as organisms, cells, bacteria, viruses, etc. can be accessed through normally closed openings such as incisions, pipettes, probes, tools, tactile feedback devices, cutters, displays, etc. As such, the term "surface", whether situated at least partially internally and/or at least partially externally relative to the at least portion of the individual, should relate to, and/or be considered relative to, and based on, the particular aspects, conditions, and/or particulars of the at least the portion of the individual. As such, there can be a large variety of access locations for certain embodiments of the X-ray fluorescence visualizer, imager, or information provider 100.

Certain embodiments of the X-ray fluorescence visualizer, imager, or information provider 100 can provide position determination, control, and/or adjustment of certain of the at least one high energy photon and/or particle emitter portion(s) 150 and/or the at least one detector portions 152 (and/or the at least one X-ray fluorescence receiving portion(s) 151). Such adjustment and/or control of the portions or entirety of the X-ray fluorescence visualizer, imager, or information provider 100 can be used to control and/or adjust the amount and/or depth of matter through which the X-ray fluorescence visualizer, imager, or information provider 100 can X-ray fluorescence visualize, image, and/or provide information, such as when X-ray fluorescence visualization, imaging, or information providing (to within the at least one X-ray fluorescence range to the at least one prescribed substantial X-ray fluorescence depth). Certain aspects of such control and/or adjustment is typically characterized by the energy level and/or frequency of the X-ray photons.

For example, consider where a particular X-ray fluorescence visualizer, imager, or information provider 100 may be configured (e.g., based on X-ray photon energy and/or frequency) to X-ray fluorescence visualize, image, and/or provide information at the at least one controllable and/or adjustable prescribed substantial X-ray fluorescence depth. If the at least one high energy photon and/or particle emitter portion(s) 150 can be arranged to direct the at least one applied high energy photon and/or particle 120 substantially perpendicular to the surface 168 of the at least the portion of the individual, the X-ray fluorescence visualization, imaging, or information providing could occur within the at least one prescribed substantial X-ray fluorescence depth of, for example, 5 mm. However, as the angle of the at least one applied high energy photon and/or particle 120 by the high energy photon and/or particle emitter portion(s) to the surface 168 of the matter changes from perpendicular to some slant from a surface of the at least the portion of the individual, such as illustrated in FIG. 21 or 22, the at least one prescribed substantial X-ray fluorescence depth also changes. The at least one prescribed substantial X-ray fluorescence depth corresponds to the maximum depth which the X-rays can pass to, X-ray fluorescence at, and return from during the X-ray fluorescence visualization, imaging, or information providing. Therefore, as the angle of the X-rays applied by the high energy photon and/or particle emitter portion(s) to the surface 168 of the at least some matter of the at least the portion of the individual changes (e.g., from perpendicular to some angle), the effective perpendicular X-ray fluorescence depth visualizing, imaging, or information providing could change, which typically changes as a cosine function of the change of angle.

With many types of individuals, most surfaces 168 are not completely planar, and many may hardly be planar at all. Consider that most surfaces of people, animals, organisms, and plants are not typically flat, but instead we have some degree of curvature over our surfaces. For the purpose of this disclosure, such X-ray fluorescence visualization, imaging, or information providing concepts can be explained and more easily modeled assuming a planar initial contact surface, which may become closer to true as the depth imaged or X-ray fluorescence visualized region becomes incrementally smaller.

Within this disclosure, "X-ray fluorescence visualization, imaging, or information providing", as may therefore be performed within some set distance from the surface 168 at which X-ray based electromagnetic radiation from the X-ray fluorescence visualizer, imager, or information provider 100 is being emitted and X-ray fluorescence, and can thereupon be detected. Certain aspects of such X-ray fluorescence visualization, imaging, or information providing may rely on the configuration and/or operation respective high energy photon and/or particle emitter portions and/or detector portions that can respectively apply X-rays proximate to, and/or receive X-rays from, the surface 168 of the at least the portion of the individual.

The matter of the at least the portion of the individual which can be X-ray fluorescence visualized, imaged, or have information provided using a variety of embodiments and/or configurations of the X-ray fluorescence visualizer, imager, or information provider 100, can vary. For instance, for X-ray fluorescence visualization, imaging, or information providing humans or animals, the soft matter that can be X-ray fluorescence visualized, imaged, or have information provided can include but is not limited to: soft tissue, fluid (blood, spinal, lymph, etc.) bone portions interspersed among tissue, tissue forming organs, muscles, fat, flesh, etc. Additionally, relatively hard matter such as: bones, bone portions, joints, spine portions, teeth, etc. can be X-ray fluorescence visualized, imaged, or have information provided using certain configurations or embodiments of the X-ray fluorescence visualizer, imager, or information provider 100. As such, the interior bones, teeth, etc. can be depth imaged to provide a considerable amount of internal X-ray fluorescence visualization, imaging, or information providing. As such, the particulars of the at least some matter can have some effect on the X-ray fluorescence visualizing, imaging, or information providing. As such, a variety of embodiments of the X-ray fluorescence visualizer, imager, or information provider 100 can be applied to a variety of visualizing, imaging, or information providing applications.

Certain embodiments of the X-ray fluorescence visualizer, imager, or information provider can additionally X-ray fluorescence visualize, image, and/or provide information relating to such matter can be associated with, or positioned in or nearby the at least the portion of the individual as plastic, metal, implants, pins, constructs, fillings, orthopedic braces, dental braces, etc. Certain embodiments of the X-ray fluorescence visualizer, imager, or information provider can be either stand-alone devices, or provide input into the at least the portion of the individual such as a tool, implant, tactile feedback providers, injecting device, probe, cutter, drill, separator, ablator, Bovie electrocautery device, material adder, material remover, etc. Certain portions of the X-ray fluorescence visualizer, imager, or information provider 100, as described in this disclosure, can pertain to X-ray fluorescence visualizing, imaging, or information providing within the medical areas, orthopedic areas, research areas, dental areas, orthodontia areas, veterinarian areas, livestock areas, wild animal or aquatic animal areas, etc.

Certain embodiments of the X-ray fluorescence visualization, imaging, or information providing of such individuals as plants or organisms can involve X-ray fluorescence depth visualizing, imaging, or information providing at least some of the various particular components or structure of the plant or organism. Such X-ray fluorescence visualization, imaging, or information providing of plants, organisms, etc. can be for research, commercial, medical, veterinarian, dental, or other purposes. For instance, certain organisms being X-ray fluorescence visualized, imaged, or have information provided can within a human, animal, or other host, can be distinct, or can be at least partially integrated in human, plant, organism, animal, etc.

There may be particular aspects of particular type of X-ray fluorescence visualization, imaging, or information providing, as can be performed by particular embodiments of the X-ray fluorescence visualizer, imager, or information provider 100 as described in this disclosure. For example, certain embodiments of the X-ray fluorescence visualizer, imager, or information provider 100 might be particularly useful in X-ray fluorescence visualization, imaging, or information providing a region within the at least the portion of the individual that is physically separated from the location where the at least one applied high energy photon and/or particle 120 initially pass through the surface. As such, certain embodiments of the X-ray fluorescence visualizer, imager, or information provider 100 may be used to image through considerable matter, tissue, etc. that may not be desired to be included in the X-ray fluorescence visualization, imaging, or information providing, such as by using image combining (e.g., image subtraction, time of flight X-ray fluorescence X-ray fluorescence depth visualization, or other technique such as by using image subtraction, image transformation, deconvolution, image subtraction, weighted subtraction, functional subtraction, and group including inverse integral transform, subtractive inverse integral transform, inverse functional transform, and subtractive inverse functional transform, or other such image processing techniques), and/or other imaging, or information providing, techniques as described in this disclosure may be utilized. Certain embodiments of the X-ray fluorescence depth visualizing or imaging effects of such matter that is not desired to be X-ray fluorescence visualized, imaged, or have information provided can be computationally limited, such as by limited processing capabilities, memory storage, and/or retrieval, etc. of the visualization, imaging, or information providing controller 97. Certain embodiments of the X-ray fluorescence visualizer, imager, or information provider 100 can be configured or operated to most effectively image the matter of the at least the portion of the individual situated nearby the external or internal surface 168 (e.g., via skin or other internal or external surface, or alternately through an incision, cut, etc.) of the at least the portion of the individual.

Certain embodiments of the X-ray fluorescence visualizer, imager, or information provider 100 are described in this disclosure as having their energy level and/or frequency of the at least one applied high energy photon and/or particle 120 that can be controlled and/or adjusted. The term controllable can, depending on context, indicate the ability of the user and/or other entity to control the X-ray fluorescence range and/or the prescribed substantial X-ray fluorescence depths relative to the matter of the at least the portion of the individual. Such control can be based at least in part on controlling the energy level and/or frequency of at least some the at least one applied high energy photon and/or particle 120. By comparison, the term adjustable can, depending on context, indicate that some adjustment can be made to the depth at which the X-ray fluorescence visualizer, imager, or information provider 100 X-ray fluorescence visualizes, images, or provides information into the matter of the at least the portion of the individual. Such adjustment can be based, at least in part, on controlling the energy level and/or frequency of at least some the at least one applied high energy photon and/or particle 120. Such control or adjustment of the prescribed substantial X-ray fluorescence depth, or X-ray fluorescence ranges, can be made during initial and/or subsequent X-ray fluorescence depth visualizing, imaging, or information providing, and can be empirically determined or not. A variety of embodiments of the X-ray fluorescence visualizer, imager, or information provider 100 may be controllable and/or adjustable based at least in part on controlling the energy level and/or frequency of at least some the at least one applied high energy photon and/or particle 120, as described in this disclosure; while other embodiments may not.

Certain embodiments of the X-ray fluorescence visualization, imaging, or information providing controller 97, of the X-ray fluorescence visualizer, imager, or information provider 100, as described in this disclosure, can utilize a variety of software, hardware, firmware, X-ray fluorescence depth visualizing or imaging technology, electronic and/or electric circuitry to facilitate the desired X-ray fluorescence visualization, imaging, or information providing. A variety of the software, hardware, firmware, X-ray fluorescence depth visualizing or imaging technology, electronic and/or electric circuitry is understood in the field of controllers, optical systems, electronics, and/or computers; and might be effectively performed by a variety of types of the X-ray fluorescence visualization, imaging, or information providing controller 97. For instance, certain embodiments of X-ray fluorescence visualization, imaging, or information providing that can rely at least partially on X-ray fluorescence visualization, imaging, or information providing image subtraction or combination, filtering, and/or processing, etc., as described in this disclosure, such as are particularly likely to involve software, hardware, firmware, and/or electronic to perform suitable image processing such as transforms, etc. As such, certain embodiments of the X-ray fluorescence visualizer, imager, or information provider 100 can allow transitioning or reconfiguration between different types of X-ray fluorescence visualization, imaging, or information providing such as by operation selection, reprogramming, modification, replacement, or reconfiguration of the X-ray fluorescence visualization, imaging, or information providing controller 97. Such modification by the X-ray fluorescence visualization, imaging, or information providing controller 97 may control operation of the at least one high energy photon and/or particle emitter portion(s) 150 and/or the at least one X-ray fluorescence receiving portion(s) 151 of FIG. 1 or 2). The operational or processing requirements of the X-ray fluorescence visualization, imaging, or information providing controller 97 may be quite demanding, for certain applications.

Figure 23:
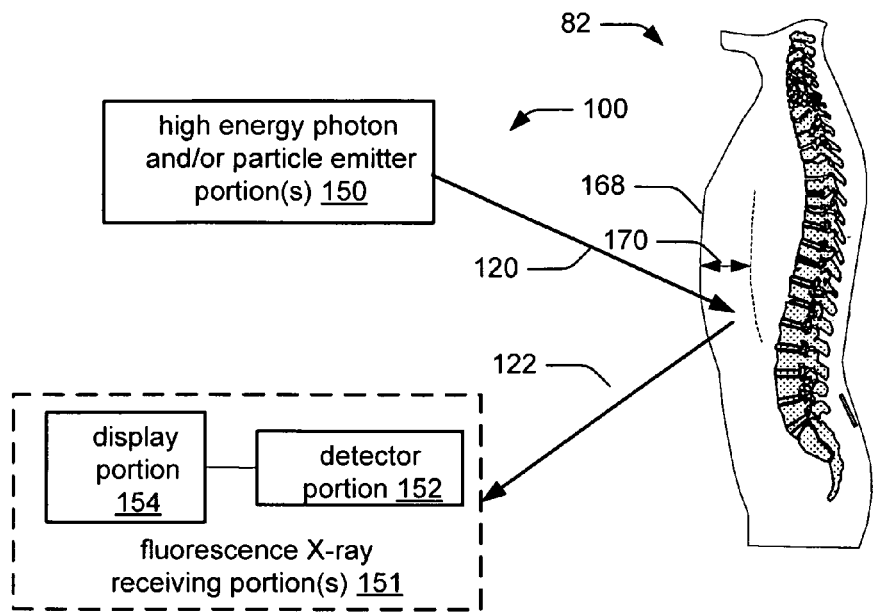
FIG. 23 shows a diagram of an at least the portion of an individual (e.g., human) being X-ray fluorescence visualized, imaged, or image provided by one embodiment of the X-ray fluorescence visualizer, imager, or information provider.
Figure 24:
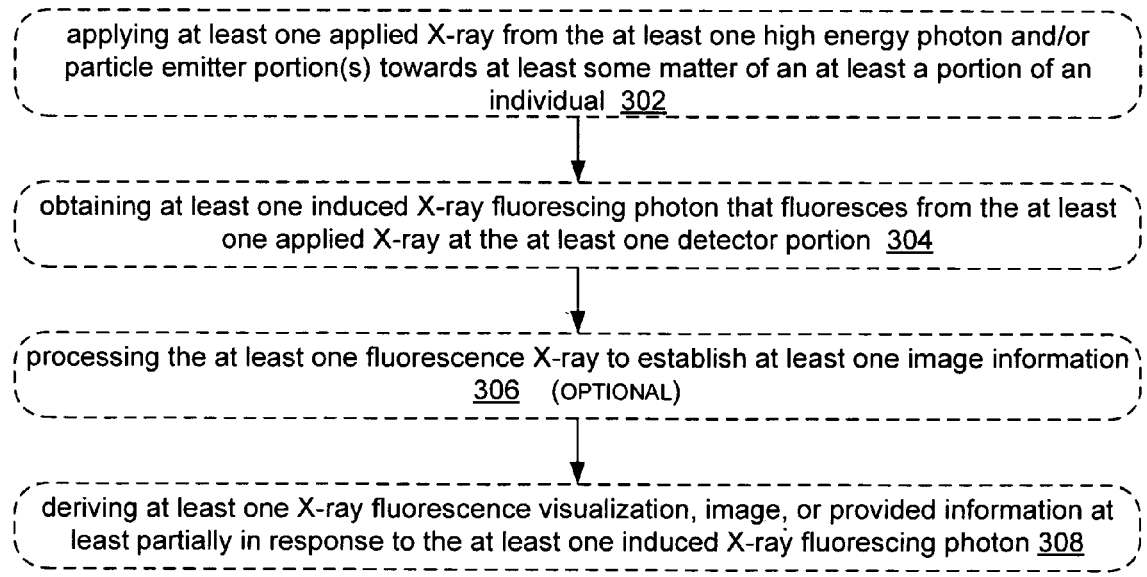
FIG. 24 shows a block diagram of a X-ray fluorescence visualization, imaging, or information providing process using the X-ray fluorescence visualizer, imager, or information provider such as described with respect to FIG. 23.
Figure 25:
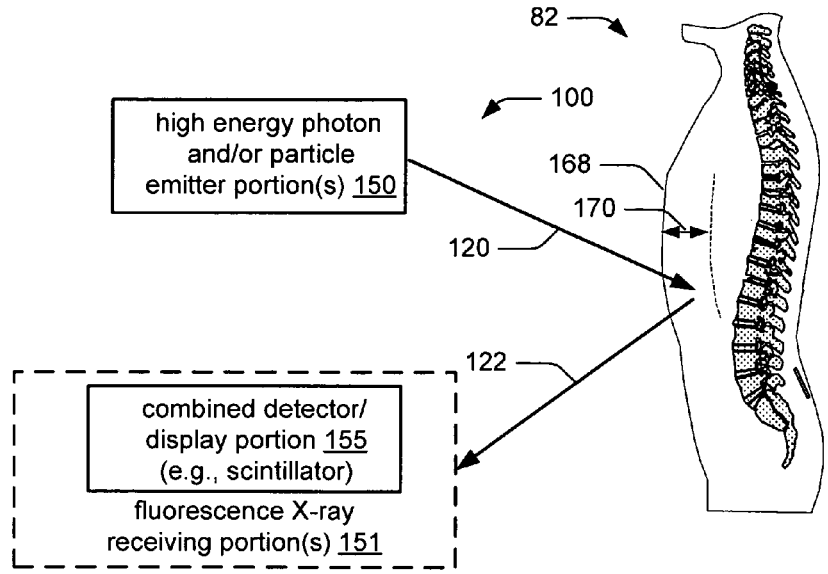
FIG. 25 is a diagram of the at least the portion of the individual being X-ray fluorescence visualized, imaged, or image provided by another embodiment of the X-ray fluorescence visualizer, imager, or information provider.

FIGS. 23 and 25 illustrate two respective exemplary but not limiting embodiments of the X-ray fluorescence visualizer, imager, or information provider 100, each embodiment conforms generally to the description on this disclosure relating to the FIG. 1 or 2 block diagram. Exemplary, but not limiting, logic pertaining to the respective FIGS. 23 and 25 embodiments of the X-ray fluorescence visualizer, imager, or information provider 100, and can be applied to certain large flow charts as described respectively relative to FIGS. 24 and 26.

It is envisioned that one or more distinct components, or portions, of certain embodiments of the X-ray fluorescence visualizer, imager, or information provider 100, can be included in one or more separate or distinct X-ray fluorescence visualizer, imager, or information provider 100 (such as described with respect to FIG. 1 or 2 and at other locations) can be operationally combined or configured as desired. Such components or portions from the one or more separate or distinct X-ray fluorescence visualizer, imager, or information provider 100 can interoperate, using known networking concepts. Each portion or component of the X-ray fluorescence visualizer, imager, or information provider can thereby perform one or more distinct functions or operations associated with the X-ray fluorescence visualizer, imager, or information provider.

As such, at least certain portions or components of different embodiments of one or more of the X-ray fluorescence visualizer, imager, or information provider 100 can interface and/or interact with each other such as to transfer, transmit, and/or receive images, X-ray fluorescence visualize, image, and/or provide information there between. Such transfer, transmission, and/or reception techniques can be provided in a manner utilizing techniques understood by those skilled in computing, hard-wired, wireless, networking, optical, communications, and other similar technologies. Such transmission, transferring, and/or receiving can be performed utilizing wireless, optical, wired based and/or other known technologies.

There can be a variety of, and embodiments of, devices and/or techniques which can be used by the at least one high energy photon and/or particle emitter portion(s) 150, that can generate the at least one applied high energy photon and/or particle 120. For example, certain embodiments of the at least one high energy photon and/or particle emitter portion(s) 150 of the X-ray fluorescence visualizer, imager, or information provider 100 can utilize X-ray devices, tubes, etc. to generate X-rays. A variety of X-ray tubes may be used to generate X-rays for a variety of conventional X-ray devices and/or conventional fluoroscopy devices, such as are generally known and are commercially available. Conventional X-ray devices, tubes, etc., such as may be utilized for conventional medical X-ray fluorescence visualizing, imaging, or information providing, are described, for example, in chapter 5 of "The Essential Physics of Medical Imaging, Second Edition", J. T. Bushburg, et al., Lippincott Williams and Wilkins, 2002 (incorporated by reference herein in its entirety). The X-ray tubes, devices, etc. can, depending on context, be considered as those devices that can be configured to produce X-rays including X-ray photons of a particular energy level or range of energy levels, frequency or range of frequencies, power or range of powers, etc. for the conventional transmissive X-ray imaging, for example, the X-rays can pass through the at least the portion of the individual 82. By comparison, certain embodiments of the at least one high energy photon and/or particle emitter portion(s) 150 of the X-ray fluorescence visualizer, imager, or information provider 100 can X-ray fluorescence visualize, image, and/or provide information utilizing such X-ray fluorescence mechanisms of the at least one applied high energy photon and/or particle 120 in a manner that can rely on X-rays that have characteristics (frequency, energy level, power, etc. of the X-ray photons).

Certain external embodiments of the X-ray fluorescence visualizer, imager, or information provider 100 may be configured such that the particular frequency or X-ray photon energy, or such other operational characteristic(s) of at least some of the X-ray photons included within the at least one applied high energy photon, can pertain to the depth of the X-ray fluorescence visualization, imaging, or information providing. As such, the frequency or energy level of a number of X-ray photons included in the at least one applied high energy photon, if controlled or adjusted, can have the effect of controlling or adjusting the depth(s) of X-ray fluorescence visualization, imaging, or information providing into the matter of the at least the portion of the individual 82. Certain embodiments of the X-ray fluorescence visualizer, imager, or information provider 100 can X-ray fluorescence visualize, image, and/or provide information down to within the at least one X-ray fluorescence range to the at least one prescribed substantial X-ray fluorescence depth which can be at least partially adjusted and/or controlled. Such determination can be either at least partially empirically, empirically, such as by calculation, derivation, or determination. Certain embodiments of the X-ray fluorescence visualizer, imager, or information provider 100 can obtain the X-ray fluorescence information in the form of information, data, X-ray fluorescence depth visualizations, images, and/or provided information, etc.

The at least one X-ray fluorescence range to the at least one prescribed substantial X-ray fluorescence depth from the surface 168 of the individual, such that the electromagnetic radiation of the at least one applied high energy photon and/or particle 120 passes into the at least the portion of the individual, fluoresce, and may therefore cause a reduction in the energy level of the X-ray upon fluoresce. The latter distance can be controlled to effectively control the X-ray fluorescence visualization, imaging, or information providing characteristics as per the former. Certain of the at least one X-ray fluorescence range to the at least one prescribed substantial X-ray fluorescence depth, which can vary along with varied surface configurations, roughness, material non-uniformities, etc.

By controlling the characteristics of the X-rays photons (e.g., frequency and/or energy level of the X-ray photons, intensity of the X-rays, angle of the X-rays, etc.), the perpendicular distance from the surface 168 of the at least the portion of the individual that the at least one applied high energy photon and/or particle 120 passes can be controlled and/or adjusted. Such control and/or adjusting of the energy level, frequency, direction, intensity, position, and/or other aspect or parameter of the at least one applied high energy photon and/or particle 120 can considerably limit the amount and type of matter of the at least the portion of the individual through which the X-rays may be applied. For instance, certain embodiments of the X-ray fluorescence visualizer, imager, or information provider can be configured to emit the X-ray based electromagnetic radiation (of the at least one applied high energy photon and/or particle 120 or the X-ray fluorescence high energy (e.g., X-ray, gamma ray, photon, particle, etc.)) at one or more selected organ(s) and/or matter, while limiting the application of the X-ray electromagnetic radiation to other organs, matter, etc. Certain embodiments of the X-ray fluorescence visualizer, imager, or information provider 100 can control the angle at which it applies its X-ray photons to the surface 168 of the at least the portion of the individual.

Due to the uncertain health effects of application of X-rays on humans, other individuals, and/or users, it may be desirable to limit the amount of X-ray electromagnetic radiation applied to the at least the portion of the individual, and/or any nearby users, when using the X-ray fluorescence visualizer, imager, or information provider 100. In general, therefore, it is desirable to limit such dosages of such electromagnetic radiation as X-rays that individual such as persons are animals are exposed to. Additionally, it would be expected to ease acceptance of certain embodiments of the X-ray fluorescence visualizer, imager, or information provider 100 by the appropriate regulatory agencies, in the amount of X-rays being applied to individuals and/or users (particularly human) could be limited considerably. As such, by the certain embodiments of the X-ray fluorescence visualizer, imager, or information provider 100 be configured to image a relatively small portion of the individual using depth-imaging techniques (e.g., imaging scan in a small portion underneath, primarily imaging matter through the prescribed substantial X-ray fluorescence depth, primarily certain organs, etc.), it can inherently limit the amount and extent of X-rays passing through the matter of the at least the portion of the individual.

For example, certain regions or locations of particular individuals (e.g., the embryo in pregnant women, certain organs, certain tissue, radiation-weakened individuals, elderly or informed, certain animals or organisms, etc.) might be particularly susceptible to the application of X-ray electromagnetic radiation, and as such are especially critical to shield from the application of X-rays. As such, it might be particularly desirable to configure at least certain embodiments of the X-ray fluorescence visualizer, imager, or information provider 100 to allow control of the particular X-ray fluorescence range of the prescribed substantial X-ray fluorescence depth of the at least one applied high energy photon and/or particle 120 (as well as their released amount) within the at least the portion of the individual. By limiting the amount of and the energy level of the at least one applied high energy photon and/or particle 120 being applied to the at least some matter of the at least the portion of the individual by such techniques as substantial bandwidth limiting, X-ray energy reduction, filtering, shielding, etc., can limit the application of the X-ray to the user and/or individual to substantially within some prescribed bandwidth.

Allowing relatively precise directional control of the at least one applied high energy photon and/or particle 120 using collimators, lenses, etc. such as emitted by the at least one high energy photon and/or particle emitter portion(s) 150, as compared with certain conventional X-ray imagers (conventional transmissive or X-ray fluorescence X-rays) can considerably reduce the X-ray dosage to the at least the portion of the individual. Also, X-ray dosages to nearby users can be limited. Such use of relatively low-energy the at least one applied high energy photon and/or particle 120, precise application of the at least one applied high energy photon and/or particle 120 to limited region of the individual, and associated reduced dosage of nearby areas, users, and/or individuals by certain embodiments of the X-ray fluorescence visualizer, imager, or information provider 100 could improve the public's and professional perception and acceptance thereof.

With certain embodiments of the X-ray fluorescence visualizer, imager, or information provider 100, the user such as a doctor, researcher, veterinarian, surgeon, etc. (each of whom may be involved in examination, surgery, and/or research, etc.) can appropriately subsurface X-ray fluorescence visualize, image, and/or provide information relating to the at least the portion of the individual 82. Depending on context, certain types of X-ray fluorescence visualization, imaging, or information providing can be applied from nearby or proximate the surface 168 down to within the at least one X-ray fluorescence range to the at least one prescribed substantial X-ray fluorescence depth. Certain embodiments of the X-ray fluorescence visualizer, imager, or information provider 100 can vary from the micron range up to and including substantially through a major portion of the individual 82.

The resolution of certain embodiments of the X-ray fluorescence visualizer, imager, or information provider 100 might be effective for certain diagnosis, examination, surgical, research, and other purposes; and certain embodiments X-ray fluorescence visualizer, imager, or information provider could provide desired or appropriate resolutions through the X-ray fluorescence visualized, imaged, or information provided portion of the individual 82.

It may be desired for certain X-ray fluorescence visualization, imaging, or information providing applications to adjust and/or control the X-ray fluorescence visualization, imaging, or information providing by certain embodiments of the X-ray fluorescence visualizer, imager, or information provider 100. Within this disclosure, the term "control", as it relates to X-ray fluorescence visualization, imaging, or information providing, can mean, but is not limited to, controlling the energy level, frequency, angle, additional matter imaged through, and/or other characteristics of the at least one applied high energy photon and/or particle 120 by certain embodiments of the X-ray fluorescence visualizer, imager, or information provider 100. Within this disclosure, the term "adjust" can mean, but is not limited to, depending on context, adjusting the at least one X-ray fluorescence range to the at least one prescribed substantial X-ray fluorescence depth. Such control or adjustment can occur by altering or adjusting certain characteristics of the at least one applied high energy photon and/or particle 120 such as energy level, frequency, depth, angle from perpendicular to the surface 168, etc.

Such control and/or adjustment of certain embodiments of the X-ray fluorescence visualizer, imager, or information provider 100 can make the X-ray fluorescence visualizer, imager, or information provider more applicable to a variety of applications. For example, certain controllable embodiments of the X-ray fluorescence visualizer, imager, or information provider 100 can X-ray fluorescence visualize, image, and/or provide information a variety of matter within the at least the portion of the individual at a variety of depths, or X-ray fluorescence range of X-ray fluorescence visualizing, imaging, or information providing depths. Certain embodiments of the X-ray fluorescence visualizer, imager, or information provider 100 can adjust the depth of X-ray fluorescence visualization, imaging, or information providing and/or their resolution based on controlling the X-ray characteristics of the at least one applied high energy photon and/or particle 120. Certain embodiments of the X-ray fluorescence visualizer, imager, or information provider 100 can therefore be configured to be adjustably tunable, such that the user can adjust the energy of the X-ray photons. By adjusting the energy of the at least one applied high energy photon and/or particle 120, for example, the at least one X-ray fluorescence range to the at least one prescribed substantial X-ray fluorescence visualizing, imaging, or information providing depth of X-ray fluorescence visualization, imaging, or information providing into the matter of the at least the portion of the individual can be adjusted.

Certain embodiments of the X-ray fluorescence visualizer, imager, or information provider 100 can utilize steered, focused, directed, filtered, scanned, and/or processed X-rays. Certain embodiments of the X-ray fluorescence visualizer, imager, or information provider 100 can X-ray fluorescence visualize, image, and/or provide information along a variety of one, two, or three dimensional patterns, in certain instances such as by scanning to create a two or three dimensional X-ray fluorescence visualize, image, and/or provide information within the at least the portion of the individual 82. Certain embodiments of the X-ray fluorescence visualizer, imager, or information provider 100 can be configured to be low or non-contact, as well as low or non-invasive, such as by utilizing one or more of the at least one high energy photon and/or particle emitter portion(s) 150 having no or limited contact with the surface 168.

Certain embodiments of the X-ray fluorescence visualizer, imager, or information provider may allow the operation and/or structure of the detector portion and the display portion to be at least partially combined. Certain embodiments of the X-ray fluorescence visualizer, imager, or information provider 100 can allow the user, or a controller, to alter the X-ray fluorescence visualization, imaging, or information providing of subsequent or sequential X-ray fluorescence depth visualizations, images, and/or provided information based at least in part on results from prior captured images. Such sequential X-ray fluorescence visualization, imaging, or information may allow such exemplary users as doctors, surgeons, veterinarians, researchers, etc. to determine the region within the at least the portion of the individual that is being X-ray fluorescence visualized, imaged, or have information provided. It may be desirable to provide for such changes in X-ray fluorescence visualization, imaging, or information providing using a variety of image processing techniques to effect such changes as magnification, zooming, changing a relative angle, depth, or position of the X-ray fluorescence visualization, image, or provided information, and/or changing a variety of other X-ray fluorescence visualizing, imaging, or information providing parameter such as may be desired or useful by the user or individual.

A variety of configurations and/or operational combinations of the at least one high energy photon and/or particle emitter portion(s) 150, the at least one X-ray fluorescence receiving portion(s) 151, the at least one detector portion, and/or the at least one display portion(s) 154 may be associated with the X-ray fluorescence visualizer, imager, or information provider 100. As described in this disclosure, certain embodiments of the at least one high energy photon and/or particle emitter portion(s) 150 can be directed such as to apply X-ray based electromagnetic radiation at a precisely controllable region of the at least the portion of the individual 82; such as may thereupon be detected by certain embodiments of the at least one detector portion 152. Such application and/or detection of the electromagnetic radiation can be done once, multiple continuous times without feedback by a user and/or controller, multiple sequential times with feedback by a user and/or controller, or other ways or combinations thereof. The application or detection of X-rays may rely on transmission of a variety of radiation such as pulse, continuous, pencil, fan, flooding, or other types of the at least one applied high energy photon and/or particle 120.

Certain embodiment(s) component(s), and/or portion(s) of the X-ray fluorescence visualizer, imager, or information provider 100 can be configured as an at least partially external emitter device, such as to depth-examine the at least some matter of the at least the portion of the individual either directly through the matter itself, or alternately below an either external or internal surface 168 of the at least the portion of the individual. For certain external embodiments of the X-ray fluorescence visualizer, imager, or information provider 100, the "subsurface" X-ray fluorescence visualization, imaging, or information providing can, depending upon context, relate to X-ray fluorescence visualization, imaging, or information providing beneath the skin or other external surface. Certain embodiment(s) component(s), and/or portion(s) of the X-ray fluorescence visualizer, imager, or information provider can be configured as an at least partially internal device, such as to examine an internal portion of the individual 82 through an incision, or alternately through a normally open opening in the at least the portion of the individual.

For certain internal embodiments of the X-ray fluorescence visualizer, imager, or information provider 100, a "subsurface" undergoing X-ray fluorescence visualization, imaging, or information providing can, depending upon context, relate to being applied through openings of the individual, such as a normally open portions of the individual, such as beneath the surface 168, within a region at least partially forming the lumen, within a cavity, or within another body opening. For internal embodiments of the X-ray fluorescence visualizer, imager, or information provider 100 that can be applied through normally closed portions of the individual (e.g., an incision, a wound, etc.), the term "subsurface" can, depending upon context, including the X-ray fluorescence visualizer, imager, or information provider 100 being applied through the normally-closed opening, incision, etc. Various embodiments of the X-ray fluorescence visualizer, imager, or information provider 100 can X-ray fluorescence visualize, image, or provide information through a variety of such matter as tissue, bone portions, fluid, blood, etc. through the X-ray fluorescence range of the prescribed substantial X-ray fluorescence depths to the prescribed substantial X-ray fluorescence depth 170, as described with respect to FIG. 23.

FIG. 24 shows one embodiment of a flowchart of a X-ray fluorescence visualization, imaging, or information providing technique 300 that can be performed by the embodiment of the X-ray fluorescence visualizer, imager, or information provider 100 as described in this disclosure of the at least one X-ray fluorescence receiving portion(s) 151. Certain embodiments of the at least one X-ray fluorescence receiving portion(s) 151 can include operationally distinct ones of the at least one detector portion 152 from the at least one display portion 154. Certain embodiments of the subsurface X-ray fluorescence visualization, imaging, or information providing technique 300 can include one or more operations 302, 304, 306, and/or 308 to be applied within the at least one X-ray fluorescence range to the at least one prescribed substantial X-ray fluorescence depth into the at least some matter.

Certain embodiments of operation 302 can include, but is not limited to, applying at least one the at least one applied high energy photon and/or particle 120 from an at least one high energy photon and/or particle emitter portion(s) 150 towards an at least some matter of an at least a portion of an individual. For example, certain embodiments of the at least one high energy photon and/or particle emitter portion(s) 150 can apply X-rays toward the desired matter (e.g., tissue, fluid, bone, teeth, joint, fat, muscle, etc.) of the at least the portion of the individual in a manner that the X-rays can be X-ray fluorescence visualizing, imaging, or information providing within the at least some matter. Such application of the at least one applied high energy photon and/or particle 120 can thereupon be used by certain embodiments of the X-ray fluorescence visualizer, imager, or information provider 100 to allow X-ray fluorescence depth visualizing, imaging, or information providing. A considerable percentage of the at least one applied high energy photon and/or particle 120 that fluoresce at the X-ray fluorescing event, and thereupon are returned to be detected by the at least one X-ray fluorescence receiving portion(s) 151 could X-ray fluorescence between within the at least one X-ray fluorescence range to the at least one prescribed substantial X-ray fluorescence depth. The value of the at least one X-ray fluorescence range to the at least one prescribed substantial X-ray fluorescence depth can be based at least partially on the energy level of the at least one applied high energy photon and/or particle 120. The energy level of the at least one applied high energy photon and/or particle 120 is considered to be directly related to frequency.

Certain embodiments of the operation 304 can include, but is not limited to, obtaining at least one X-ray fluorescence that X-ray fluorescence from the at least one the at least one applied high energy photon and/or particle 120 at the at least one detector portion 152. In effect, certain of the at least one induced X-ray fluorescing photon 122 can be received at the detector portion 152, at least partially based on the X-ray fluorescence of the at least one applied high energy photon and/or particle 120 at the fluorescing event (e.g., within the at least some matter of the at least the portion of the individual). Certain of the at least one applied high energy photon and/or particle 120 can be applied by the at least one high energy photon and/or particle emitter portion(s) 150 during operation 302.

Certain embodiments of the operation 306 (which is optional) can include, but are not limited to, processing the at least one X-ray fluorescence received during operation 304, to X-ray fluorescence visualize, image, and/or provide information about the at least the portion of the individual. For example, certain embodiments of the X-ray fluorescence visualization, imaging, or information providing controller 97 can derive X-ray fluorescence visualizations, images, and/or provide information such as can be displayed.

Certain embodiments of the operation 308 can include, but is not limited to, deriving the at least one X-ray fluorescence visualization, image, and/or provided information at least partially responsive to the induced X-ray fluorescing photon, as can be at least partially processed and/or captured during operation 304. For example, certain embodiments of the display portion 154 and/or the at least one X-ray fluorescence receiving portion(s) 151 (which may be a scintillator and/or fluoroscope embodiment) can display a X-ray fluorescence visualization, image, and/or provide information of at least a portion of the matter of the at least the portion of the individual.

Figure 26:
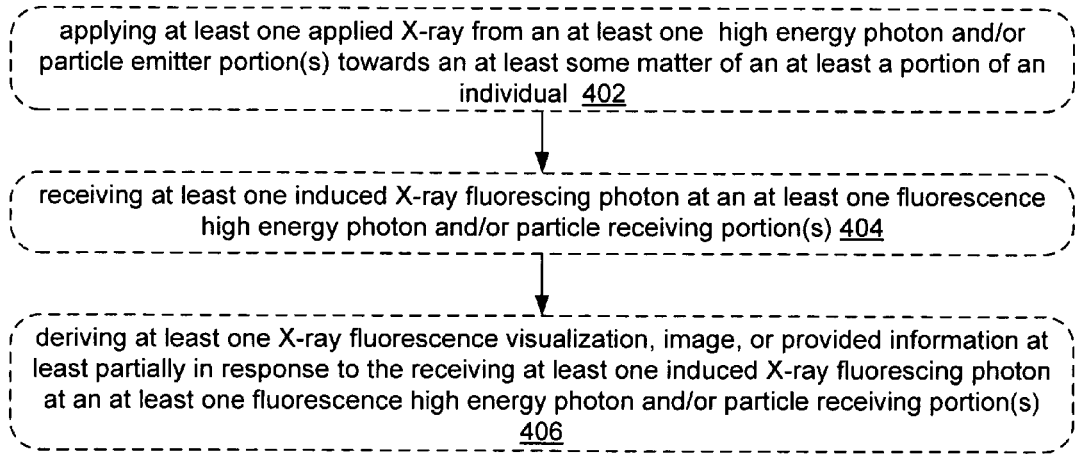
FIG. 26 shows a block diagram of another X-ray fluorescence visualization, imaging, or information providing process using the X-ray fluorescence visualizer, imager, or information provider such as described with respect to FIG. 25.

Certain embodiments of the X-ray fluorescence visualizer, imager, or information provider may be configured to, at least partially, convert X-ray fluorescence high energy (e.g., X-ray, gamma ray, photon, particle, etc.) directly into viewable or visible light, without the processing the X-ray fluorescence high energy (e.g., X-ray, gamma ray, photon, particle, etc.) such as may be provided with certain scintillator embodiments of the X-ray fluorescence visualizer, imager, or information provider 100 as described with respect to FIG. 25. FIG. 26 shows one embodiment of a flowchart of a X-ray fluorescence visualization, imaging, or information providing technique 400 that can be performed by the embodiment of the X-ray fluorescence visualizer, imager, or information provider 100 without processing. Certain embodiments of the subsurface X-ray fluorescence visualization, imaging, or information providing technique 400 can include one or more of operations 402, 404, and/or 406 as described in this disclosure to X-ray fluorescence visualize, image, and/or provide information using a scintillator (and/or fluoroscope) embodiment of the at least one X-ray fluorescence receiving portion(s) 151. Certain scintillator (and/or fluoroscope) embodiments of the at least one X-ray fluorescence receiving portion(s) 151 can X-ray fluorescence visualize, image, or provide information within the at least one X-ray fluorescence range to the at least one prescribed substantial X-ray fluorescence depth into the matter of the at least the portion of the individual.

Certain embodiments of the operation 402 can include, but is not limited to, applying at least one the at least one applied high energy photon and/or particle 120 from the at least one high energy photon and/or particle emitter portion(s) towards the at least some matter of the at least the portion of the individual. For example, certain embodiments of the at least one high energy photon and/or particle emitter portion(s) 150 can apply X-rays toward the desired matter (e.g., tissue, fluid, bone, teeth, joint, fat, muscle, etc.) of the at least the portion of the individual in a manner that the X-rays can be X-ray fluorescence within the matter.

Certain embodiments of the operation 404 can include, but is not limited to, receiving at least some X-ray fluorescence at the at least one X-ray fluorescence receiving portion(s) 151 as described in this disclosure, in response to the at least one applied high energy photon and/or particle 120 applied by the at least one high energy photon and/or particle emitter portion(s) 150. A considerable percentage of the at least one applied high energy photon and/or particle 120 that X-ray fluoresces and are returned that can be detected by the at least one X-ray fluorescence receiving portion(s) 151 will X-ray fluorescence through the at least one X-ray fluorescence range to the at least one prescribed substantial X-ray fluorescence depth. Such X-ray fluorescence depth can be based at least partially on the energy level (or frequency, which is related thereto) of the at least one applied high energy photon and/or particle 120, as described in this disclosure.

Certain embodiments of the operation 406 can include, but is not limited to, deriving at least one X-ray fluorescence visualization, image, or provided information at least partially in response to the receiving the at least one X-ray fluorescence high energy (e.g., X-ray, gamma ray, photon, particle, etc.) at the at least one X-ray fluorescence receiving portion(s) 151. For example, certain scintillator (and/or fluoroscope) embodiments of the display portion 154 and/or the at least one X-ray fluorescence receiving portion(s) 151 can display a X-ray fluorescence depth visualization or image of at least a portion of the matter of the individual based at least partially on the elements, chemicals, compounds, and/or biological materials.

Certain embodiments of the X-ray fluorescence visualizer, imager, or information provider 100 thereby can provide a mechanism to X-ray fluorescence visualize, image, and/or provide information down to, or at, one or more prescribed substantial X-ray fluorescence depths (in many instances controllably) into at least partially X-ray matter such as to capture X-ray fluorescence depth visualizations, images, and/or provided information based at least partially on the elements, chemicals, compounds, and/or biological materials. Within this disclosure, much of the matter being depth-imaged by certain embodiments of the X-ray fluorescence visualizer, imager, or information provider 100 can be expected to be interspersed, mixed, compounded, or at least partially combined with other matter such as bones, metal, etc. within the individual such as typically exists in at least certain portions of the individual 82. Certain embodiments of the X-ray fluorescence, such as can be performed by certain embodiments of the X-ray fluorescence visualizer, imager, or information provider 100, can thereby be used to X-ray fluorescence visualize, image, and/or provide information matter that can be at least partially combined with relatively electromagnetic radiation-X-ray fluorescence matter.

Certain embodiments of the X-ray fluorescence visualizer, imager, or information provider 100 can be configured to be used to X-ray fluorescence visualize, image, and/or provide information of the elements, chemicals, compounds, and/or biological materials that is relatively dense within the at least portions of certain matter. Such density may indicate the matter includes, e.g., bones, bone fragments or portions, spinal portions, cranial portions, metal, implants, etc. Such reconfigurations as altering the frequencies of the at least one applied high energy photon and/or particle 120 may be used to configure the X-ray fluorescence visualizer, imager, or information provider 100 to X-ray fluorescence visualize, image, and/or provide information matter(s) having varied characteristics or transitions thereof. By X-ray fluorescence depth visualizing, imaging, or information providing of hard matter such as bones, spinal portions, certain implants, etc., it can become possible to examine a two-dimensional, or three-dimensional portion of the bone, etc. with considerable resolutional accuracy. Such X-ray fluorescence depth visualizing, imaging, or information providing of hard matter can be controlled and/or adjusted as described in this disclosure. Such X-ray fluorescence visualization, imaging, or information providing of hard matter or dense matter can be performed prior to surgery or examination, during surgery or examination, following surgery or examination. Certain embodiments of the X-ray fluorescence visualizer, imager, or information provider 100 can X-ray fluorescence visualize, image, and/or provide information hard matter in combination with other matter. For example, a bone can be imaged in combination with at a junction with associated tissue, joints, muscles, tendons, surgical pins, plates, etc. Such junctions of dissimilar matter can be particularly emphasized based on differences between the elements, chemicals, compounds, and/or biological materials included in or forming the matter of either side of the junction. Additionally, a brain portion can be X-ray fluorescence visualized, imaged, or have information provided relative to associated cranial portions (e.g., skull), etc. Providing such adjustability or control of X-ray fluorescence visualization, imaging, or information providing can allow doctors, surgeons, dentists, etc. to obtain accuracy of X-ray fluorescence visualization, imaging, or information providing of a variety of matter within the at least the portion of the individual, particularly by certain embodiments of the X-ray fluorescence visualizer, imager, or information provider 100 using low power/dosage techniques.

Certain embodiments of the X-ray fluorescence visualizer, imager, or information provider 100 can be configured to X-ray fluorescence visualize, image, or provide information relating to a combination of at least some soft matter such as tissue, blood cells, bodily fluids, etc. as combined with certain embodiments of the at least some hard matter such as bones, teeth, etc. Such X-ray fluorescence visualization, imaging, or providing information of a combination of at least some hard matter with at least some soft matter (or low density matter) may be particularly useful when considering junction matter regions that are likely to be distinguishable based at least partially on the elements, chemicals, compounds, and/or biological materials of the matter such as the intersection of gums with teeth; the intersection of bones with tendons, ligaments, muscles, tissue, the intersection of pins or implants with surrounding tissues or bones, etc.

A variety of embodiments of the X-ray fluorescence visualizer, imager, or information provider 100 can be configured to image edges, sides, inconsistencies, or non-uniformities of matter, tissue, organs, etc. It may therefore be possible to locate particular organs, matter, tissue, etc. based on such aberrations, inconsistencies, or non-uniformities of the organs, matter, tissue, etc. For example, as the at least one applied high energy photon and/or particle 120 are applied to X-ray fluorescence visualize, image, and/or provide information a region of the at least the portion of the individual where an organ is situated, the edge portion of the organ may X-ray fluorescence the at least one applied high energy photon and/or particle 120 in a direction that differs from the remainder of the organ. Such X-ray fluorescence along the edge may lead into a detectable difference of the X-ray fluorescence depth image at the edge of the X-ray fluorescence organ. Such differences of characteristics of X-ray fluorescence based at least in part on angle, position, or other aspect of the matter can be used by certain embodiments of the X-ray fluorescence visualizer, imager, or information provider 100, as described in this disclosure.

Figure 13:
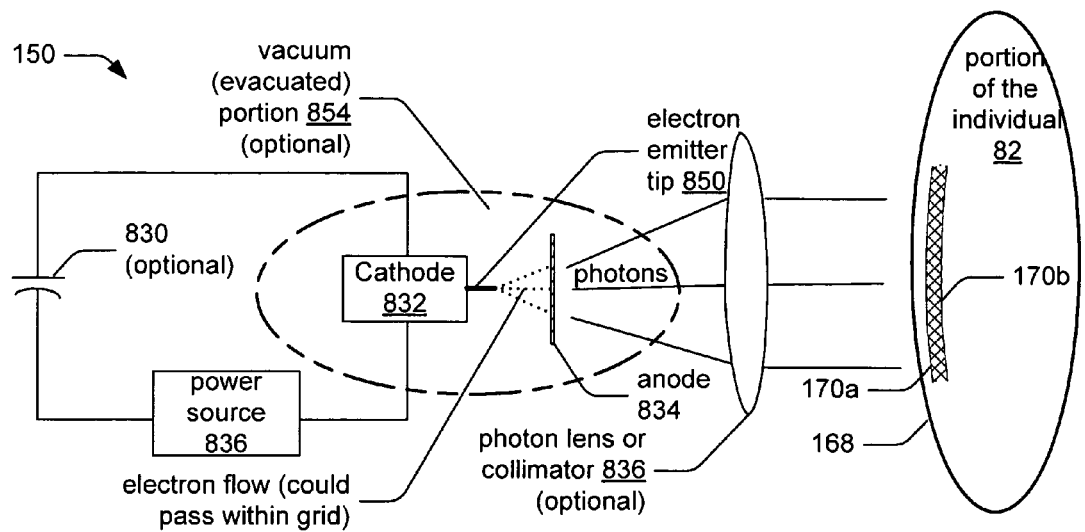
FIG. 13 shows a diagram of one embodiment of an at least one high energy photon and/or particle emitter portion(s) that can be included in certain embodiments of the X-ray fluorescence visualizer, imager, or information provider.
Figure 14:
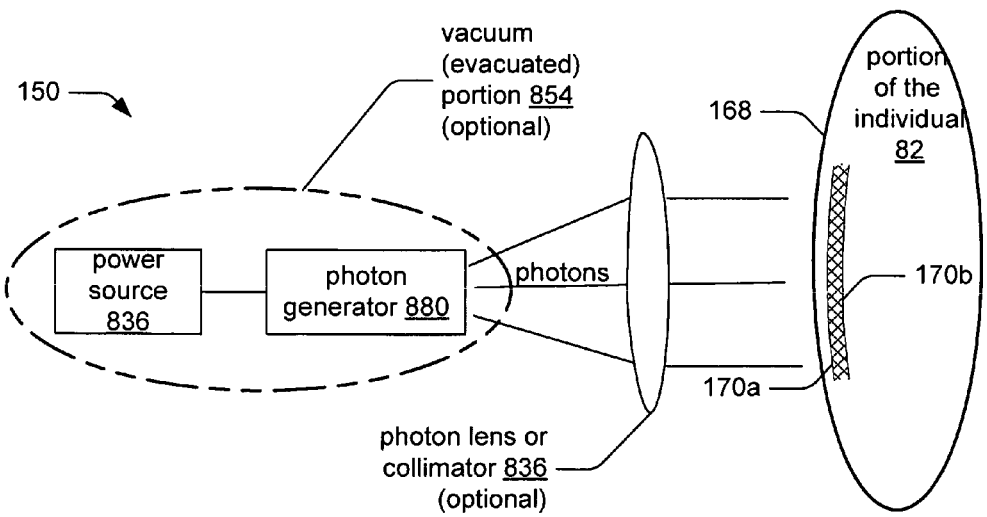
FIG. 14 shows a diagram of another embodiment of the high energy photon and/or particle emitter portion(s) that can be included in certain embodiments of the X-ray fluorescence visualizer, imager, or information provider.

FIG. 13 shows one embodiment of the at least one high energy photon and/or particle emitter portion(s) 150 that can be included in certain embodiments of the X-ray fluorescence visualizer, imager, or information provider 100, as described in this disclosure, while FIG. 14 shows another embodiment. Certain embodiments of the at least one high energy photon and/or particle emitter portion(s) 150 can emit the at least one applied high energy photon and/or particle 120 toward the at least the portion of the individual 82 over some specified angle and/or scan that can effect the X-ray fluorescence visualizing, imaging, or information providing such as with a pencil radiation, fan radiation, area radiation, or other radiation pattern. For example, certain emitters of certain embodiments of the X-ray fluorescence visualizers, imagers, or information providers 100 can emit the at least one applied high energy photon and/or particle 120 in a narrow radiation pattern such as the pencil radiation pattern; or a wide radiation pattern such as a fan or flooding pattern. Certain embodiments of the at least one high energy photon and/or particle emitter portion(s) 150 can emit collimated X-rays, while others can emit disperse X-rays. Certain embodiments of the at least one high energy photon and/or particle emitter portion(s) 150 can include such adjustable optical elements as Bragg optics elements to adjust the pattern/direction of the at least one applied high energy photon and/or particle 120 emission, while others may not be adjustable or controllable. The configuration, design, and usage of certain embodiments of the at least one high energy photon and/or particle emitter portion(s) 150 can depend, at least in part, on the particular characteristics of the X-ray fluorescence visualization, imaging, or information providing (as well as the characteristics of the at least the portion of the individual being X-ray fluorescence visualized, imaged, or have information provided).

Certain embodiments of the at least one high energy photon and/or particle emitter portion(s) 150 are therefore configured to direct at least one X-ray towards the at least the portion of the individual. Certain embodiments of the at least one high energy photon and/or particle emitter portion(s) 150, can include, but are not limited to, a power source 836, a cathode 832, a field emission tip 850, and/or an anode 834. Other illustrative potential structures of the at least one high energy photon and/or particle emitter portion(s) 150 are described in this disclosure, while still others are generally understood by those skilled with X-ray tubes and generating devices. Certain embodiments of the power source 836 and the cathode 832 can be arranged in an electron circuit such as to provide an electric (e.g., electron) flow from the cathode 832, such as can be at least partially discharged via the electron emitter tip 850 and the anode 834. Certain embodiments of the electron emitter tip 850 can be in electrical communication with the cathode, such as to be configured as to be capable of discharging the electron flow that can be at least partially directed at the anode 834.

Certain embodiments of the electron emitter tip 850 may be configured as an electron discharge region that can generate and/or direct the electron flow in a pattern, frequency, energy level, configuration, or other parameter as described with respect to FIG. 13. Certain embodiments of the electron emitter tip 850 are configured to establish the electron flow, and as such may include such elements as a triode, antenna, nanostructure, or other such component. Certain embodiments of the electron emitter tip 850 can also be configured to include one or more (carbon) nanotubes, which may be effectively configured as electromagnetic radiation antennas. Certain embodiments of the electron emitter tip 850 can thereby utilize one or more discrete elements, while other embodiments can utilize a number or array of carbon nanotubes, etc.

Certain embodiments of the electron emitter tip 850 can be fixed, while other embodiments can be adjusted or displaced such as to change such as to alter the pattern of electron emission, such as by moving the electron source. One example of a movable or adjustable electron emitter tip 850 can include, for example, utilizing adjustment or displacement of a flexible carbon nanotube electrically coupled to the cathode.

Certain embodiments of the anode 834 can be configured and/or biased during operation as to attract electrons from the combination of the cathode 832 and/or the electron emitter tip 850. Upon contact of the electron flow into certain embodiments of the anode 834, certain embodiments of the anode can thereupon generate X-ray photons of the desired frequency and/or energy level. In certain embodiments of the at least one high energy photon and/or particle emitter portion(s) 150, the electron flow emanating from the electron emitter tip 850 can remain substantially static, and as such may not be directable or scannable. With other embodiments of the at least one high energy photon and/or particle emitter portion(s) 150, the electron emitter tip 850 of the cathode 832 can steer, scan, or otherwise displace the electron flow to the desired location relative to the anode 834. Certain embodiments of the X-ray fluorescence visualizer, imager, or information provider 100 can be configured to include a stepper motor, or other motor or displacement mechanism (not shown) to control or adjust the positions of the at least one high energy photon and/or particle emitter portion(s) 150 and/or the detector portion 152. The respective at least one high energy photon and/or particle emitter portion(s) 150 and/or detector portion 152 may be configured to operationally pan and tilt during operation such as to provide a desired degree of adjustability. Certain embodiments of the electron emitter tip 850 can be configured as an X-ray source (e.g., in certain instances the size may be in the small mm range such that it may, in certain instances, fit within certain blood vessels or lumens such as to allow X-ray fluorescence depth visualizing, imaging, or information providing from these locations). In other embodiments, the size of the electron emitter tip 850 may be considerably larger such as to interface with an external or larger portion of the individual 82.

Certain embodiments of the electron emitter tip 850 radiation can be configured to be displaceable or moveable such as to allow control and/or adjustment of the X-ray fluorescence visualizer, imager, or information provider 100, such as by scanning, shifting, axially moving, radiation focusing control, rotating, panning, or otherwise moving to alter the path of the electron flow. For example: one or more Micro Electro-Mechanical System (MEMS) devices, a rotating crystal, an electromechanical or X-ray scanning mechanism, or other suitable means may be included in the certain embodiments of the electron emitter tip 850 such as to provide control and/or adjustment of the electron emitter tip. Certain embodiments of the at least one high energy photon and/or particle emitter portion(s) 150 can be configured to produce X-rays that are at least partially incident on a lens (not shown, but which may include a crystal which is configured as a lens) that can be displaceable to move and/or scan the X-ray radiation. Alternately, certain embodiments of the at least one high energy photon and/or particle emitter portion(s) 150 can be configured as an array type device, with different ones are different groups of the elements being a controlled either manually or at least partially by the X-ray fluorescence depth visualization, imaging, or information providing controller 97. Such scanning of the X-ray radiation can follow a raster-type scan, use a fan type radiation, pencil type radiation, or other scan, perhaps similar to those utilize to in certain other conventional tomography scanners, or may follow some other pattern. In certain instances, the scanning of the at least one high energy photon and/or particle emitter portion(s) 150 may be coordinated with the scanning of the at least one detector portion 152, or alternately a scanning detector portion may be associated with the high energy photon and/or particle emitter portion(s) that generates X-rays which effectively "flood" the at least the portion of the individual 82 being X-ray fluorescence visualized, imaged, or have information provided. The selection of the particular scanning, pencil, flooding, or other configuration may affect X-ray dosage of the user and/or nearby individuals, as described in this disclosure.

Various embodiments of the power source 836, as described with respect to FIG. 13, may be configured as desired, as long as it provides adequate power to the cathode to establish the electron flow from the particular embodiment of the electron emitter tip 850, depending on the configuration of electron emitter tip as well as the anode. Certain embodiments of the at least one high energy photon and/or particle emitter portion(s) 150 can thereby be configured to direct electrons, as provided by the power source 836, the cathode 832, and/or the electron emitter tip 858. The electrons may therefore be directed from the electron emitter tip 850 to the anode 834 as described with respect to FIG. 13. Altering or controlling the electron flow may have a corresponding effect on the generation of photons by the anode 834. Certain embodiments of the at least one high energy photon and/or particle emitter portion(s) 150 may alternately be powered optically, such as to include the photon generator 880 as applied to the power source 836, as described with respect to FIG. 14.

Certain embodiments of the photon generator 880 can alternately utilize, for example, an optically fed photoelectric stack, an optical fed battery, an energy accumulator (e.g., battery or capacitor), a solar panel, or a variety of other device that can generate X-ray photons such as may be used directly or indirectly as the applied high energy photon and/or particle 120. Certain embodiments of the at least one high energy photon and/or particle emitter portion(s) 150 utilizing the photon generator 880 as described with respect to FIG. 14, can be adjustable, controlled, fixed, dispersed, and/or focused, etc. as to control and/or adjust generation of X-ray photons as described with respect to the FIG. 13 embodiment of the high energy photon and/or particle emitter portion.

With certain embodiments of the at least one high energy photon and/or particle emitter portion(s) 150, as described with respect to FIG. 13, an electron grid (not shown) may be positioned, adjusted, and/or controlled from a location such as operationally proximate to the electron flow. For example, the electron grid may be situated adjacent a path at least partially situated between the electron emitter tip 850 and the anode 834. Certain embodiments of the electron grid may be configured, upon activation, to steer, scan, or otherwise control the flow or velocity of electrons passing from the electron emitter tip 850 to the anode 834. Such steering, scanning, accelerating, decelerating, or otherwise controlling the flow or velocity of electrons can in addition control or alter the characteristics or position(s) at which the photons generated contact the particular anode 834.

Certain basic embodiments of the anode 834 can be configured in a variety of forms. For example, the anode can include a thin metal foil, or other configuration, that can be positioned in suitable proximity to the electron emitter tip 850. Certain embodiments of the anode 834 can be provided to be controllable and/or adjustable such as to include at least one anode wheel, cassette, cartridge, etc. (not shown) that can emit X-ray photons whose characteristics can be adjusted and/or controlled, such as by displacement, rotation, etc., such as to provide varied anode metals or other materials anodes (or having different shapes, dimensions, or other configurations) in communication with the electron flow.

By using an anode wheel, cartridge, canister, or other such mechanism that can alter the material and/or configuration of the anode, the characteristics of the X-ray photons (such as energy level and/or frequency) being generated by the at least one high energy photon and/or particle emitter portion(s) can be controlled or altered. Such controlling and/or altering of the X-rays being emitted can control and/or alter the at least one X-ray fluorescence range to the at least one prescribed substantial X-ray fluorescence depth being performed by certain embodiments of the X-ray fluorescence visualizer, imager, or information provider 100 as described in this disclosure. Certain other uses of anode wheels is known in certain conventional X-ray tubes, which can function largely to maintain all portions of the anode within acceptable temperature ranges by altering the portion of the anode wheel which the electron flow contacts, and is therefore being instantaneously heated by the electron flow. The anode wheels could also include a motive mechanism (not shown) to allow suitable rotation and/or displacement of the anode wheel (either rotationally and/or axially) such as may utilize a stepper motor, a pneumatic drive, an electric motor, etc. Certain embodiments of the anode wheel could also include a variety of control mechanisms (not shown) to control such rotation and/or displacement. A variety of such control, rotation, and/or displacement mechanisms are generally understood by those skilled in the anode wheel art.

Certain embodiments of the anode 834 can thereby be configured to generate the X-ray photons at controllable and/or adjustable energy levels, frequencies, or other characteristic based at least in part on the characteristic of the electron flow being applied to the anode 834, and additionally on the material of the anode 834. As such, it may be possible to generate X-rays having particular characteristics by selecting particular materials (e.g., different metals) or configurations of the anode that can be either shifted in position relative to (e.g., in front of) the electron flow. Additionally, moving or angling the anode relative to the electrons (or vice versa) may result in different characteristics of the at least one applied high energy photon and/or particle 120. Certain embodiments of the X-ray fluorescence visualizer, imager, or information provider 100 can thereby be adjusted or controlled by shifting or steering the electron flow relative to the anode 834 such that the portion of the anode which the electron flow contacts may be made of multiple varied materials and/or configurations. Certain embodiments of the anode 834 can be configured in the shape of a wheel (e.g., to form an anode wheel) that when rotated can result in positioning of the desired metal in contact with the electron flow such as to provide control and/or adjustment of the at least one applied high energy photon and/or particle 120.

There can be a variety of additional components that can be applied to certain embodiments of the at least one high energy photon and/or particle emitter portion(s) 150 within certain embodiments of the X-ray fluorescence visualizer, imager, or information provider 100 as described with respect to FIGS. 13 and/or 14. Certain embodiments of the at least one high energy photon and/or particle emitter portion(s) 150 can further include a collimator or X-ray lens 842 that can focus, angle, or direct the photons emitted from the high energy photon and/or particle emitter portion(s) as desired. Certain embodiments of the X-ray lens or collimator 842 can be controllable such as to provide control of such X-ray fluorescence visualization, imaging, or information providing processes as high energy photon and/or particle emitter portion(s) directability, signal or image filtering, image zooming, starting, stopping, or pausing X-ray fluorescence visualization, imaging, or information providing, signal or image processing, etc.

Certain embodiments of the X-ray fluorescence visualizer, imager, or information provider 100 can utilize an optional vacuum (at least partially evacuated) portion 854, as described with respect to FIGS. 13 and/or 14, which can be utilized to limit contact of the electrons of the electron flow traveling from the cathode 832 to the anode 834 with extraneous gas, air, suspended solids, liquid, and/or other minute particles suspended in the air. As such, certain embodiments of the optional vacuum (at least partially evacuated) portion 854 can limit interaction of the photons with additional particles. Additionally, certain embodiments of the vacuum portion 854 may thereby be configured to at least partially limit combustion of certain of the electronic components contained therein as a result of the heat being generated upon the exposure to air. Certain embodiments of the vacuum (at least partially evacuated) portion 854 can thereby be configured as a vacuum tube, such as may be configured as an interlumenal X-ray source and is generally understood by those skilled in the X-ray tube technologies.

Certain embodiments of a capacitor 830 can optionally be arranged in an electronic circuit including the power source 836 and the cathode 832 as described with respect to FIG. 13. Certain embodiments of the cathode 832 can be configured with the capacitor 830 to store particular levels of electric voltage such as can be applied to the cathode 832, and subsequently released as desired as the electron flow via the electron emitter tip 850.

While this disclosure describes certain embodiments of the at least one high energy photon and/or particle emitter portion(s) 150, it is to be understood that any mechanism that can transmit X-rays whose frequency, energy level, or other characteristic can be controlled or adjusted may be used in certain embodiments of the X-ray fluorescence visualizer, imager, or information provider 100. The embodiments of the at least one high energy photon and/or particle emitter portion(s) 150 as described in this disclosure with respect to FIGS. 1, 2, 13, 14, as well as other locations in this disclosure, is intended to be illustrative in nature, but not limiting in scope. As mentioned in this disclosure, for example, certain embodiments of the at least one high energy photon and/or particle emitter portion(s) 150 could be at least partially replaced by an optical-generating portion as described with respect to FIG. 14. It is envisioned that the at least one high energy photon and/or particle emitter portion(s) 150 can thereby be configured slightly differently in operation and/or configurations, such as to generate photons in a different manner, but are still intended to be within the scope of the present disclosure as being within the claimed limitations. For example, the vacuum (evacuated) portion 854, such as a vacuum tube, may include one or more discrete emitter tip elements or one or more (carbon) nanotubes be configured as the electron emitter tip 850 as described with respect to FIG. 13.

Certain embodiments of the at least one high energy photon and/or particle emitter portion(s) 150 of the X-ray fluorescence visualizer, imager, or information provider 100, as described with respect to FIGS. 13 and 14, may therefore be adjustable and/or controllable such as by being configured for repositioning, angling, filtering, or some other suitable technique. For instance, certain embodiments of the X-ray fluorescence visualizer, imager, or information provider 100 can include a stepper motor such as may be configured such that it can pan and tilt, thereby providing some control and/or adjustment to emitted photons that can be emitted by the at least one high energy photon and/or particle emitter portion(s) 150. Such stepper motors may thereupon be considered to represent one illustrative embodiment of an adjustment or control portion that can also be accomplished by use of a photon lens or collimator 842.

Figure 27:
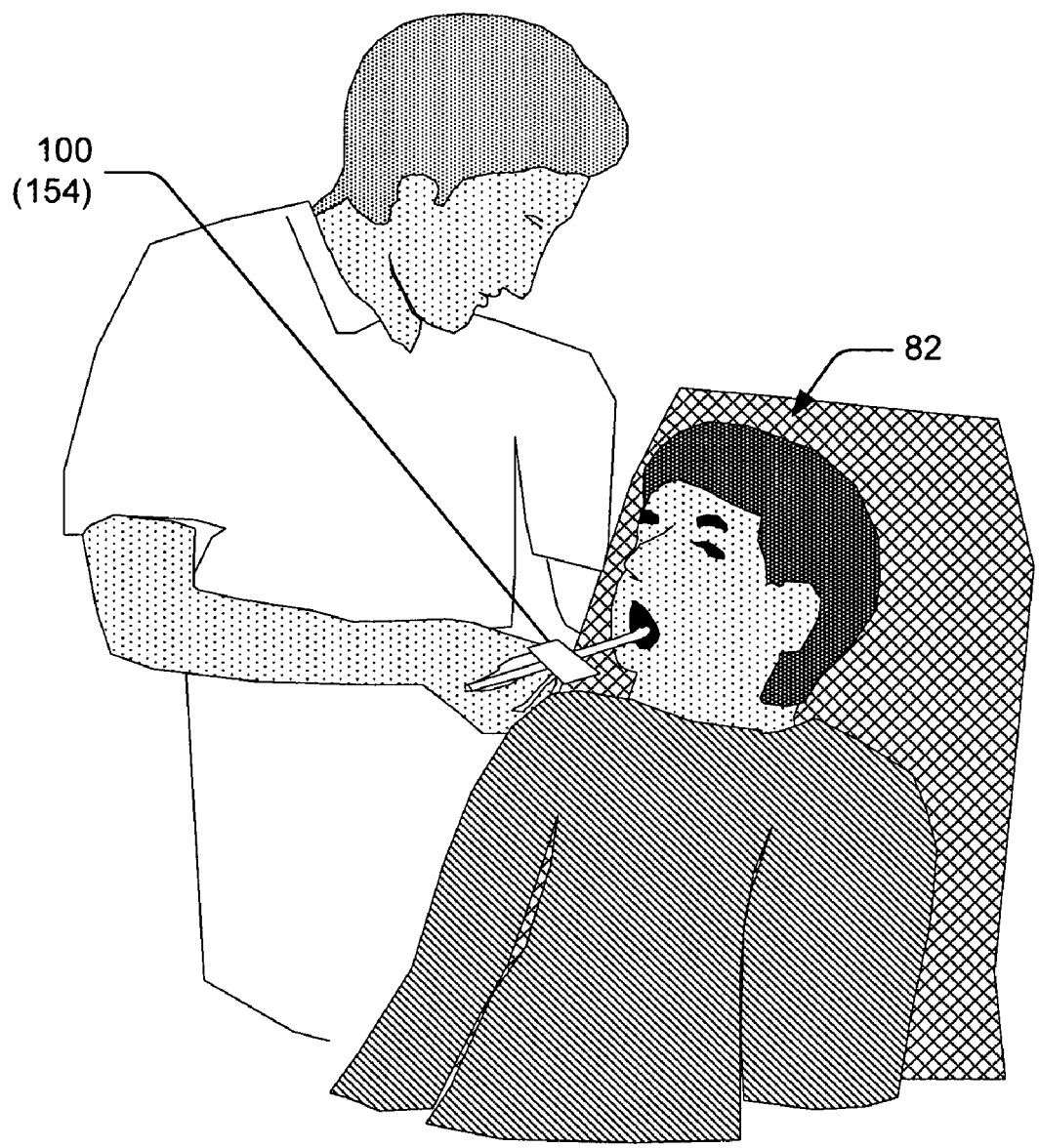
FIG. 27 is a diagram of an embodiment of the X-ray fluorescence visualizer, imager, or information provider as used by a dentist.

Certain embodiments or configurations of the X-ray fluorescence visualizer, imager, or information provider 100, as described with respect to FIG. 1 or 2, can X-ray fluorescence visualize, image, and/or provide information teeth, dental plates or surfaces 168, etc. based at least partially on the elements, chemicals, compounds, and/or biological materials of the matter; such as may be operated or used by dentists, oral hygienists, etc. as described with respect to FIG. 27. Certain embodiments of the X-ray fluorescence visualizer, imager, or information provider 100 can allow X-ray fluorescence visualization, imaging, or information providing of at least one tooth at one or more angles, positions, magnifications, etc. as desired. The particular display for the X-ray fluorescence visualizer, imager, or information provider 100 that may be selected may be based upon user preference, ease of use, design choice, etc. The embodiment of the X-ray fluorescence visualizer, imager, or information provider 100, as illustrated in FIG. 27, could be attached to a probe, for example. Similar user configurations of certain embodiments of the X-ray fluorescence visualizer, imager, or information provider 100 can be applied to tools being used by doctors, surgeons, veterinarians, as well as other users as described in this disclosure. As the X-ray fluorescence visualization, imaging, or information providing can be performed by certain embodiments of the X-ray fluorescence visualizer, imager, or information provider 100 from a number of different angles, positions, etc., it may be desired to display at least the display portion reflect the change in angle, position, etc.

The configuration of a display portion 154 of certain embodiments of the X-ray fluorescence visualizer, imager, or information provider may vary depending upon its use or user. For example, a dental embodiment of the X-ray fluorescence visualizer imager, or information provider is likely to have a smaller display (perhaps providing lesser dosage) than a full-body tomographic-type embodiment.

As the user/dentist, as illustrated in FIG. 27, moves or repositions the probe or drill, etc., it might be preferred to have the X-ray fluorescence visualizer, imager, or information provider 100 to adequately reflect the angle or position of the X-ray fluorescence visualization, imaging, or information providing. With sufficient changes of the angle, material of the anode, and/or position of the X-ray fluorescence visualization, imaging, or information providing, certain embodiments of the X-ray fluorescence visualizer, imager, or information provider 100 can derive and/or display a three-dimensional model of the one or more teeth. Certain embodiments of the X-ray fluorescence visualizer, imager, or information provider 100 can therefore provide information or images such as to determine where and/or how to treat the at least the portion of the individual (patient). Certain dental embodiments of the X-ray fluorescence visualizer, imager, or information provider 100 can be applied to a dental drill or other tool, and thereupon be displayed at a location and magnification such as can be made viewable and/or visible to the user such as to differentiate between types of matter based at least partially on the elements, chemicals, compounds, and/or biological materials of or in the matter. Certain embodiments of the X-ray fluorescence visualizer, imager, or information provider 100 that are operatively associated with certain tools, tactile providers, etc. need not be directly connected (or may be removably connected, to the tool, tactile provider, etc.

Certain of the images can also be provided to the patient as well using the same or other X-ray fluorescence visualizer, imager, or information provider 100. Certain embodiments of the X-ray fluorescence visualizer, imager, or information provider 100, when attached to a tool performing a desired operation, can act as a double check to ensure the tooth being imaged by the user is indeed the one that should be dealt with at least partially by viewing the actual condition as compared with the expected condition. For example, a dentist can check that the correct tooth is being drilled by, for example, ensuring a cavity be situated by X-ray fluorescence visualizing, imaging, or information providing in a tooth that is being considered to be drilled based at least partially on the density, elements, chemicals, compounds, and/or biological materials of the matter. A doctor can ensure the correct arm, leg, or other body part is being treated, etc. There can be a large variety of tools that may be used by such users as surgeons, assistants, veterinarians, dentists, etc. as generally understood to be used in each particular area. It is envisioned that certain embodiments of the X-ray fluorescence visualizer, imager, or information provider 100 may be applied to a variety of tools and/or tactile feedback devices that could benefit by use with X-ray fluorescence visualization, imaging, or information providing, as described in this disclosure.

The location of the drill or other tool including certain embodiments of the X-ray fluorescence visualizer, imager, or information provider 100 as taken relative to the decayed or damaged portions of the teeth can be detected on a substantially real-time, intermittent, or as desired basis. Certain embodiments of the X-ray fluorescence visualizer, imager, or information provider 100 can be configured to provide tactile feedback, which in the case of a dentists are dental assistant would be useful in determining the security of a tooth, the degree of tooth decay within a particular tooth, the security of braces, caps, filling, dental plates, or other device within the individual. By using certain dental X-ray fluorescence depth visualizing, imaging, or information providing embodiments of the X-ray fluorescence visualizer, imager, or information provider 100, it may not be necessary for dental patients to use conventional X-ray plates (positioned between the teeth of the person that has to be bitten down by the person) during dental X-rays thereby making dental visits more pleasant.

Such dental X-ray fluorescence depth visualizing, imaging, or information providing can be performed substantially parallel to or at some other angle relative to the tool operation, the path of drilling or cutting, or other tool parameter. As such, the user such as the dentist or dental hygienist can be provided an improved indication of where they are drilling or treating relative to damaged or decayed teeth. Certain embodiments the X-ray fluorescence visualizer, imager, or information provider 100 can be configured as clinic, emergency, or home-test kits, by which people could check the state of certain illness shows, sicknesses, injuries, painful or uncertain orthodontia, gum, dental, skin, or other conditions, etc. based at least partially on the density, elements, chemicals, compounds, and/or biological materials of the matter. The user can thereby be provided with considerable detail as to the condition of, or decay within the teeth from particularly desired angles.

Additionally, certain embodiments of the X-ray fluorescence visualizer, imager, or information provider 100 can allow X-ray fluorescence depth visualizing, imaging, or information providing of the gums, portion of teeth hidden by the gum, and other matter and portions within or close to the mouth that may be useful for dental use. Certain embodiments of the X-ray fluorescence visualizer, imager, or information provider 100 can X-ray fluorescence visualize, image, and/or provide information the relating to teeth, gums, tongue, blood vessels or pools, or other general aspects, etc. Certain dental embodiments of the X-ray fluorescence visualizer, imager, or information provider 100 can operate through the cheeks, and as such the X-ray fluorescence visualizer, imager, or information provider 100 can be situated either at partially external to, or at least partially internal of the at least the portion of the individuals mouth.

Certain embodiments of the X-ray fluorescence visualizer, imager, or information provider 100 can provide "freezing" or halting motion the state of certain X-ray fluorescence depth visualizations, images, and/or provided information as desired by the user or operator, or alternately as controlled by the X-ray fluorescence visualization, imaging, and/or information providing controller. Such freezing of the X-ray fluorescence depth visualizations, images, and/or provided information can include maintaining an image of the at least the portion of the individual displayed on the display portion 154 and/or the at least one X-ray fluorescence receiving portion(s) 151. Since generating new images may require an application of the at least one applied high energy photon and/or particle 120 to the at least the portion of the individual, it may be desired to limit such application of the at least one applied high energy photon and/or particle 120. As such, certain users can judiciously control the application of X-rays to the at least the portion of the individual, the user, and/or others in the vicinity during the X-ray fluorescence visualization, imaging, or information providing by certain embodiments of the X-ray fluorescence visualizer, imager, or information provider.

Certain dental or orthodontia embodiments of the X-ray fluorescence visualizer, imager, or information provider 100 of FIG. 27 can also be used to X-ray fluorescence visualize, image, or provide information relating to teeth of human individuals wearing braces. It is presently difficult, if not impossible, to accurately X-ray image teeth covered by brace bands, wires, etc. due to the distortions caused by the wires, bands, etc. Certain embodiments of the X-ray fluorescence visualizer, imager, or information provider 100 can provide visualize, image, or provide information based on such elements, chemicals, compounds, and/or biological materials that differ from those present in the braces, wires, etc., and can therein limit the effect of the braces, wires, fillings, pins, etc. Certain embodiments of the X-ray fluorescence visualizer, imager, or information provider 100 can provide visualize, image, or provide information using such accuracy and limited spatial scope of X-ray fluorescence visualization, imaging, or information providing, as to allow X-ray fluorescence visualization, imaging, or information providing from a single uncovered face of a tooth (e.g., biting surface). As such, certain teeth covered by braces, bands, etc can be X-ray fluorescence visualized, imaged, or have information provided thereto, potentially from a variety of controllable and/or adjustable angles, positions, etc., during orthodontia treatment that can thereby enhance the dental health of the patient during the treatment. Teeth, dental surfaces, fillings, etc. can be X-ray fluorescence visualized, imaged, or have information provided from a variety of angles, positions, etc. based at least partially on the elements, chemicals, compounds, and/or biological materials such as to provide an improved indication of their configuration, solidity, dental health, etc. The amount of, and reliability of, dental treatment that can be performed based at least in part on X-rays can thereby be increased during orthodontia treatment.

While this disclosure have described certain embodiments of the X-ray fluorescence visualizer, imager, or information provider 100 as being substantially externally-applied devices, it should also be understood that certain embodiments of the X-ray fluorescence visualizer, imager, or information provider can be an at least partially internal device. Such at least partially internal devices can be applied to within the at least the portion of the individual using a scope, a needle, through an incision, via a normally open opening, and/or via a normally closed opening. Certain embodiments of the X-ray fluorescence visualizer, imager, or information provider 100 can therefore be integrated at least partially a scope devices such as an endoscope embodiments of the X-ray fluorescence visualizer, imager, or information provider 100, as described with respect to FIG. 28. Such scope-based embodiments could be applied via normally open openings, incisions, punctures, etc. to the interior of the at least the portion of the individual.

Figure 28:
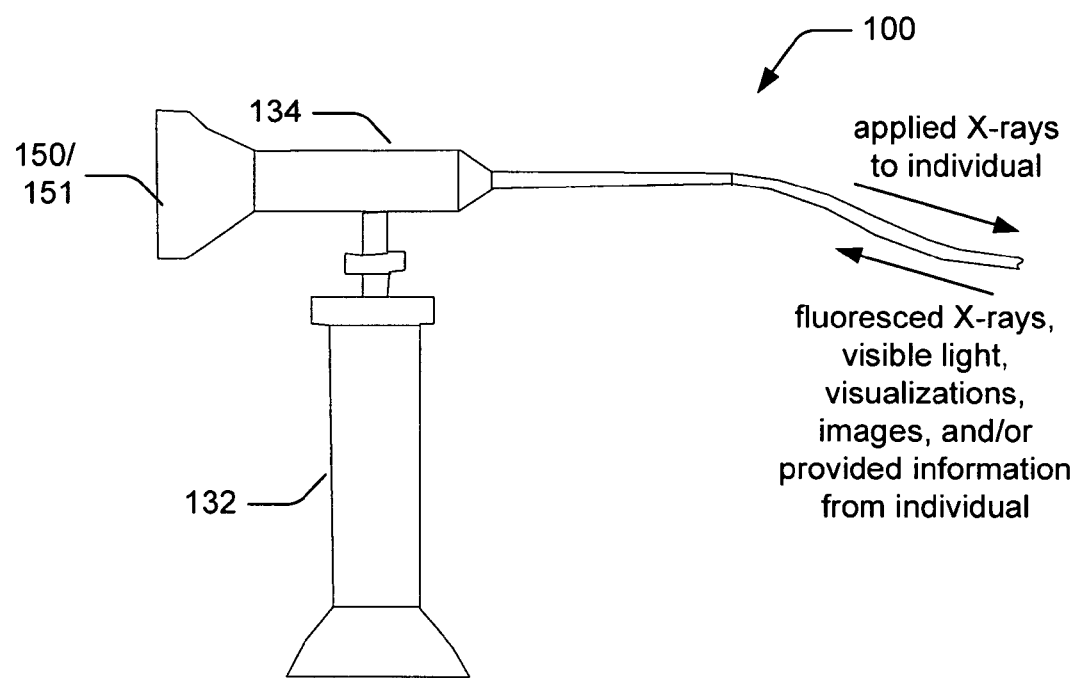
FIG. 28 is a diagram of an internal embodiment (e.g., endoscope-based) of the X-ray fluorescence visualizer, imager, or information provider.

Certain endoscope embodiment of the X-ray fluorescence visualizer, imager, or information provider 100, as illustrated in FIG. 28, can include a scope portion 134 or an illumination portion 136, whose operation and structure is generally understood to those skilled in the scope arts. The illumination portion 134 could be used to provide the at least one applied high energy photon and/or particle 120 as described elsewhere to the individual, which thereupon can fluoresce. Certain endoscope embodiments of the X-ray fluorescence visualizer, imager, or information provider 100 can thereupon be configured to receive the X-ray fluorescence high energy (e.g., X-ray, gamma ray, photon, particle, etc.), viewable and/or visible light, X-ray fluorescence visualization, image, or provided information from the individual.

The scope embodiments of the X-ray fluorescence visualizer, imager, or information provider 100 can include a variety of the at least one X-ray fluorescence receiving portion(s) 151. Certain embodiments of the at least one X-ray fluorescence receiving portion(s) 151 can include a scintillator (and/or fluoroscope), perhaps with a photomultiplier as described in this disclosure to amplify a relatively weak viewable and/or visible-light output. Certain embodiments of the at least one X-ray fluorescence receiving portion(s) 151 can include a fluoroscope as generally known in the art which may operate in certain ways similar to the scintillator (and/or fluoroscope). Certain embodiments of the at least one X-ray fluorescence receiving portion(s) 151 can include a detector portion in combination with a display portion as described with respect to FIG. 1 or 2 in this disclosure. Certain embodiments of the X-ray fluorescence visualizer, imager, or information provider 100 can be at least partially adapted with, or at least partially configured to act as, a variety of tools. Such tools can include, but are not limited to: a Bovie electrocautery device as generally understood in the art, an ablator, a cutter, a scalpel, a saw, a tactile feedback provider, a contact-type probe, a dental drill, a probe, a material adder, a material remover, etc.

Certain embodiments of the X-ray fluorescence visualizer, imager, or information provider 100 may be configured as being attached a scope, tube, catheter, or other instrument or tool that can be configured to be inserted into the at least the portion of the individual to act as an at least partially internal device. For example, certain endoscope embodiments of the X-ray fluorescence visualizer, imager, or information provider can be configured as described with respect to FIG. 28. Certain configurations of the X-ray fluorescence visualizer, imager, or information provider 100 may be provided with the high energy photon and/or particle emitter portion(s) being situated relative to an endoscope via a surgical implant, and thereby may be similar to other embodiments of the X-ray fluorescence visualizer, imager, or information provider in certain ways, but with the high energy photon and/or particle emitter portion(s) placed inside the individual.

Certain scope-based embodiments of the at least one high energy photon and/or particle emitter portion(s) 150, as described with respect to FIG. 28, may be largely applied to an internal portion of the individual such as to include an interluminal X-ray source; while other embodiments of the high energy photon and/or particle emitter portion(s) may be applied to an external portion of the individual. Certain embodiments of the at least one high energy photon and/or particle emitter portion(s) 150 may be powered by a variety of power sources (traditional or non-conventional) including, but not limited to, solar cells, batteries, power sources, etc. that may include traditional or untraditional power sources. For example, the high energy photon and/or particle emitter portion(s) may be fed by one or more optical fibers, for example to power the at least one high energy photon and/or particle emitter portion(s) 150, the at least one detector portion 152, and/or the at least one display portion 154. Certain optically fed embodiments of the at least one high energy photon and/or particle emitter portion(s) 150 may also include automated shutdown or other safety aspects relating to emission of X-ray based electromagnetic radiation. Certain embodiments of the at least one high energy photon and/or particle emitter portion(s) 150 may be implanted within the at least the portion of the individual such as to allow X-ray fluorescence visualization, imaging, or information providing (using certain embodiments of the at least one X-ray fluorescence receiving portion(s) 151) on a more continuous basis. Such implants of at least portions of the X-ray fluorescence visualizer, imager, or information provider 100 can be particularly useful for difficult to access portions of the body, such as the heart, brain, or certain other organs or regions of the body, etc.

Certain embodiments of the X-ray fluorescence visualizer, imager, or information provider 100 can be configured to control X-ray generation and/or direction at least partially by accelerating or directing electrons for X-ray production. Such directing the electrons can effectively reduce X-ray path length, and hence limit multiple fluorescing events. Certain embodiments of the at least one high energy photon and/or particle emitter portion(s) 150, and/or at least one detector portion 152 can be configured such as by being placed by a scope or other such device in a normally open opening, normally closed opening, or other lumen, such as colon, esophagus, mouth, throat, stomach, blood vessels, lungs, gut, etc.

Certain embodiments of the X-ray fluorescence visualizer, imager, or information provider 100 can also be applied to cranial, brain, or spinal X-ray fluorescence depth visualizing, imaging, or information providing. It may be difficult to X-ray fluorescence visualize, image, and/or provide information within the skull using certain conventional imaging modalities, as a result of deflections of certain electromagnetic radiation within the interior (e.g., substantially concave) surface 168 of the skull and the associated distortions. Certain embodiments of the X-ray fluorescence visualizer, imager, or information provider 100 can be configured to access the brain via such openings in the skull as the ear sockets, mouth opening, and/or sinuses. Such X-ray fluorescence visualization, imaging, or information providing of the brain through such key-hole opening should experience relatively limited X-ray fluorescence visualization, imaging, or information providing distortion, as compared with X-ray fluorescence visualization, imaging, or information providing at least partially through the skull, bony matter, or other such X-ray distorting or shielding regions.

Certain embodiments of the X-ray fluorescence visualizer, imager, or information provider 100 can be configured to be applied to relatively small regions of the body, and thereby apply relatively small overall dosages of X-rays. Certain embodiments of the X-ray fluorescence visualization, imaging, or information providing can be controllably or adjustably applied in small regions, from different angles, etc., than certain conventional full-scale X-ray or certain conventional tomography imagers.

For instance, certain X-ray tomography-type X-ray fluorescence visualization, imaging, or information providing imagers can capture a X-ray fluorescence visualization, image, or provide information by scanning a series of scans relatively shallow into the at least some matter of the at least one portion of the individual from a variety of angles and/or positions. Such scanning can be performed using a variety of respective the at least one applied high energy photon and/or particle 120 and/or X-ray fluorescence high energy (e.g., X-ray, gamma ray, photon, particle, etc.) that can be respectively applied/received using respective arrays of at least one high energy photon and/or particle emitter portion(s) 150 or at least one X-ray fluorescence receiving portion(s) 151; or alternately one or more of the respective high energy photon and/or particle emitter portion(s) and/or the at least one X-ray fluorescence receiving portion(s) 151 that can be moved, scanned, angled, or otherwise repositioned. For instance, the certain array embodiments of the at least one high energy photon and/or particle emitter portion(s) 150 or at least one X-ray fluorescence receiving portion(s) 151 can be configured to roughly conform to the general shape of the portion of the individual being imaged, or alternately in some other configuration. As the distinct elements of the at least one high energy photon and/or particle emitter portion(s) 150 are actuated to provide the at least one applied high energy photon and/or particle 120, then the corresponding embodiment of the at least one X-ray fluorescence receiving portion(s) 151 can collect the data corresponding to the X-ray fluorescence visualization, image, or provided information for each element(s) of the high energy photon and/or particle emitter portion(s) including some unknowns relating to particular X-ray fluorescence visualization, imaging, or information providing limitations. As a number of the distinct element(s) of the at least one high energy photon and/or particle emitter portion(s) 150 that direct the at least one applied high energy photon and/or particle 120 under different directions, positions, energy levels, or other conditions decreases, the number of unknowns relating to particular X-ray fluorescence visualization, imaging, or information providing limitations for at least some matter of the at least the portion of the individual correspondingly decreases, and a more complete and accurate X-ray fluorescence visualization, image, or provided information can be obtained using tomographic techniques.

A similar tomographic technique or embodiment of the of the X-ray fluorescence visualizer, imager, or information provider 100 can be applied to directing at least one high energy photon and/or particle emitter portion(s) 150 or at least one X-ray fluorescence receiving portion(s) 151 at different positions, angles, energy levels, etc. Such techniques can involve physically repositioning and/or angling of the at least one high energy photon and/or particle emitter portion(s) 150 and/or the at least one X-ray fluorescence receiving portion(s) 151 itself/themselves such as to follow a scan, circular motion around the at least the portion of the individual, or other type of translation, angling, repositioning, changing of energy levels, etc. Alternately, a redirecting device of the at least one applied high energy photon and/or particle 120 or X-ray fluorescence can be used, such as a filter, lens, modulator, shield, collimator, endoscope or other bendable, movable, or twistable scope or other high energy photon and/or particle emitter portion(s) could be used in different embodiments, as described in this disclosure.

Certain embodiments of the X-ray fluorescence visualizer, imager, or information provider 100 can, by using relatively low energy version of the at least one applied high energy photon and/or particle 120, provide a relatively low-power version of the at least one applied high energy photon and/or particle 120 which can be highly suited for intracranial X-ray fluorescence visualization, imaging, or information providing and examination or other radiation-sensitive regions of the human or other individual. The power of the at least one applied high energy photon and/or particle radiation 120 may generally be configured or set at a level to be insufficient to penetrate, in large numbers, to another region that may not be X-ray fluorescence depth visualized, imaged, or information provided. Such would be the case of brain X-ray fluorescence depth visualizing, imaging, or information providing to limit transmission of excessive doses of such high-energy photons as X-rays, gamma rays, etc. to the cranium, brain, brainstem, embryo, or other such the region, etc.

Certain embodiments of the X-ray fluorescence visualizer, imager, or information provider 100 can therefore be configured to X-ray fluorescence visualize, image, and/or provide information in the brain, or other intracranial tissue. Certain embodiments of the X-ray fluorescence visualizer, imager, or information provider 100 could operate with relatively high resolution, or alternately with lower resolution as desired or designed compared to other imaging modalities that may be similar in resolution and certain other aspects to that of conventional MRI. Certain embodiments of the X-ray fluorescence visualizer, imager, or information provider 100 that can visualize, image, or provide information based at least partially on the elements, chemicals, compounds, and/or biological materials of or in the matter of the at least the portion of the individual may provide for a richer or more indicative visualization, image, or provided information. Certain embodiments of the at least one high energy photon and/or particle emitter portion(s) 150 can thereby be configured to use mono-energetic, collimated, or other sources. When using at least partially internal (e.g., in-body) embodiments of the at least one high energy photon and/or particle emitter portion(s) 150, it may be possible to increase X-ray capture fraction by having multiple in-body detector portions 152, not just a single detector portion associated with the high energy photon and/or particle emitter portion. With the different embodiments of the X-ray fluorescence visualizer, imager, or information provider 100, it is likely to be desired to limit dosages of X-rays as applied to the at least the portion of the individual 82 and/or the user (e.g., physician, dentist, veterinarian, assistant, researcher, etc.).

A variety of embodiments of the at least one detector portion 152 can be associated with the X-ray fluorescence visualizer, imager, or information provider 100 as described at various locations in this disclosure. Certain embodiments of the at least one detector portion 152 may be considered as functionally associated with the at least one display portion 154, since the at least one display portion may be configured to display a version (which may be resized, filtered, scanned, computed, and/or otherwise modified) of what was detected by the at least one detector portion.

Certain embodiments of the at least one detector portion 152 and/or the at least one X-ray fluorescence receiving portion(s) 151, as included in certain embodiments of the X-ray fluorescence visualizer, imager, or information provider 100, can be configured of various sizes, shapes, configurations, and may include a single detector portion or an array of detector portion elements. For example, those embodiments of the at least one X-ray fluorescence receiving portion(s) 151 utilizing a distinct detector portion 152 and 154 as described with respect to FIG. 23 differ from those scintillator (and/or fluoroscope) embodiments of the X-ray fluorescence receiving assembly utilizing a combined detector and display portion as described with respect to FIG. 25. The dimensions of each detector portion element and/or the at least one X-ray fluorescence receiving portion(s) 151 can be selected based on such criteria as the desired application, usage, and/or the desired or designed X-ray fluorescence visualization, imaging, or information providing resolution.

A variety of X-ray fluorescence depth visualizations, images, and/or provided information including, but not limited to, tomography X-ray fluorescence depth visualizations, images, and/or provided information can be constructed by scanning the X-ray radiation received at the at least one detector portion 152 over a volume of interest of the at least the portion of the individual 82. As such, the at least one detector portion 152 may be considered as detecting the X-ray fluorescence rays, with time-of-flight, spectral, and/or spatial resolution of the X-ray fluorescences or other electromagnetic radiation. Specific X-ray energies can be used by the at least one detector portion to detect spectral features (e.g., absorption edges or X-ray fluorescence spectra) of specific X-rays received (e.g., X-ray fluorescence) from particular ones of the at least the portion of the individual 82. The targeted portion of the individual can be at least partially endogenous, such as being produced from within the at least the portion of the individual (such as iron in blood, or calcium in tumors). Alternately, the targeted portion can be at least partially exogenous such as being produced outside of the at least the portion of the individual (e.g., high-Z contrast agents that migrate, bind, or are otherwise introduced into regions of interest). The emitted flux, energy level, or frequency of each X-ray photon can be tuned as to detect particular structures, organs, materials, etc. at certain depths and/or regions, as being detected by the at least one detector portion 152.

Certain embodiments of the X-ray fluorescence visualizer, imager, or information provider can thereby capture a series of X-ray fluorescence depth visualizations, images, and/or provided information, in which the at least one high energy photon and/or particle emitter portion(s) and/or the at least one detector portion can operate sequentially utilizing feedback by the user and/or X-ray fluorescence visualization, imaging, or information providing controller 97. Such control and subsequent feedback can be used as to alter and/or control the relative position, angle, magnification, or other aspect of the subsequent X-ray fluorescence depth visualizations, images, and/or provided information. The initial X-ray fluorescence depth visualizations, images, and/or provided information that have been captured can thereupon be displayed to the user at least partially using the at least one display portion 154 and/or the at least one X-ray fluorescence receiving portion(s) 151. The location, magnification, angle, and/or other characteristics of the subsequent X-ray fluorescence depth visualizations, images, and/or provided information can be determined, at least in part, from the results of the prior X-ray fluorescence depth visualizations, images, and/or provided information based at least partially on user input.

By allowing capturing of sequentially adjustable X-ray fluorescence depth visualizations, images, and/or provided information, the users and/or individuals can observe the at least the portion of the individual 82 as they may desire. As such, the X-ray fluorescence depth visualizing, imaging, or information providing being performed by the X-ray fluorescence visualizer, imager, or information provider 100 can be adjusted and/or controlled. Consider that with certain embodiments of the X-ray fluorescence visualizer, imager, or information provider 100, a user such as a physician, dentist, technician, assistant, etc. can obtain some preliminary X-ray fluorescence depth visualizations, images, and/or provided information from certain embodiments of the X-ray fluorescence visualizer, imager, or information provider to locate a desired examining feature. Thereupon, the X-ray fluorescence depth visualizing, imaging, or information providing can be adjusted in subsequent images such as more closely or more accurately scan or examine at a desired location, angle, etc., such as to scan or examine for a cancerous growth, abscesses, infections, etc.

Alternately, the user can use some embodiments of the X-ray fluorescence visualizer, imager, or information provider to locate a desired organ or the at least the portion of the individual 82. Thereupon, the X-ray fluorescence visualization, imaging, or information providing as performed by certain embodiments of the X-ray fluorescence visualizer, imager, or information provider 100 can be modified, altered, repositioned, magnified, etc. such as to more closely or more accurately examine some aspect of the desired examining feature at a variety of angles, positions, magnifications, etc. Each one of the respective at least one high energy photon and/or particle emitter portion(s) 150, at least one detector portion 152, at least one display portion 154, and/or the at least one combined detector/display portion 155 (e.g., scintillator and/or fluoroscope), can be respectively fabricated and/or respectively formed.

Certain embodiments of the X-ray fluorescence visualizer, imager, or information provider 100, as described at a variety of locations through this disclosure, may alternately be scintillator-based and/or fluoroscope-based. Certain embodiments of the X-ray fluorescence visualizer, imager, or information provider 100 may allow feedback techniques to allow users and/or X-ray fluorescence visualization, imaging, or information providing controller 97. Such feedback techniques may alter and/or control X-ray fluorescence visualization, imaging, or information providing of subsequent X-ray fluorescence depth visualizations, images, and/or provided information based at least in part on results or user input based on prior captured X-ray fluorescence visualization, imaging, or information providing. Certain embodiments of the at least one X-ray fluorescence receiving portion(s) 151, including the at least one display portion 154 as combined with the at least one detector portion 152, can therefore be configured as a scintillator and/or fluoroscope, as described with respect to FIG. 25. With scintillator or fluoroscope embodiments of the X-ray fluorescence receiving assembly, X-ray photons can be converted to viewable and/or visible photons as described with respect to this disclosure.

Certain embodiments of the scintillators or fluoroscopes can be configured including a substance that can absorb such electromagnetic radiation as X-rays, and thereupon can fluoresce, or otherwise provide such as by X-ray fluorescence or other imaging mechanism, viewable and/or visible light (viewable and/or visible photons) at a characteristic X-ray frequency or energy level depending upon the received X-ray radiation. The fluorescing of the viewable and/or visible light may, as generally understood by those skilled in the art, be viewed as releasing induced X-ray fluorescing photon 122 generated at least partially from the previously absorbed energy associated with previously absorbed applied high energy photon and/or particle 120.

Certain embodiments of the at least one X-ray fluorescence receiving portion(s) 151 of the X-ray fluorescence visualizer, imager, or information provider 100 can therefore be configured to include scintillators and/or fluoroscopes can convert the X-ray fluorescence high energy (e.g., X-ray, gamma ray, photon, particle, etc.) directly to viewable and/or visible light, without associated detectors and displays associated with certain embodiments of the at least one X-ray fluorescence receiving portion(s) 151. Certain configurations of conventional scintillators or fluoroscopes can be configured as optical detectors, displays, X-ray fluorescence visualization, imaging, or information providing, etc. such as described with respect to U.S. Pat. No. 7,057,187 to Yun et al., entitled Scintillator Optical System and Method of Manufacture (incorporated herein by reference in its entirety). Certain embodiments of scintillator can be used for medical X-ray fluorescence depth visualizing, imaging, or information providing as described with respect to U.S. Pat. No. 6,895,077 to Karellas et al., entitled System and Method for X-Ray Fluoroscopic Imaging (incorporated herein by reference in its entirety). Certain conventional CAT scanners may utilize scintillator technology.

It is likely that the scintillator (and/or fluoroscope) embodiments of the X-ray fluorescence visualizer, imager, or information provider 100 might be useful in screening the at least the portion of the individual, perhaps at shallow prescribed substantial X-ray fluorescence depths and/or for homogeneous matter (using X-ray fluorescence, or fluoroscopy techniques), for matter or skin aberrations, such as cancers, tumors, abscesses, infections, lesions, etc. As such, the user might scan the users for such aberrations that might occur near the surface 168, and the image processing associated with X-ray fluorescence depth visualizing, imaging, or information providing such aberration with particular concern about processing X-ray fluorescences at different prescribed substantial X-ray fluorescence depth being limited.

Certain scintillator (and/or fluoroscope) embodiments of the X-ray fluorescence visualizer, imager, or information provider 100 may be characterized in this disclosure by the characteristics of their viewable and/or visible photonic output. The characteristics of their viewable and/or visible photonic output can include, but are not limited to, e.g., strength, energy level, and/or frequency of emitted viewable and/or visible photons as a function of absorbed X-ray electromagnetic radiation, X-ray fluorescence decay times, and/or optical transparency at wavelengths of their emitted viewable and/or visible electromagnetic radiation and/or other such factors. Scintillators (and/or fluoroscopes) may thereby be considered as operating by translating X-ray electromagnetic radiation into viewable and/or visible light electromagnetic radiation. As such, at least certain X-rays detected by the at least one detector portion 152 may be viewed by the user (or individual) without the necessity of at least one distinct display portion(s) 154.

The lower the decay time of certain embodiments of the scintillator and/or fluoroscopes (i.e., the shorter the duration of its flashes of X-ray fluorescence), the less so-called "dead time" or delay the detector portion will have and the more ionizing events per unit of time it will be able to detect. The excited atoms can thereupon lose some of this excess energy resulting from the dead time by emitting some viewable and/or visible photons. The amount of viewable and/or visible light produced by the scintillator and/or fluoroscope (and thereby the intensity of viewable and/or visible light output by the display portion) can, in certain embodiments, be amplified by a "photomultiplier" that is operationally included in the scintillator and/or fluoroscope. Certain embodiments of the scintillator and/or fluoroscope of the X-ray fluorescence visualizer, imager, or information provider 100, as described in this disclosure with respect to FIG. 25, can include the at least one X-ray fluorescence receiving portion(s) 151 including a combined detector portion 152 and/or display portion 154. Such combined embodiments of the at least one X-ray fluorescence receiving portion(s) 151 can X-ray fluorescence visualize, image, and/or provide information based at least in part on the received photons X-ray fluorescence off the at least the portion of the individual.

The scintillator-based and/or fluoroscope-based embodiments of the X-ray fluorescence visualizer, imager, or information provider 100 can be useful to provide real-time or near real time X-ray fluorescence visualization, imaging, or information providing of the at least the portion of the individual. Additionally, certain scintillator-based and/or fluoroscope-based embodiments of the X-ray fluorescence visualizer, imager, or information provider 100 can be configured to be adjusted to alter subsequent X-ray fluorescence visualization, imaging, or information providing based on user or controller feedback, or other such aspects. For example, a region that is being X-ray fluorescence visualized, imaged, or have information provided can be modified, angled, magnified, filtered, etc. such as to provide closer examination or X-ray fluorescence visualization, imaging, or information providing. Certain "scintillator" and/or fluoroscope embodiments of X-ray fluorescence visualizer, imager, or information provider 100 can be computationally intensive, while other embodiments can view the image directly. By angling the emission of the at least one applied high energy photon and/or particle 120 by the at least one high energy photon and/or particle emitter portion(s) 150, the reception of the X-ray fluorescence high energy (e.g., X-ray, gamma ray, photon, particle, etc.) by the at least one X-ray fluorescence receiving portion(s) 151 and/or the at least one X-ray fluorescence receiving portion(s) 151, certain ambiguity as to the shape or configurations or aberrations, junctions, dissimilarities, etc. of the matter can be determined. Such angling, etc. can be provided either visually by the user, or by using image process techniques by the X-ray fluorescence visualization, imaging, or information providing controller 97.

Certain scintillator and/or fluoroscope embodiments of the X-ray fluorescence visualizer, imager, or information provider 100 can utilize such optical processing "downstream" of the scintillator to limit distortion effects, etc. Examples of such "optical" signal processing techniques can include filtering, amplifications, distortion limiting, optical signal processing, optical image processing, etc.

Certain scintillator and/or fluoroscope embodiments of the X-ray fluorescence visualizer, imager, or information provider 100 can thereby be fabricated from, and therefore include, certain materials which can "convert" an X-ray photon to a viewable and/or visible photon. Certain embodiments of scintillators and/or fluoroscopes can additionally amplify a relatively weak photonic X-ray signal such as by utilizing a photomultiplier (typically for each scintillator and/or fluoroscope element). One advantage of amplifying a relatively weak photonic signal is that an adequate X-ray fluorescence depth visualization, image, or provided information can be obtained while subjecting the patient to a much lower dose of X-rays. Certain embodiments of Charge Coupled Devices (CCDs) may be associated with certain embodiments of the at least one detector portion 152 and/or the at least one X-ray fluorescence receiving portion(s) 151. Such embodiments of the at least one X-ray fluorescence receiving portion(s) 151 may be referred to in this disclosure as scintillators, fluoroscopes, film screens, or scintillation counters. Certain embodiments of scintillators and/or fluoroscopes may thereby be considered as direct semiconductor detector portions since they may not be largely computational-based to derive X-ray fluorescence depth visualizations, images, and/or provided information. Certain embodiments of scintillators and/or fluoroscopes can be generated using signal amplification or computer amplification techniques.

Certain exemplary embodiments of scintillators and/or fluoroscopes may be configured as semiconductor detector portions 152, which may be based on converting X-ray photons to electron-hole pairs in the semiconductor, and the electron-hole pairs are thereupon obtained to detect the X-rays. It may be is possible to directly determine the X-ray energy spectrum using so-called called energy dispersive X-ray spectroscopy; and such techniques may additionally be used in small X-ray fluorescence spectrometers. These detector portions are sometimes called "solid detectors". Medical X-ray fluorescence visualization, imaging, or information providing applications using scintillators and/or fluoroscopes that can rely on the concept that certain semiconductor diodes will thereby produce a small amount of current when placed in an X-ray radiation.

Certain types of silicon drift detectors (SDDs), such as may be produced by semiconductor fabrication, can provide a relatively high resolving X-ray radiation detection measurement, and thereby be useful for certain embodiments of the at least one X-ray fluorescence receiving portion(s) 151. Certain scintillators and/or fluoroscopes, when combined with semiconductor detectors, can provide indirect detection of X-ray radiation. With the advent of large semiconductor array detectors it has become possible to design detector systems using a scintillator and/or fluoroscope screen to convert from X-rays to viewable and/or visible light which is then converted to electrical signals in an array detector, such as may be used to provide visibility to the human eye. Such signal processing and image processing techniques as filtering, amplifying, resizing, etc. can be applied to scintillator-based and/or fluoroscope-based embodiments of the X-ray fluorescence visualizer, imager, or information provider 100, such as to improve X-ray fluorescence visualization, imaging, or information providing.

Certain embodiments of the at least one high energy photon and/or particle emitter portion(s) 150 can be dispersive such as to apply X-ray based electromagnetic radiation at the at least the portion of the individual 82; such as may thereupon be detected by certain embodiments of the at least one detector portion 152. As such, certain portions of the X-ray fluorescence visualizer, imager, or information provider 100 can be associated with or include the at least one high energy photon and/or particle emitter portion(s) 150; while certain embodiments of the X-ray fluorescence visualizer, imager, or information provider 100 can be associated with or include the at least one detector portion 152.

Certain embodiments of the X-ray fluorescence visualizer, imager, or information provider 100 can therefore X-ray fluorescence visualize, image, and/or provide information relating to the at least the portion of the individual that is physically separated from the surface 168 of the at least the portion of the individual. Such X-ray fluorescence visualization, imaging, or information providing can rely on image combination (e.g., image subtraction, time of flight, image transformation, deconvolution, image subtraction, weighted subtraction, functional subtraction, and group including inverse integral transform, subtractive inverse integral transform, inverse functional transform, and subtractive inverse functional transform, or other such image processing techniques). The quality of such X-ray fluorescence visualization, imaging, or information providing can improve if the matter being imaged becomes more consistent across the thickness of the imaged portion 352 (e.g., horizontally across the thickness 352 as shown in FIG. 20). As such, as the thickness 352 of the at least one prescribed substantial X-ray fluorescence depth becomes thinner, and its consistency across the thickness becomes more uniform, its X-ray fluorescence depth visualizing, imaging, or information providing consistency generally increases and the associated quality and/or reliability of the X-ray fluorescence visualizing, imaging, or information providing quality generally increases.

Selection or control of a desirable or suitable thickness to X-ray fluorescence visualize, image, of provide information relating to particular matter (e.g., tissue, bones, teeth, etc.) within a particular type of individual may depend, at least in part, on empirical results. For example, scanning skin, muscle, or other tissue across, may be performed in relatively thick X-ray fluorescence visualizing, imaging, or information providing slices as compared with X-ray fluorescence depth visualizing, imaging, or information providing bone parts, nodules, or other matter that has a considerable amount of void space or may be inconsistent across its imaged thickness based at least partially on at least one element of the matter of the at least the portion of the individual. Suitable data, information, X-ray fluorescence visualizations, images, etc. pertaining at least partially to X-ray fluorescence visualization, imaging, or information providing of certain types of matter can be stored in the X-ray fluorescence visualization, imaging, and/or information providing controller 97 (e.g., in a memory, database, or other suitable location), as described with respect to FIG. 1 or 2. Or alternately, the X-ray fluorescence visualization, imaging, or provided information can be provided as a written reference to the users and/or operators of the X-ray fluorescence visualizer, imager, or information provider 100, such as could be accessed and/or set by the user and/or operator.

Figure 29:
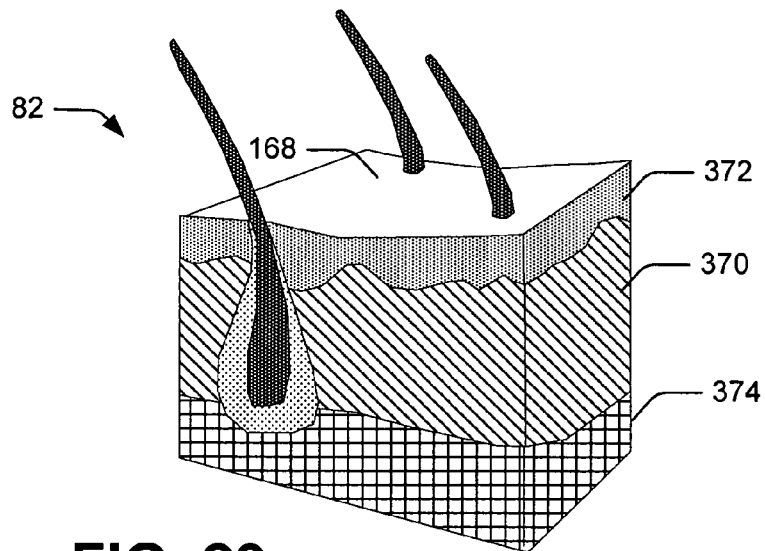
FIG. 29 is a partial cross-section of certain skin and sub-surface layers of an individual (e.g., human) that can be X-ray fluorescence visualized, imaged, or have information provided.
Figure 30:
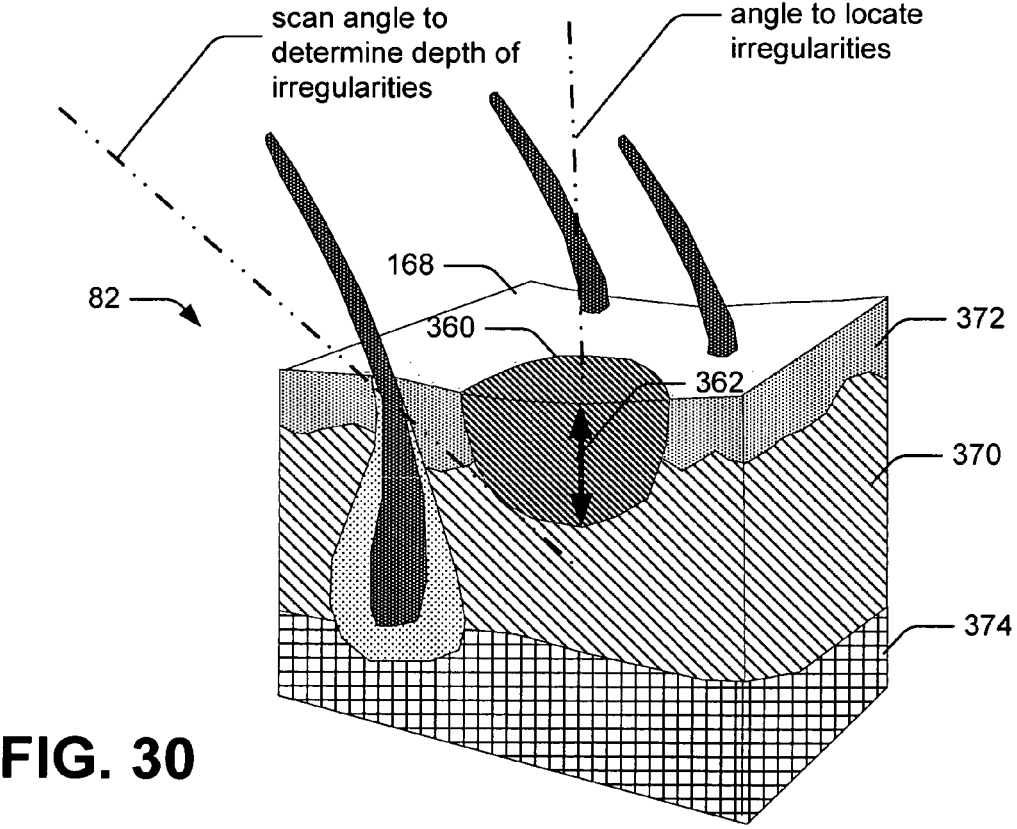
FIG. 30 is a partial cross-section of certain skin and sub-surface layers of the individual including a skin aberration (e.g., a melanoma)

There may be a variety of surgical applications of certain embodiments of the X-ray fluorescence visualizer, imager, or information provider 100 that are now described with respect to FIGS. 29 and 30. The particular suitable applications for certain embodiments of the X-ray fluorescence visualizer, imager, or information provider 100 may be dependent upon the frequency, energy, or other characteristics of the at least one applied high energy photon and/or particle 120, as well as the energy level and frequency of the at least one applied high energy photon and/or particle 120 can be used for the X-ray fluorescence visualization, imaging, or information providing. Certain embodiments of the X-ray fluorescence visualizer, imager, or information provider 100, for example, can be particularly suited or configured for treatment and/or examination near the surface 168 such as skin of the at least the portion of the individual 82, with normal skin being illustrated in FIG. 29. By comparison, certain embodiments of the X-ray fluorescence visualizer, imager, or information provider 100 can be particularly suited or configured for treatment and/or examination of at least a portion of the individual; even if the portion of the matter being X-ray fluorescence visualized, imaged, or information provided is spaced a considerable depth distance from a surface into matter of the individual 82 (as illustrated in FIGS. 23 and 25). This may be the case for treating person wishing to examine or locate a particular individual's organ(s), bone(s), and/or other regions that may be situated subsurface utilizing the at least one X-ray fluorescence range to the at least one prescribed substantial X-ray fluorescence depth from the surface 168.

For example, certain X-ray fluorescence visualizer, imager, or information provider 100 can be utilized to X-ray fluorescence visualize, image, or provide information relating to some matter aberrations, such as to a tumor, abscess, tissue contour, etc. (such as may be useful to resect the X-ray fluorescence visualized, imaged, or information provided aberration). Certain embodiments of the X-ray fluorescence visualizer, imager, or information provider 100 can be configured to control or adjust the at least one X-ray fluorescence range to the at least one prescribed substantial X-ray fluorescence depth during resection of a tumor or aberrative matter. This may be accomplished by varying the energy level, frequency, or other characteristics of the at least one applied high energy photon and/or particle 120 (which may require reconfiguring of the at least one high energy photon and/or particle emitter portion(s) 150). Such resection can be accomplished in certain instances by allowing the surgeon to X-ray fluorescence visualize, image, and/or provide information relating to tissue margins of the tumor using certain embodiments of the X-ray fluorescence visualizer, imager, or information provider 100 based on its differential matter density and/or the element of the at least the portion of the individual. The differential matter density and/or the elemental composition may, in certain instances, be either endogenous to the tissue, or enhanced by a contrast agent which may not otherwise be viewable and/or visible using normal human visual observation.

This use of certain X-ray fluorescence visualizer, imager, or information providers 100 therefore could allow the surgeon to resect a lesion, tumor, etc. while limiting harm and manipulation (or even removal) to adjacent healthy matter or tissue, such as may be indicated based at least partially on the matter density and/or the element composition of the matter. This can be useful in X-ray fluorescence depth visualizing, imaging, or information providing organs such as the brain that are particularly sensitive to harm, manipulation, or removal of matter. Additionally, certain embodiments of the X-ray fluorescence visualizer, imager, or information provider 100 might be configured to allow the user (e.g., surgeon or assistant) to view the matter aberration of the matter at a number of different angles. By allowing the viewing at different angles, etc., it may be easier for the user to appreciate the shape of the aberration, as well as its proximity to adjacent structures such as nerves, blood vessels, or other sensitive or other areas during particular operations or procedures. By limiting manipulation, bruising, contact, or removal, etc. of sensitive matter during particular operations and/or procedures, certain embodiments of the X-ray fluorescence visualizer, imager, or information provider 100 might likely be configured or designed to perform more radical surgeries or procedures (that might hurt the patient using other imaging techniques) than presently allowable.

Certain embodiments of the X-ray fluorescence visualizer, imager, or information provider 100 can be configured to X-ray fluorescence visualize, image, and/or provide information relating to the depth of certain layers of the at least the portion of the individual near the surface 168 (e.g., skin) as described with respect to FIG. 29. This may be used to examine or X-ray fluorescence visualize, image, and/or provide information relating to the depth of aberrative matter such as tumors in skin or other tissue or matter as described with respect to FIG. 30. With certain conventional imaging techniques, boundaries and/or depth from the surface 168 may not be clear between different types of matter (such as aberrative matter or tissue and normal matter or tissue, different types of cells, etc.). With X-ray based technologies, such as certain embodiments of the X-ray fluorescence visualizer, imager, or information provider 100, certain types of aberrative matter such as certain cancers, tumors, etc. can be detected as a result of the associated calcification of the matter of the cancers, tumors, etc.

For example, it is likely that the calcified aberrative matter or tissue of such aberrative matter as breast cancer nodules in skin will absorb a considerable amount of the X-ray based electromagnetic radiation being applied as compared to the non-cancerous matter. As such, certain embodiments of the X-ray fluorescence visualizer, imager, or information provider 100 can be configured to indicate outlines, depths, regions, volumes, or other such aberrative matter based on aberrative X-ray and/or photonic characteristics of the aberrative matter as compared to the normal matter (e.g., tissue). Additionally, aberrative matter also may have different contrast enhancing properties from normal matter. An example being a brain tumor can reduce the effectiveness of the blood brain barrier, and thereby absorb certain contrast agents to have X-ray fluorescence visualization, imaging, or information provided characteristics unlike adjacent brain tissue.

Certain users using certain embodiments of the X-ray fluorescence visualizer, imager, or information provider 100 can be used to more easily detect or X-ray fluorescence visualize, image, and/or provide information relating to certain aberrative matter, etc. Such ease of detection can allow for more easily location of a position, extent, depth, and/or other aspects of the aberrative matter such as can enhance simplification or effectiveness of examination, removal, and/or treatment thereof. Removal of certain aberrative matter can be performed using certain matter removal techniques that may or may not be performed by certain embodiments of the X-ray fluorescence visualizer, imager, or information provider, or associated equipment, including but not limited to: surgical cutting techniques, abrasive techniques, ablative techniques (such as laser ablation), etc.

Consider that certain surgeons, doctors, veterinarians, dentists, etc. may wish to completely locate and remove all (or at least as much as practicable), or only portion of a particular amount of such aberrations as aberrative or undesired matter interspersed in normal matter or tissue (such as a tumor interspersed in tissue, a cavity interspersed in a tooth, etc.). For example, it may be desired to remove a melanoma (i.e., skin cancer) completely as described with respect to FIG. 30 (or other skin aberration), while leaving behind as much matter or tissue as practicable. Certain cancers, for example, may spread in a dispersive manner through some tissue, blood, bones, or other matter. As such, it may be desired to allow for visualizing, imaging, or providing in a manner that can precisely locate and identify (and/or perhaps even remove, ablate, or otherwise treat) the matter based at least partially on the element composition of the matter being analyzed, screened, or treated.

It may be desirable to X-ray fluorescence visualize, image, and/or provide information relating to the aberrative matter (e.g., associated with the melanoma, tumor, etc.) one or more subsequent times such as to determine its precise extent. An initial X-ray fluorescence visualization, imaging, or information providing scan may be useful in locating regions where certain matter aberrations such as melanomas may exist, and subsequent X-ray fluorescence visualization, imaging, and/or information providing scans may be applied to each potential located aberration as to be useful in determining the depth or extent of each aberration such as to act as a biopsy, etc. In addition, certain tomography type or volumetric type embodiments of the X-ray fluorescence visualizer, imager, or information provider 100 can be used to map or determine, as accurately as practical or desirable, such aberrations, etc. Certain skin aberrations may include aberrative cells, colonies of cells, growths, or other dissimilar matter as compared to neighboring normal matter, and the aberrative (e.g., cancerous) matter can be based at least partially on the depth to which it has developed. Certain embodiments of the X-ray fluorescence visualizer, imager, or information provider 100 can be configured to determine a depth of dissimilar matter feature within the at least one normal matter.

Additionally, a brain tumor might be suitable for being X-ray fluorescence visualized, imaged, or information provided by certain embodiments of the X-ray fluorescence visualizer, imager, or information provider 100, including those embodiments of surgical tools including the X-ray fluorescence depth visualizer, imager, tactile feedback provider, or information provider 100 that can resect the tumor. As such, the tumor can be resected, with limited adjacent brain tissue that is not infiltrated with tumor effected by the resection. A low grade glioma is one example of a tumors which the X-ray fluorescence visualizer, imager, or information provider 100 may assist in visually differentiating.

If the feature of an aberration or dissimilar matter, such as a tumor, cancerous matter, tooth decay, abscesses, infections, etc. is not removed completely, the aberration may continue to grow. Such aberrations as cancer or tumors may even grow uncontrollably, and even metastasize. The surgeon may not be able to determine the depth from a visual inspection or even one-time imaging techniques that use certain conventional imagers. An aberrative growth could be quickly examined, and the depth of the aberrative growth could be reliably determined by a skilled user utilizing certain embodiments of the X-ray fluorescence visualizer, imager, or information provider 100. A dissimilar matter representing an aberration such as a melanoma, if not treated and/or removed in time, may thereby grow to an extent to be dangerous or even deadly.

The depth of certain matter aberrations such as melanomas may correspond to their seriousness. For example, if a melanoma has reached below a particular depth 362 as described with respect to FIG. 30, then the probability that it has metastasized may increase considerably. As such, there are a variety of medical situations that vital information as to the seriousness of a patient's condition could be obtained relatively and accurately using certain embodiments of the X-ray fluorescence visualizer, imager, or information provider 100. By utilizing a series of successive images, such aberrations or abnormalities as melanomas could be examined from a variety of angles, magnifications, and/or positions such as to make certain of their extent. It is likely that at least certain melanomas, breast cancers, other tumors or cancers, etc. can be imaged relative to adjacent matter either based on different densities of the dissimilar matter or alternately using certain contrast agent and/or fluoroscopy techniques.

As such, FIG. 29 shows an example of a partial cross-sectional view of normal matter such as skin; while matter such as skin including a dissimilar matter a melanoma is shown in FIG. 30. Normal skin, for example, is typically made up of layers, including the epidermis 370 and the dermis 372. As illustrated in FIG. 30, a skin aberration or tumor such as a melanoma 360 can develop within the skin, and can be measured by a number of quantitative systems, two of which are referred to as "Breslow Depth" and "Clark's Levels". Breslow Depth quantifies the top-to-bottom measurement of the melanoma in millimeters, similar to as shown by the arrow 362 in FIG. 30. By comparison, Clark's Levels describe how far the melanoma has extended into the particular layers of the skin. Certain embodiments of the X-ray fluorescence visualizer, imager, or information provider 100, as described in this disclosure, can therefore be used to determine the characteristics of a melanoma using the Breslow Depth and/or the Clark's Level. Certain embodiments of the X-ray fluorescence visualizer, imager, or information provider 100 as can be applied to aberrative matter, such as tumors such as melanomas, are intended to be illustrative in nature but not limiting in scope. Determination of a suitable matter thickness or X-ray fluorescence visualizing, imaging, or information providing based on element composition may relate to slice thickness for X-ray fluorescence visualization, imaging, or information providing may pertain to the likely presence or absence of matter aberrations or inconsistencies.

As such, by viewing a matter aberration such as a tumor or cancer at a number of angles, positions, magnifications, thicknesses, etc. using certain embodiments of the X-ray fluorescence visualizer, imager, or information provider 100 as described with respect to FIG. 30, it is likely that the true extent, depth, and condition of their growth can be determined. Such re-examination or subsequent X-ray fluorescence visualization, imaging, or information providing of the at least the portion of the individual 82 can be performed at a desired angle, position, etc. Such re-examination (perhaps while providing for examination or scanning for different elements, chemicals, compounds, and/or biological materials, etc.) can be based or selected, at least in part, on input from the user, the individual, or a controller or computerized portion such as to closely examine those regions of interest under a suitable magnification, angle, position, etc.

Certain embodiments of the X-ray fluorescence visualizer, imager, or information provider 100 can be configured to visualize, image, or provide information relating to such nontissue matter as blood, bone, etc. As such, certain embodiments of the X-ray fluorescence visualizer, imager, or information provider 100 can be applied to leukemia (one type of cancer of the blood), lymphoma (one type of cancer of the lymph nodes), Hodgkin's disease, myeloma other blood, lymph, bone, or other cancers, infections, impurities, sicknesses, etc. based at least partially on the element composition.

Certain embodiments of the X-ray fluorescence visualizer, imager, or information provider 100 can rely on advantages of X-ray technology. X-ray technology may provide advantages of being well developed, researched, understood, trusted, etc. X-ray technology can be less expensive than certain other X-ray fluorescence visualization, imaging, or information providing technologies. While certain aspects of X-ray fluorescence technology may be less developed than conventional X-ray (e.g., transmissive) technologies, both types of X-ray technologies can be utilized in a variety of medical or non-medical applications including, but not limited to, medical, examination, surgery, geological, security, structural, and other technologies.

By allowing subsequent controllable X-ray fluorescence visualization, imaging, or information providing as is the case with certain embodiments of the X-ray fluorescence visualizer, imager, or information provider 100 as described in this disclosure, the users such as physicians, surgeons, dentists, etc. can interactively examine the at least the portion of the individual 82, in a manner as desired. For example, after a desired at least the portion of the individual 82 is located by an initial X-ray fluorescence visualization, imaging, and/or information providing scan, subsequent X-ray fluorescence visualization, imaging, or information providing scan(s) can further or more closely examine the located portion. With certain embodiments of the X-ray fluorescence visualizer, imager, or information provider, the at least the portion of the individual with at least part of their body part being examined can interactively X-ray fluorescence visualize, image, and/or provide information relating to their condition using subsequent X-ray fluorescence visualization, imaging, or information providing if the output/display is provided to the at least the portion of the individual 82. Such subsequent X-ray fluorescence visualization, imaging, or information providing can be performed on a variety of matter in the at least the portion of the individual.

As with a variety of radiographic X-ray fluorescence visualization, imaging, or information providing techniques, and particularly those utilizing X-rays, it is important to consider the dosage effects of certain electromagnetic radiation provided by the X-ray fluorescence visualizer, imager, or information provider 100 to the at least the portion of the individual and/or the user. Certain embodiments of the X-ray fluorescence visualizer, imager, or information provider 100 can X-ray fluorescence visualize, image, and/or provide information relating to a series of X-ray fluorescence depth visualizations, images, and/or provided information sequentially, on a real time basis, at a variety of resolutions, or over a large or small portion of the individual. By judicious X-ray fluorescence visualization, imaging, or information providing using certain embodiments of the X-ray fluorescence visualizer, imager, or information provider 100, the radiation doses as applied to the at least the portion of the individual and/or the user can be limited considerably, particularly as compared with many conventional X-ray imaging modalities.

Certain embodiments of the X-ray fluorescence visualizer, imager, or information provider 100 are configured to image by allowing X-rays to pass into, X-ray fluorescence from, and return from a localized organ, matter, etc. Conventional transmissive X-ray devices, by comparison, typically pass through the entire thickness of the at least the portion of the individual being imaged. For example, certain embodiments of the X-ray fluorescence visualizer, imager, or information provider 100 can be configured by X-ray fluorescence visualization, imaging, or information providing a first general area, and thereupon depending upon the initial X-ray fluorescence visualization, image, or provided information. A relatively minor number of X-ray fluorescence visualizations, images, and/or provided information (perhaps localized to small regions) can be examined to consider in considerable degree, for example, one or more regions of interest that have been located by the initial depth interest. Such subsequent X-ray fluorescence depth visualizations, images, and/or provided information may be configured to limit exposure of the at least the portion of the individual or the user to the doses of the original X-ray fluorescence depth visualizations, images, and/or provided information.

By allowing subsequent X-ray fluorescence visualization, imaging, or information providing with certain embodiments of the X-ray fluorescence visualizer, imager, or information provider 100, the condition of the at least the portion of the individual may be clearly imaged and/or examined to determine the condition of the at least the portion of the individual. In certain instances, perhaps less drastic treatment (e.g., radiation therapy, chemotherapy) and/or less imaging, X-ray fluorescence visualizing, and/or tests may need to be applied to the at least the portion of the individual based on the more complete or accurate X-ray fluorescence visualization, imaging, or provided information results. Such results may be obtained by (or the relatively precise locating, X-ray fluorescence visualizing, and/or imaging of) certain embodiments of the X-ray fluorescence visualizer, imager, or information provider 100. In certain instances, perhaps the growths, once clearly examined, can be more accurately treated such as by direct treatment of the relevant location, ablation, etc.

A variety of X-ray based electromagnetic radiation (applied, returning/reflected, etc.) can be utilized for X-ray fluorescence visualization, imaging, or information providing purposes when X-ray fluorescence visualization, imaging, or information providing the at least the portion of the individual. Certain embodiments of the X-ray fluorescence visualizer, imager, or information provider 100, as described with respect to this disclosure, the at least one high energy photon and/or particle emitter portion(s) 150 can apply an the at least one applied high energy photon and/or particle 120 to the at least the portion of the individual. FIG. 23 shows one representative embodiment of the X-ray fluorescence visualizer, imager, or information provider applying the X-ray (photonic-based electromagnetic radiation) down to the at least one X-ray fluorescence range to the at least one prescribed substantial X-ray fluorescence depth within the at least the portion of the individual 82 (e.g., human, shown in cross section).

Certain embodiments of the at least one high energy photon and/or particle emitter portion(s) 150 can thereby be positioned relative to the at least the portion of the individual 82, either at least partially internally or at last partially externally to the individual. Certain embodiments of the at least one high energy photon and/or particle emitter portion(s) can be configurable to emit the at least one applied high energy photon and/or particle 120 for a controllable depth into the matter of the at least the portion of the individual 82. The subsequent X-ray fluorescence (X-ray fluorescence from the at least one applied high energy photon) can be detected by the at least one detector portion 152 and/or the at least one display portion. The X-ray fluorescence visualization, imaging, and/or provided information relating to information can thereby be derived at least partially in response to X-ray fluorescence of the X-ray based electromagnetic radiation.

The at least one high energy photon and/or particle emitter portion(s) 150 of certain embodiments of the X-ray fluorescence visualizer, imager, or information provider 100 can be configured to generate at least some of the at least one applied high energy photon and/or particle 120, that can be applied and/or directed to the at least the portion of the individual 82. Some of the at least one applied high energy photon and/or particle 120 can be applied by the at least one high energy photon and/or particle emitter portion(s) 150 such as to at least partially penetrate into the at least the portion of the individual. During such instances as when penetrating into matter of the at least the portion of the individual 82, the X-ray based electromagnetic radiation of the at least one applied high energy photon and/or particle 120 can be at least partially deflected, at least partially X-ray fluorescence, and/or at least partially passed through the at least the portion of the individual 82. X-ray fluorescence (at a variety of angles) of at least some of the at least one applied high energy photon and/or particle 120 can result in detection of the at least one induced X-ray fluorescing photon 122 (based at least partially on element composition of the matter) which can be detected by certain embodiments of the at least one detector portion 152, and/or the at least one X-ray fluorescence receiving portion(s) 151.

Certain examples of the other matter that can effect the X-ray fluorescence can include, for example: tissue, bones, portions of bones, metal, etc. Certain embodiments of the X-ray fluorescence visualizer, imager, or information provider 100 may be configured for X-ray fluorescence visualization, imaging, or information providing matter not normally associated with X-ray fluorescence visualization, imaging, or information providing. Such would be the case with locating interfaces between two different types of matter including, but not limited to: "normal" or "regular" opaque matter (such as tissue), as compared with other aberration matter.

Certain embodiments of the X-ray fluorescence visualizer, imager, or information provider 100 can be configured to combine X-ray fluorescence visualization, imaging, or information providing at least partially by combining information obtained from the X-ray fluorescence visualizer, imager, or information provider 100 with image information from another source (e.g., MRI, conventional X-rays, other X-ray fluorescence-based systems or portions thereof, other embodiments of the X-ray fluorescence visualizer, imager, or information provider 100, etc.). Such combinations may take the form or function, for example, of depth, position, varying X-ray fluorescence depth visualizing, imaging, or information providing modalities, etc.; and may include previously gathered X-ray fluorescence depth visualizing information.

Certain of such combined embodiments of X-ray fluorescence visualizer, imager, or information provider 100 can be useful for instance where the imaging capabilities of the X-ray fluorescence visualizer, imager, or information provider 100 may be more limited such as to produce a real-time X-ray fluorescence visualization, imaging, or information providing, and thereupon integrating more detail imaging from other imaging modalities. Although certain aspects of the X-ray fluorescence visualization, images, or provided information of particular matter such as tissue, organs, bones, or other portions of the individuals may not precisely match between certain embodiments of the X-ray fluorescence visualizer, imager, or information provider 100 and the other conventional X-ray fluorescence visualization, imaging, or information providing modalities, it is likely that each visualizing, imaging, or information providing modality could be expected to be particularly useful for particular applications, illnesses, injuries, infections, conditions, etc.

Certain embodiments of the X-ray fluorescence visualizer, imager, or information provider 100 may also be configured as to be able to X-ray fluorescence visualize, image, or provide information at a suitable rate considering the matter being imaged and/or the ability of the user to be able to view the distortions. There might be a variety of distortions of the matter which may be particularly useful to X-ray fluorescence visualize, image, or provide information. For example, certain surgeons might be particularly interested in considering the rate at which the heart beating causes deformation of the heart muscle, or alters blood flow through portions of the heart such as the aorta, valves, etc. By comparison, other surgeons may be interested in considering somewhat slower motion of their patients, such as how changes in the body position (e.g., leg or arm position) may be reflected in variation in the associated skeletal bones between successive X-ray fluorescence depth visualization, imaging, or providing information. Certain dentists or orthodontists might be interested in how movement of the jaw can be reflected by changes in the bite of the teeth of their patients.

As described with respect to FIG. 23, certain embodiments of the at least one high energy photon and/or particle emitter portion(s) 150 can apply at least one the at least one applied high energy photon and/or particle 120 at a desired, or controllable, angle. The X-ray fluorescence depth visualizing, imaging, or information providing angle of the at least one applied high energy photon and/or particle 120 radiation may range from almost parallel, but still incident, to a surface 168 of the at least the portion of the individual 82, to substantially perpendicular to the surface 168 of the at least the portion of the individual 82, and any angle there between). The characteristics of the at least one applied high energy photon and/or particle 120 may include, but are not limited to, a suitable and/or desired position, power, frequency, energy level, duration, as well as a variety of other such characteristics.

Certain embodiments of the X-ray fluorescence visualizer, imager, or information provider 100 can be configured to include at least one detector portion 152 and/or display portion 154 that can be operable to be at least partially inserted into the at least the portion of the individual. Such configurations can be used to receive at least one X-ray fluorescence that has been X-ray fluorescence in an at least one opaque matter of the at least the portion of the individual. Certain embodiments of the detector portion can be configured to be adjustable, alignable, scannable, or otherwise modifiable;

and may include such scopes as endoscopes that may alternately be inserted through insertion or normally open opening of the individual as is generally understood by the use of an endoscope.

Certain embodiments of the at least one X-ray fluorescence receiving portion(s) 151 might preferably be configured as combined detector portion/display portions as described in this disclosure, such that the X-ray fluorescence visualizer, imager, and/or information provider might suitably change as the user moves their vantage point, etc. relative to the at least the portion of the individual. It may be desired to reduce or limit the involved computation associated with X-ray fluorescence depth visualizing, imaging, or information providing. By comparison, those embodiments of the X-ray fluorescence visualizer, imager, or information provider 100 involved in X-ray fluorescence depth visualizing, imaging, or information providing relatively deep into the at least the portion of the individual may include the distinct detector portions and display portions. Additionally, certain embodiments of the X-ray fluorescence visualizer, imager, or information provider 100 can be applied in the at least one X-ray fluorescence range to the at least one prescribed substantial X-ray fluorescence depth relatively near the surface 168. Recall that such image combining may utilize image subtraction, time of flight, image transformation, deconvolution, image subtraction, weighted subtraction, functional subtraction, and group including inverse integral transform, subtractive inverse integral transform, inverse functional transform, and subtractive inverse functional transform, or other such image processing techniques. Such distinct detector portions and display portions may be configured to computationally differentiate images, X-ray fluorescence visualizations, information, etc. using certain image information. Additionally, such computationally complex X-ray fluorescence visualization, imaging, or information providing displays as time of flight embodiments of the X-ray fluorescence visualizer, imager, or information provider 100 (or high resolution display portions) may benefit from the distinct detector portions and display portions, which may also simplify the associated image processing. These design choices are intended to be illustrative in nature, but not limiting in scope.

Certain embodiments of the detector portion 152 may be situated within the at least the portion of the individual 82, adjacent to the at least the portion of the individual 82, or external to the at least the portion of the individual 82. Either one detector portion 152, or a plurality of detector portions, may be provided either within the at least the portion of the individual 82, adjacent to the at least the portion of the individual 82, and/or external to the at least the portion of the individual 82.

Within this disclosure, certain embodiments of the at least one display portion 154 can be configured to display the X-ray based electromagnetic radiation such as it has at least been partially received from the at least the portion of the individual 82 by the at least one detector portion. As such, certain embodiments of the at least one display portion 154 can be configured to display X-ray illumination that can be X-ray fluorescence at least partially from the at least the portion of the individual 82. Such X-ray fluorescence illumination can be based on the X-ray fluorescence based electromagnetic radiation that can be detected by the at least one detector portion 152.

Certain embodiments of the at least one X-ray fluorescence receiving portion(s) 151 can include a variety of the at least one display portion 154. Certain embodiments of the display portion 154 can take a variety of forms that can include, but are not limited to: a cathode ray tube (CRT) display portion, a liquid crystal display portion (LCD) display portion, a personal display or information provider portion (configured to display to one person), a glasses-based display portion, a group display or information provider portion (that can display X-ray fluorescence depth visualizations, images, and/or provided information to more than one person), a plasma display portion, a medical display portion, a computer display portion, a personal display assistant (PDA) display portion, or such other displays that can at least partially provide a display of at least the portion of the individual based at least in part on the at least one induced X-ray fluorescing photon 122.

The selection as to whether the at least one X-ray fluorescence receiving portion(s) 151 includes distinct detector portions and display portions, or combined detector portion/display portions can be based at least partially based on functionality and/or desired computation. For example, certain X-ray fluorescence visualization, imaging, or information providing applications involving depth imaging, X-ray fluorescence visualizing, or providing information from the surface 168 to the at least one X-ray fluorescence range to the at least one prescribed substantial X-ray fluorescence depth.

Figure 31:
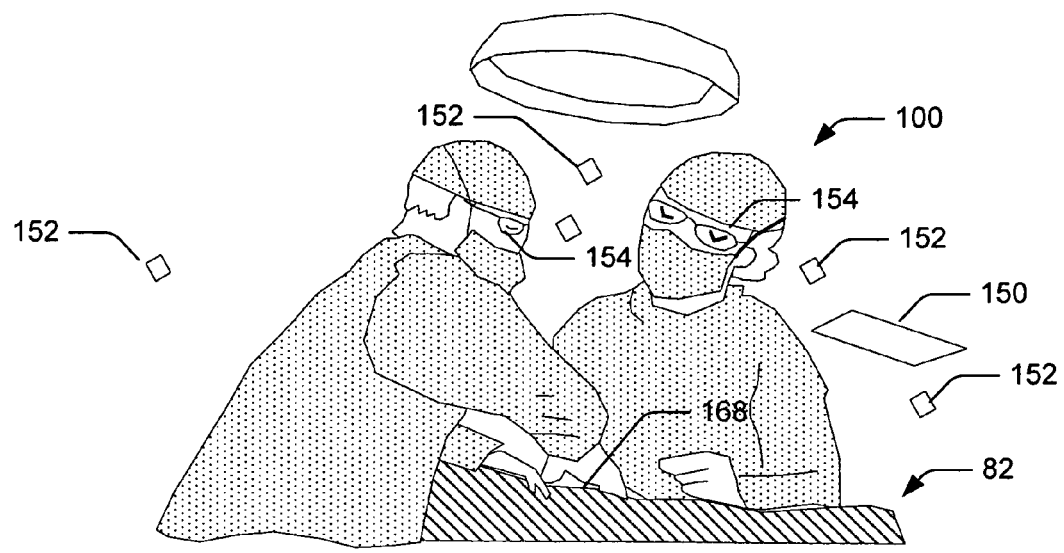
FIG. 31 shows another embodiment of the X-ray fluorescence visualizer, imager, or information provider including an embodiment of an at least one display portion configured as a personal display or information provider portion.

Certain embodiments of the at least one X-ray fluorescence receiving portion(s) 151 may be referred to as surgeon's glasses that can be worn by an individual surgeon or doctor, or other configuration, as illustrated in FIG. 31. Certain embodiments of the X-ray fluorescence visualizer, imager, or information provider 100 can be configured as personal devices, which can thereby be used primarily by one person. By comparison, certain embodiments of the X-ray fluorescence visualizer, imager, or information provider 100 can be used as group devices such as can be used by two or more persons or users. Particularly, FIG. 31 shows one embodiment of the X-ray fluorescence visualizer, imager, or information provider 100 including an embodiment of the at least one display portion 154 configured as a personal display (in this instance, surgeon glasses, dentist glasses, veterinarian glasses, etc.), as described in this disclosure. Certain embodiments of the X-ray fluorescence visualizer, imager, or information provider 100 can thereby be configured as augmented vision glasses. For instance, certain embodiments of the X-ray fluorescence visualizer, imager, or information provider 100 can utilize glasses, such as can be worn by surgeons in which at least a portion of the glasses can be configured as a display, such display portion could be viewed by the user. Certain embodiments of the X-ray fluorescence visualizing, imaging, or information provided as provided by certain embodiments of the X-ray fluorescence visualizer, imager, or information provider 100 can be optically aligned to the user. Certain embodiments of the X-ray fluorescence visualizer, imager, or information provider 100 can therefore be configured as an X-ray fluorescence device is used to deliver a real-time 2D or 3D X-ray fluorescence depth visualization, image, or information to the surgeon. The X-ray fluorescence depth visualizations or images can be presented to the surgeon by means of an external monitor, head-mounted display, or stereoscopic projection. The surgeon can select the depth (from millimeters to substantially through the X-ray fluorescence visualized, imaged, or have information provided portion of the individual 82) at which the X-ray fluorescence visualization, image, or provided information is taken, captured, etc.; the selected depth can be targeted by tuning the intensity, energy level, or frequency of the X-ray photons in the X-ray radiation.

There may be a variety of configurations and/or utilizations of certain embodiments of the X-ray fluorescence visualizer, imager, or information provider 100. For example, certain personalized embodiments of the X-ray fluorescence visualizer, imager, or information provider 100 can present X-ray fluorescence depth visualization, image, or information to at least one person particularly associated with the X-ray fluorescence visualizer, imager, or information provider, similar to as described with respect to FIG. 31. Certain personalized embodiments of the X-ray fluorescence visualizer, imager, or information provider 100 can be configured to be worn as personal devices, such that each of the at least the portion of the individual 82 can obtain the X-ray fluorescence depth visualization, image, or information of the at least the portion of the individual 82 in a manner similar to glasses. For instance, in the embodiment of the X-ray fluorescence visualizer, imager, or information provider 100 as described with respect to FIG. 31, the at least one high energy photon and/or particle emitter portion(s) 150 can be situated proximate the glasses-based embodiment of the X-ray fluorescence visualizer, imager, or information provider 100 (e.g., on the frame); adhered to the user at a remote location from the glasses (e.g., on cloth, clothes, fabric, metal, or other material); or alternatively situated at a remote location from the user.

Certain embodiments of the detector portion 152 of the X-ray fluorescence visualizer, imager, or information provider 100, as described with respect to FIG. 31, can thereby be described as surgeons' glasses. The terms surgeon's glasses or surgical glasses is intended to be illustrative and not limiting since these devices can be worn by the user and illustrate X-ray fluorescence visualizations and/or images, as well as provide information, to the user or other person. Certain surgical glass embodiments of the X-ray fluorescence visualizer, imager, or information provider 100 may or may not contain optical glasses at all. Certain surgical glasses are understood to perhaps include an additional display portion (which may function as typical optical glasses) such as can be viewed by a surgeon, or alternatively may be provided as only a frame without the optical glasses. Certain embodiments of the surgical glasses, can include, for example, at least one liquid crystal display (LCD), at least one light emitting diode (LED) or an embodiment of the at least one X-ray fluorescence receiving portion(s) 151 that can be secured by a variety of mechanisms to nearby are to the user, such as can be viewed by the user. With surgeon's glasses, a variety of display portions can be provided to surgeons, etc. through a portion of glasses, while other portions of the glasses allow the surgeon to see during the operation.

Figure 32:
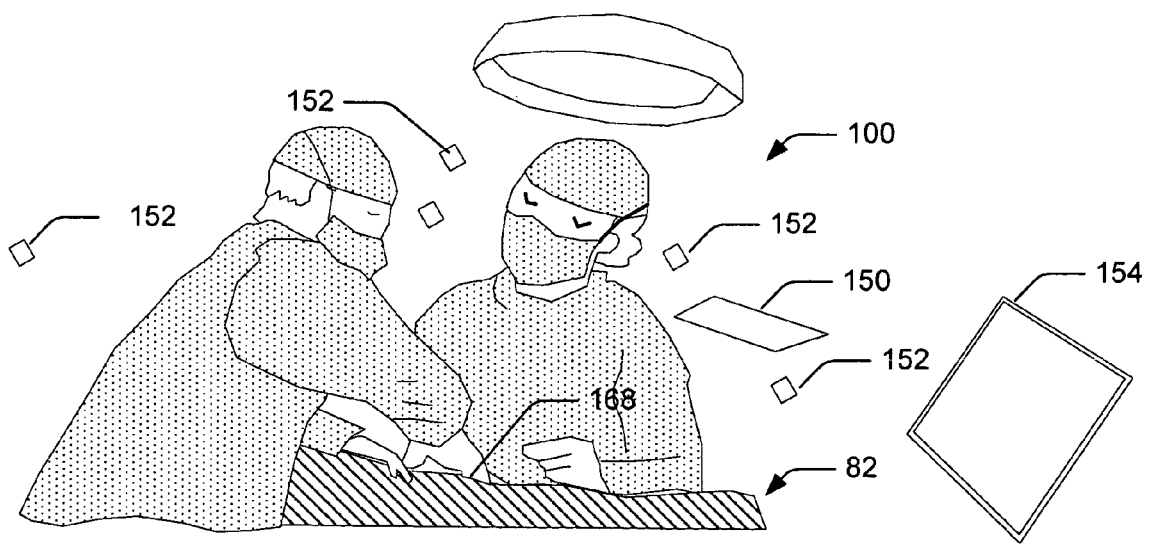
FIG. 32 shows one embodiment of the X-ray fluorescence visualizer, imager, or information provider including an embodiment of the at least one display portion configured as a group display or information provider portion.

By comparison, a number of embodiments of the X-ray fluorescence visualizer, imager, or information provider 100 could include at least one display portion 154 can be configured as a group display or information provider portion. For example, FIG. 32 illustrates an instance in which a number of users could view selected portion(s) of the individual through a group display 154, as described in this disclosure such as could be viewed by a number of users. For instance, the X-ray fluorescence visualizer, imager, or information provider 100 can include an LCD display portion, a CRT display portion, a television display portion, a medical display portion, or other applicable embodiments of the X-ray fluorescence visualizer, imager, or information provider.

Certain of the at least one applied high energy photon and/or particle 120, that are generated and/or applied to the at least the portion of the individual 82 by certain embodiments of the at least one high energy photon and/or particle emitter portion(s) 150, may thereupon after at least partially passing into the at least the portion of the individual 82 be subsequently X-ray fluorescence and/or deflected. Such X-ray fluorescence and/or deflection can thereupon be detected by the at least one detector portion 152, as described with respect to FIG. 1 or 2. Certain embodiments of the X-ray fluorescence visualizer, imager, or information provider 100, can include a considerable number of detector portions 152 positioned, for example, around an operation or examination room in which the individual 82 is situated. The particular arrangement of a number of the at least one high energy photon and/or particle emitter portion(s) 150 is largely considered to be a design choice.

Certain embodiments of the X-ray fluorescence visualizer, imager, or information provider 100 can be configured to be adjustable, tunable, and/or controllable. Such adjustability, tunability, and/or controllability can be used to adjust the energy level or frequency of the at least one applied high energy photon and/or particle 120; and thereby affect the depth of X-ray fluorescence visualization, imaging, or information providing, into the at least some matter of the at least the portion of the individual. Certain external embodiments of the X-ray fluorescence visualizer, imager, or information provider 100 may be configured to be non-contact, with a probe of the at least one high energy photon and/or particle emitter portion(s) 150 and/or probe of the detector portion 152 that does not contact the surface 168 of the matter of the at least the portion of the individual. Other embodiments adjustable, tunable, and/or controllable do permit contact of the at least one high energy photon and/or particle emitter portion(s) 150 probe and/or detector portion 152 probe with the matter of the at least the portion of the individual. Certain embodiments of the X-ray fluorescence visualizer, imager, or information provider 100 can provide a number of modalities of X-ray fluorescence depth visualizing, imaging, or information providing (traditional X-ray images, X-ray fluorescence visualization, imaging, or information providing, etc.) including, but not limited to, density and elemental X-ray fluorescence depth visualizing, imaging, or information providing mode. Certain embodiments of the X-ray fluorescence visualizer, imager, or information provider 100 can be configured to provide considerable contrast, and thereby may be less dependent on such variables as user skill in X-ray fluorescence depth visualizing, imaging, or information providing, etc.

Certain embodiments of the X-ray fluorescence visualizer, imager, or information provider 100 can be configured to combine image information with that being performed by different imagers that can produce images in one or a variety of different formats and configurations. Certain embodiments of the X-ray fluorescence visualizer, imager, or information provider 100 can be applied externally or internally, such as described relative to certain locations in this disclosure. Certain external configurations of the X-ray fluorescence visualizer, imager, or information provider 100 can utilize either full-body tomography imaging enclosures or partial body tomography imaging enclosures, similar to as generally used during MRIs, CAT scans, PET scans, Compton backscattering devices, etc. By comparison, certain embodiments of the at least one X-ray fluorescence receiving portion(s) 151 for certain embodiments of the X-ray fluorescence visualizer, imager, or information provider 100 can be positioned around the room where the individual is situated. Such configurations can be configured to improve the application of the at least one applied high energy photon and/or particle 120 towards the at least the portion of the individual being imaged. Certain embodiments of the X-ray fluorescence visualizer, imager, or information provider could be used to obtain a CAT-grade or PET-grade tomography scan, based at least in part on the configuration and structure of the at least one high energy photon and/or particle emitter portion(s) 150 and/or the at least one X-ray fluorescence receiving portion(s) 151.

Certain embodiments of the X-ray fluorescence visualizer, imager, or information provider 100 may be configured to provide X-ray fluorescence depth visualizing, imaging, or information providing flexibility, as well as to conform to the at least the portion of the individual being imaged as described with respect to FIG. 32. Certain embodiments of the X-ray fluorescence visualizer, imager, or information provider 100 can be attached to a flexible securing member (perhaps even being attached to the individual using belts, Velcro, straps, or some other known fastener), such as can be used to limit relative displacements between the X-ray fluorescence visualizing components and the at least the portion of the individual. For example, certain embodiments of the X-ray fluorescence visualizer, imager, or information provider 100 can be configured as a fabric or jointed sleeve that can be at least partially tied to, worn by, or attached to surround the at least part of the patient, as described with respect to FIG. 32. Certain embodiments of the X-ray fluorescence visualizer, imager, or information provider can be embedded in, or attached to, clothing, fabric or other material that can be made distinctly for each individual, or can be used by a number of individuals. Such flexible attachment members may be especially desirable for monitoring or examining, or otherwise X-ray fluorescence visualizing, imaging, or providing information relating to particular portion or organ of the individual, such as the heart, brain, or other organs, tissue, or other matter.

For example, at least portions of the X-ray fluorescence visualizer, imager, or information provider 100 may be applied to securing elements which can be maintained or secured with respect to the at least the portion of the individual. Certain embodiments of the X-ray fluorescence visualizer, imager, or information provider 100 can be flexibly applied to a more extensive portion of the individual such as the torso; or a smaller portion of the individual such as an arm, leg, finger, etc. Certain embodiments of the X-ray fluorescence visualizer, imager, or information provider 100 can at least partially include a sleeve or other flexible portion that at least partially be affixed to and/or surrounds the individual. For example, certain embodiments of the X-ray fluorescence visualizer, imager, or information provider 100 can be configured to limit relative motion between at least one portion of the at least one X-ray fluorescence receiving portion(s) 151 relative to the at least the portion of the individual. By limiting the relative motion between the at least one high energy photon and/or particle emitter portion(s) 150 and/or the at least at least one X-ray fluorescence receiving portion(s) 151 with respect to the at least the portion of the individual, a number of aspects of X-ray fluorescence depth visualizing, imaging, or information providing can be improved, such as clarity and perhaps improved resolution.

Certain embodiments of the X-ray fluorescence visualizer, imager, or information provider 100 can be configured to act as a shield to limit transmission of X-rays outside of the at least the portion of the individual. Certain embodiments of the X-ray fluorescence visualizer, imager, or information provider 100 (particularly those flexible configurations as described with respect to FIG. 32) can be configured to include X-ray shielding material to shield users and/or individuals from the X-rays. Consider that the X-ray fluorescence visualizer, imager, or information provider 100 as described in this disclosure could include an X-ray shielding material such as could limit excessive stray X-rays from passing away towards the user such as a doctor, veterinarian, etc. Such users may be exposed to a higher total dosage of X-rays after X-ray fluorescence depth visualizing, imaging, or information providing a number of individual patients, etc., as compared with the individuals who are seldom imaged. Certain embodiments of the X-ray fluorescence visualizer, imager, or information provider 100 may also shield at least some of the X-rays from passing to the at least the portion of the individual. In certain instances, such shielding may be removable, replaceable, and/or shiftable such as to shield at least certain portions of the individual at one or more locations depending on which at least one high energy photon and/or particle emitter portion(s) 150 and/or detector portions 152 are being utilized.

Figure 34:
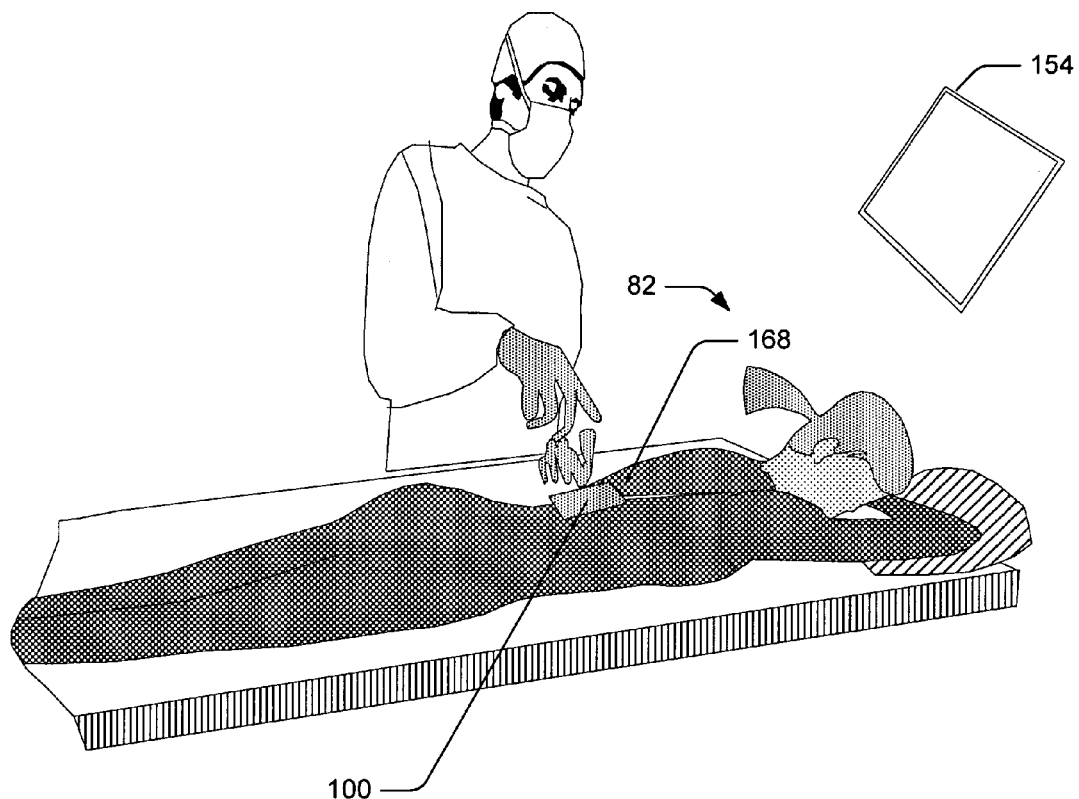
FIG. 34 shows an embodiment of the X-ray fluorescence visualizer, imager, or information provider that can be positioned by the user.

Certain embodiments of the at least one high energy photon and/or particle emitter portion(s) 150 and/or the at least one detector portion 152 can thereby be configured as a hand-held and positional device as described with respect to FIG. 34 such as can be positioned and/or used by the user, the individual, or another person. It is envisioned that at least portions of certain embodiments of the X-ray fluorescence visualizer, imager, or information provider 100 can be configured similar to a computer mouse (e.g., in dimension and/or position), such as to allow a user to position the device from a useful (and/or non-obstructive) user-selectable vantage point relative to the individual. Certain hand-held devices can transmit data to other detector or display devices, such as can be displayed over displays, glasses, plasma, or a variety of at least portions of certain embodiments of the at least one X-ray fluorescence receiving portion(s) 151.

Certain portable or repositionable embodiments of at least portions of the X-ray fluorescence visualizer, imager, or information provider 100 can utilize wireless and/or wired-based communications relative to other controller and/or computer portions associated therewith to effect data transfer, image transfer, etc. Alternately, certain embodiments of the constant X-ray fluorescence high energy (e.g., X-ray, gamma ray, photon, particle, etc.) X-ray fluorescence visualized, imaged, or information provided 100 can include the display and/or simulator as to provide for X-ray fluorescence visualization, imaging, and/or provide information directly there from. Certain user-selectable positionable X-ray fluorescence visualizer, imager, or information provider 100 could be securable in position by some securement or locking structure relative to the matter of the at least the portion of the individual. Such securement or fastener techniques can be used to limit excessive motion of the X-ray fluorescence visualizer, imager, or information provider 100 relative to the at least the portion of the individual and/or improve X-ray fluorescence depth visualizing, imaging, or information providing capability or quality of the X-ray fluorescence visualizer, imager, or information provider. As such, the high energy photon and/or particle emitter portion(s) could be positioned and located as desired. Certain embodiments of the at least one high energy photon and/or particle emitter portion(s) 150 could include a mount that might hold the at least one high energy photon and/or particle emitter portion(s) 150 in position, such as might limit the displacements of the high energy photon and/or particle emitter portion(s) to improve the X-ray fluorescence visualization, imaging, or information providing capabilities of the X-ray fluorescence visualizer, imager, or information provider 100. By providing a hand-held and/or positionable device, certain users can obtain a desired X-ray fluorescence depth visualization or image at a desired location without while the remainder of the user remains in a desired viewing or other position and/or location.

With certain hand-held positionable embodiment of the X-ray fluorescence visualizer, imager, or information provider 100, relatively quick feedback rates may be particularly desirable for X-ray fluorescence visualization, imaging, or information providing. Certain hand-held, positionable, or movable devices may also be useful in providing X-ray fluorescence visualization, imaging, or information providing at a variety of locations and/or angles of the individual such as may be controlled or adjusted by the user, the individual, a machine (e.g., robot), or another person.

The at least one high energy photon and/or particle emitter portion(s) 150 and/or detector portion 152 can thereby be configured as a remote device, or even a movable device such as can be a hand-held device (perhaps similar in size or shape as a computer mouse, or a digital camera as described with respect to FIG. 34). Such movable, frame secured, securable, or other embodiments of the X-ray fluorescence visualizer, imager, or information provider 100 can thereby provide the at least one applied high energy photon and/or particle 120 and/or receive X-ray fluorescence high energy (e.g., X-ray, gamma ray, photon, particle, etc.) from desired or controllable positionable locations. For instance, a doctor could position certain embodiments of the high energy photon and/or particle emitter portion(s) adjacent the at least the portion of the individual 82, such that particular subsurface regions of the at least the portion of the individual can be illuminated by or receive the X-ray based electromagnetic radiation adjacent the at least the portion of the individual 82. Such controllability or positionability of X-ray fluorescence visualizing, imaging, or information providing can be performed in a similar manner as a user of a flashlight might apply the flashlight to certain locations to optionally illuminate particular regions at which the flashlight is directed based at least partially on element composition of the at least some matter. Similarly, a physician might position the at least one detector portion 152 in close proximity to the portion(s) of the individual being X-ray fluorescence visualized, imaged, or information provided based at least partially on element composition of the at least some matter. By comparison, certain embodiments of the high energy photon and/or particle emitter portion(s) can be configured as applying a relatively disperse X-ray source that can generally apply X-rays against large regions (or at least regions of interest) of the at least the portion of the individual 82. Different embodiments of the X-ray fluorescence visualizer, imager, or information provider 100 (i.e., surgeon positioning and/or region of room filling embodiments of the at least one high energy photon and/or particle emitter portion(s) 150, etc.) can be used separately or in combination, and are intended to be illustrative in nature but not limiting in scope.

Figure 33:
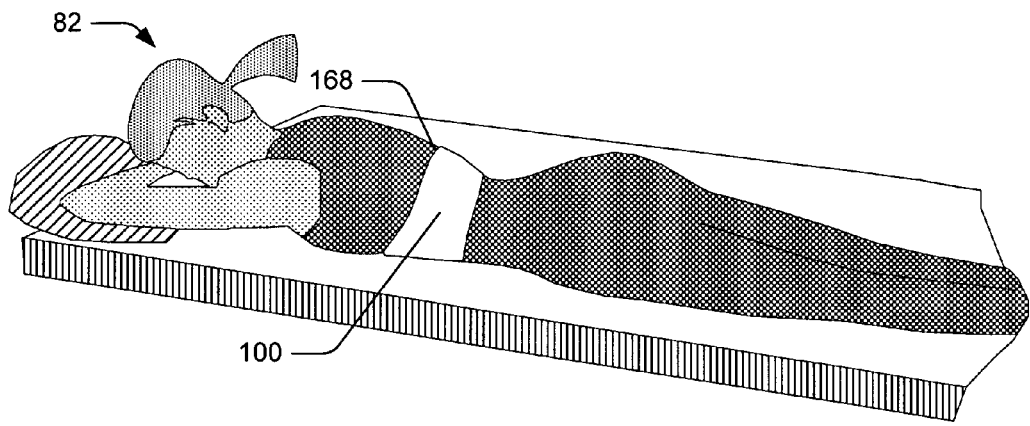
FIG. 33 shows a flexible embodiment of the X-ray fluorescence visualizer, imager, or information provider.
Figure 35:
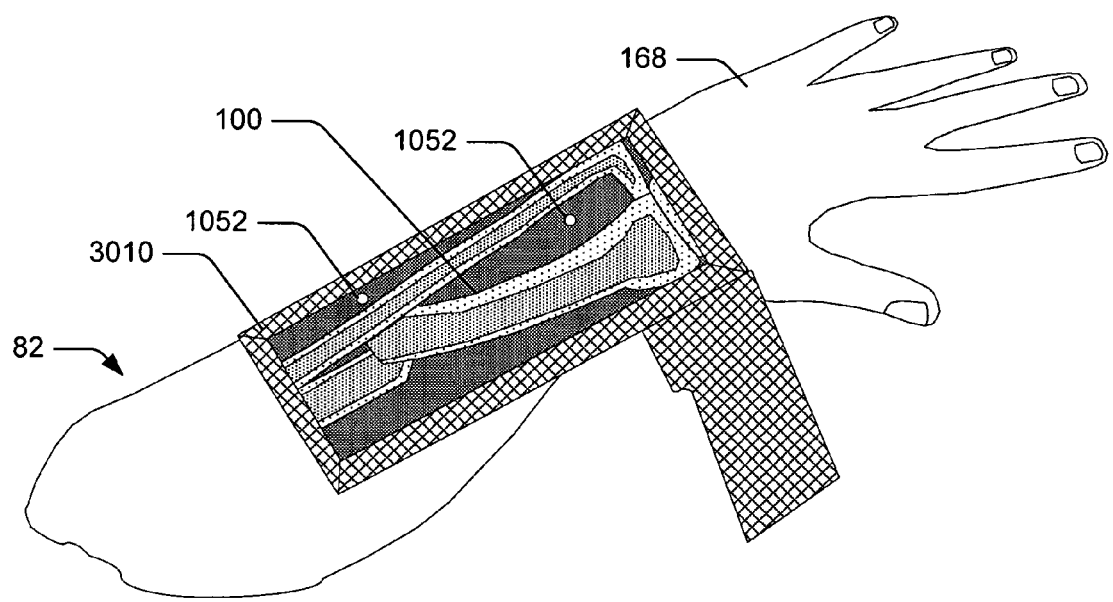
FIG. 35 shows another embodiment of the X-ray fluorescence visualizer, imager, or information provider.

Certain embodiments of the at least one X-ray fluorescence receiving portion(s) 151 and/or the display can be positioned in close proximity to the at least the portion of the individual, as described with respect to FIG. 35. For example, the at least one X-ray fluorescence receiving portion(s) 151 that is X-ray fluorescence visualization, imaging, or information providing a bone in a forearm may be positioned adjacent the forearm, perhaps even in a position that may be viewable by the user and/or the user. Certain embodiments of the X-ray fluorescence visualizer, imager, or information provider 100 can utilize at least one fiducial 1052 to assist in locating the X-ray fluorescence visualized, imaged, or information provided portion. The embodiments of the at least one X-ray fluorescence receiving portion(s) 151 as described with respect to FIG. 36 can be configured for X-ray fluorescence depth visualizing, imaging, or information providing relatively deep portions of the individual, such as skeletal systems, organs, certain internal blood vessels, etc. based at least partially on element composition of the at least some matter. It is likely that such embodiments of the X-ray fluorescence visualizer, imager, or information provider 100 that act deep into the matter of the individual based at least partially on element composition of the at least some matter can also apply the at least one applied high energy photon and/or particle 120 including at least some X-ray photons having sufficient energy level that can pass deep into the individual. Such deep X-ray fluorescence visualizing, imaging, or information providing would likely utilize the image processing techniques as described with respect to FIGS. 33 and 34, for example.

Figure 36:
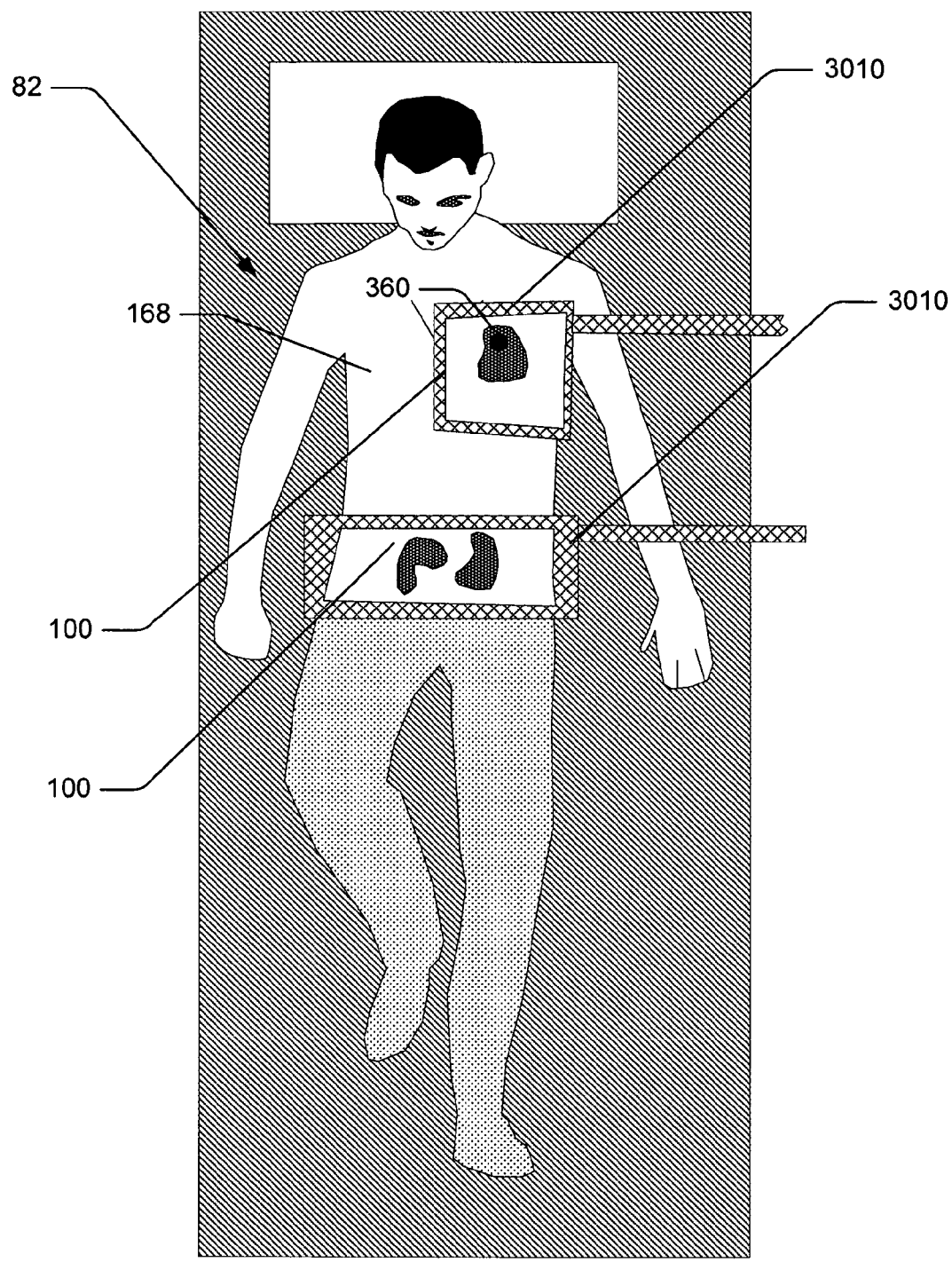
FIG. 36 shows yet another embodiment of the X-ray fluorescence visualizer, imager, or information provider.

Certain embodiments of the X-ray fluorescence visualizer, imager, or information provider 100, as described with respect to FIGS. 35 and 36, can include a framework 3010 and be configured such as to contain at least the at least one X-ray fluorescence receiving portion(s) 151 (not shown in these figures). Certain embodiments of the framework can be used to be positioned by the user, or secured by a securing device (rigid frame, arm, flexible belt, strap, or other). As described with respect to FIG. 36 and at other locations through the disclosure, the matter aberration 360 can be X-ray fluorescence visualized, imaged, or information provided such as can be provided or enhanced based at least partially on the elemental composition (or chemical composition, compound composition, or biological material composition with the use of X-ray fluorescence enhancing additives, taggants, or contrast agents, etc.).

Certain embodiments of the entire X-ray fluorescence visualizer, imager, or information provider 100 as described with respect to FIG. 1 or 2 can therefore be configured as a single unitary member utilizing similar technology as is known in graphical user interface (GUI), display, and controller technology such as to integrate all the portions of devices into combined units. By comparison, certain embodiments of the X-ray fluorescence visualizer, imager, or information provider 100 can be configured as distinct units, only certain ones of which may include their distinct framework 3010 if desired, or practicable. There are a variety of potential advantages to frameworks which include, but are not limited to, allowing a user to hold or providing a securement point (certain ones of which can be adjusted and controlled) to at least certain portions of the X-ray fluorescence visualizer, imager, or information provider 100.

Certain conventional transmissive X-rays can image three-dimensional matter across the extent of the portion of the person to a two-dimensional image. Certain embodiments of the X-ray fluorescence visualizer, imager, or information provider 100, by imaging a two-dimensional X-ray fluorescence visualizing, imaging, or information providing slice of the individual (e.g., imaging through the bone), might be particularly useful in X-ray fluorescence visualizing, imaging, or providing information pertaining to the individual for orthopedics, knees, bones, joints, organs, and other structural aspects of the individual.

Certain embodiments of the X-ray fluorescence visualizer, imager, or information provider 100 can be configured to operate based at least in part on tomography. Tomography can be based, at least partially, on obtaining at least one material characterizing distribution function. Within this disclosure, the material characterizing distribution function can be considered as a measurement of electron density, which more or less corresponds to the density of the matter. As such, a variety of X-ray fluorescence visualizations, images, or provided information of at least some matter of at least the portion of the individual based at least upon the material characterizing distribution function. Conventional tomography, such as CAT scan, PET scan, etc. may rely upon obtaining at least some type of distribution function. Those electrons of the outer shells of the matter, thereby are loosely held to the molecule, in such a manner to quantifiably correspond largely to the material characterizing distribution function. By comparison, those electrons of the inner shell of the matter thereby are more securely held to the molecule, and therefore correspond to a lesser degree to the material characterizing distribution function.

Certain embodiments of the at least one X-ray fluorescence receiving portion(s) 151 can receive a number of X-ray fluorescence in such a manner that there exists a number of uncertainties as to certain characteristics (e.g., in density, mass, structure, component, etc.) of the matter that may be based at least partially on element composition of the at least some matter. For example, a particular at least one X-ray fluorescence receiving portion(s) 151 that receives X-ray fluorescence high energy (e.g., X-ray, gamma ray, photon, particle, etc.) from a specific angle and/or position may receive a large number of X-ray fluorescence high energy (e.g., X-ray, gamma ray, photon, particle, etc.) that correspond to that angle and/or position, corresponding to the material characterizing distribution function that may depend, at least partially, on the element composition of the matter. It may be difficult to differentiate between X-ray fluorescence high energy (e.g., X-ray, gamma ray, photon, particle, etc.) from a number of different depths that correspond to a given angle and/or position within the at least some matter of the at least some portion of the individual, upon consideration of the material characterizing distribution function. Conventional tomography can similarly utilizes a material characterizing distribution function.

Certain embodiments of the X-ray fluorescence visualizer, imager, or information provider 100 can capture a X-ray fluorescence visualization, image, or provided information based on a number of material characterizing distribution function that are obtained from a number of positions, angles, etc. based at least partially on element composition of the at least some matter. For example, certain embodiments of the X-ray fluorescence visualizer, imager, or information provider 100 can utilize the material characterizing distribution function obtained when applying an the at least one applied high energy photon and/or particle 120 substantially through a considerable portion of the individual that are fluorescing, similar to as described relative to FIG. 5 to 12, for example, and other locations through this disclosure. Certain embodiments of the X-ray fluorescence visualizer, imager, or information provider 100 can utilize the material characterizing distribution function obtained when applying the at least one applied high energy photon and/or particle 120 substantially through a considerable portion of the individual that can thereupon X-ray fluorescence similar to as described relative to FIG. 6, for example, and other locations through this disclosure.

Certain embodiments of the X-ray fluorescence visualizer, imager, or information provider 100 can differentiate between X-ray fluorescence high energy (e.g., X-ray, gamma ray, photon, particle, etc.) from different X-ray fluorescence locations and/or angles, based at least partially on tomographic/volumetric considerations based at least partially on element composition of the at least some matter. Certain embodiments of the X-ray fluorescence visualizer, imager, or information provider 100 can differentiate between X-ray fluorescence high energy (e.g., X-ray, gamma ray, photon, particle, etc.) from different energy levels, based at least partially on tomographic considerations.

The embodiments of the X-ray fluorescence visualizer, imager, or information provider 100 that are secured to the at least the portion of the individual, using a sleeve or other such mechanism, will likely be preferred by individuals undergoing imaging as compared with certain MRI images, CAT scans, tomography imagers, and/or other conventional imagers in which the patient is expected to remain substantially motionless. In addition, certain conventional tomography imaging techniques require positioning of the individual in a claustrophobic tube during the relatively extended duration.

Certain types of tomography imagers (both conventional and included as certain embodiments of X-ray fluorescence visualizer, imager, or information provider 100), may tend to be quite computer-software and processor intensive. Much of the work by the computer software, hardware, or firmware is associated with repositioning, focusing, zooming, angling, refreshing, and other controlling and adjusting aspects of the displayed X-ray fluorescence visualization, image, or provided information. Certain of the X-ray fluorescence depth visualizing, imaging, or information providing components of certain embodiments of the X-ray fluorescence visualizer, imager, or information provider 100 can be indexed relative to the portion of the individual. Such indexing can be performed such that if a region of interest (e.g., a cancer node) is located, the location can be determined relative to the X-ray fluorescence visualizer, imager, or information provider 100, such as by longitude or latitude markings on the sleeve in certain embodiments of the X-ray fluorescence visualizer, imager, or information provider 100. Certain instances of such X-ray fluorescence visualization, imaging, or information providing can be provided on a real time (or near real time) basis.

A considerable portion of this disclosure describes applying X-ray fluorescence visualizer, imager, or information providers to image to locate, analyze, and/or treat a variety of aberrations such as cancers, abscesses, infections, etc. It is also envisioned that a number of embodiments of the X-ray fluorescence visualizer, imager, or information provider 100 can be applied to a variety of surgical, medical examination, medical diagnosis, medical forensics, autopsies and other such applications. Certain embodiments of the X-ray fluorescence visualizer, imager, or information provider 100 may X-ray fluorescence visualize, image, and/or provide information relating to blood that can be configured to provide high contrast with this technique since it has iron and fluoresces considerably based at least partially on element composition of the at least some matter.

As such, certain embodiments of the X-ray fluorescence visualizer, imager, or information provider may be particularly appropriate for brain X-ray fluorescence visualization, imaging, or information providing and/or surgery, heart X-ray fluorescence visualization, imaging, or information providing and/or surgery, lung X-ray fluorescence visualization, imaging, or information providing and/or surgery, etc. Certain embodiments of the X-ray fluorescence visualizer, imager, or information provider 100 may be configured to examine aberrations of such dissimilar matter such as calcium concentration of portions of matter for X-ray fluorescence visualization, imaging, or information providing or examination for breast tumors, iodine for thyroid X-ray fluorescence visualization, imaging, or information providing or examination based at least partially on element composition of the at least some matter. Additionally, certain contrast agents may be used to enhance the contrast for X-ray fluorescence visualization, imaging, or information providing, for example iodine in blood vessels.

Certain embodiments of the X-ray fluorescence visualizer, imager, or information provider 100 can include a relatively weak powered X-ray based at least one high energy photon and/or particle emitter portion(s) 150, such that much of the X-rays generated therefrom may not be transmitted through the at least the portion of the individual. Such relatively weak powered X-ray at least one high energy photon and/or particle emitter portion(s) 150 may be desirable since they limit the dosage being applied to the at least the portion of the individual, as well as others near the individual such as the user.

There are a number of X-ray fluorescence visualization, imaging, or information providing techniques that can be utilized by certain embodiments of the X-ray fluorescence visualizer, imager, or information provider 100, each of which should consider limiting the overall dosage of X-rays being applied to the at least the portion of the individual and/or other persons. Certain embodiments of the X-ray fluorescence visualizer, imager, or information provider 100 can be configured to operate on a temporal/positional reflective basis. This may, depending on context, be considered as X-ray fluorescence visualization, imaging, or information providing at a rate sufficient to indicate accurately the current position of the portion of the individual 82 undergoing X-ray fluorescence visualization, imaging, or information providing (considering the intended purpose of the at least one X-ray fluorescence visualization, image, or provided information).

Real time depth imaging, X-ray fluorescence visualizing, or information providing, and near real time depth imaging, X-ray fluorescence visualizing, or information providing may be considered as one embodiment of temporal/positional reflective X-ray fluorescence depth visualizing, imaging, or information providing. As such, temporal/positional X-ray fluorescence visualization, imaging, or information providing by certain embodiments of the X-ray fluorescence visualizer, imager, or information provider 100 can involve updating of X-ray fluorescence visualization, imaging, or information providing within such a duration as to accurately reflect a state of the at least the portion of the individual 82. By using certain types of temporal/positional reflective X-ray fluorescence visualization, imaging, or information providing using certain embodiments of the X-ray fluorescence visualizer, imager, or information provider, certain users may be able to locate a region, organ, etc. within the at least the portion of the individual either manually or using a tool. Examples of such tools as described in this disclosure can include, but are not limited to, an endoscope attachment, a tactile feedback provider, an attachment to a framework, etc.

As such, certain embodiments of the X-ray fluorescence information can be utilized or operated by the user and/or the individual on a substantially temporal/positional reflective basis. At the time of operation, X-ray fluorescence visualization, imaging, or information providing and/or X-ray fluorescence visualize, image, and/or provide information updating can be performed at a substantially temporal/positional reflective basis. Alternatively, certain X-ray fluorescence visualization, imaging, or information providing and/or X-ray fluorescence visualize, image, and/or provide information updating could be performed sequentially a number of times, or only one or more times using certain embodiments of the X-ray fluorescence visualizer, imager, or information provider 100 based at least partially on element composition of the at least some matter.

A number of illustrative but not limiting applications of temporal X-ray fluorescence depth visualizing, imaging, or information providing by certain embodiments of the subcutaneous X-ray fluorescence visualizer, imager, or information provider 100. One application of temporal X-ray fluorescence depth visualizing, imaging, or information providing by certain embodiments of the X-ray fluorescence visualizer, imager, or information provider 100 could include functional brain X-ray fluorescence depth visualizing, imaging, or information providing or functional tomography, in which certain regions of brain activation may be reflected with increases in blood flow based at least partially on element composition of the at least some matter of the brain. This type of X-ray fluorescence depth visualizing, imaging, or information providing could be used during brain surgeries to detect an area associated with a given cognitive action or sensory stimulation by monitoring or detecting alterations in blood flow. Another application of temporal X-ray fluorescence depth visualizing, imaging, or information providing by certain embodiments of the X-ray fluorescence visualizer, imager, or information provider 100 may be associated with vascular surgery. Whether the vascular surgery be for clipping an aneurysm or creating a vascular graft, one could use the subcutaneous X-ray fluorescence visualizer, imager, or information provider 100 to detect alterations in blood flow in the brain, heart, liver, or other organ, tissue, or region of the individual.

Yet another X-ray fluorescence depth visualizing, imaging, or information providing application of certain embodiments of the subcutaneous X-ray fluorescence visualizer, imager, or information provider 100 could include implantation of orthopedic instrumentation. A user such as a surgeon could image, examine, and/or utilized the implant during installation to ensure that it is being installed properly. As such, the user could insure the implant is not being positioned are located in properly or in the wrong place during attachment or securement. Dentists could similarly image, examine, and/or utilize images relating to their dental work. An example of such installation-based X-ray fluorescence visualization, imaging, or information providing might include installing a pedicle screw to be used in a spinal construct and/or plate. Certain embodiments of the subcutaneous X-ray fluorescence visualizer, imager, or information provider 100 may be used to ensure the screw has not breached and gone into the spinal canal, or alternately exited to hit a blood vessel, a nerve root, or another sensitive region. Certain embodiments of the subcutaneous X-ray fluorescence visualizer, imager, or information provider 100 could thereby help watch the implant placement progression.

Certain embodiments of the X-ray fluorescence visualizer, imager, or information provider 100 can be applied to different individuals such as a variety of humans of different conditions, sexes, ages (e.g., a human adult, child, or embryo), etc. Additionally, certain embodiments of the X-ray fluorescence visualizer, imager, or information provider 100 can be applied to at least one other non-human individuals 82 including, but not limited to: at least one animal (domestic, wildlife, livestock as described with respect to FIGS. 37 and 38), at least one organism (natural or synthetic, such as can be X-ray fluorescence visualized, imaged, or have information provided for medical, scientific, clinical or other purposes), at least one plant, etc. By X-ray fluorescence visualization, imaging, or information providing animals such as pets, wild animals, or livestock, for example, certain embodiments of the X-ray fluorescence visualizer, imager, or information provider 100 can obtain useful information thereabout based at least partially on element composition of the at least some matter, without the necessity of the user having to come into close contact, or only limited contact, with the animal. Such users who often have to come in contact with animals might include, but are not limited to: veterinarian, wildlife managers, zookeepers, other people associated with wild or domestic animals, etc. Such close contact is also possible during use by certain X-ray fluorescence visualization, imaging, or information providing embodiments. In addition, such X-ray fluorescence visualization, imaging, or information providing can be done relatively routinely, or in a non-evident manner, such as to make scanning the animals, or a relatively large number of animals, relatively easy without them necessarily being aware of the X-ray fluorescence depth visualizing, imaging, or information providing. Such X-ray fluorescence depth visualizing, imaging, or information providing of certain animals may preferably be performed in a manner that reduces the animal's awareness that anything unusual is occurring, such as may easily be accomplished using certain embodiments of the X-ray fluorescence visualizer, imager, or information provider 100.

The above-mentioned components or embodiments of the X-ray fluorescence visualizer, imager, or information provider 100, as described with respect to FIG. 1 or 2 as well as in other locations in this disclosure, could be distributed or operated outside, in a forest, etc. to view a variety of individual animals, humans, organisms, plants, etc., such as to monitor their conditions. Such configurations could allow X-ray fluorescence visualization, imaging, or information providing of wild animals (perhaps controlled and/or adjusted by remote control), livestock, fish, etc. that may be based at least partially on the density, elements, chemicals, compounds, and/or biological materials included in or contained within the matter. Such embodiments of the X-ray fluorescence visualizer, imager, or information provider 100 could be useful in detecting illnesses, infections, injuries, conditions, etc. in wildlife, whales, dolphins, etc. that may be based at least partially on the densities, elements, chemicals, compounds, and/or biological materials included in or contained within the matter. The matter aberration 360 can be X-ray fluorescence visualized, imaged, or information provided, and can be provided or enhanced based at least partially on the elemental composition (or chemical composition, compound composition, or biological material composition with the use of X-ray fluorescence enhancing additives, taggants, or contrast agents, etc.).

Figure 37:
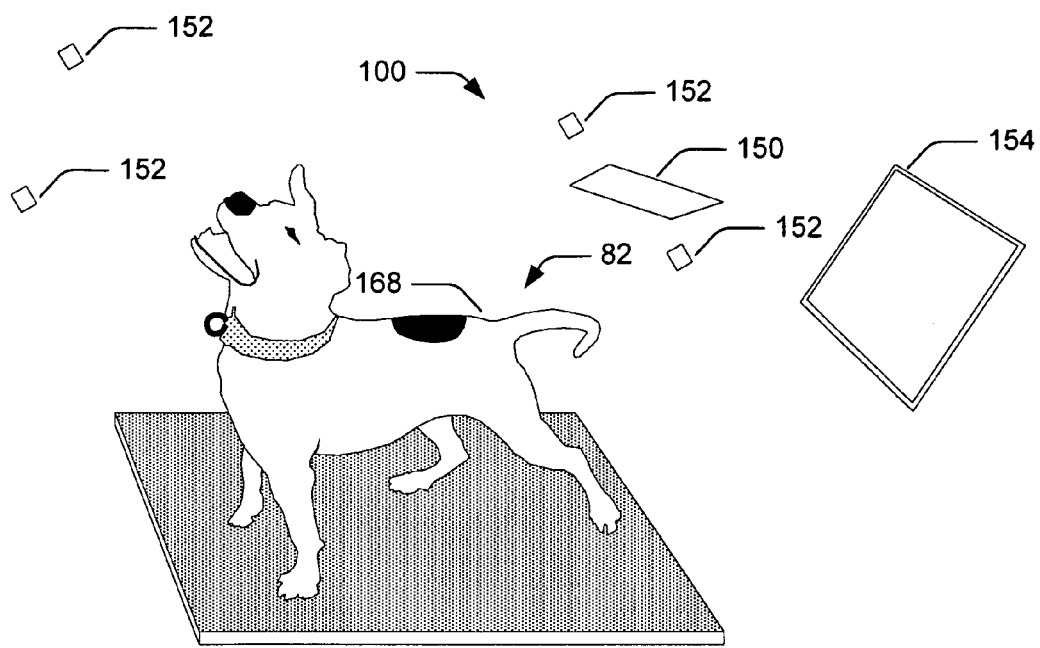
FIG. 37 shows one animal-based embodiment of the X-ray fluorescence visualizer, imager, or information provider.
Figure 38:
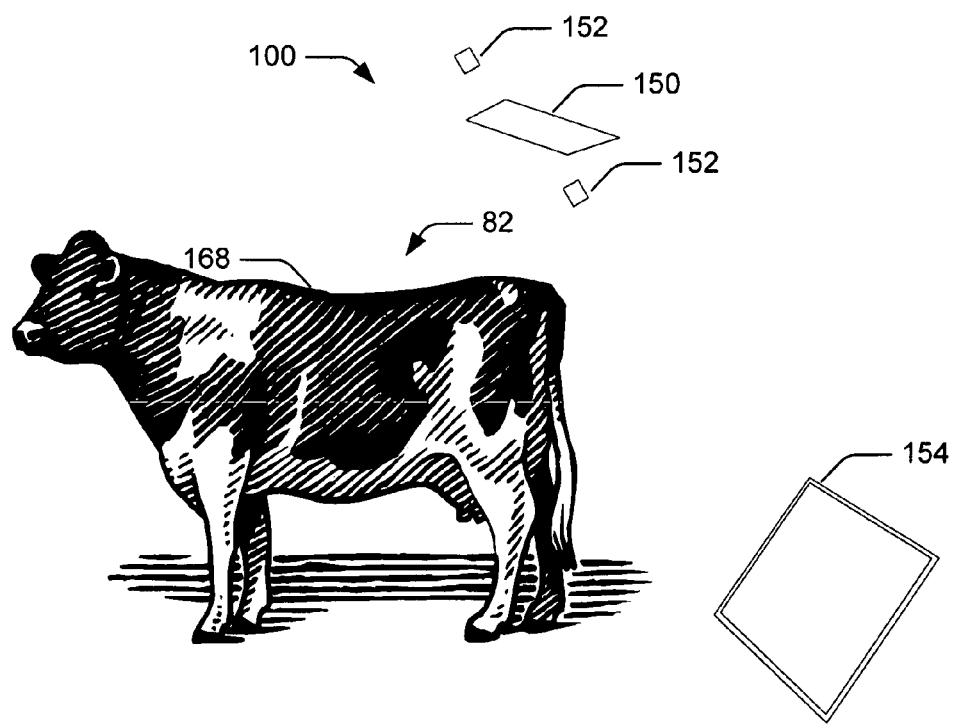
FIG. 38 shows another animal-based embodiment of the X-ray fluorescence visualizer, imager, or information provider.

Certain embodiments of the X-ray fluorescence visualizer, imager, or information provider 100 can be applied to animals such pets, livestock, wild animals, aquatic animals and fish, etc. as described with respect to FIGS. 37 and 38, for example. Since animals do not understand conventional imaging or other medical processes, they may be difficult to handle or become agitated or confused under certain conventional imaging circumstances. As such, it may be very difficult to image portions of animals to determine their condition using certain conventional imagers. Certain embodiments of the X-ray fluorescence visualizer, imager, or information provider 100 could be applied in such manner such as the animal may not even be aware of the ongoing X-ray fluorescence visualization, imaging, or information providing. Veterinarians could utilize certain embodiments of the X-ray fluorescence visualizer, imager, or information provider 100 that may be based at least partially on the densities, elements, chemicals, compounds, and/or biological materials included in or contained within the matter to obtain considerable X-ray fluorescence visualization, imaging, or information providing information previously unobtainable while keeping a safe distance from uncooperative, uncertain, or dangerous animals.

Certain embodiments of the X-ray fluorescence visualizer, imager, or information provider 100 could be applied to livestock, such as may be situated in a corral or even a field as described with respect to FIG. 38. Such livestock embodiments of the X-ray fluorescence visualizer, imager, or information provider may be able to scan them for certain illnesses, infections, conditions, sicknesses, etc. (e.g., mad cow disease) that may be based at least partially on the densities, elements, chemicals, compounds, and/or biological materials included in or contained within the matter. Certain users of the X-ray fluorescence visualizer, imager, or information provider 100 could be characterized by relative speed, limited expense, reliability, and effectiveness.

As such, certain embodiments of the X-ray fluorescence visualizer, imager, or information provider 100 can X-ray fluorescence visualize, image, and/or provide information of a wide variety of individuals from the surface 168 of the at least the portion of the individual down to the within the at least one X-ray fluorescence range to the at least one prescribed substantial X-ray fluorescence depth (that may be based at least partially on the densities, elements, chemicals, compounds, and/or biological materials included in or contained within the matter). As described herein, the surface that is being visualized, imaged, or information provided across could be internal and/or external to the individual. The particular X-ray fluorescence visualization, imaging, or information providing modality being utilized should be configured based on the matter, region, structure, and other characteristics, of the at least the portion of the individual as well as the condition of the at least the portion of the individual, etc.

Certain embodiments of X-ray fluorescence visualization, imaging, or information providing of distinct matter relatively can be based at least partially on different X-ray based characteristics of the distinct matter, the junction location of the different matters, etc. that may be based at least partially on the densities, elements, chemicals, compounds, and/or biological materials included in or contained within the matter. One X-ray characteristic can be based, at least partially, on X-ray absorbance differences between different types of matter that may be based at least partially on the densities, elements, chemicals, compounds, and/or biological materials, included in or contained within the matter. Bones, bone fragments, etc. when being exposed to transmissive X-rays are generally understood to absorb more X-ray based electromagnetic radiation (e.g., X-ray photons) than softer human matter (such as skin, tissue, muscle, blood, bodily fluid, etc.), for example. Even with X-ray fluorescence, such as utilized by certain embodiments of the X-ray fluorescence visualizer, imager, or information provider 100, the bone or bone fragments would be expected to be more dense, and would be expected to absorb more X-rays of certain frequencies/energy levels than other matter such as tissue that may be based at least partially on the densities, elements, chemicals, compounds, and/or biological materials included in or contained within the matter. As such, certain matter will X-ray fluorescence a greater percentage of the applied or the at least one applied high energy photon and/or particle 120 than bone or bone fragments, which will absorb a greater percentage of X-rays that may be based at least partially on the densities, elements, chemicals, compounds, and/or biological materials included in or contained within the matter.

Similarly, each type of matter such as tissue, muscle, bones, fat, etc. should have distinct X-ray characteristics that can be imaged directly using X-ray fluorescence techniques, and/or by using certain particular contrast agents or fluoroscopy using certain embodiments of the X-ray fluorescence visualizer, imager, or information provider that may be based at least partially on the densities, elements, chemicals, compounds, and/or biological materials included in or contained within the matter. Another X-ray characteristic can be based, at least partially, on X-ray fluorescence or reflectance differences between different types of matter. Yet another X-ray characteristic can be based, at least partially, on a ratio of photons transmission compared to photons return between different types of matter that may be based at least partially on the densities, elements, chemicals, compounds, and/or biological materials included in or contained within the matter.

Certain embodiments of the X-ray fluorescence visualizer, imager, or information provider 100 can utilize a single the at least one applied high energy photon and/or particle 120 during X-ray fluorescence visualization, imaging, or information providing such as can be provided by at least one high energy photon and/or particle emitter portion(s) 150, as described in this disclosure. By comparison, certain embodiments of the X-ray fluorescence visualizer, imager, or information provider can utilize multiple the at least one applied high energy photon and/or particle 120 which may at least partially intersect with each other during X-ray fluorescence visualization, imaging, or information providing such as can be provided by the at least one high energy photon and/or particle emitter portion(s) 150, as described in this disclosure. With certain embodiments of the X-ray fluorescence visualizer, imager, or information provider 100, the intersection of the multiple the at least one applied high energy photon and/or particle 120 can be applied at a location that may be desired to be X-ray fluorescence visualized, imaged, or information provided, such as at a particular prescribed substantial X-ray fluorescence depth, etc.

With certain embodiments of the X-ray fluorescence visualizer, imager, or information provider 100, the intersection location of the multiple the at least one applied high energy photon and/or particle 120 can be controllably moved to a desired location such as may be controlled by the user of certain embodiments of the subsurface X-ray fluorescence visualization, imaging, or information providing controller 97 as described in this disclosure with respect to FIG. 1 or 2. Alternately, such movement of the intersection can effect a scan, similar to a raster scan such as is generally known by those skilled with displays. Certain embodiments of the X-ray fluorescence visualizer, imager, or information provider 100 can thereby be configured to provide a variety of different X-ray fluorescence depth visualizations, images, and/or provided information depending on the X-ray fluorescence visualization, imaging, or information providing techniques that may be based at least partially on the densities, elements, chemicals, compounds, and/or biological materials included in or contained within the matter. For instance, by X-ray fluorescence visualization, imaging, or information providing, certain individuals could be X-ray fluorescence visualized, imaged, or have information provided in a manner appearing similar to (but perhaps having different resolution or characteristics from) imaging by conventional X-ray, fluoroscopy, MRI, CAT scans, or other X-ray fluorescence visualization, imaging, or information providing modalities that may be based at least partially on the densities, elements, chemicals, compounds, and/or biological materials included in or contained within the matter.

One aspect of certain embodiments of the X-ray fluorescence visualizer, imager, or information provider 100 is that relatively small X-ray fluorescence depth visualizations, images, and/or provided information can be captured, displayed, analyzed, and if desired recaptured without waiting for durations associated with processing, or developing, the images are X-ray fluorescence visualizations for a larger region. In certain circumstances, the X-ray fluorescence visualizing, imaging, and/or providing information can be performed without having to wait for processing or developing, and the necessity of having to move or reposition the patient. During certain conventional imaging techniques, the at least the portion of the individual must remain virtually motionless during the conventional imaging process to maintain the image quality. Additionally, certain conventional image techniques take a considerable duration to capture, develop, process, display, etc. By comparison, certain embodiments of the X-ray fluorescence visualizer, imager, or information provider can capture and/or display certain localized or shallow X-ray fluorescence depth visualizations, images, and/or provided information that may be based at least partially on the densities, elements, chemicals, compounds, and/or biological materials included in or contained within the matter relatively quickly. As such, the user such as the physician, veterinarian, dentist, or other user can quickly examine the X-ray fluorescence visualize, image, and/or provide information and/or obtain additional subsequent X-ray fluorescence depth visualizations, images, and/or provided information that show desired features, positions, etc.

Certain embodiments of the X-ray fluorescence visualizer, imager, or information provider 100 may not require maintaining the at least the portion of the individual nearly motionless in an encircling enclosure or tunnel, such as with CT scans, PET scans, or MRI. Certain embodiments of the X-ray fluorescence visualizer, imager, or information provider 100 might involve a change in X-ray fluorescence visualization, imaging, or information providing techniques by the users, surgeons, etc. that may be based at least partially on the densities, elements, chemicals, compounds, and/or biological materials included in or contained within the matter, but would likely not diminish X-ray fluorescence visualization, imaging, or information providing capabilities or resolution as compared with other conventional imaging techniques.

Certain embodiments of the X-ray fluorescence visualizer, imager, or information provider 100 can be configured such that the at least one matter associated with the at least the portion of the individual 82. For example, the matter of the portion of the human can include at least some, or combination of: flesh, muscle, fat, tissue, bone, teeth, blood, fluids, or other such matter that may be based at least partially on the densities, elements, chemicals, compounds, and/or biological materials included in or contained within the matter. As such, certain embodiments of the X-ray fluorescence visualizer, imager, or information provider 100 can X-ray fluorescence visualize, image, and/or provide information relating to not only matter in general, but also different types of matter and junctions between different types of matter that may be based at least partially on the densities, elements, chemicals, compounds, and/or biological materials included in or contained within the matter. Such X-ray fluorescence visualization, imaging, or information providing matter can be performed at the range of resolutions as described in this disclosure, and may at least partially rely on additional agents, components, etc. such as may enhance X-ray fluorescence visualization, imaging, or information providing.

Certain embodiments of the X-ray fluorescence visualizer, imager, or information provider 100 can allow physicians a number of opportunities to detect certain types of distinct matter, such as tumors, cancers, abscesses, infections, etc. that may be situated in a region of generally normal matter that may be based at least partially on the densities, elements, chemicals, compounds, and/or biological materials included in or contained within the matter. Certain X-ray fluorescence visualization, imaging, or information providing modalities may be more successful to detect certain types of cancers, abscesses, infections, etc. as compared with certain X-ray fluorescence visualizers, imagers, or have information providers that may be based at least partially on the densities, elements, chemicals, compounds, and/or biological materials included in or contained within the matter. It may therefore be useful to provide a X-ray fluorescence visualization, imaging, or information providing modality that can detect at least one or a considerable number and types of cancers, tumors, abscesses, infections, and/or other matter aberrations as described in this disclosure. For instance, certain X-ray fluorescence visualization, imaging, or information providing modalities may not detect certain cancers, abscesses, infections, etc. or other matter aberrations, while other X-ray fluorescence visualization, imaging, or information providing modalities (perhaps including certain embodiments of the X-ray fluorescence visualizer, imager, or information provider 100) may detect the cancers or other matter aberrations.

Certain embodiments of the X-ray fluorescence visualizer, imager, or information provider 100 can be configured or designed to detect at least one of a variety of cancers or tumors such as, but not limited to: breast cancer, skin cancer, colon cancer, bladder cancer, prostate cancer, etc. Such cancer cells or tumors may be situated in the matter at a location that certain conventional imagers may not be able to image, or may be expensive to image well. Certain cancers, such as certain breast cancer and certain melanomas, may be characterized by calcium nodules, which may be difficult be detect using a variety of conventional imaging techniques and/or devices.

Certain embodiments of the X-ray fluorescence visualizer, imager, or information provider 100 can be well suited to X-ray fluorescence visualize, image, and/or provide information relating to a variety of cancer and/or tumors. Certain tumors or cancers may exhibit angiogenesis that allow X-ray fluorescence depth visualizing, imaging, or information providing by certain X-ray fluorescence visualizer, imager, or information providers 100. The blood vessel of the patient individual nearby the cancer or tumor may be grown to allow for an increase in blood flow to the tumor or cancer as the tumor or cancer tends to expand and grow outward. Cancer cells or tumor cells may lose their ability to divide in a controlled fashion that can result in the angiogenesis. Tumors can induce blood vessel growth (angiogenesis) by secreting various growth factors, e.g., Vascular Endothelial Growth Factor (VEGF). Such growth factors can induce capillary growth into the tumor, which some researchers suspect supply required nutrients, thereby allowing for tumor expansion. Other clinicians believe that angiogenesis really serves as a waste pathway, taking away the biological end products put out by rapidly dividing cancer cells. In either case, angiogenesis is a necessary and required step for cancer cells to transition and grow from a small harmless cluster of cells to the size of a large tumor. Angiogenesis is also required for the spread of a tumor, or metastasis. The depth of the X-ray fluorescence visualization, imaging, or information providing can be controlled or adjusted as to localize the area being examined.

Certain types of cancer can proliferate to different regions, areas, organs, etc. based on metastasis. Metastasis can occur, for example, when single cancer cells break away from an established solid tumor, enter the blood vessel, and be carried to a distant site, where they can implant and begin the growth of a secondary tumor. Evidence now suggests that the blood vessel in a given solid tumor may in fact be mosaic vessels, comprised of endothelial cells and tumor cells. This mosaicity can allow for substantial shedding of tumor cells into the vasculature. The subsequent growth of such metastases will also require a supply of nutrients and oxygen or a waste disposal pathway as provided by subsequent angiogenesis. A tumor thereby typically consists of a population of rapidly dividing and growing cancer cells. Mutations may rapidly accrue within the population of many cancer cells. These mutations of the cancer cells often allow at least some of the cancer cells to develop drug resistance.

Tumors including certain cancer cells cannot grow beyond a certain size, while permitting the internal cancer cells deep within the tumor to survive (typically as a result of a lack of oxygen and other essential nutrients that can be provided to the interior cancer cells). Certain tumors or cancers may thereby exhibit necrosis, in which, as the size of the tumor or cancer increases, the original cancer cells that are situated deep within the tumor, and thereby distant from the outer boundary of the tumor or cancer may starve and die as a result of lack of nutrients such as may be provided by the healthy cells. Such starvation or dying may occur since the cell is no longer in contact with healthy cells or supplies of nutrients or oxygen. As such, certain necrotic cancer cells may tend to exhibit different photonic and X-ray characteristics than the living cancer cells, as well as the healthy cells. Certain embodiments of the X-ray fluorescence visualizer, imager, or information provider 100 can therefore be utilized to detect such necrotic cancer cells. Such X-ray fluorescence depth visualizing, imaging, or information providing of tumors and/or cancer provides only one illustrative embodiment of a use of certain embodiments of the X-ray fluorescence visualizer, imager, or information provider 100.

In addition, certain embodiments of the X-ray fluorescence visualizer, imager, or information provider 100 can X-ray fluorescence visualize, image, and/or provide information on a temporal/positional reflective basis that may be based at least partially on the densities, elements, chemicals, compounds, and/or biological materials included in or contained within the matter, and may be performed without positioning the individual in the claustrophobic enclosures, or applying the high-scale electromagnetic radiation associated with, for example, conventional MRI, conventional PET scans, and certain other conventional images.

Certain embodiments of the X-ray fluorescence visualizer, imager, or information provider 100 can provide different X-ray fluorescence depth visualizing, imaging, or information providing modalities and/or techniques than that of conventional X-ray imaging. For example, conventional X-ray imaging can X-ray fluorescence visualize, image, and/or provide information relating to differences based at least in part on density or atomic number of the matter of the portion of the X-ray fluorescence visualized, imaged, or information provided object, such as differences on density between bone and skin for a person. By comparison, certain embodiments of the X-ray fluorescence visualizer, imager, or information provider 100 can X-ray fluorescence visualize, image, and/or provide information based at least partially on density of matter such as tissue, as well as providing an additional X-ray fluorescence visualization, imaging, or information providing modality. Certain embodiments of the X-ray fluorescence visualizer, imager, or information provider 100 can be expected to X-ray fluorescence visualize, image, and/or provide information that may be based at least partially on the densities, elements, chemicals, compounds, and/or biological materials included in or contained within the matter to a resolution down to approximately 100 microns, or even less as technology improves.

Certain embodiments of the X-ray fluorescence visualizer, imager, or information provider 100 can be configured to utilize contrast agents such as, for example, iodine that may be based at least partially on the densities, elements, chemicals, compounds, and/or biological materials included in or contained within the matter. Certain embodiments of the X-ray fluorescence visualizer, imager, or information provider 100 can be configured to apply a contrast agent at least partially within the confined depth region that may be based at least partially on the densities, elements, chemicals, compounds, and/or biological materials included in or contained within the matter. Also, certain embodiments of fluorophores (that when accepted by matter may allow the matter to X-ray fluorescence under the application of certain X-rays), as well as other electromagnetic responsive material, can be utilized in a similar manner as contrast agent to matter to enhance the X-ray fluorescence visualization, imaging, or information providing that may be based at least partially on the densities, elements, chemicals, compounds, and/or biological materials included in or contained within the matter.

Certain embodiments of the X-ray fluorescence visualizer, imager, or information provider can be configured to X-ray fluorescence visualize, image, and/or provide information relating to certain fluids and/or fluid locations such as blood (e.g., an element of hemoglobin) that may be based at least partially on the densities, elements, chemicals, compounds, and/or biological materials included in or contained within the matter. Certain blood locations, such as arteries, veins, blood pooling regions, body parts, organs, capillaries, regions, etc., can provide good X-ray contrast based at least partially on iron or other materials in the blood that may be based at least partially on the densities, elements, chemicals, compounds, and/or biological materials included in or contained within the matter. Therefore, the iron in the blood can cause deflection, absorption, reflection, or X-ray fluorescence of the X-rays passing there through by some detectable amount. Using conventional techniques, many surgeons, etc. have considerable uncertainty as to the precise location of many blood vessels that they must operate around without contacting or damaging. Such effort by the surgeons, etc. in avoiding the blood vessels may not only be dangerous, but also expensive, time consuming, laborious, and tedious. Certain embodiments of the X-ray fluorescence visualizer, imager, or information provider 100 can detect blood vessels, as well as other bodily fluid conduits, etc. such as to in many instances allow the surgeons, etc. to operate more safely, quickly, effectively, and efficiently in a manner such as may be based at least partially on the densities, elements, chemicals, compounds, and/or biological materials included in or contained within the matter.

Certain embodiments of the X-ray fluorescence visualizer, imager, or information provider 100 can thereby be configured to observe calcium concentration, such as may exist in certain cancers or tumors that may be based at least partially on the densities, elements, chemicals, compounds, and/or biological materials included in or contained within the matter. Certain embodiments of the X-ray fluorescence visualizer, imager, or information provider 100 can be configured to X-ray fluorescence visualize, image, and/or provide information relating to iodine such as may be present and varying concentrations in portions of the brain, such as may be provided by the thyroid. Certain embodiments may be used in combination with a X-ray fluorescence visualization, imaging, or information providing agent that can be added to the at least the portion of the individual, either intravascular or otherwise that may be based at least partially on the densities, elements, chemicals, compounds, and/or biological materials included in or contained within the matter.

Certain organs and matter such as tissue that have considerable blood flow either flowing through or contained therein can be X-ray fluorescence visualized, imaged, or have information provided based, at least in part, on the blood situated within the organ or matter that may be based at least partially on the densities, elements, chemicals, compounds, and/or biological materials included in or contained within the matter. Examples of such organs or matter that can be X-ray fluorescence visualized, imaged, or have information provided as a result of blood can include, but are not limited to: the brain (accounting for approximately 20 percent of the blood flow in the human body at any given time), the heart, the liver, the lung, the appendix, the intestine, as well as certain muscles. The heart therefore is an example of an organ that can be X-ray fluorescence visualized, imaged, or have information provided particularly well based on blood situated relative to the heart that may be based at least partially on the densities, elements, chemicals, compounds, and/or biological materials included in or contained within the matter. The heart acts to circulate blood throughout the body, and such blood flow through the aorta, the ventricles, and other chambers and regions of the heart can be X-ray fluorescence visualized, imaged, or have information provided (in certain instances in a substantially real-time basis). In addition, the heart additionally includes arteries, veins, and capillaries which can be distinctly X-ray fluorescence visualized, imaged, or have information provided.

There may be variety of heart aspects and/or conditions that can be imaged using certain embodiments of the X-ray fluorescence visualizer, imager, or information provider 100 that may be based at least partially on the densities, elements, chemicals, compounds, and/or biological materials included in or contained within the matter. For example, the myocardium could be imaged, as can the heart valves, the coronary arteries, the blood vessels, as well as other matter and/or fluid of or within the heart. Certain blood flows through the valves, the aorta, etc. can be imaged, such as to indicate regurgitation and (that workflow) of blood through a valve; as well as valve stenosis (when blood flows through leaky valves) that may be based at least partially on the densities, elements, chemicals, compounds, and/or biological materials included in or contained within the matter. Certain embodiments of the X-ray fluorescence visualizer, imager, or information provider 100 can X-ray fluorescence visualize, image, and/or provide information relating to portions of the myocardium, such as to screen persons for increased risk of myocardial infractions (heart attacks) that may be based at least partially on the densities, elements, chemicals, compounds, and/or biological materials included in or contained within the matter. Certain embodiments of the X-ray fluorescence visualizer, imager, or information provider 100 can utilize external and/or Bluetooth image and, such as by utilizing scopes, etc. They can be positioned as desired relative to the heart that may be based at least partially on the densities, elements, chemicals, compounds, and/or biological materials included in or contained within the matter. Certain embodiments of the X-ray fluorescence visualizer, imager, or information provider can thereby be extended via scopes or other techniques following blood vessels, lumens, etc. to a desired location within the heart. Certain embodiments of the subsurface X-ray fluorescence visualizer, imager, or information provider 100 can utilize open-heart or closed surgery or procedures.

Certain embodiments of the X-ray fluorescence visualizer, imager, or information provider 100 can image at least portions of other organs, such as long as, liver, brain, etc. that may be based at least partially on the densities, elements, chemicals, compounds, and/or biological materials included in or contained within the matter. The lung and liver include internal nodules whose condition can be detected using certain embodiments of the X-ray fluorescence visualizer, imager, or information provider. As such, certain organs and matter can be X-ray fluorescence visualized, imaged, or have image provided by certain embodiments of the X-ray fluorescence visualizer, imager, or information provider 100 based, at least in part, on density or atomic number of the matter that may be based at least partially on the densities, elements, chemicals, compounds, and/or biological materials included in or contained within the matter. For example, bones, spine portions, cartilage, tendons, ligaments, etc. can be X-ray fluorescence visualized, imaged, or have information provided that may be based at least partially on the densities, elements, chemicals, compounds, and/or biological materials included in or contained within the matter. Certain embodiments of the X-ray fluorescence visualizer, imager, or information provider 100 can be utilized by orthopedic surgeons, for example, to determine how bones, bone fragments, bony portions, etc. are situated relative to each other that may be based at least partially on the densities, elements, chemicals, compounds, and/or biological materials included in or contained within the matter. For example, during a spinal construct or bone fracture surgery, the surgeon could determine whether the bone portions are properly aligned or situated as desired; such as to be able to apply a construct, apply a pin, set, etc. that may be based at least partially on the densities, elements, chemicals, compounds, and/or biological materials included in or contained within the matter. Following surgery, the individual (e.g., patient) could be examined using certain embodiments of the X-ray fluorescence visualizer, imager, or information provider 100 to determine a variety of orthopedic considerations. For example, are the bones in the desired location such as being aligned that may be determined based at least partially on the densities, elements, chemicals, compounds, and/or biological materials included in or contained within the matter? Alternately, are any pins, fasteners, etc. that have been applied within the individual properly situated or affixed relative to the portions of the individual, etc. that may be based at least partially on the densities, elements, chemicals, compounds, and/or biological materials included in or contained within the matter? Such post-operative examination can be performed with the bone portion(s) exposed, closed up and within the at least the portion of the individual, as well as also contained within a cast or other body part stabilizer. Following surgery, certain embodiments of the X-ray fluorescence visualizer, imager, or information provider 100 could be used to ensure that there has been no retained surgical instruments, sponges, tools, needles, tactile feedback providers, etc. within the at least the portion of the individual that may be determined based at least partially on the densities, elements, chemicals, compounds, and/or biological materials included in or contained within the matter.

A variety of organs and/or matter can be X-ray fluorescence visualized, imaged, or have information provided based at least partially on density image combination (e.g., image subtraction, time of flight, image transformation, deconvolution, image subtraction, weighted subtraction, functional subtraction, and group including inverse integral transform, subtractive inverse integral transform, inverse functional transform, and subtractive inverse functional transform, or other such image processing techniques) across the organ. Certain organs can be formed non-uniformly, such as alveoli being formed within lungs, blood vessels, non-uniform heart matter or tissue, etc. that may be based at least partially on the densities, elements, chemicals, compounds, and/or biological materials included in or contained within the matter. Certain organs and matter can include gases, liquids, and/or solids in portions of the organ or matter, such as to make the matter of the organ or tissue non-uniform.

As such, whether the X-ray fluorescence visualization, imaging, or information providing of the organ or matter is based at least partially on the blood or blood component situated therein, the density image combination (e.g., image subtraction, time of flight, image transformation, deconvolution, image subtraction, weighted subtraction, functional subtraction, and group including inverse integral transform, subtractive inverse integral transform, inverse functional transform, and subtractive inverse functional transform, or other such image processing techniques) across the organ or matter, or the liquid, solid, or gasses contained in at least portions of the organ or matter. Certain embodiments of the X-ray fluorescence visualizer, imager, or information provider 100 can be configured to X-ray fluorescence visualize, image, and/or provide information with considerable definition and at relatively low resolution, while others can be configured with relatively low definition at relatively high resolution. Such definitions, resolutions, and/or other X-ray fluorescence depth visualizing, imaging, or information providing characteristics can be controlled and/or adjusted with certain embodiments of the X-ray fluorescence visualizer, imager, or information provider 100.

The operation and structure of the certain embodiments of the X-ray fluorescence visualizer, imager, or information provider 100 can, depending on context, have a considerable number of similarities independent of the type of individual 82. Certain embodiments of the X-ray fluorescence visualizer, imager, or information provider 100 can be operated and/or scaled differently, however, depending upon the condition and/or portion of the individual being X-ray fluorescence visualized, imaged, or having information provided, desired resolution of X-ray fluorescence visualization, imaging, or information providing, rate of successive X-ray fluorescence visualization, imaging, or information providing, temporal duration of X-ray fluorescence visualization, imaging, or information providing, cooperation or consciousness of the individual, and other such factors.

Certain embodiments of the X-ray fluorescence visualizer, imager, or information provider 100 can thereby utilize a variety of X-ray fluorescence visualization, imaging, or information providing techniques similar to those that can at least partially include, but are not limited to: conventional X-ray imaging (e.g., transmission and/or fluoroscopy), X-ray Computed Tomography (CT or CAT) scans, Positron Emission Tomography (PET) scans, X-ray imaging at least partially using X-ray fluorescence, X-ray backX-ray fluorescence imaging, X-ray forward-X-ray fluorescence imaging, and/or other combinations, modifications, and/or developments of X-ray imaging, and/or X-ray based imaging modalities. Certain embodiments of the X-ray fluorescence visualization, imaging, or information providing technologies could be configured to represent affordable and technically useful X-ray fluorescence visualization, imaging, or information providing technologies for a variety of medical applications. The more affordable particular X-ray fluorescence visualizing, imaging, or information providing modality are provided similar success rates, safety records, etc., the more likely it is to be routinely used, and thereupon ultimately developed and accepted.

Certain embodiments of the X-ray fluorescence visualizer, imager, or information provider 100 therefore can rely on a variety of X-ray technologies that may be based at least partially on the densities, elements, chemicals, compounds, and/or biological materials included in or contained within the matter. X-ray technologies, in general, can be characterized as particle bombardment, in which the particle includes emitted photons following interaction of the target atom situated at the anode with electrons directed at (or near) the target atom. Certain embodiments of the X-ray fluorescence visualizer, imager, or information provider 100 therefore can rely on emission and detection of X-rays, which can take the form of directed or bombarded particles such as photons (and/or X-ray fluorescence photons there from).

As such, X-ray fluorescence visualization, imaging, or information providing technology can be associated and/or operatively combined with certain other imaging modalities such as particle bombardment imaging mechanisms (i.e., the particles including photons), as well as other conventional imaging methodologies as described in this disclosure. Such combination of the X-ray fluorescence visualizer, imager, or information provider 100 with other imaging modalities are intended to be considered as another embodiment of X-ray fluorescence visualizer, imager, or information provider, for the purpose of this disclosure, depending on context. As such, the X-rays can be characterized as including photons, which represent a form of electromagnetic radiation, which may be characterized by Maxwell's Equations.

There can be a variety of X-ray fluorescence visualization, imaging, or information providing modalities can be utilized to provide some level of X-ray fluorescence visualization, imaging, or information providing (which together can be considered for purpose of this disclosure, depending on context, to be referred to as X-ray fluorescence visualization, imaging, or information providing). Certain conventional transmission X-ray visualizing, imaging, or information providing modality can rely largely on those X-rays that can be applied to the soft matter or tissue of the at least the portion of the individual 82, to be transmitted there through (while being absorbed, diffracted, reflected, etc. off bones or other matter). The electromagnetic radiation of the transmitted X-rays can thereupon be received at a distant location of the at least the portion of the individual 82, after it has passed through the at least the portion of the individual 82. Such techniques can be used to form the X-ray on the opposite side of the at least the portion of the individual 82. X-ray fluorescence visualization, imaging, or information providing, as performed by certain embodiments of the X-ray fluorescence visualizer, imager, or information provider 100, can refer to those modalities that relies primarily on the X-ray based electromagnetic radiation that is at least partially reflected, or redirected, as it passes through the soft matter or tissue (or other opaque matter) of the at least the portion of the individual 82.

The term "X-ray fluorescence visualization, imaging, or information providing", as described in this disclosure, can be performed by one or more of certain embodiments of the X-ray fluorescence visualizer, imager, or information provider 100. Depending on context, certain type of X-ray fluorescence visualization, imaging, or information providing can include, but is not limited to, X-ray fluorescence visualization, imaging, or information providing, photography, displaying, X-ray fluorescence visualization, imaging, or information generation, computer generation, partial X-ray fluorescence visualization, imaging, or information integration, X-ray fluorescence visualization, imaging, or information capturing, X-ray fluorescence visualization, imaging, or information synthesizing, and other techniques that can at least partially capture X-ray fluorescence depth visualizations, images, and/or provided information that may be based at least partially on the densities, elements, chemicals, compounds, and/or biological materials included in or contained within the matter.

A sufficient amount of the at least one applied high energy photon and/or particle 120 can penetrate into the at least portion of the individual 82 for a prescribed substantial X-ray fluorescence depth 170 to accomplish the desired X-ray fluorescence visualization, imaging, or information providing that may be based at least partially on the densities, elements, chemicals, compounds, and/or biological materials included in or contained within the matter. By limiting the amount of X-rays, the dosage can be limited as well. A certain amount of the at least one applied high energy photon and/or particle 120 will likely be X-ray fluorescence or otherwise deflected throughout the penetration region from the surface 168 (e.g., skin) subsurface down to, and including, the prescribed substantial X-ray fluorescence depth 170.

Certain embodiments of the at least one high energy photon and/or particle emitter portion(s) 150 can be associated with a variety of embodiments of X-ray based electromagnetic radiation that can operate at a variety of frequencies and/or energy levels, which may therefore X-ray fluorescence visualize, image, and/or provide information down to or at a variety of prescribed substantial X-ray fluorescence depths into the at least the portion of the individual 82 within a first of view of the X-ray fluorescence visualizer, imager, or information provider 100. Certain embodiments of the at least one high energy photon and/or particle emitter portion(s) 150 may be situated within the at least the portion of the individual 82, adjacent to the at least the portion of the individual 82, or external to the at least the portion of the individual 82. Either one, or a plurality of, the at least one high energy photon and/or particle emitter portion(s) 150 may be provided either within the at least the portion of the individual 82, adjacent to the at least the portion of the individual 82, and/or external to the at least the portion of the individual 82 that may be based at least partially on the densities, elements, chemicals, compounds, and/or biological materials included in or contained within the matter.

Certain embodiments of the detector portion 152 can be configured, by comparison, to receive X-ray electromagnetic radiation in the form of X-ray fluorescence high energy (e.g., X-ray, gamma ray, photon, particle, etc.) that can X-ray fluorescence from the at least one applied high energy photon and/or particle 120 provided by the high energy photon and/or particle emitter portion(s) of the X-ray fluorescence visualizer, imager, or information provider 100, or another device configured to emit the at least one applied high energy photon and/or particle 120 that may be based at least partially on the densities, elements, chemicals, compounds, and/or biological materials included in or contained within the matter. Within this disclosure, certain embodiments of the at least one detector portion 152 can be adjustable such as to receive certain embodiments of the X-ray based electromagnetic radiation such as can be applied to the at least the portion of the individual from the at least one high energy photon and/or particle emitter portion(s) 150 (and X-ray fluorescence at least partially within the at least the portion of the individual). Such adjustment of the at least one detector portion 152 can be based on such parameters as direction, signal strength, frequency, energy level, or other such characteristics of the X-ray photons.

Certain embodiments of the at least one high energy photon and/or particle emitter portion(s) 150, that is not associated with any particular X-ray fluorescence visualizer, imager, or information provider 100, may be utilized that can be detected by one or more distinct detector portions 152 and/or one or more distinct at least one X-ray fluorescence receiving portion(s) 151. For example, certain embodiments of the at least one high energy photon and/or particle emitter portion(s) 150 may be configured as a "flooding" embodiment that can provide X-rays within a relatively larger area of the individual, and perhaps a surrounding area. For instance, a remote or local source of the at least one applied high energy photon and/or particle 120 can include the at least one high energy photon and/or particle emitter portion(s) 150, and the at least one applied high energy photon and/or particle 120 can be at least partially directed at the at least the portion of the individual 82 from a distant high energy photon and/or particle emitter portion, or other device, such as could be detected by the detector portion 152 that may be based at least partially on the densities, elements, chemicals, compounds, and/or biological materials included in or contained within the matter. Certain embodiments of operating rooms, examination rooms, medical offices, research facilities, etc. may be provided with a dispersive embodiment of the at least one high energy photon and/or particle emitter portion(s) 150, such that each user (doctor, medical assistant, technician, dentist, etc.) operationally nearby may utilize their distinct or combined personal or group detector portion 152, and/or personal or group display or information provider portion 154.

Certain embodiments of the at least one detector portion 152 can be hand-held, and may thereupon be positioned by the user of the X-ray fluorescence visualizer, imager, or information provider 100. For instance, if a doctor or dentist would like to examine the subsurface of certain at least the portion of the individual, then certain embodiments of the embodiments of the at least one detector portion 152 could be positioned as proximate the at least the portion of the individual as desired to provide the desired X-ray fluorescence depth visualizing, imaging, or information providing quality and images. Such positionable embodiments of the at least one high energy photon and/or particle emitter portion(s) 150, the detector portion 152, the at least one X-ray fluorescence receiving portion(s) 151, or other components of the X-ray fluorescence visualizer, imager, or information provider 100 can be useful to image relatively small portions of the individual in a manner to substantially limit application of X-rays to those regions. For example, in a surgical operating room, medical examination room, veterinarian, etc., certain positionable embodiments of the X-ray fluorescence visualizer, imager, or information provider 100 can be situated closely adjacent the at least the portion of the individual.

The level of the at least one applied high energy photon and/or particle 120 can be thereupon be relatively small as compared with flooding-type high energy photon and/or particle emitter portions. The user (and/or the X-ray fluorescence visualization, imaging, or information providing controller 97) can thereupon control or adjust the X-ray fluorescence depth visualizing, imaging, or information providing. By allowing precise control of the limited at least some matter in the at least a portion of the individual that is being imaged by capturing one or more sequential, adjustable, controllable, or continuous X-ray fluorescence visualizations, images, or provided information, less X-ray electromagnetic radiation may be applied to the individual, the user, and/or others in the vicinity. Certain embodiments of the detector portion could be mechanically mounted, or motion-stabilized (such as is understood in computer graphic systems), such as to limit relative motion of the X-ray fluorescence visualize, image, and/or provide information on the display portion.

Certain embodiments of the at least one display portion 154, as described in this disclosure, can display at least one X-ray fluorescence visualize, image, and/or provide information based at least partially on the X-ray fluorescence based electromagnetic radiation that has been received by the at least one detector portion 152. Certain embodiments of the at least one display portion 154 can be adjusted such that the user can observe what they desire, adjust the X-ray fluorescence visualization, image, or provided information, and/or otherwise control a variety of operations of the X-ray fluorescence visualizer, imager, or information providers 100.

Certain embodiments of the at least one display portion 154 can display at least portion of the X-ray fluorescence visualize, image, and/or provide information relating to the portion of the individual 82 to the individual, such as a patient either alone or in combination with a physician, etc. The fact that certain embodiments of the X-ray fluorescence visualizer, imager, or information providers 100 can operate on a substantially real-time basis can make the individual more aware of their condition based on an accurate X-ray fluorescence visualization, imaging, or information providing of at least a portion of their body. Consider certain individuals who may have an injury, illness, sickness, medical condition, etc. who can have an X-ray fluorescence visualize, image, and/or provide information relating to an appropriate location likely be provided with a near-temporal/positional reflective X-ray fluorescence visualize, image, and/or provide information relating to an appropriate location. As such, they can have more knowledge of their treatment or condition, understand their treatment, and/or perhaps even participate in their treatment. Certain embodiments of the X-ray fluorescence visualizer, imager, or information provider 100 can be configured to control a treating mechanism that can be used to treat the at least the portion of the individual 82 at least partially in response to the X-ray fluorescence information.

In certain injuries or conditions such as ligament tears, joint or bone injuries/fractures, organ conditions, etc., certain embodiments of the X-ray fluorescence visualizer, imager, or information providers 100 could X-ray fluorescence visualize, image, and/or provide information in a substantially continuous manner as the at least the portion of the individual undergoes motion of an affected joint or location. For example, an orthopedic surgeon could consider or examine a knee joint or bone of a patient during flexure, relaxation, or other motion of that body part. In certain instances, X-ray fluorescence enhancing additives, taggants, or contrast agents, etc. could be applied to at least the portion of the individual such as to improve the X-ray fluorescence visualization, imaging, or information providing of certain embodiments of the X-ray fluorescence visualizer, imager, or information provider 100.

Certain embodiments of the X-ray fluorescence visualizer, imager, or information providers 100 can interface and/or interact with each other to provide X-ray fluorescence visualization, imaging, or information providing operation(s) between a number of the at least portions of the X-ray fluorescence visualizer, imager, or information providers. For example, certain embodiments of the X-ray fluorescence visualizer, imager, or information provider 100 (or portions thereof) can include the at least one high energy photon and/or particle emitter portion(s) 150. Certain embodiments of the X-ray fluorescence visualizer, imager, or information provider 100 can include the one or more detector portion 152, or alternately at least one X-ray fluorescence receiving portion(s) 151. Still yet other embodiments of the X-ray fluorescence visualizer, imager, or information provider 100 can include one or more display portions 154. Various of the at least one high energy photon and/or particle emitter portion(s) 150, detector portions 152, and/or display portions 154 can be combined as desired, and utilized in an appropriate configuration for the desired X-ray fluorescence visualization, imaging, or information providing application, only certain illustrative embodiments of which are described in this disclosure.

Within this disclosure, certain embodiments of the at least one high energy photon and/or particle emitter portion(s) 150 can be configured to apply X-ray based electromagnetic radiation at least partially toward the at least the portion of the individual 82. The frequency, energy level, or other operational characteristics and/or structural characteristics of the X-ray based electromagnetic radiation may differ considerably (and be less objectionable or dangerous) than as applied to patients by conventional X-ray (fluoroscopy) techniques.

This is largely a result of lower X-ray dosages being applied to the individual since the X-rays can X-ray fluorescence from the at least the portion of the individual 82 after it has passed through only a relatively short distance within the at least the portion of the individual. As such, electromagnetic shielding that is applied to patients undergoing fluoroscopy can be limited, or at least considerably reduced, by using certain embodiments of the X-ray fluorescence visualizer, imager, or information provider 100. Certain airport screening systems, for example, use X-ray fluorescence X-ray fluorescence visualization, imaging, or information providing from security screening without undue concern of excessive radiation being applied to the travelers of users of the X-ray scanning systems.

The at least one applied high energy photon and/or particle of limited strength could be useful in X-ray fluorescence depth visualizing, imaging, or information providing sensitive at least portions of individuals such as embryos, fetuses, etc. within pregnant women. Certain embodiments of the X-ray fluorescence visualizer, imager, or information provider 100 could image in a manner such that the X-rays stop just short of sensitive matter or tissue, organ, or other matter (e.g., the uterus, heart, brain, etc.) and thereby limit exposure of ionizing radiation to the embryos, fetuses, etc. for example. In actuality, almost any matter within the individual can be considered as sensitive to some degree, particularly relative to desirability of limiting exposure of X-rays there to. As such, certain embodiments of the X-ray fluorescence visualizer, imager, or information provider 100 are particularly suited to correcting or applying the at least one applied high energy photon and/or particle 120 and/or X-ray fluorescence high energy (e.g., X-ray, gamma ray, photon, particle, etc.) to controllably limited regions within the individual. Additionally, there may be a considerable number and variety of organs, portions, or segments of the body that would do better with limited the at least one applied high energy photon and/or particle 120. As such, certain embodiments of the X-ray fluorescence visualizer, imager, or information provider 100 can limit transmission of X-rays during depth imaging to certain of such matter, organs, portions, or segments of the body. Certain embodiments of the X-ray fluorescence visualizer, imager, or information provider 100 can thereby be configured to X-ray fluorescence visualize, image, and/or provide information relating to areas as desired within the particular individual, and limit exposure of X-ray radiation to other (perhaps sensitive) regions.

Within this disclosure, the X-ray fluorescence detected by certain embodiments of the detector portion 152 can be back X-ray fluorescence, forward X-ray fluorescence, deflected, or other distortions of the path of the X-ray based electromagnetic radiation that fall within the scope of the present disclosure, while remaining within the intended scope of X-ray fluorescence. Certain embodiments of the detector portion 152 can be associated with a variety of embodiments of X-ray based electromagnetic radiation, which can operate at a variety of frequencies and/or energy levels, and may therefore X-ray fluorescence visualize, image, and/or provide information down to or at a variety of depths into the at least the portion of the individual 82.

Certain embodiments of the X-ray fluorescence visualizer, imager, or information provider 100, as described in this disclosure, can be configured with one or more of the at least one high energy photon and/or particle emitter portion(s) 150, the at least one X-ray fluorescence receiving portion(s) 151, the detector portion 152, and/or the display portion 154, or any combination thereof. With those embodiments of the X-ray fluorescence visualizer, imager, or information provider 100 having no at least one high energy photon and/or particle emitter portion(s) 150, the X-ray based electromagnetic radiation can be at least partially provided by another device. For instance, a number of the display portion(s) 154 (or alternately at least one display portion that can be viewed by numerous persons), can be utilized by or controlled by a number of persons such as surgeons, technicians, assistants, etc. that can be applied by a single strategically located at least one high energy photon and/or particle emitter portion(s) 150. The at least one high energy photon and/or particle emitter portion(s) 150 may, or may not, be included as a portion of at least one of the X-ray fluorescence visualizer, imager, or information provider(s) 100.

Certain embodiments of the X-ray fluorescence visualizer, imager, or information provider 100 can be controlled, such as to allow its operator to select different substantial X-ray fluorescence depths 170 (or range of substantial X-ray fluorescence depths) to which the X-ray fluorescence visualizer, imager, or information provider can X-ray fluorescence visualize, image, or provide information. Within certain embodiments of the X-ray fluorescence visualizer, imager, or information provider 100, the substantial X-ray fluorescence depth 170 for X-ray fluorescence visualizing, imaging, and/or information providing may vary as a function of the energy applied to or contained within the at least one applied high energy photon, and/or the frequency, energy level, or other characteristics of the at least one applied high energy photon and/or particle 120. The matter (e.g., skin, tissue, bone, etc) to which the at least one applied high energy photon and/or particle 120 is being applied will also affect the X-ray fluorescence visualizing, imaging, or information providing characteristics. As certain characteristics of the at least one applied high energy photon and/or particle 120 are increased, it may likely effect the maximum prescribed substantial X-ray fluorescence depth 170 (see FIGS. 23 and/or 25) to which the at least one applied high energy photon and/or particle 120 X-ray fluorescence radiation will likely travel to prior to X-ray fluorescence, or thereby X-ray fluorescence visualize, image, and/or provide information down to that may be based at least partially on the densities, elements, chemicals, compounds, and/or biological materials included in or contained within the matter. While a limited number of X-rays might travel within the at least the portion of the individual to a depth greater than the prescribed substantial X-ray fluorescence depth 170, certain embodiments of the X-ray fluorescence visualizer, imager, or information provider 100 can be configured to limit the effects of those few X-rays relative to the X-ray fluorescence visualization, imaging, or information providing.

Certain embodiments of the X-ray fluorescence visualizer, imager, or information provider 100 can provide for image combination (e.g., image subtraction, time of flight, image transformation, deconvolution, weighted subtraction, functional subtraction, and group including inverse integral transform, subtractive inverse integral transform, inverse functional transform, and subtractive inverse functional transform, or other such image processing techniques) that may be based at least partially on the densities, elements, chemicals, compounds, and/or biological materials included in or contained within the matter, as described with respect to FIG. 21. Within this disclosure, such image combining techniques as relating to X-ray fluorescence visualization, imaging, or information providing techniques can, depending on context, refer to X-ray fluorescence visualization, imaging, or information providing between two of the at least one prescribed substantial X-ray fluorescence depths 170a and 170b that may be based at least partially on the densities, elements, chemicals, compounds, and/or biological materials included in or contained within the matter. Each prescribed substantial X-ray fluorescence depth 170a and 170b can be situated at least some distance from the skin or surface 168 of the individual (such as illustrated in FIGS. 21 and/or 22). Certain embodiments of the X-ray fluorescence visualizer, imager, or information provider 100 can obtain multiple sampled X-ray fluorescence visualize, image, and/or provide information relating to data pertaining to X-ray fluorescence visualization, imaging, or information providing at different depths either sequentially or in parallel. As such, the multiple sampled X-ray fluorescence visualize, image, and/or provide information relating to data can be considered as X-ray fluorescence visualization, imaging, or information providing a similar sample space down to different prescribed substantial X-ray fluorescence depths 170a and 170b.

Certain ones of the multiple sampled X-ray fluorescence visualize, image, and/or provide information relating to data can thereupon be compared at least partially by image combination (e.g., image subtraction, time of flight, image transformation, deconvolution, weighted subtraction, functional subtraction, and group including inverse integral transform, subtractive inverse integral transform, inverse functional transform, and subtractive inverse functional transform, or other such image processing techniques) that may be based at least partially on the densities, elements, chemicals, compounds, and/or biological materials included in or contained within the matter. As such, those details, images, information, X-ray fluorescence visualizations, etc. that are situated in the shallower prescribed substantial X-ray fluorescence depth 170a, and not in the deeper prescribed substantial X-ray fluorescence depth 170b, as described with respect to FIG. 21, can be digitally subtracted out, transformed out, or otherwise computed out. By digitally differentiating the matter, tissue, objects, etc. being X-ray fluorescence visualized, imaged, or have information provided at the shallower prescribed substantial X-ray fluorescence depth 170a from the deeper prescribed substantial X-ray fluorescence depth 170b, the X-ray fluorescence depth visualizations, images, and/or provided information or other information relating to matter between the shallower and deeper prescribed substantial X-ray fluorescence depths can be obtained.

Certain embodiments of the X-ray fluorescence visualizer, imager, or information provider 100 can be configured to obtain a X-ray fluorescence information at least partially using X-ray fluorescence to derive X-ray fluorescence visualize, image, and/or provide information through at least one matter (e.g., tissue or other matter) of the at least the portion of the individual 82. Such X-ray fluorescence visualizing, imaging, or providing information can be provided at least at both a first depth region and at a second depth region, both associated with the at least a common portion of the individual 82. The depth difference between the first depth regions that extends to a first prescribed substantial X-ray fluorescence depth 170a and the second depth region that extends to a second prescribed substantial X-ray fluorescence depth 170b can be used for subtraction or combination X-ray fluorescence visualization, imaging, or information providing techniques, as described in this disclosure.

Certain embodiments of the X-ray fluorescence visualizer, imager, or information provider 100 that utilize subtraction or combination X-ray fluorescence visualization, imaging, or information providing techniques can therefore act to X-ray fluorescence visualize, image, and/or provide information at different prescribed substantial X-ray fluorescence depths 170a and 170b. As such, adjustment of the subtraction or combination X-ray fluorescence visualization, imaging, or information providing technique can be performed at least partially by, for example, controlling and/or adjusting the frequency of energy level of the X-ray photons at two levels to provide two X-rays. Each of the controlling and/or adjusting the frequency or energy level of the X-ray photons can be detected distinctly to the at least one prescribed substantial X-ray fluorescence depths 170a and 170b. Thereupon, the difference of the shallower level image undergoes image combination (e.g., image subtraction, time of flight, image transformation, deconvolution, image subtraction, weighted subtraction, functional subtraction, and group including inverse integral transform, subtractive inverse integral transform, inverse functional transform, and subtractive inverse functional transform, or other such image processing techniques) from that of the deeper image. The image subtraction or combination X-ray fluorescence depth visualizing, imaging, or information providing techniques can thereby be used to provide information about matter within range of volumes between two prescribed substantial X-ray fluorescence depths 170a and 170b in FIGS. 21 and 22 from the surface 168, etc.

Certain embodiments of the X-ray fluorescence visualizer, imager, or information provider 100 can be configured to X-ray fluorescence visualize, image, and/or provide information at a first controllable one of the at least one X-ray fluorescence range to the at least one first prescribed substantial X-ray fluorescence depth to obtain the first X-ray fluorescence image information. Certain of these embodiments of the X-ray fluorescence visualizer, imager, or information provider 100 can X-ray fluorescence visualize, image, and/or provide information at a second controllable one of the at least one X-ray fluorescence range to the at least one second prescribed substantial X-ray fluorescence depth to obtain the second X-ray fluorescence information. Certain embodiments of the X-ray fluorescence visualizer, imager, or information provider 100 can be configured to computationally differentiating the data associated with the first X-ray fluorescence information and the second X-ray fluorescence information.

Certain embodiments of the X-ray fluorescence visualizer, imager, or information provider 100 can also utilize a time of flight measurement to X-ray fluorescence visualize, image, and/or provide information at the at least one X-ray fluorescence range to the at least one prescribed substantial X-ray fluorescence depth, as described with respect to FIG. 22. Such time of flight measurement can utilize precise pulse signals which can be characterized as at least one input pulse signal and at least one return pulse signal (allowing fractional-second temporal X-ray fluorescence visualization, imaging, or information providing resolution so as to achieve suitable X-ray fluorescence visualization, imaging, or information providing resolution). The briefer the duration of the emitted pulse signal and the detected pulse signal, the lesser the achievable resolution (lesser resolution leading to improved X-ray fluorescence visualization, imaging, or information providing characteristics). Using time of flight techniques, the emitted pulse signals can be applied by certain embodiments of the X-ray fluorescence visualizer, imager, or information provider 100 to the surface 168 of the at least the portion of the individual 82 that may be based at least partially on the densities, elements, chemicals, compounds, and/or biological materials included in or contained within the matter. Providing the time of flight of the return signal can be measured with sufficient accuracy (e.g., resolution in picoseconds for certain embodiments, such as those that utilize streak cameras, pixelated streak cameras, avalanche detectors, CCDs, etc.) then the time of the detected pulse signal can be gated to provide sufficient accuracy, and the time of flight can be determined, from which the distance or depth can be determined that may be X-ray visualized, imaged, or information provided based at least partially on the densities, elements, chemicals, compounds, and/or biological materials included in or contained within the matter.

By using the time of flight embodiments of the X-ray fluorescence visualizer, imager, or information provider 100, the at least one high energy photon and/or particle emitter portion(s) 150 can transmit the at least one input pulse and the detector portion 152 can detect the return time of the at least one return pulse signal. As described with respect to FIG. 22, a time of flight calculation 160 can be determined based on the amount of time required for the at least one input pulse signal to be applied to the at least the portion of the individual; which can thereupon each be X-ray fluorescence into one or more return pulse signal. The X-ray fluorescence return pulse signal(s) will be modified based at least in part on the characteristics of the matter of the individual through which the pulse signals pass (e.g., pulse the at least one applied high energy photon and/or particle 120 and/or pulse X-ray fluorescence high energy (e.g., X-ray, gamma ray, photon, particle, etc.)).

One use of combination of X-ray fluorescence visualization, imaging, or information providing (including subtracting, and other such processes) may involve X-ray fluorescence visualization, imaging, or information providing matter, an organ, etc. that is located within a region that is situated a considerable depth from the surface 168. During X-ray fluorescence depth visualizing, imaging, or information providing of such a deep organ, matter, etc., additional matter, organs, etc. that are positioned between the X-ray fluorescence depth visualizing, imaging, or information providing component(s) of the X-ray fluorescence visualizer, imager, or information provider 100 and the imaged region may not be necessarily be displayed. Therefore, additional matter, organs, tissue, etc. may not be X-ray fluorescence visualized, imaged, or have information provided using image combination (e.g., image subtraction, time of flight, image transformation, deconvolution, weighted subtraction, functional subtraction, and group including inverse integral transform, subtractive inverse integral transform, inverse functional transform, and subtractive inverse functional transform, or other such image processing techniques).

As such, certain organs, matter, etc. that are situated deep within the at least the portion of the individual may be imaged without X-ray fluorescence depth visualizing, imaging, or information providing interference from shallower matter using subtraction or combination of X-ray fluorescence visualization, imaging, or information providing techniques, such as with image combination (e.g., image subtraction, time of flight, image transformation, deconvolution, weighted subtraction, functional subtraction, and group including inverse integral transform, subtractive inverse integral transform, inverse functional transform, and subtractive inverse functional transform, or other such image processing techniques). Alternately, certain matter, tissue, organs, etc. can be imaged by positioning the at least one high energy photon and/or particle emitter portion(s) 150, the at least one detector portion 152, and/or the at least one X-ray fluorescence receiving assembly internally at a suitable position relative to the imaged organs, matter, etc. One skilled with the various embodiments, configurations, and uses of the X-ray fluorescence visualizer, imager, or information provider 100 could determine which X-ray fluorescence depth visualizing, imaging, or information providing technique would provide the better quality X-ray fluorescence depth visualizations, images, and/or provided information or images, less invasively, thereby lowering the X-ray dosages to the user and/or individual.

Certain embodiments of the X-ray fluorescence visualizer, imager, or information provider 100 can at least partially rely on X-ray fluorescence visualization, imaging, or information providing matter within the at least the portion of the individual 82, such as muscle, skin, blood vessels, fluids (e.g., blood, lymph), etc. Within this disclosure, the soft X-ray fluorescence visualization, imaging, or information providing may be compared to hard imaging such as occurs in conventional fluorescing imaging that may occur when the visualizing, imaging, or information providing modality encounters a hard or reflective surface such as bones, metals, etc. By providing X-ray fluorescence-based X-ray fluorescence visualization, imaging, or information providing of soft matter, certain embodiments of the X-ray fluorescence visualizer, imager, or information provider 100 can allow detection of variations of certain characteristics of the soft matter, such as may be the case of calcification of the skin such as occurs relative to a matter aberration. Such matter aberrations as certain breast cancers can be identified due to the calcification of the tumor or cancer. By allowing X-ray fluorescence-based X-ray fluorescence visualization, imaging, or information providing of at least some soft matter, certain embodiments of the X-ray fluorescence visualizer, imager, or information provider 100 can provide for locating that may be based at least partially on the densities, elements, chemicals, compounds, and/or biological materials included in or contained within the matter. Such locating or positioning based at least partially on matter aberration can be applied to such varied applications as positioning organs, circulatory portions (e.g., veins, arteries, etc), blood flows, nerves, bones, etc. relative to the at least some matter of the at least the portion of the individual 82 that may be based at least partially on the densities, elements, chemicals, compounds, and/or biological materials included in or contained within the matter.

Certain embodiments of the X-ray fluorescence visualizer, imager, or information provider 100 can be configured to limit certain contact or damage of arteries, veins, capillaries, or other blood (or other fluid) vessels, etc. that may be based at least partially on the densities, elements, chemicals, compounds, and/or biological materials included in or contained within the matter. Consider the difficulty during surgery, etc., of avoiding such contact that may be at some uncertain location within the individual. Considering the number of blood or other fluid vessels within the body, as well as the likelihood of damage using scopes, tools within incisions, cutting tools, tactile feedback providers, other tools, etc., the scope of the difficulty during surgery, etc. becomes evident. In certain instances, a surgeon may even be unaware if they have damaged a hidden blood vessel or other fluid capillary. Certain embodiments of the X-ray fluorescence visualizer, imager, or information provider 100 can be positioned to X-ray fluorescence visualize, image, and/or provide information the region in which the physician or veterinarian is working. Alternately, certain embodiments of the X-ray fluorescence visualizer, imager, or information provider 100 can be connected to, or otherwise associated with, tools being applied to the at least the portion of the individual. Certain embodiments of the X-ray fluorescence visualizer, imager, or information provider 100 can also allow surgeons, and/or their tools, to avoid or limit contact with particular nerves, organs, matter, etc. Such X-ray fluorescence depth visualizing, imaging, or information providing which allows users such as surgeons, dentists, veterinarians are likely to come in proximity with blood vessels, fluid vessels, nerves, organs, matter, etc. to limit contact their with. Such imaging or X-ray fluorescence visualization to limit contact with certain portions of the body can be performed on a substantially real-time basis, or another basis as desired, and would be expected to considerably reduce the duration of operations, procedures, etc, by such users as doctors, dentists, veterinarians, etc.

Certain embodiments of the X-ray fluorescence visualizer, imager, or information provider 100 can also be configured to locate, analyze, and/or treat blood pooling or other fluid pooling. With certain injuries from bombs, explosives, injuries, vehicular and other crashes, certain illnesses, certain infections, etc., it can be difficult with conventional imagers to locate blood pooling within portions of such individuals as humans, animals, fish, etc. Certain embodiments of the X-ray fluorescence visualizer, imager, or information provider 100 could determine, for example, a trajectory of a bullet, explosive, bomb, etc. such as could be located by determining the location (such as in a trail or pool) of blood through organs, matter, etc. Other naturally occurring blood or fluid pools could be located, examined, and/or treated.

Another example of a bodily fluid which might be located using certain embodiments of the X-ray fluorescence visualizer, imager, or information provider 100 is lymph fluid. Following certain cancers, for example, certain lymph nodes may have to be removed. Lymph nodes function to largely remove lymph fluid from the body. With lymph nodes removed, there can be a considerable collection of the lymph fluid in the body, which can add to weight gain to the individual and/or eventually become infected. Other types of bodily fluids may be X-ray fluorescence visualized, imaged, or have information provided.

Certain embodiments of the at least one detector portion 152, as described at various locations through this disclosure, can be controlled and/or adjusted to receive photons at least partially emitted from the at least one high energy photon and/or particle emitter portion(s) 150. Such control and/or adjustment can be performed in a manner that can be used to provide X-ray fluorescence visualization, imaging, or information providing using certain embodiments of the at least one display portion 154.

Certain embodiments of the X-ray fluorescence depth visualization, imaging, or information providing controller 97 can thereby include, but is not limited to, at least one control and/or adjustment portion 934. Certain embodiments of the detector portion 152 of the at least one X-ray fluorescence receiving portion(s) 151 can be configured to measure the amount of X-ray based electromagnetic radiation (e.g., X-ray fluorescence high energy (e.g., X-ray, gamma ray, photon, particle, etc.) in the form of photons) that is received by the at least one detector portion 152. Certain embodiments of the control and/or adjustment portion 934 can be configured to control and/or adjust the position, angle, or other operating parameter of at least a portion of the at least one X-ray fluorescence receiving portion(s) 151. Certain embodiments of the control and/or adjustment portion 934 can be used to enhance, modify, filter, or otherwise effect reception of the X-ray based electromagnetic radiation (e.g., in the form of photons), such as may be emitted from the at least one high energy photon and/or particle emitter portion(s) 150. Certain detector portions 152 of certain embodiments of the at least one X-ray fluorescence receiving portion(s) 151 can be omnidirectional, multi-directional, or at least have a suitable directional range as to suitable detect the X-ray based electromagnetic radiation being emitted towards the at least the portion of the individual. Certain embodiments of the control and/or adjustment portion 934 can be configured to the relative angle(s), frequencies, and/or positions of the at least one high energy photon and/or particle emitter portion(s) 150, and/or the at least the portion of the individual 82. Certain embodiments of the control and/or adjustment portion 934 can be configured to ensure suitable transmission or reception of X-ray based electromagnetic radiation to allow proper X-ray fluorescence depth visualizing, imaging, or information providing.

Certain embodiments of the at least one X-ray fluorescence receiving portion(s) 151 can also include a detector portion transfer portion, not shown, in which the detected photons, X-ray fluorescence visualization, imaging, or information providing information, data, etc. relating to the X-rays that can be at least partially X-ray fluorescence at/within the at least the portion of the individual. Certain data, information, images, X-ray fluorescence visualizations, etc. as obtained at least partially be the at least one X-ray fluorescence receiving portion(s) 151 can be displayed by the at least one display portion 154, perhaps in a form of the at least one X-ray fluorescence visualization, image, or provided information.

Certain embodiments of the X-ray fluorescence visualizer, imager, or information provider 100 can be configured to X-ray fluorescence visualize, image, and/or provide information at a substantially real-time basis, while other embodiments can be configured to X-ray fluorescence visualize, image, and/or provide information at a slower repetitive rate. Certain embodiments of the X-ray fluorescence visualizer, imager, or information provider 100 can even be configured to X-ray fluorescence visualize, image, and/or provide information relating to one or more non-repetitive X-ray fluorescence depth visualizations, images, and/or provided information that may be based at least partially on the densities, elements, chemicals, compounds, and/or biological materials included in or contained within the matter. Such selection of X-ray fluorescence visualization, imaging, or information providing on substantially temporal/positional reflective can allow such users as a surgeon, doctor, veterinarian, dentist, etc. to obtain conditional information, X-ray fluorescence event information, etc. at desired subsurface locations of the at least the portion of the individual 82 as quickly as desired. Within this disclosure, the term "subsurface", can, depending on context, refer to X-ray fluorescence depth visualizing, imaging, or information providing matter underneath, or across, the surface 168 of the at least the portion of the individual 82 (possibly X-ray fluorescence depth visualizing, imaging, or information providing the surface of the individual). Certain of the surfaces 168 can include skin, internal surfaces, etc. that can be in communication with outside via an opening such as one which a scope that could be applied, such as mucous membranes, at least partially endothelium, internal membranes or skin(s) at least partially defining or surrounding a lumen, via blood vessels, etc. Certain embodiments of at least portion of the X-ray fluorescence visualizer, imager, or information provider 100 (such as the at least one high energy photon and/or particle emitter portion(s) 150 or the at least one X-ray fluorescence receiving portion(s) 151) could be applied to within the at least the portion of the individual 82 using such technologies as a scope, a needle, an injected or implanted device.

Certain embodiments of the X-ray fluorescence visualizer, imager, or information provider 100 could be configured to, for example, image a moving organ as described with respect to FIG. 36. Such X-ray fluorescence visualization, imaging, or providing information relative to moving organs can be applied to, for example, at least a portion of the heart, kidney, brain, stomach, intestine, or other organ that can be defined based on X-ray fluorescence visualization, imaging, or information providing, or variations such as by edges of the particular organs being X-ray fluorescence visualized, imaged, or information provided.

Consider that a moving two dimensional or three dimensional image of a portion of the heart could be provided using certain embodiments of the X-ray fluorescence visualizer, imager, or information provider 100. Such X-ray fluorescence depth visualizing, imaging, or information providing could be useful for diagnosis purposes, during surgery, during screening of susceptible individuals, etc. X-ray fluorescence depth visualizing, imaging, or information providing could be performed on a heart valve, as well as the associated X-ray fluorescence depth visualizing, imaging, or information providing through that heart valve. Heart-based X-ray fluorescence depth visualizing, imaging, or information providing could be provided by positioning the at least one high energy photon and/or particle emitter portion(s) 150 and the at least one detector portion 152 in suitable proximity to (or within) the heart utilizing suitable scopes, implants, etc. along with wireless and/or wired-based technology. The configuration, position, motion, reflex of the heart, aorta, arteries, valves, etc. can be used with suitable resolution and refresh rates using certain X-ray fluorescence visualizer, imager, or information provider 100 configurations.

Certain embodiment the X-ray fluorescence visualizer, imager, or information provider 100 could be applied to image matter or tissue contained within such internal lumens to the human body (and/or image from the internal lumens). Such internal lumens can include, but are not limited to, those at least partially defining: the respiratory tract, the cardiovascular system (e.g., heart, blood vessels), at least a portion of a CSF-space of the nervous system (e.g., the spinal canal, the ventricles of the brain, the sub-arachnoids space, etc.), at least a portion of the urinary tract (for example a urethra), at least a portion of the lymphatic system, at least a portion of the abdominal cavity, at least a portion of the thoracic cavity, at least a portion of the gastrointestinal tract, at least a portion of a reproductive tract (either the female reproductive tract—e.g., a lumen of a fallopian tube), or the male reproductive tract (including various lumens including but not limited to the epidermis, vas deferens or ductile deferens, efferent duct, ampoule, seminal duct, ejaculatory duct, or urethra), the biliary tract, a nostril or nasal cavity, the oral cavity, the digestive tract, the tear ducts, a glandular system, and/or the reproductive tract. Other body lumens may be found in the auditory or visual system, or in interconnections thereof, e.g., the Eustachian tubes. As such, three can be a considerable variety of applications for certain embodiments of the X-ray fluorescence visualizer, imager, or information provider 100 that may be based at least partially on the densities, elements, chemicals, compounds, and/or biological materials included in or contained within the matter.

Certain embodiments of the X-ray fluorescence visualizer, imager, or information provider 100 can be configured to X-ray fluorescence visualize, image, and/or provide information at a single resolution device, such as may be appropriate for a particular X-ray fluorescence visualization, imaging, or information providing application, a particular resolution, or a particular use. Certain embodiments of the X-ray fluorescence visualizer, imager, or information provider 100 can be configured to X-ray fluorescence visualize, image, and/or provide information at a variety of resolutions or applications, such as can be controlled by certain embodiments of the X-ray fluorescence visualization, imaging, or information providing controller 97 as described in this disclosure with respect to FIG. 1 or 2. Such variation of the X-ray fluorescence visualization, imaging, or information providing resolution may vary depending on use. For instance, in those instances where the embodiments of the X-ray fluorescence visualizer, imager, or information provider 100 is being used to determine a location or position of an organ, bone, etc., relatively high resolution (e.g., low quality) X-ray fluorescence visualization, imaging, or information providing can be utilized. By comparison, in those instances where the embodiments of the X-ray fluorescence visualizer, imager, or information provider 100 are being used to detect tumors or the like, a relatively improved resolution (high quality) X-ray fluorescence visualize, image, and/or provide information may be obtained and utilized.

Certain embodiments of the X-ray fluorescence visualization, imaging, or information providing can thereby utilize one or more at least one high energy photon and/or particle emitter portion(s) 150 that can apply X-ray radiation which can be X-ray fluorescence and/or reflected off at least the portion of the individual 82. As such, certain conventional X-ray fluorescence visualization, imaging, or information providing may be referred to as "soft X-ray fluorescence visualization, imaging, or information providing" since it is reflective (relying at least partially on reflection/refraction of X-ray based electromagnetic radiation-photons), instead of being at least partially transmissive as with certain embodiments of the X-ray fluorescence visualizer, imager, or information provider 100. Certain transmissive types of conventional X-ray fluorescence visualization, imaging, or information providing can also utilize fluoroscopy. In addition, X-ray fluorescence visualization, imaging, or information providing may often utilize less powerful X-ray signals then conventional X-ray imaging since the photons of the former do not have to pass through the at least the portion of the individual 82.

Certain embodiments of the X-ray fluorescence visualizer, imager, or information provider 100 therefore provide a mechanism to examine or view an aberration in the surface 168 that can be provided in temporal/positional reflective, real time or near real time, or in a controllable repeatable or non-repeatable fashion. Certain embodiments of the X-ray fluorescence visualization, imaging, or information providing time (duration) can be controlled or adjusted based, at least in part, on such factors as: input from the user, X-ray fluorescence visualization, imaging, or information providing detail. Other operational characteristics of certain embodiments of the X-ray fluorescence visualizer, imager, or information provider 100 can be adjusted and/or controlled by certain embodiments of the X-ray fluorescence visualization, imaging, or information providing controller 97, as described in this disclosure.

It is to be understood that the included description(s) of the at least one high energy photon and/or particle emitter portion(s) 150, the at least one detector portion 152, and/or the at least one display portion 154, as described in this disclosure, are intended to be illustrative in nature but not limiting in scope. Modifications and/or alterations of one or more of the devices 150, 151, 152, and/or 154 from those described in this disclosure are within the intended scope of the present disclosure, depending they still are within the scope of the claims.

As such, certain embodiments of the X-ray fluorescence visualizer, imager, or information provider 100 may be configured such that the physician, dentist, etc. using them can observe a subsurface X-ray fluorescence visualization, image, and/or provide information of the region of the at least the portion of the individual 82. Certain particulars of the X-ray fluorescence visualization, imaging, or information providing and/or the region can vary depending on the embodiment of the X-ray fluorescence visualizer, imager, or information provider 100. For example, certain X-ray fluorescence visualization, imaging, or information providing can correspond to where they are looking, wherein they desire to look, or alternatively where they direct the X-ray fluorescence visualizer, imager, or information provider 100 to X-ray fluorescence visualize, image, or provide information. Certain embodiments of the X-ray fluorescence visualizer, imager, or information provider 100 can present X-ray fluorescence visualizations, images, and/or provide information to a group of persons particularly associated with the X-ray fluorescence visualizer, imager, or information provider.

With conventional X-rays that are transmitted through the at least the portion of the individual 82, including fluoroscopy as well as conventional transmissive X-rays techniques, X-rays may be configured to be applied such that the electromagnetic radiation is applied with sufficient energy level and/or frequency of the X-ray photons to be applied through the portion of the at least some matter. The X-ray photons resulting from X-ray fluorescence is traditionally not utilized in conventional fluoroscopy-based imaging modalities. As such, with certain embodiments of the X-ray fluorescence visualizer, imager, or information provider 100, the at least one applied high energy photon and/or particle 120 does not have to be applied exclusively, but can represent a percentage (even a minority) of the electromagnetic radiation being applied to the at least the portion of the individual 82.

Certain embodiments of the X-ray fluorescence visualizer, imager, or information provider 100 can utilize X-ray fluorescences that do not have to X-ray fluorescence from within the at least the portion of the individual 82. Instead, certain embodiments of the X-ray fluorescence visualizer, imager, or information provider 100 can pass at least partially through the at least the portion of the individual 82 and be somewhat deflected or fluoresce, such that as described within the at least the portion of the individual 82. The X-ray based electromagnetic radiation that is detected as "X-ray fluorescence" information may thereby at least partially X-ray fluorescence by the at least the portion of the individual 82. Certain embodiments of the at least one applied high energy photon and/or particle 120 from the X-ray fluorescence visualizer, imager, or information provider 100 can be applied can be applied at various angles (ranging from perpendicular to substantially parallel to the contacting surface 168 of the at least the portion of the individual 82) relative to the surface of the matter of the at least the portion of the individual 82.

The X-ray fluorescence visualization, imaging, or information can be presented to the user such as a surgeon, veterinarian, dentist, researcher, etc. by a variety of display portion means that can include, but are not limited to: an external monitor, a head-mounted display, stereoscopic projection, a scope device (i.e., endoscope, etc.). Certain portions of different embodiments of the X-ray fluorescence visualizer, imager, or information provider 100 can be used in combination, such as a scope-based at least one high energy photon and/or particle emitter portion(s) 150 which can be used in combination with an at least partially external-based or internal-based detector portion 152 from another embodiment of the X-ray fluorescence visualizer, imager, or information provider.

Certain embodiments of the X-ray fluorescence visualizer, imager, or information provider 100 can be usable or are adjustable to X-ray fluorescence visualize, image, and/or provide information to various controllable and/or adjustable prescribed substantial X-ray fluorescence depths that may be based at least partially on the densities, elements, chemicals, compounds, and/or biological materials included in or contained within the matter. For example, certain embodiments of the X-ray fluorescence visualizer, imager, or information provider 100 could be configured to X-ray fluorescence visualize, image, and/or provide information to a prescribed substantial X-ray fluorescence depth of a few millimeters. Other embodiments could be configured to X-ray fluorescence visualize, image, and/or provide information to a prescribed substantial X-ray fluorescence depth through the at least the portion of the individual 82, if provided with X-ray electromagnetic radiation having sufficient energy or of a suitable X-ray photon frequency or energy level. The prescribed substantial X-ray fluorescence depth of X-ray fluorescence visualization, imaging, or information providing of certain embodiments of the X-ray fluorescence visualizer, imager, or information provider 100 can be a function of frequency, energy level, or other characteristic of the X-ray photons used to generate the X-ray fluorescence visualization, image, type of matter of the individual, as well as power applied to generate the X-ray fluorescence visualization, image, or provided information.

For example, a user or operator can utilize certain embodiments of the X-ray fluorescence visualizer, imager, or information provider 100 to X-ray fluorescence visualize, image, and/or provide information at a variety of prescribed substantial X-ray fluorescence depths. It is envisioned that a variety of X-ray fluorescence depth visualizing, imaging, or information providing modalities can be utilized for the different embodiments of the debt-controllable X-ray fluorescence visualizer, imager, or information provider 100. With certain embodiments of the X-ray fluorescence visualizer, imager, or information provider 100, as described in this disclosure, the X-ray fluorescence visualization, imaging, or information providing can X-ray fluorescence visualize, image, and/or provide information from the surface 168 down to and including the controlled prescribed substantial X-ray fluorescence depth of the at least the portion of the individual 82.

Certain embodiments of a robotic or automated system can utilize certain embodiments of the X-ray fluorescence visualizer, imager, or information provider 100, such as to allow a wide variety of automated or robotic devices to operate at least partially in response to X-ray fluorescence visualization, imaging, or provided information. For instance, certain embodiments of the X-ray fluorescence visualizer, imager, or information provider could scan the at least the portion of the individual for suspicious areas such as melanomas automatically, and indicate any suspicious region to a doctor or operator to be more closely considered. Certain embodiments of the X-ray fluorescence visualizer, imager, or information provider 100 can be configured to control a robotic device at least partially in response to the X-ray fluorescence information. It may be envisioned that certain automated devices or robotic devices could be configured to allow surgery, internal procedures (e.g., scope-based or other), and/or other internal operations based at least in part on X-ray fluorescence visualization, imaging, or information providing information obtained at least in part from the X-ray fluorescence visualizer, imager, or information provider 100. Such automated or robotic procedures hold out the promise of considerable precision, as well as a variety of automated or remotely-controlled operation.

A variety of embodiments of the X-ray fluorescence visualizer, imager, or information provider 100 can be configured to allow control and/or adjustment of the within the at least one X-ray fluorescence range to the at least one prescribed substantial X-ray fluorescence depth of the X-ray fluorescence visualization, imaging, or information providing. Certain embodiments of the X-ray fluorescence visualizer, imager, or information provider 100 can allow an operator such as a surgeon, support person, other person, machine, robot, etc. to provide input, or manually, to control and/or adjust the depth at which the at least one depth-adjustable embodiment of the X-ray fluorescence visualizer, imager, or information provider 100. With certain depth-adjustable embodiment of the X-ray fluorescence visualizer, imager, or information provider 100, at least one of the selected depth that is being X-ray fluorescence visualized, imaged, or have information provided can be targeted (for example, by tuning the X-ray radiation intensity, energy level, frequency, or other characteristics) either manually and/or automatically.

One such technique that can be used to adjust and/or control the within the at least one X-ray fluorescence range to the at least one prescribed substantial X-ray fluorescence depth at least partially by angling the at least one applied high energy photon and/or particle 120 relative to the surface 168 of the at least the portion of the individual. Provided the X-ray fluorescence visualizer, imager, or information provider 100 is configured to pass through a prescribe depth of matter, the greater the angle at which the at least one applied high energy photon and/or particle 120 contacts the surface 168, the lesser the travel distance of the at least one X-ray fluorescence range to the at least one prescribed substantial X-ray fluorescence visualizing, imaging, or information providing depth into the matter.

Another such technique that can be used to adjust and/or control the at least one X-ray fluorescence range to the at least one prescribed substantial X-ray fluorescence visualizing, imaging, or information providing depth by certain embodiments of the X-ray fluorescence visualizer, imager, or information provider 100 can involve providing a depth equivalent material or device between that the at least one applied high energy photon and/or particle 120 should pass through. For example, assume that the depth equivalent material or device represents the equivalent of 2 mm, and assuming the X-ray fluorescence visualizer, imager, or information provider 100 is configured to image at 5 mm, the image subtraction or combination effect of the depth equivalent material would result in X-ray fluorescence visualization, imaging, or information providing down to a prescribed substantial X-ray fluorescence depth of, for example, 3 mm. A number of depth equivalent material of devices can be provided such as to allow control and/or adjustment over the desired X-ray fluorescence range to the at least one prescribed substantial X-ray fluorescence visualizing, imaging, or information providing depth.

Certain embodiments of the X-ray fluorescence visualizer, imager, or information provider 100 may be configured to obtain the X-ray fluorescence information in a manner capable of temporally reflecting motion (conscious or reflexive) of portion(s) of the individual 82 than are deeper than those described up to this point. For example, certain embodiments of the aberrative matter, etc. may be configured to X-ray fluorescence visualize, image, and/or provide information at least one organ(s), bone(s), bone portion(s), blood vessel(s), blood capillar(ies), etc. that may be spaced relatively deeply subsurface. By altering certain operational characteristics of the X-ray based electromagnetic radiation that may be applied by the at least one high energy photon and/or particle emitter portion(s) 150 as described with respect to FIG. 1 or 2, as well as received by certain embodiments of the at least one detector portion(s) 152, the substantial X-ray fluorescence depth can thereby be controlled.

Considering that conventional X-rays can image by X-rays passing completely through the at least the portion of the individual, it should be understood that X-ray fluorescence technologies can be used to X-ray fluorescence visualize, image, and/or provide information a considerable depth into the at least the portion of the individual provided the X-rays are configured to travel with a suitable frequency of the X-ray photons at a suitable energy level, etc. Such X-ray fluorescence visualization, imaging, or information providing of at least partially internal organs, bones, etc. can better be performed in some internal location that is not at least partially hidden, distorted, or obscured by bones, metal or other X-ray diffusive matter that may be based at least partially on the densities, elements, chemicals, compounds, and/or biological materials included in or contained within the matter. Certain embodiments of the X-ray fluorescence visualizer, imager, or information provider 100 may be configured such that the obtaining the X-ray fluorescence information such as can be obtained visually.

Certain embodiments of the X-ray fluorescence visualizer, imager, or information provider 100 can X-ray fluorescence visualize, image, and/or provide information from a variety of perspectives. For instance, certain embodiments of the X-ray fluorescence visualizer, imager, or information provider 100 can provide different types of views. Certain embodiments of the X-ray fluorescence visualizer, imager, or information provider 100 can be configured to provide X-ray fluorescence depth visualizations, images, and/or provided information and/or X-ray fluorescence visualize, image, and/or provide information in substantially temporal and/or positional reflective condition, such as could be detected by the user based at least partially on the densities, elements, chemicals, compounds, and/or biological materials included in or contained within the matter.

Certain embodiments of the X-ray fluorescence visualizer, imager, or information provider 100 could provide X-ray fluorescence depth visualizations, images, and/or provided information and/or X-ray fluorescence visualize, image, and/or provide information at absolute locations in space. For instance, a particular bone, joint, portion of an organ, etc. could be located or situated at a precise position with respect to the at least the portion of the individual 82, a device, a location in space, a building or room, etc. Such determination of a position, situation, or location could be determined using a global positioning system (GPS), another global positional program or device, or using a coordinate system or device relative to the at least the portion of the individual, or the location thereof. In addition to the location or position, there may be an indication of the condition of the particular bone, joint, portion of the organ, etc. at that location. Once such positional information is obtained, certain embodiments of the X-ray fluorescence visualizer, imager, or information provider 100 could utilize, implant, generate at least portions of the X-ray fluorescence depth visualizations, images, and/or provided information such as may be provided using an additional or alternate X-ray fluorescence visualization, imaging, or information providing modality, another application, other maps, etc.

Certain embodiments of the X-ray fluorescence visualizer, imager, or information provider 100 that are so configured to provide good resolution should be capable of providing 100 micron, or better, resolution based on the X-ray fluorescence technology. As described in this disclosure, streak camera, pixelated streak cameras, CCDs, avalanche detectors, and other detector-type devices can be used to provide very good resolution and accuracy. With such resolution, certain embodiments of the X-ray fluorescence visualizer, imager, or information provider could be used to determine positional information precisely and accurately. Such combining of multiple imaging and/or X-ray fluorescence visualizing modalities may limit the X-ray fluorescence depth visualizing, imaging, or information providing computation necessary by certain embodiments of the X-ray fluorescence visualizer, imager, or information provider 100 by, for example, inputting image information already derived from other sources.

Certain embodiments of the X-ray fluorescence visualizer, imager, or information provider 100 can thereby provide for overlaying of combining of the X-ray fluorescence visualization, imaging, or information providing with other conventional and/or imaging modalities. For example, MRI could be overlaid on certain embodiments of the X-ray fluorescence visualizer, imager, or information provider 100. Conventional MRI can be used in combination with certain embodiments of the X-ray fluorescence visualizing, imaging, or information providing modality that can be used in combination with X-rays, since MRI is generally understood to be highly accurate, provide considerable X-ray fluorescence visualizations, images, and/or provided information in the medical area, and can be quite expensive. As such, certain embodiments of the X-ray fluorescence visualizer, imager, or information provider 100 can capture or otherwise obtain temporal/positional reflective X-ray fluorescence visualization, imaging, or information providing, and a variety of locative techniques in utilized to match recently obtained MRI or other visualizing, imaging, or information providing modality can visualize, image, or provide information (e.g., in one, two, or three dimensions) in the imaged region. For example, certain fiducials could provide position information for MRI (or other visualizing, imaging, or information providing modality) such as could also provide position information for certain embodiments of the X-ray fluorescence visualizer, imager, or information provider 100.

As such, the location of the fiducials they can provide position information for MRI could be used to co-locate the MRI and/or the subsurface X-ray fluorescence. Certain embodiments of the X-ray fluorescence visualizer, imager, or information provider 100, once the X-ray subsurface X-ray fluorescence X-ray fluorescence depth visualizations, images, or provided information has been located with respect to the other visualizing, imaging, or information providing modality such as MRI, the X-ray fluorescence depth visualizations, images, and/or provided information, X-ray fluorescence depth visualizations, images, or provided information relating to MRI can be imported, utilized, and/or displayed by certain embodiments of the X-ray fluorescence visualizer, imager, or information provider 100. Certain of the fiducial can be endogenous (such as blood within the blood vessel); while other fiducials can be exogenous (such as a bead which is implanted under the skin.

Certain embodiments of the X-ray fluorescence visualizer, imager, or information provider 100 can allow providing inputting higher energy, such as may result in demarcated finer structures within the X-ray fluorescence visualized, imaged, or information provided regions that are located deeper into the at least the portion of the individual. This control or adjustment of the X-ray fluorescence visualization, imaging, or information providing can result since a larger percentage of the X-ray based electromagnetic radiation (e.g., photons) have the ability to be applied by the at least one high energy photon and/or particle emitter portion(s) 150 to travel within the at least the portion of the individual to the deeper regions, fluoresce, and travel out again to be detected. Certain embodiments of the X-ray fluorescence visualizer, imager, or information provider 100 can provide some amount of adjustment, control, and/or shift to the X-ray based electromagnetic radiation, which with certain embodiments can be varied, adjusted, or controlled, especially when X-ray fluorescence visualization, imaging, or information providing deeper matter, bones, or organs, etc. that may be based at least partially on the densities, elements, chemicals, compounds, and/or biological materials included in or contained within the matter.

Certain embodiments of the X-ray fluorescence visualizer, imager, or information provider 100 are therefore useful in providing relatively detailed X-ray fluorescence visualizations, images, and/or provided information about one or more of: matter, aberrative matter embedded in tissues, bones, organs, etc. that may be based at least partially on the densities, elements, chemicals, compounds, and/or biological materials included in or contained within the matter. A considerable number of conventional imaging modalities may be useful for X-ray fluorescence visualization, imaging, or information providing at least some of the matter within the body of the individual with suitable resolution.

Certain embodiments of the X-ray fluorescence visualizer, imager, or information provider 100 can provide some quantification, automated observation, and/or feedback associated with the X-ray fluorescence in a temporal/positional reflective basis, and in certain instances at a variety of controllable prescribed substantial X-ray fluorescence depth(s). In certain instances, the X-ray fluorescence visualization, imaging, or information providing can be performed through modifiable (in-vivo) matter with low latency. Illuminating electromagnetic characteristics selected with characteristics having intensity and wavelengths selected to limit transmission of excessive electromagnetic radiation (e.g., X-ray) into the body of the individual, and thereby limit X-ray dosages.

Certain embodiments of the X-ray fluorescence visualizer, imager, or information provider 100 can be configured to scan across the surface 168 (or through a region) of the at least the portion of the individual 82. By comparison, certain embodiments of the X-ray fluorescence visualizer, imager, or information provider 100 can be configured to capture at least one X-ray fluorescence visualization, at least one image, and/or provide information substantially at the same time. The particular characteristics of the X-ray fluorescence visualizer, imager, or information provider 100 visualizing, imaging, or information providing modality are intended to be illustrative in nature, but not limiting in scope.

At least portions of certain embodiments of the X-ray fluorescence visualizer, imager, or information provider 100 can include scopes such as endoscopes as described with respect to FIG. 30. Within this disclosure, the term "endoscope" can, depending on context, refer to an one of a variety of scopes that can be applied at least partially internally or externally, such as to one or more of the tracts that are at least partially open that can include, but are not limited to: the gastrointestinal tract, the respiratory tract, the urinary tract, the female reproductive system, etc. Such X-ray fluorescence visualization, imaging, or information providing relative to the tracts can be for a variety of purposes including, but not limited to, examination for health, research, or medical purposes, screening for cancers or tumors, injuries, illnesses, infections, or sicknesses, reproductive conditions, abscesses, etc. For example, certain embodiments of the X-ray fluorescence visualizer, imager, or information provider can be configured as an "endotracheal tube (ET), or other tube, that can have had the appropriate components as described with respect to FIG. 1 or 2. Certain embodiments of the endoscopes can be applied to normally closed lumens, cavities, and portions of the individual such as via a small incision. Certain embodiments of the X-ray fluorescence visualizer, imager, or information provider 100 can be used, for instance, to determine where such small incisions may be situated, for example.

Certain embodiments of the endoscope-based embodiment of the X-ray fluorescence visualizer, imager, or information provider 100 can include, but are not limited to, a rigid or flexible tube 1102, a light delivery system 1104, and the X-ray fluorescence visualizer, imager, or information provider component(s). For instance, certain endoscope-based embodiments of the X-ray fluorescence visualizer, imager, or information provider 100 can be configured to include zero, one, or more at least one high energy photon and/or particle emitter portion(s) 150; zero, one, or more at least one X-ray fluorescence receiving portion(s) 151; zero, one, or more detector portion 152; and/or zero, one, or more display portion 154, as described with respect to FIG. 1 or 2. Other components component of the X-ray fluorescence visualizer, imager, or information provider 100 that are not situated in the scope-based embodiment of the X-ray fluorescence visualizer, imager, or information provider can be included in other associated embodiments of the X-ray fluorescence visualizer, imager, or information provider.

FIGS. 38 to 41 show four embodiments of certain components of the X-ray fluorescence visualizer, imager, or information provider 100 that can X-ray fluorescence visualize, image, or provide information relative to the at least the portion of the individual 82 that may be based at least partially on the densities, elements, chemicals, compounds, and/or biological materials included in or contained within the matter. Certain embodiments of the X-ray fluorescence visualizer, imager, or information provider 100 can utilize either wire-based or wireless communications to transfer data between related devices, such as the at least one detector portion 152 and the at least one display portion, as described in this disclosure. In addition, certain networking, computing, imaging, and other well known techniques may be used to facilitate certain embodiments of the X-ray fluorescence visualizer, imager, or information provider 100, as described in this disclosure.

Figure 39:
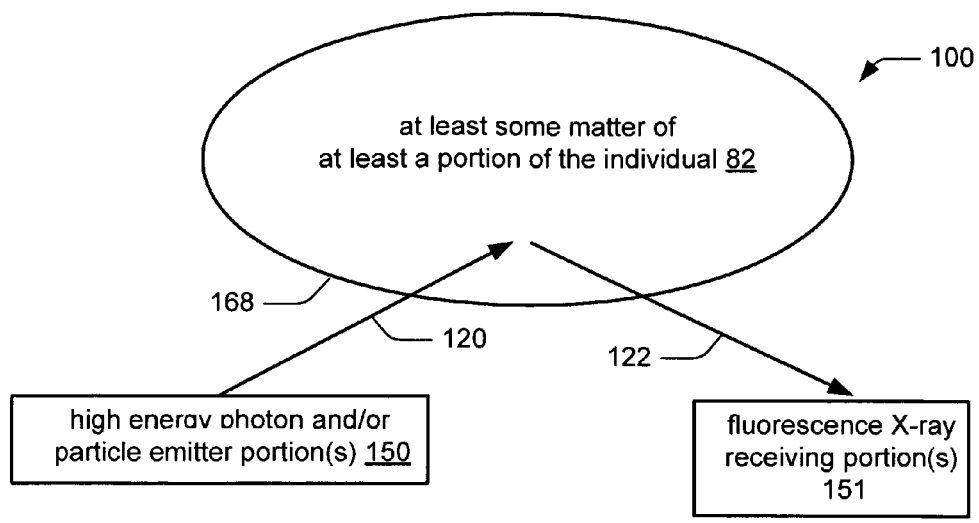
FIG. 39 shows one embodiment of the X-ray fluorescence visualizer, imager, or information provider in which the at least one high energy photon and/or particle emitter portion(s) is situated at least partially externally to the at least the portion of the individual while the at least one X-ray fluorescence receiving assembly is situated at least partially externally to the at least the portion of the individual.

As described in this disclosure with respect to FIGS. 38 to 41, certain embodiment(s) component(s), and/or portion(s) of the X-ray fluorescence visualizer, imager, or information provider 100 can be configured as an at least partially external device, while other embodiments can be configured as an at least partially internal device (and/or combination thereof). FIG. 39 shows one embodiment of the X-ray fluorescence visualizer, imager, or information provider 100, in which the at least one high energy photon and/or particle emitter portion(s) 150 is situated at least partially externally to the at least the portion of the individual 82; while at least a portion of the at least one X-ray fluorescence receiving portion(s) 151 is situated at least partially externally to the at least the portion of the individual.

Figure 40:
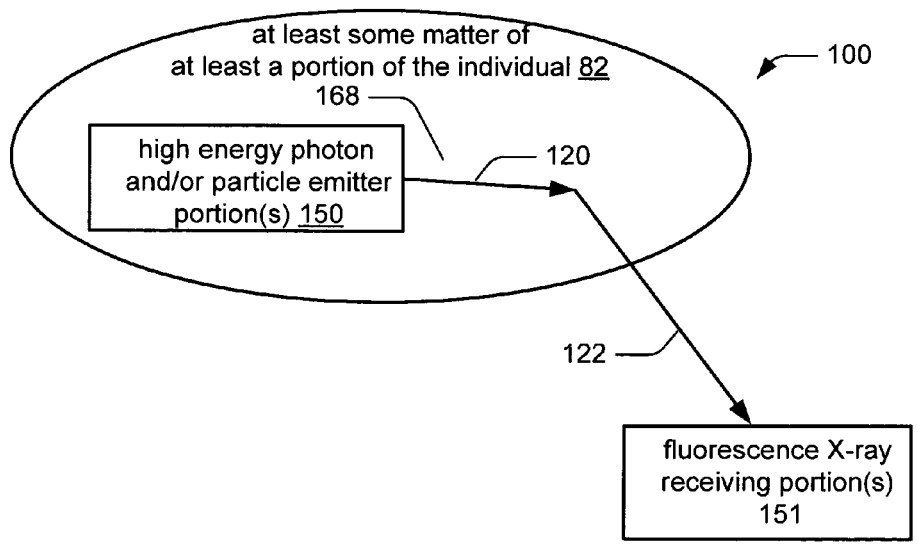
FIG. 40 shows one embodiment of the X-ray fluorescence visualizer, imager, or information provider in which the at least one high energy photon and/or particle emitter portion(s) is situated at least partially internally to the at least the portion of the individual while the at least one X-ray fluorescence receiving assembly is situated at least partially externally to the at least the portion of the individual.

FIG. 40 shows one embodiment of the X-ray fluorescence visualizer, imager, or information provider 100, as described with respect to FIG. 1 or 2, in which the at least one high energy photon and/or particle emitter portion(s) 150 is situated at least partially internally to the at least the portion of the individual 82; while the at least a portion of the at least one X-ray fluorescence receiving portion(s) 151 is situated at least partially externally to the at least the portion of the individual that may be based at least partially on the densities, elements, chemicals, compounds, and/or biological materials included in or contained within the matter.

Figure 41:
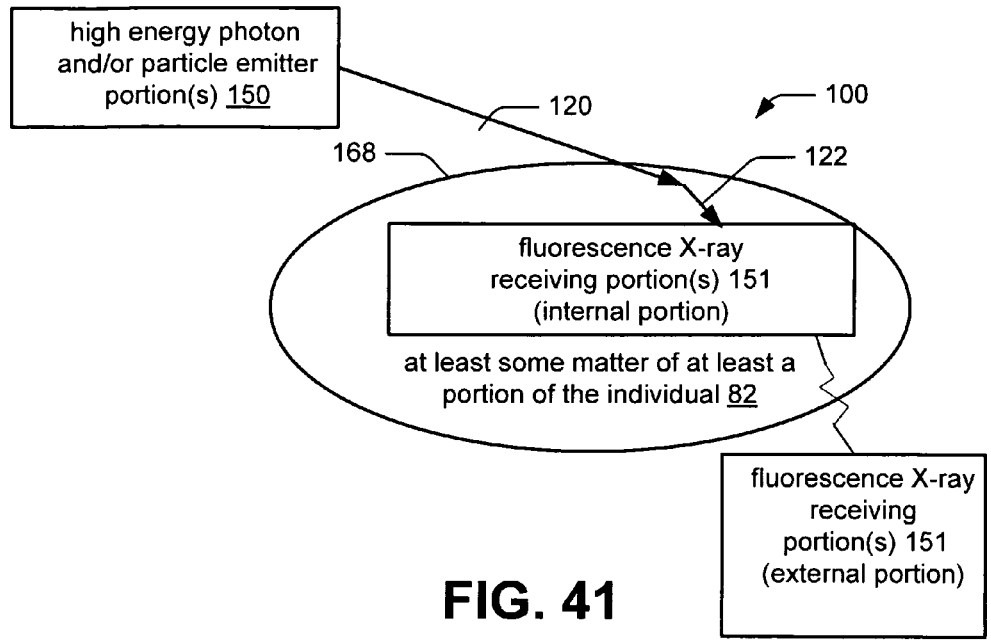
FIG. 41 shows one embodiment of the X-ray fluorescence visualizer, imager, or information provider in which the at least one high energy photon and/or particle emitter portion(s) is situated at least partially externally to the at least the portion of the individual while the at least one X-ray fluorescence receiving assembly is situated at least partially internally to the at least the portion of the individual.

FIG. 41 shows one embodiment of the X-ray fluorescence visualizer, imager, or information provider 100, as described with respect to FIG. 1 or 2, in which the at least one high energy photon and/or particle emitter portion(s) 150 is situated at least partially externally to the at least the portion of the individual 82; while the at least a portion of the at least one X-ray fluorescence receiving portion(s) 151 is situated at least partially internally to the at least the portion of the individual that may be based at least partially on the densities, elements, chemicals, compounds, and/or biological materials included in or contained within the matter. For example, as illustrated in FIG. 40, certain portions of the at least one X-ray fluorescence receiving portion(s) 151 (e.g., corresponding perhaps to the detector portion 152 of FIG. 1 or 2), could be at least partially internally applied while other portions of the at least one X-ray fluorescence receiving portion(s) 151 (e.g., corresponding perhaps to the display portion 154 of FIG. 1 or 2) can be at least partially externally applied. Certain embodiments of wireless, wired-based, data-transfer, image transfer, or other similar mechanism can allow for communication between the internal and external portions of the at least one X-ray fluorescence receiving portion(s) 151.

Figure 42:
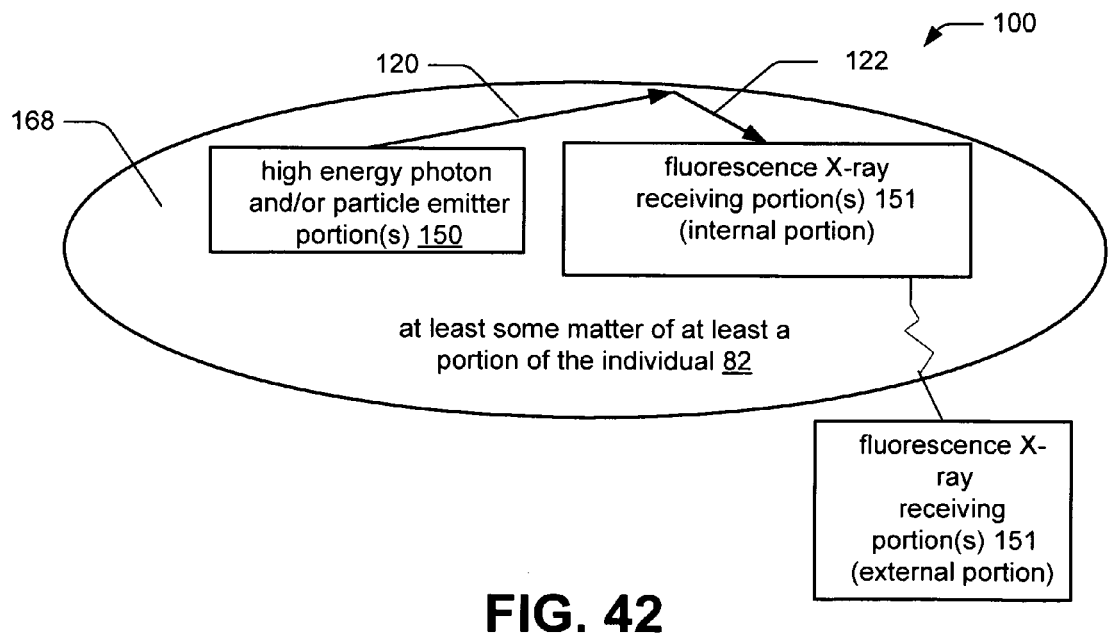
FIG. 42 shows one embodiment of the X-ray fluorescence visualizer, imager, or information provider in which the at least one high energy photon and/or particle emitter portion(s) is situated at least partially internally to the at least the portion of the individual while the X-ray fluorescence receiving assembly is situated at least partially internally to the at least the portion of the individual.

FIG. 41 shows one embodiment of the X-ray fluorescence visualizer, imager, or information provider 100, as described with respect to FIG. 1 or 2, in which the at least one high energy photon and/or particle emitter portion(s) 150 is situated at least partially internally to the at least the portion of the individual 82; while the at least a portion of the at least one X-ray fluorescence receiving portion(s) 151 is situated at least partially internally to the at least the portion of the individual that may be based at least partially on the densities, elements, chemicals, compounds, and/or biological materials included in or contained within the matter. For example, as illustrated in FIG. 42, certain portions of the at least one X-ray fluorescence receiving portion(s) 151 (e.g., corresponding perhaps to the detector portion 152 of FIG. 1 or 2), could be at least partially internally applied while other portions of the at least one X-ray fluorescence receiving portion(s) 151 (e.g., corresponding perhaps to the display portion 154 of FIG. 1 or 2) can be at least partially externally applied. Certain embodiments of wireless, wired-based, data-transfer, image transfer, or other similar mechanism can allow for communication between the internal and external portions of the at least one X-ray fluorescence receiving portion(s) 151.

There can be a variety of embodiments of the X-ray fluorescence visualizer, imager, or information provider 100 which may utilize a tactile feedback such as to "transfer" some type of feel or touch sensation to the user. Such tactile feedback embodiments of the X-ray fluorescence visualizer, imager, or information provider 100 may be considered as one embodiment of the tool, as described in this disclosure such as relative to FIG. 28 and at other locations, for example. For instance, certain embodiments of the X-ray fluorescence visualizer, imager, or information provider 100 may include, or be associated with, that can allow the operator such as a physician to "feel" at least some of the nodules such as to provide an indication as to whether they may wish to further examine by touch or feel, such as with patients having cancer. The importance of the interrelationship between sight and touch is well-recognized in many medical or health fields. For example, doctors, veterinarians, dentists, assistants, researchers, etc. often provide their analysis of combination of feeling and seeing at least a portion of the individual, in combination.

Certain embodiments of the X-ray fluorescence visualizer, imager, or information provider 100, as described in this disclosure, thereby provide considerable sight (at least partially internally and/or at least partially externally) in the form of imaging, X-ray fluorescence visualization, and/or information providing. Such "sight" as can be provider by certain embodiments of the X-ray fluorescence visualizer, imager, or information provider 100 can be combined with "touch", which can be provider by certain embodiments of tactile feedback mechanisms. Such embodiments of the tactile feedback mechanism may include various components are mechanisms of automation, tactile feedback, remote-control, robotics, etc., as generally understood in those respective arts, and will not be described more fully in this disclosure. Certain embodiments of the tactile feedback mechanism may be particularly useful when the particular X-ray fluorescence visualizer, imager, or information provider 100 is being applied at least partially internally to the individual, such that the user cannot always see the internal location. Such tactile feedback embodiments are especially useful for certain doctors, surgeons, veterinarians, dentists, assistants, researchers, etc. with somewhat limited senses of touch and/or sight.

In certain instances, the tactile feedback may be partially associated with the diagnosis from a medical user such as a surgeon or doctor. A number of medical diagnosis, examination, treatment, and other practices rely on a combination of sight in combination with touch. It is to be understood that during conventional breast cancer examinations, the "feel" or "touch" of the physician to detect breast cancer nodules in an important portion of examination and/or diagnosis. Proctologists, for example, are often forced to rely on touch or feel, since the ability to see potential medical situations or conditions may be limited. As such, providing certain embodiments of the X-ray fluorescence visualizer, imager, or information provider with tactile capabilities may be particularly important in the diagnosis or treatment phases. For example, certain doctors may more directly locate or tactile "feel" for cancers, tumors, or which may be relatively hard as compared with the surrounding matter, nodules, organs, tissue, fat, muscle, or other matter. For dental users, the tactile feedback may by utilized in conjunction with a dental drill or pick, etc., such that the X-ray fluorescence visualizer, imager, or information provider 100 can be used to indicate the degree and/or area of dental decay, etc. during drilling, etc. It is to be understood that many types of users may similarly benefit from the tactile feedback being provided by certain tools by certain embodiments of the X-ray fluorescence visualizer, imager, or information provider 100.

Certain embodiments of the X-ray fluorescence visualizer, imager, or information provider 100 could be configured to provide a variety of types of tactile feedback. Tactile feedback may be based on hardness or softness of the matter, such as iron or calcium concentration, or concentration of other matter. The tactile feedback system could involve feeding a signal representing some aspect of touchability (e.g., the matter is hard, soft, resilient, etc.) from the tactile system back to the instrument, such as can be displayed, and/or provided as some tactile output to the user. Certain embodiments of the instrument may not be able to "feel" the feedback information in a similar manner as a person, and as such certain tactile output information can be returned from the at least one X-ray fluorescence visualization, image, and/or provided information in image or data form. As such, the user of certain embodiments of the X-ray fluorescence visualizer, imager, or information provider could receive feedback either visually and/or tactually.

In addition, certain types of tools can be configured to be actuated based on user input. Such tools may be configured as an endoscope, or alternately some devoted type of tool such as a cutter, scalpel, separator, tactile feedback provider, ablator, surgical suction, etc. Such actuation of at least portions of tool based on user input may be considered as a version of robotics, remote control, amplification, and/or automation. Certain embodiments of the X-ray fluorescence visualizer, imager, or information provider 100 can be configured as allow controlled (e.g., robotic surgery), as well as image processing to precisely detect organs, make incisions, cut matter away, ablate matter, X-ray fluorescence visualize, image, and/or provide information relating to a region in matter, etc.

Certain embodiments of the tactile feedback could be provided on a probe or other portion of the X-ray fluorescence visualizer, imager, or information provider 100 itself, such as in an endoscope. The greater the tactile feedback can enhance certain surgical techniques for surgeons, certain dental techniques for dentists, certain veterinarian techniques for veterinarians, etc. Certain embodiments of the X-ray fluorescence visualizer, imager, or information provider 100 can be configured as to generate a tactile response that can be detected by a person at least partially in response to the X-ray fluorescence information. Certain embodiments of the X-ray fluorescence visualizer, imager, or information provider 100 can be configured to be minimally invasive to locate organ, and confirm whether it is at a perceived location. Certain embodiments of the X-ray fluorescence visualizer, imager, or information provider 100 could allow surgeons, etc. to X-ray fluorescence visualize and/or operate such as to perform more complex surgeries using "keyholes", or incisions, within the patient.

Certain embodiments of the X-ray fluorescence visualizer, imager, or information provider 100 with tactile feedback can be configured to X-ray fluorescence visualize, image, and/or provide information from a location at least partially external to the at least the portion of the individual. Certain embodiments of the X-ray fluorescence visualizer, imager, or information provider with tactile feedback can be configured to X-ray fluorescence visualize, image, and/or provide information from a location at least partially internal to at least the portion of the individual (either via a normally open location such as using an endoscope or via a normally closed location such as with an incision).

Certain embodiments of the X-ray fluorescence visualizer, imager, or information provider 100 could therefore be utilized for a variety of applications and X-ray fluorescence visualization, imaging, or information providing techniques outside of scope of confessional X-ray. For example, certain embodiments of the X-ray fluorescence visualizer, imager, or information provider 100 could be situated, or made viewable to the at least the portion of the individual at their bedside such as they may view. As such, certain embodiments of the X-ray fluorescence visualizer, imager, or information provider 100 may be utilized as a relatively inexpensive alternative to MRI, for example, which doesn't necessarily enclose the body of the at least the portion of the individual as is the case with MRI, CT, etc. Certain embodiments of the X-ray fluorescence visualizer, imager, or information provider 100 may therefore serve as a direct replacement, in certain applications, for such imaging technologies as MRI, CT, etc. In addition, certain embodiments of the X-ray fluorescence visualizer, imager, or information provider 100 might be preferred, in certain applications, to ultrasound because of the considerable contrast of the X-ray fluorescence visualizer, imager, or information provider.

As described in this disclosure, certain embodiments of the at least one high energy photon and/or particle emitter portion(s) 150 may be at least partially steerable. Additionally, certain embodiments of the detector portion 152 may be at least partially adjustable to control the direction which it best receives X-ray-based electromagnetic radiation. Certain embodiments of the X-ray fluorescence visualizer, imager, or information provider 100 may therefore be configured such that the at least one high energy photon and/or particle emitter portion(s) 150 is relatively closely aligned with the detector portion 152. Similarly, certain embodiments of the X-ray fluorescence visualizer, imager, or information provider 100 may be configured to such that the at least one high energy photon and/or particle emitter portion(s) 150 moves into an approximate alignment with the detector portion 152, in certain embodiment as to create a standing pattern such as may be utilized to X-ray fluorescence visualize, image, and/or provide information relating to a region utilizing scanning, such as is generally known with certain display technologies. By utilizing such scanning embodiments of the X-ray fluorescence visualizer, imager, or information provider 100, relatively good-quality X-ray fluorescence visualization, imaging, or information providing can be provided. Additionally, relatively low power may be necessary (as compared to other medical imaging modalities), such as may be useful in limiting the exposure of the at least the portion of the individual to relatively high-powered X-rays, as described in this disclosure.

Certain embodiments of the X-ray fluorescence visualizer, imager, or information provider 100 can be configured to identify a trend of pattern correlating to the change in state to a pattern corresponding to a macrostate. These patterns can be correlated to a target indicative of a particular condition. By comparing the X-ray fluorescence visualized, imaged, or information provided pattern with the pattern recognized as representing a condition, illness, etc. The information, data, patterns, etc. can be maintained in a database, the pattern of information can be used for a prognosis of the condition, illness, etc. The use of information, data, patterns, etc. as can be received by or pr processed from X-ray fluorescence high energy (e.g., X-ray, gamma ray, photon, particle, etc.) from X-ray fluorescence can therefore be quite useful for a variety of purposes.

Certain embodiments of the X-ray fluorescence visualizer, imager, or information provider 100 can be configured to use selected portion of new X-ray fluorescence visualizing, imaging, or information providing slice information, and higher resolution info to produce composite X-ray fluorescence visualize, image, and/or provide information (having enhanced resolution) as compared to original X-ray fluorescence visualizations, images, or provided information. Also, producing this can be responsive to matter deformation modeling. Certain embodiments of the X-ray fluorescence visualizer, imager, or information provider 100 can be configured to consider information that can be not only anatomically obtained, but also functionally obtained. (Instead or in addition to displaying info, correlate to a bio-state, or change in state. Change in state from a plurality of locations).

Figure 44:
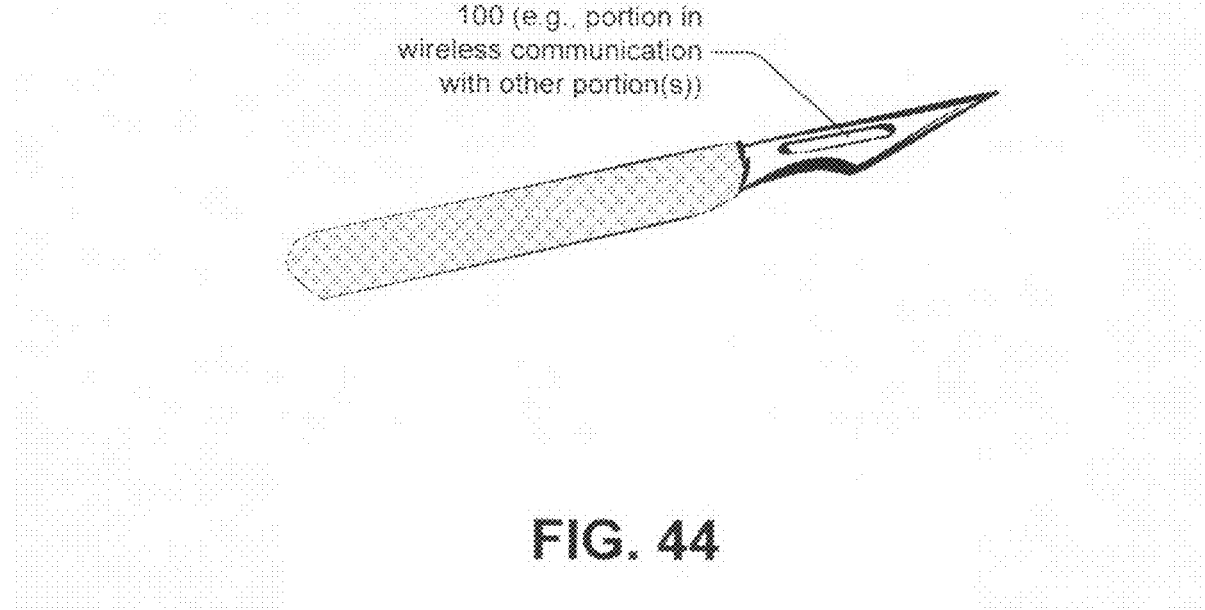
FIG. 44 shows another embodiment of the X-ray fluorescence receiving assembly that is associated with a tool.

Certain embodiments of the X-ray fluorescence visualizer, imager, or information provider 100 can be configured such as their at least one high energy photon and/or particle emitter portion(s) 150 and their at least one detector portion 152 integral to a tool (surgical, examination, positioning, scope-type, tactile feedback provider, luminal, etc.). In certain instances, the X-ray fluorescence visualizer, imager, or information provider 100 may provide a proximity sensor function to the tool. For example, the at least one high energy photon and/or particle emitter portion(s) 150 may be sized such as to emit (in substantially $4\pi$ or $2\pi$ steradians) at a desired frequency and/or energy level based on the prescribed substantial X-ray fluorescence depth that is being examined or that the tool is being positioned, and the detector portion may be a pixelated X-ray detector portion array, an avalanche detector array, a CCD array, etc. Examples of X-ray detectors may include, but are not limited to, pixelated streak cameras, streak cameras, CCD devices, avalanche detectors, or other devices. With certain embodiments of the X-ray fluorescence visualizer, imager, or information provider 100, the high energy photon and/or particle emitter portion(s) may produce radiation, where the detector portion is not a pixelated array (e.g., including a Kulikov lens, and/or a Bragg lens). Certain embodiments of the X-ray fluorescence visualizer, imager, or information provider 100 might include the high energy photon and/or particle emitter portion(s) at the distal end of the tool, and the detector portion separated there from either in close proximity or by a considerable distance in a manner desirable to provide suitable X-ray fluorescence visualization, imaging, or information providing. Certain embodiments of the X-ray fluorescence visualizer, imager, or information provider 100 might be particularly useful if positioned on, integrated into, or otherwise associated with the tool (e.g., situated on the tip of a probe or cutter, on at least one tip of scissors, on forceps, on needles, etc.). FIG. 44, for example, illustrates one embodiment of the tool (surgical knife) including an embodiment of the X-ray fluorescence visualizer, imager, or information provider 100. For the purpose of this disclosure, certain endoscopes as described with respect with FIG. 28 can be considered as tools that can include certain embodiments of the X-ray fluorescence visualizer, imager, or information provider 100. Certain embodiments of tools may also be associated with a tactile feedback mechanism that provides at least some tactile feedback, which by themselves may be considered as another embodiment of tool within this disclosure. It may therefore be desirable to position certain embodiments of the X-ray fluorescence visualizer, imager, or information provider 100 on, proximate to, or to provide viewability of, operative surfaces of a variety of such tools as surgical tools, tactile feedback providers, etc. Such embodiments of the X-ray fluorescence visualizer, imager, or information provider 100 can thereby provide a X-ray fluorescence visualization, imaging, or information providing from the viewpoint of the tool.

Implants, constructs, pins, screws, etc. such as may be positioned within the individual may be considered as one embodiment of the tool, which may include certain embodiments of the X-ray fluorescence visualizer, imager, or information provider 100. Additionally, certain implants, constructs, pins, screws, etc. can be viewed as tools that in include certain embodiments of the X-ray fluorescence visualizer, imager, or information provider 100. Certain embodiments of the X-ray fluorescence visualizer, imager, or information provider 100 can provide an added benefit, such that when a user such as a surgeon is placing a pedicle screw, it is highly desired to stay within the pedicle because if the surgeon goes outside they may contact a nerve root. As such, the embodiment of the X-ray fluorescence visualizer, imager, or information provider 100 can act as a pedicle guide. Certain embodiments of the X-ray fluorescence visualizer, imager, or information provider 100 can thereby be considered to combine with a warning system that can utilize certain embodiments of the X-ray fluorescence depth visualizing, imaging, or information providing controller 97. Certain embodiments of the X-ray fluorescence depth visualizing, imaging, or information providing controller 97 can include, as data or information, a variety of individual information, such as patient information, injury, illness, and if the user (doctor, dentist, veterinarian, etc.) is positioning the tool at an undesired location or performing some undesired procedure (e.g., at the wrong side of the patient's body), in which instance a suitable alarm may be actuated in the event of a suitable event.

Certain embodiments of the X-ray fluorescence visualizer, imager, or information provider 100 can thereby be configured as a surgical tool, certain of which may be configured to act as a proximity sensor, while output from others may be displayed. It is envisioned that the at least one high energy photon and/or particle emitter portion(s) 150 and/or the at least one X-ray fluorescence receiving portion(s) 151 could be integral to the surgical tool and/or tactile feedback provider. Certain embodiments of the X-ray fluorescence visualizer, imager, or information provider 100 can be configured to image once, multiple times, or can include a number of or at least one displaceable high energy photon and/or particle emitter portion(s) to provide scanning. In certain instances, upon the surgical tool being positioned relative to the at least the portion of the individual is configurable to emit X-ray based electromagnetic radiation suitable to image to a controllable prescribed substantial X-ray fluorescence depth into an at least one matter of at least a portion of the individual to be used to derive X-ray fluorescence depth visualizations, images, or provided information at least partially in response to X-ray fluorescence of the X-ray based electromagnetic radiation. The detector portion may also be integral to the surgical tool and/or tactile feedback provider that is operable, and as such may be alignable and/or controllable. Certain embodiments of the high energy photon and/or particle emitter portion(s) may include scopes, but may also be at least partially externally situated. Certain of the at least partially internal embodiments may be inserted through insertion or via a normally open opening to be at least partially applied relative to at least a portion of the individual such as to receive at least one X-ray fluorescence that has been X-ray fluorescence in an at least one matter, etc. of the at least the portion of the individual.

Certain embodiments of the X-ray fluorescence visualization, imaging, or information providing controlling 97 are configured particularly to generate the X-ray fluorescence depth visualizations or images that can be displayed over the display portion 154 of the X-ray fluorescence visualizer, imager, or information provider 100, as described with respect to FIG. 1 or 2, and other locations through this disclosure. By comparison, certain embodiments of the X-ray fluorescence visualization, imaging, or information providing controlling 97, as described with respect to FIG. 43, can be configured to produce information that can be displayed over certain embodiments of the X-ray fluorescence visualizer, imager, or information provider 100, which can be observed by the user and/or individual (human). Consider, for example, the embodiment of the X-ray fluorescence visualizer, imager, or information provider 100 that can scan individuals for such aspects as cancers (e.g., breast cancer, melanomas), tumors, blood vessel locations (perhaps in diabetics to provide insulin shots), heart condition, bone fragments or portions (especially useful at certain sporting events, etc.), burn victim examination, and/or a variety of emergencies or situations which a variety of emergency, rescue, medical, as well as individuals who wish to examine themselves at locations remote from conventional imaging equipment are likely to encounter.

Certain embodiments of the X-ray fluorescence visualizer, imager, or information provider can utilize lower power requirements and conventional imagers since they rely on X-ray fluorescence of X-rays instead of transmission X-rays (i.e., the latter requires providing enough energy to the X-ray photons to pass the X-ray photons through the image portion of the individual, instead of X-ray fluorescence within the individual as with the former). Since less energies required for typical operation of the X-ray fluorescence depth and X-ray fluorescence visualizer, imager, or information provider 100; they can thereby be configured to operate with reduced input voltages.

It is feasible that certain embodiments of the X-ray fluorescence visualizer, imager, or information provider 100 can be made lighter and/or to use less power than conventional power supplies in medical clinics, homes, offices, vehicles, etc. Certain embodiments of the X-ray fluorescence visualizer, imager, or information provider 100 can thereby be made considerably more portable than conventional imaging equipment. There are a variety of use of the term "portable" within this disclosure. Within this disclosure, certain uses of the term "portability" can, depending on context, relate to those embodiments of the X-ray fluorescence visualizer, imager, or information provider 100 that can be carried by a person. As such, an ambulance attendant, a fireman, a ski patrol, a rescue worker, or other user could carry, roll, or move certain embodiments of the X-ray fluorescence visualizer, imager, or information provider 100 to where the individual is by carrying it themselves. Certain embodiments of the X-ray fluorescence visualizer, imager, or information provider 100 could be brought out to a sporting event, car race, etc. where an individual (such as a football player, horseback rider, etc.) is likely to be located and/or injured to gauge the injuries to the person. It is also desirable that certain embodiments of the X-ray fluorescence visualizer, imager, or information provider 100 can be removed from a vehicle, such as an ambulance or other car or truck, and could be removed portably to allow relatively simplified transit to the person.

Within this disclosure, other uses of the term "portability" can, depending on context, relate to those embodiments of the X-ray fluorescence visualizer, imager, or information provider 100 that can be transported portably as a self-contained and self-powered unit. As such, the energy source (which may include a battery device and/or a capacitor device, etc.) may provide suitable primary or auxiliary power to certain embodiments of the X-ray fluorescence visualizer, imager, or information provider 100 be transported to a remote location and operate thereat that location. In general, more complex and sophisticated imagers will utilize more power and/or electricity than lower resolution visualizers or information providers, and as such the lesser power consuming devices might be more appropriate for portable transporting.

Certain embodiments of the X-ray fluorescence visualizer, imager, or information provider 100 can therefore be configured to be portable in a manner as to be transportable based at least partially on the conventional techniques of transportation/commuting. For example, certain remote portions of many countries are accessible primarily by foot or animal, and as such a person or animal would have to carry the embodiments of the X-ray fluorescence visualizer, imager, or information provider 100 where needed. Certain embodiments of the X-ray fluorescence visualizer, imager, or information provider 100 could be transported by a ship, car, truck, military vehicle, ambulance, animal, etc. as to allow relatively high quality imaging, visualizing, or information providing even at very remote locations or separate from consistent or reliable electrical supplies.

Certain embodiments of the X-ray fluorescence visualizer, imager, or information provider 100 can include an electrical adaptor to allow operation based at least partially on one or more local electrical sources. Certain embodiments of the adapter to be used in conjunction with the X-ray fluorescence visualizer, imager, or information provider 100 could utilize a transformer (which might be controllable) as to allow the current or voltage source to the X-ray fluorescence visualizer, imager, or information provider 100 to be adapted, if desired. This adapter may be particularly useful for certain embodiments of the X-ray fluorescence visualizer, imager, or information provider 100 which may be applied to a primary power source during certain operations, and then electrically disconnected and applied to transported to another location (such as remote, in a vehicle, or at a different voltage/current supply) where there might be a varied power source, an inconsistent or non-existent power source.

By allowing certain embodiments of the X-ray fluorescence visualizer, imager, or information provider 100 to operate using relatively low power as compared to conventional imaging systems, is likely that the X-ray fluorescence visualization, imaging, and/or information providing systems can be utilized in regions remote from sophisticated electrical infrastructure. As such, certain embodiments of the X-ray fluorescence visualizer, imager, or information provider 100 can be applied to remote medical facilities, or regions, sporting events, office locations, relatively poor or remote regions, villages, islands, etc. Certain embodiments of the X-ray fluorescence visualizer, imager, or information provider 100 can thereby be situated where the medical, dental, rescue, emergency, or other need is (e.g., where sick, injured, or other individuals to be examined may be situated), as compared to where relatively large power supplies or complex or expensive imaging equipment may be located.

As such, certain portable embodiments of the at least the portion of the X-ray fluorescence visualizer, imager, or information provider 100 can utilize such portable energy-provided devices as fuel cells, batteries, generator, etc. By allowing a wide range of portable energy sources, such as allowed by relatively low power usage by certain embodiments of the X-ray fluorescence visualizer, imager, or information provider 100, relatively portable embodiments of X-ray fluorescence visualizing, imaging, or information providing solutions can be provided.

Various embodiments of the X-ray fluorescence visualizer, imager, or information provider 100 can include a variety of memory for a portable device. The different embodiments of memories can be configured to limit the energy usage by the embodiments of the X-ray fluorescence visualizer, imager, or information provider 100 during portable (or non-portable) X-ray fluorescence visualizing, imaging, or information providing. For instance, the memory capacity may in certain instances limit the images acquired.

One example of a scenario for certain embodiments of the X-ray fluorescence visualizer, imager, or information provider 100 is that the images could be viewed in real time, and nothing is stored. Another example of a scenario for certain embodiments of the X-ray fluorescence visualizer, imager, or information provider 100 is that the image can be stored in a memory device within the device either before, during, or after displaying (or the images may not even be displayed). Another example of a scenario for certain embodiments of the X-ray fluorescence visualizer, imager, or information provider 100 is that the images can be transmitted to a storage device distant from the portable unit. These examples are intended to be illustrative in nature, but not limiting in scope.

As such, certain user-operated embodiments of the X-ray fluorescence visualizer, imager, or information provider 100 can be configured to be used in, and are designed to be suitable to be used in, the particular location of the user (e.g., doctor's office, operating room, emergency center, rescue vehicle, ambulance, dentist office, veterinarian, a vehicle, the individual's home or office, a remote village, etc.) to X-ray fluorescence visualize, image, and/or provide information at least a portion of the individual, or receive information relating to the individual. Certain individual-operated, home-based, office based, or other remote embodiments of the X-ray fluorescence visualizer, imager, or information provider 100 can be configured to be used in, and are designed to be suitable to be used in) the home, office, or other location of the user that can be used by the user (who may be the individual) as a home-style version to X-ray fluorescence visualize, image, and/or provide information at least a portion of the individual, or receive information relating to the individual. The different user-operated or individual-operated embodiments of the X-ray fluorescence visualizer, imager, or information provider 100 can each have varied functions and/or operations.

Considering the privacy issues, and the time required for patients to visit doctors, etc., the individual-operated embodiments of the X-ray fluorescence visualizer, imager, or information provider 100 can be configured to allow people, and other individuals, to monitor a variety of aspects of their own condition. Consider the privacy, flexibility, independence, and other benefits that home pregnancy tests have provided for women. Certain embodiments of the X-ray fluorescence visualizer, imager, or information provider 100 can be configured to provide X-ray fluorescence depth visualization, images, and/or associated information related to a variety of other conditions, illnesses, injuries, infections, sicknesses, and other conditions, medical, and/or routine check-up aspects. Certain embodiments of the X-ray fluorescence visualizer, imager, or information provider 100 could even be designed based, at least partially, on X-ray radiation limiting, user input, ergonomics, quality of imaging, and other such factors; and might be updated, improved, and changed as appropriate based on usage and feedback considerations.

Certain embodiments of the individual-operated embodiments of the X-ray fluorescence visualizer, imager, or information provider 100 can be configured to be devoted to only one, or a relatively few, devoted task (e.g., cancer or tumor scans, blood vessel locator, bone fragment detector, etc.). By being devoted to a few specific tasks, these devoted embodiments of the individual-operated embodiments of the X-ray fluorescence visualizer, imager, or information provider 100 can be made relatively inexpensively, and relatively simple, for the individual and/or other person using it. Consider that patients, family members, friends, etc. would typically be expected to have relatively little training and/or experience with imaging systems, and as such, certain embodiments should be made relative straight forward to understand with relatively little training.

By applying certain embodiments of the X-ray fluorescence visualizer, imager, or information provider 100 to conventional imaging equipment, certain devoted tasks, logic, computer programming, electronic circuitry, and/or other processing circuitry can make relatively clear analysis, determinations, prognosis, etc. as compared certain relatively expensive and multi-use conventional imaging equipment such as MRIs and CAT scan devices. As such, a particularly exemplary embodiment of the X-ray fluorescence visualizer, imager, or information provider 100 can be configured for a particular of a few devoted operations such as examining for such conditions, infections, illnesses, or injuries as melanomas, cancers, tumors, bone condition, tissue condition, ligament or tendon condition, etc. Certain embodiments of the X-ray fluorescence visualizer, imager, or information provider 100 can be designed, for example, to scan region of the individual for such aberrations as they may occur.

Thereupon, certain embodiments of the X-ray fluorescence visualization, imaging, or information providing controller 97 can be configured to determine logically (using a combination of hardware, software, firmware, as described in this disclosure) whether the condition falls within limits as to require further examination, for example. Certain embodiments of the X-ray fluorescence visualizer, imager, or information provider 100 can be configured to provide such devoted tasks with output in the form of imaging and/or X-ray fluorescence visualization. Although certain embodiments of these devoted devices can more suitably, and less expensively, output one or more of a variety of information resulting at least partially from some analysis and processing in a non-image-based mode (e.g., text, graphics, analysis output, etc.) which could be of considerable use both to trained and/or untrained users.

There are a variety of techniques by which certain embodiments of the X-ray fluorescence visualizer, imager, or information provider 100 that can X-ray fluorescence visualize, image, or provide information to within the X-ray fluorescence range to a prescribed substantial X-ray fluorescence visualizing, imaging, or information providing depth in at least some matter of the at least the portion of the individual. Certain of these techniques are illustrated in FIGS. 45 and 46, for example.

Figure 45:
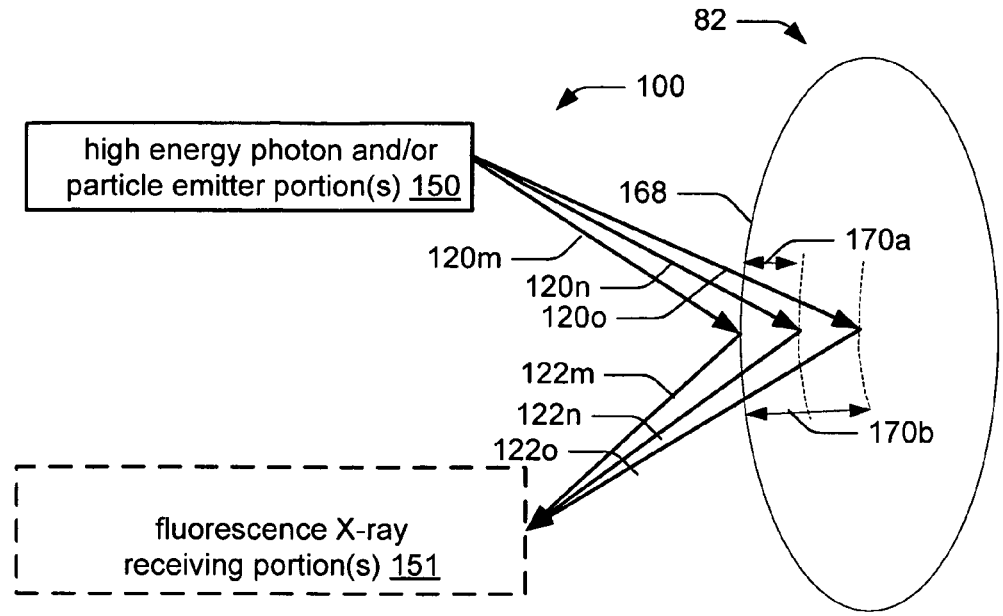
FIG. 45 shows one embodiment of the X-ray fluorescence visualizer, imager, or information provider that is being utilized for image combination.

FIG. 45, for example, illustrates an embodiment of the X-ray fluorescence visualizer, imager, or information provider 100 that can X-ray fluorescence visualize, image, or provide information to within the X-ray fluorescence range between the prescribed substantial X-ray fluorescence visualizing, imaging, or information providing depth 168, 170a, 170b in at least some matter of the at least the portion of the individual by applying a number of the at least one applied high energy photon and/or particle 120m, the at least one applied high energy photon and/or particle 120n, and the at least one applied high energy photon and/or particle 120o that respectively X-ray fluorescence at respective fluorescing events situated at differing respective prescribed substantial X-ray fluorescence visualizing, imaging, or information providing depth 168, 170a, 170b to provide respective at least one induced X-ray fluorescing photon 122 as can travel along paths 122m, 122n, and 122o. Though the number of the at least one applied high energy photon and/or particle 120 the at least one applied high energy photon and/or particle 120m, 120n, and 120o are illustrated as being applied at different angles (such as from multiple high energy photon and/or particle emitter portions are different angles, or from a single high energy photon and/or particle emitter portion(s) through several collimators), it should be understood that though these the at least one applied high energy photon and/or particle 120m, 120n, and 120o can be applied parallel or spaced from each other, such as being provide from an array. The respective at least one induced X-ray fluorescing photon 122 as traveling along respective paths 122m, 122n, and 122o can be detected by certain embodiments of the at least one X-ray fluorescence receiving portion(s) 151.

Figure 46:
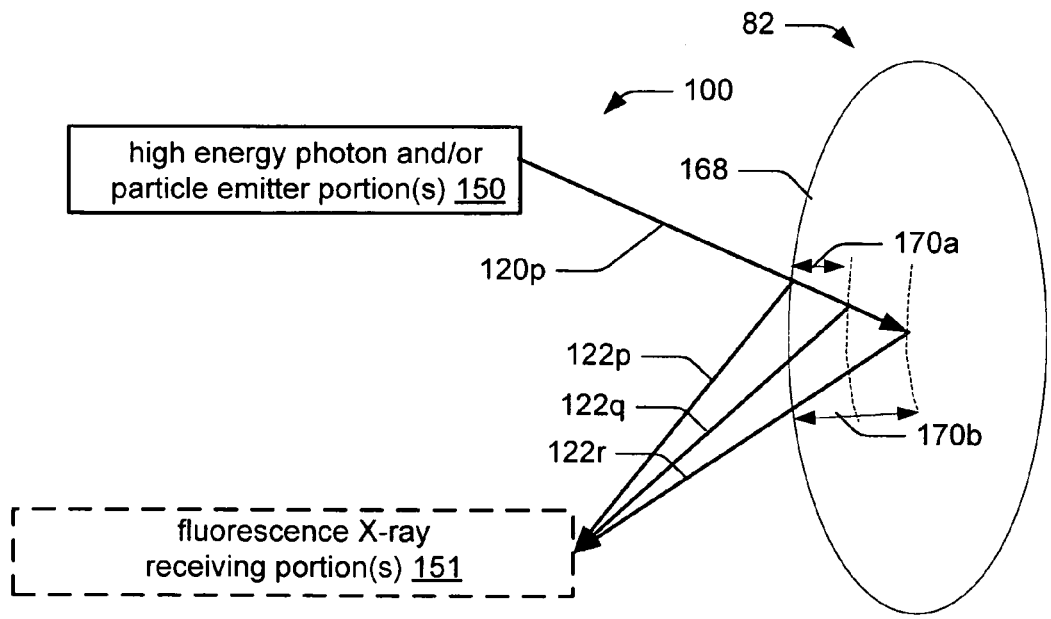
FIG. 46 shows a diagram of one embodiment of the X-ray fluorescence visualizer, imager, or information provider that is configured to provide a time of flight measurement.

FIG. 46, for example, illustrates an embodiment of the X-ray fluorescence visualizer, imager, or information provider 100 that can X-ray fluorescence visualize, image, or provide information to within the X-ray fluorescence range between the prescribed substantial X-ray fluorescence visualizing, imaging, or information providing depth 168, 170a, 170b in at least some matter of the at least the portion of the individual by the at least one high energy photon and/or particle emitter portion(s) 150 applying a single the at least one applied high energy photon and/or particle 120p that fluoresces at respective fluorescing events situated at differing respective prescribed substantial X-ray fluorescence visualizing, imaging, or information providing depth 168, 170a, 170b to provide respective at least one induced X-ray fluorescing photon 122 that can travel along paths 122p, 122q, and 122r. The respective paths 122p, 122q, and 122r can be detected by certain embodiments of the at least one X-ray fluorescence receiving portion(s) 151.

Certain characteristics of electromagnetic waves, currents, flows, fields, etc. (including aspects relating to X-rays, X-ray photons, electrons, etc.) is described in *The Electrical Engineering Handbook, Second Edition*, Richard C. Dorf, CRC Press/IEEE Press. Certain types of X-rays, which may be characterized broadly as electromagnetic waves, particles, fields, currents, etc., can be controlled, adjusted, varied, weakened, intensified, directed, etc. utilizing certain shielding, shaping, and/or electromagnetic controller techniques; such as are generally understood by those skilled in electrical engineering and/or electromagnetics. Certain embodiments of the X-ray fluorescence visualizer, imager, or information provider 100 can utilize X-rays, electromagnetic signals, particles, waves, etc. for X-ray fluorescence visualization, imaging, or information providing.

2. Controllable and/or Adjustable Embodiments of the X-Ray Fluorescence Visualizer, Imager, or Information Provider As described with respect to FIGS. 1 and 2 and at other locations in this disclosure, certain embodiments of the X-ray fluorescence visualizer, imager, or information provider 100 can utilize a variety of the high energy photon and/or particle emitter portion(s) (as well as associated elements) to direct controllable amounts such as energy levels of the at least one applied high energy photon and/or particle 120 toward and/or through matter of at least a portion of the individual. The at least one applied high energy photon and/or particle 120 can X-ray fluorescence by the matter of the at least a portion of the individual based on X-ray fluorescence aspects and equations, and at least partially on element composition of the at least some matter, as described in this disclosure. Based upon the amount of X-ray fluorescence, the energy level of the X-ray photons following the X-ray fluorescing event (corresponding to the characteristic frequency of the target atom 151, and other such X-ray fluorescence characteristics, can be utilized during a variety of embodiments of the X-ray fluorescence visualization, imaging, or information providing.

There are a variety of techniques by which and parameters of which the certain embodiments of the X-ray fluorescence visualizer, imager, or information provider 100 can be controlled and/or adjusted. For example, known image processing, optical, X-ray, and other techniques may be used to zoom, rotate, move in or out along a focal axis, or perform other such techniques. Such mechanisms to control at least some aspects of the X-ray fluorescence visualizing, imaging, or information provided may be particularly useful to allow the user to obtain the desired X-ray fluorescence visualization, image, or provided information. Such adjusted or controlled X-ray fluorescence visualizing, imaging, or information providing techniques can be performed with motion images (e.g., video), or a series of still images. Certain embodiments of such adjusted or controlled X-ray fluorescence visualizing, imaging, or information providing techniques can be used to examine the desired at least some matter of the at least the portion of the individual, at the desired magnification, and/or at the desired angle, etc.

In the instance of a surgeon, for example, the adjusting and/or control can be used to examine the desired at least some matter of the at least the portion of the individual at the desired rate such that the desired region of the at least some matter of the at least the portion of the individual can be X-ray visualized, imaged, or information provided in the desired manner.

There are a variety of controllability of adjustability aspects for a variety of embodiments of X-ray fluorescence visualizing, imaging, or information providing to a variety of prescribed depths. For instance, certain embodiments of the X-ray fluorescence visualizer, imager, or information provider 100 can provide control and/or adjustment of the X-ray fluorescence visualize, image, or provide information down to a prescribed depth, such that certain elements, chemicals, or compounds that are being particularly scanned for that are within that depth from the surface (e.g., iron for hemoglobin, or certain elements characteristic of particular types of cancer or tissue, etc.) should be indicated. While such scans within a range of depths may lack the clarity of scans limited to a relatively thin depth, certain embodiments of the X-ray fluorescence visualizer, imager, or information provider 100, such techniques for scanning for particular elements, as described in this disclosure, can be effectively performed and reliably indicated even through a prescribed depth range of matter. Such control and/or adjustment can be applied to surface scans through a prescribed depth can be from outside the individual, or at least partially internal to the individual such as via a surgical opening, a naturally occurring opening, or a minimally invasive opening such as for a scope-type device that may or may not be associated with a tool.

By comparison, certain embodiments of the control and/or adjustment of the X-ray fluorescence visualizer, imager, or information provider 100 can X-ray fluorescence visualize, image, or provide information within a prescribed depth range. For instance, it may be desired to determine what is in some matter of the at least the portion of the individual at some prescribed depth from a surface (at least partially internal or at least partially external) from a tool being used. Such control or adjustment of the range of prescribed depths being X-ray fluorescence visualized, imaged, or information provided can be under control of the user, or alternately under control of a controller, computer, hardware and/or software component, etc. as may be included in certain embodiments of the X-ray fluorescence visualization, imaging, or information providing controller 97 as described in this disclosure.

In certain instances, the energy level of the X-ray photons being applied to the matter of the individual can be ramped up, decreased, modified, maintained, etc. as described in this disclosure with respect to FIGS. 47 to 50. Certain embodiments of the X-ray fluorescence visualizer, imager, or information provider 100 can thereby X-ray fluorescence visualize, image, or provide information relating to particular matter based at least partially on increasing, reducing, modifying, or maintaining the energy levels of the X-ray photons (and thereby conversely decreasing the frequency of the X-ray photons) included in the at least one applied high energy photon and/or particle 120, and thereby controlling and/or adjusting the operation of the X-ray fluorescence visualizer, imager, or information provider. As the energy level of the X-ray photons respectively increases or decreases, within the at least one X-ray fluorescence range to the at least one prescribed substantial X-ray fluorescence depth of a considerable majority of the photons can thereupon generally correspondingly increase or decrease, though not typically in a linear fashion.

While the embodiments of the X-ray fluorescence visualizer, imager, or information provider 100 as described with respect to FIGS. 47 to 50 illustrate the at least one high energy photon and/or particle emitter portion(s) 150 whose output is controlled by an additional device; in actuality the distinct added device can be considered as an integral portion of the at least one high energy photon and/or particle emitter portion. As such, certain embodiments of the at least one high energy photon and/or particle emitter portion(s) may be considered as configured to apply adjustable and/or controllable the at least one applied high energy photon and/or particle 120 toward the at least some matter of the at least the portion of the individual.

As described above, there can be a variety of mechanisms that can be used to adjust and/or control certain embodiments of the X-ray fluorescence visualizer, imager, or information provider 100, largely based on operation of the X-ray fluorescence visualization, imaging, or information providing controller 97 to control and/or adjust the energy level, frequency, or other characteristics of the X-ray photons included in the at least one applied high energy photon and/or particle 120 and/or the at least one induced X-ray fluorescing photon 122. By controlling the energy level, frequency, or other characteristics of the X-ray photons included in the at least one applied high energy photon and/or particle 120 and/or the at least one induced X-ray fluorescing photon 122, the respective distance which a prescribed percentage of the at least one applied high energy photon and/or particle 120 and/or the at least one induced X-ray fluorescing photon 122 can pass through the at least some matter of the at least the portion of the individual can be adjusted or controlled (thereby controlling the depth of X-ray fluorescence visualizing, imaging, or information providing. For instance, controlling or adjusting the energy level of the at least one applied high energy photon and/or particle 120 can control or adjust the percentage of the at least one applied high energy photon and/or particle 120 that passes for certain prescribed distances through the at least some matter of the at least the portion of the individual. By comparison, controlling or adjusting the energy level of the at least one induced X-ray fluorescing photon 122 can control or adjust the percentage of the at least one induced X-ray fluorescing photon 122 that passes for certain prescribed distances through the at least some matter of the at least the portion of the individual. There are other mechanisms which may be utilized to control and/or adjust this X-ray fluorescence depth visualizing, imaging, or information providing of certain embodiments of the X-ray fluorescence visualizer, imager, or information provider 100.

The modification, control, adjustment, etc. in the characteristics of X-ray fluorescence visualization, imaging, or information providing into the matter of the at least the portion of the individual may not necessarily follow a linear function relative to the increasing energy levels of the X-ray photons making up the at least one applied high energy photon and/or particle 120. In addition, since the matter of such individuals is not homogenous, the rate of X-ray fluorescence visualization, imaging, or information providing may vary as a function of the material within the individual being imaged. For example, certain embodiments of the X-ray fluorescence visualizer, imager, or information provider 100 can be configured for imaging at least partially through bone would be expected to differ considerably (e.g., requiring different, likely increased, energy levels of the photons) as compared to the imaging characteristics required for less dense matter such as tissue, fluids such as blood or water, tumors, gums (dental), various organs, etc. As such, certain embodiment of the X-ray fluorescence visualizer, imager, or information provider 100 can be configured to adjust and/or control the at least one X-ray fluorescence range to the at least one prescribed substantial X-ray fluorescence depth such as by using a variety of techniques as described in this disclosure.

Figure 47:
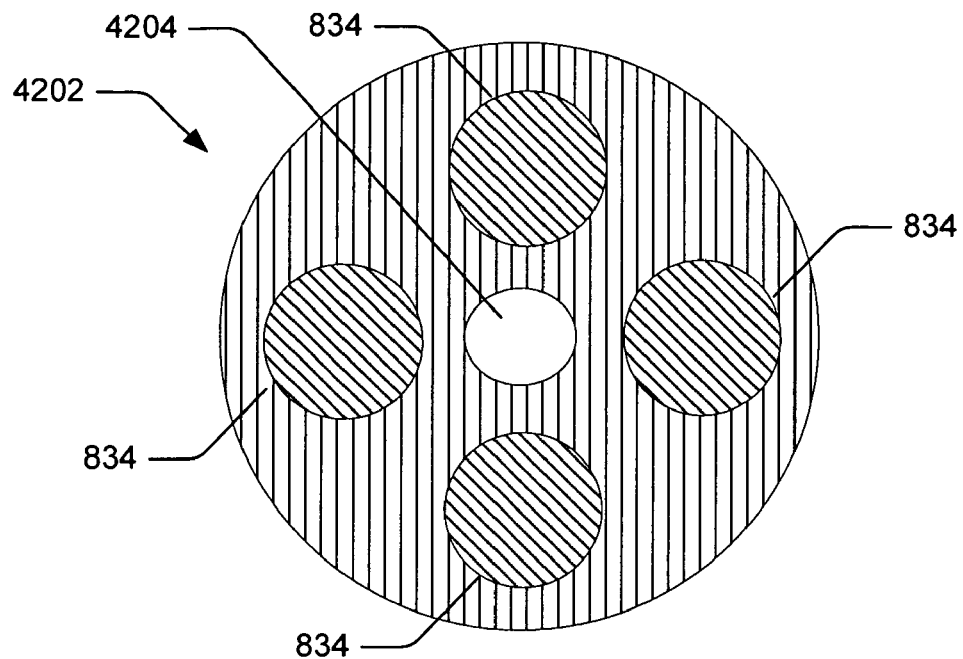
FIG. 47 shows another embodiment of the X-ray fluorescence visualizer, imager, or information provider including an embodiment of a control or adjustment mechanism.

FIG. 47 shows another embodiment of the control or adjustment mechanism 302, in which an anode switching or modifying mechanism (e.g., to include an adjustable anode wheel, or varying photon generator, as described with respect to FIG. 13 or 14) can allow for physically altering or changing of the anode 834. Certain embodiments of the anode 834 have been described with respect to FIG. 13 or 14. For instance, certain embodiments of the anode wheel as described with respect to FIG. 13 is described with respect to FIG. 47. The anode wheel can be rotated (e.g., using a step or motor, etc.), such as to align a different anode such as might have different materials, configurations, and/or dimensions, etc. such as to allow a change in the anode that is in communication with the electron stream, thereby providing varied energy levels (e.g., frequencies of X-ray photons) for the at least one applied high energy photon and/or particle 120. Certain embodiments of the anode wheel 4202 can be rotated or displaced about an axis 4204, such as by using a stepper motor or other suitable actuator, such as to operably position at least one anode 834 of the desired material, size, shape, configuration, etc. within the high energy photon and/or particle emitter portion(s) as desired. Positioning an anode having the desired characteristics within the high energy photon and/or particle emitter portion(s) as described with respect to FIG. 13 effectively generates the at least one applied high energy photon and/or particle 120 having the desired characteristics (e.g., X-ray photon energy level and corresponding frequency). Additionally, certain embodiments of the photon generator 880, as described with respect to FIG. 14, can be configured to provide X-ray photons having varied intensities and/or frequencies, such that could be used to control and/or adjust certain embodiments of the X-ray fluorescence visualizer, imager, or information provider 100. For example, the photon generator as described with respect to FIG. 14 could include multiple distinct photons generators, each of which could be individually actuated as to provide a controllable and/or adjustable version of the at least one applied high energy photon and/or particle 120 having the desired X-ray photon frequency and/or energy level characteristics.

Figure 48:
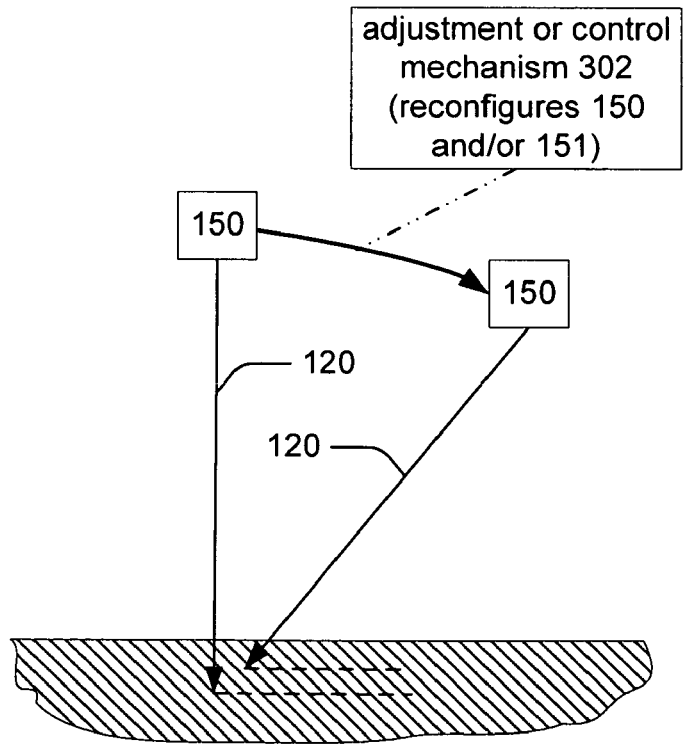
FIG. 48 shows another embodiment of the X-ray fluorescence visualizer, imager, or information provider including another embodiment of the control or adjustment mechanism.

FIG. 48 shows another embodiment of the X-ray fluorescence visualizer, imager, or information provider 100 including one embodiment of a control or adjustment mechanism 302 that can be utilized by certain embodiments of the X-ray fluorescence visualizer, imager, or information provider, in which the angle of the at least one applied high energy photon and/or particle 120 can be adjusted or controlled by varying the angle relative to the surface 168 of the at least the portion of the individual 82. As the angle of the at least one applied high energy photon and/or particle 120 changes, the at least one X-ray fluorescence range to the at least one prescribed substantial X-ray fluorescence depth can vary as a cosine function of the angle. As such, increasing the angle at which the at least one applied high energy photon and/or particle 120 is applied can therefore increase the distance of the matter through which the at least one applied high energy photon and/or particle 120 passes, and correspondingly reduce the at least one X-ray fluorescence range (measured perpendicular to the surface) to the at least one prescribed substantial X-ray fluorescence depth in a predictable, adjustable, and/or controllable fashion.

Figure 49:
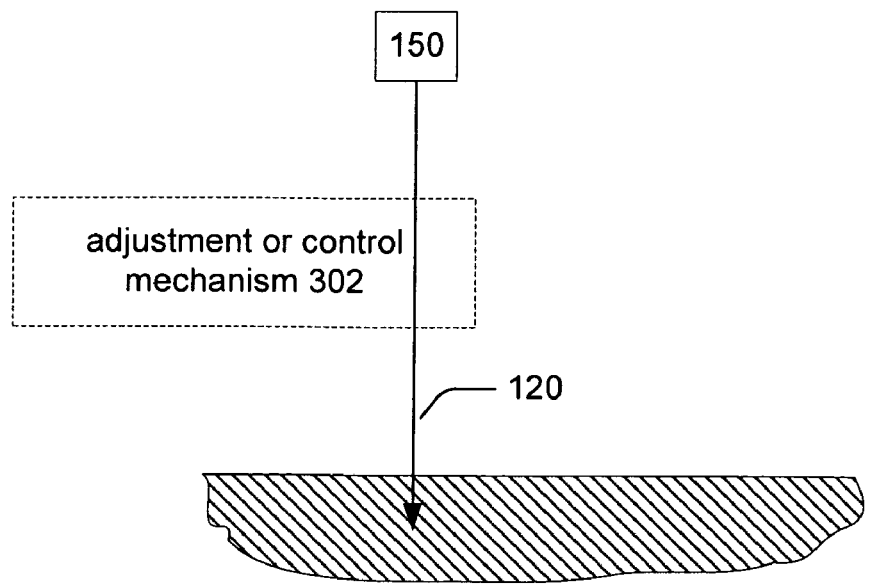
FIG. 49 shows another embodiment of the X-ray fluorescence visualizer, imager, or information provider including yet another embodiment of the control or adjustment mechanism.
Figure 50:
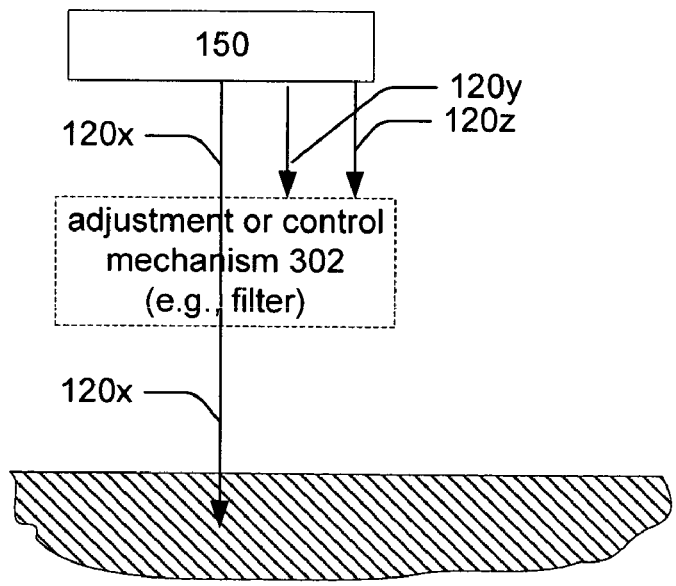
FIG. 50 shows another embodiment of the X-ray fluorescence visualizer, imager, or information provider including another embodiment of the control or adjustment mechanism.

FIG. 49 shows another embodiment of the X-ray fluorescence visualizer, imager, or information provider 100 including another embodiment of the control or adjustment mechanism 302, in which an X-ray depth-imaging depth reducing mechanism can be operationally applied between the at least one high energy photon and/or particle emitter portion(s) 150 the surface of the at least the portion of the individual (or at some other locations) as to limit the at least one X-ray fluorescence range to the at least one X-ray fluorescence visualizing, imaging, or information providing depth to reduce the energy level of the X-ray photons being applied to the at least the portion of the individual. Consider that, in general, as the at least one applied high energy photon and/or particle 120 travel through the matter of the at least the portion of the individual, they typically lose energy. As such, the X-ray depth-imaging depth reducing mechanism can be configured is any device or mechanism that can similarly reduce the energy level of the at least one applied high energy photon and/or particle 120 prior to being applied to the at least the portion of the individual. Certain embodiments of the adjustment or control mechanism 44 as illustrated in FIG. 49 could include an X-ray energy level or frequency modulator or modifier.

As such, the effective at least one substantial X-ray fluorescence within the at least one X-ray fluorescence range to the at least one X-ray fluorescence visualizing, imaging, or information providing depth of the at least one applied high energy photon and/or particle 120 can enter into the matter of the at least the portion of the individual can be reduced by initially passing through certain embodiments of the X-ray depth-imaging depth reducing mechanism can be reduced. Certain X-ray depth-imaging depth reducing mechanism to embodiments of the control or adjustment mechanism 302 can effectively decrease the energy level and/or frequency of the X-ray photons included in the at least one applied high energy photon and/or particle 120. Various X-ray depth-imaging depth reducing mechanism to arrange for a layer of material that at least partially dissipates the energy of the X-ray photons, to at least one semiconductor device or other mechanism that can modulate X-ray frequencies and thereby reduce energies, etc.

FIG. 49 shows another embodiment of the adjustable or controllable mechanism 302 by which a variety of filters would be applied to the at least one applied high energy photon and/or particle 120 to filter out at least certain frequency X-rays, while allowing at least other frequency X-rays to pass. Certain embodiments of the at least one high energy photon and/or particle emitter portion(s) 150 thereby can include multiple X-ray generators, multiple anodes, or multiple devices that each can generate X-rays photons having a distinct frequency. Alternately, certain embodiments of the at least one high energy photon and/or particle emitter portion(s) 150 can generate a broadband X-ray including X-rays having a range of frequencies, only certain ones of which are allowed to pass through the filter embodiment of the adjustment or control mechanism 302. For instance, FIG. 49 shows one filtering embodiment of the adjustment or control mechanism 302 that allows X-ray photons having frequency corresponding to the at least one applied high energy photon and/or particle 120$x$ to pass, while limiting the ability of X-ray photons having frequencies corresponding to the at least one applied high energy photon and/or particle 120$y$ and 120$z$ to pass.

There are therefore a variety of configurations of various embodiments of the X-ray fluorescence visualizer, imager, or information provider 100 that can include a variety of types of adjustment or control mechanism 302 by which the energy level of X-ray photons can be controlled or adjusted. Certain embodiments of the at least one high energy photon and/or particle emitter portion(s) 150 and/or the at least one X-ray fluorescence receiving portion(s) 151 can be configured in arrays, or by having slightly different operating characteristics. As such, one or more of the at least one high energy photon and/or particle emitter portion(s) 150 and/or the at least one X-ray fluorescence receiving portion(s) 151 can be actuated and/or deactuated, depending on characteristic, position, angle, etc. such as to allow for control and/or adjustment of the X-ray fluorescence visualizing, imaging, or providing information modalities.

Additionally, certain embodiments of the at least one X-ray fluorescence receiving portion(s) 151 can be directed, positioned, angled, filtered, or otherwise operated to only receive certain X-ray fluorescence high energy (e.g., X-ray, gamma ray, photon, particle, etc.). While these embodiments of the X-ray fluorescence visualizer, imager, or information provider 100 are not illustrated, it is to be understood that certain embodiments of the adjustment or control mechanism 302 can be situated relative to the at least one high energy photon and/or particle emitter portion(s) 150, relative to the at least one X-ray fluorescence receiving portion(s) 151, at some median location, or elsewhere. Certain embodiments of the adjustment or control mechanism 302 can be software, hardware, firmware, and/or processor intensive such as to only consider certain of the X-ray fluorescence high energy (e.g., X-ray, gamma ray, photon, particle, etc.) as received by certain embodiments of the at least one X-ray fluorescence receiving portion(s) 151.

The various exemplary embodiments of the adjustment or control mechanism 302 as described with respect to FIGS. 47 to 50 are intended to be illustrative in nature, but not limiting in scope. Any of a variety of techniques by which the frequency (and the corresponding energy level) of the at least one applied high energy photon and/or particle 120 being applied to the at least some matter of the at least a portion of the individual may be considered as another embodiment of the adjustment or control mechanism, within the scope of the present disclosure.

Additionally, certain embodiments of the adjustment or control mechanism can be applied to respectively adjust or control the at least one induced X-ray fluorescing photon 122 fluorescing from the fluorescing event within the matter of the at least the portion of the at least a portion of the individual. A variety of such adjustment or control techniques such as filtering, correlating, controlling, or selectively monitoring certain X-ray photon frequency or energy levels of the X-ray fluorescence high energy (e.g., X-ray, gamma ray, photon, particle, etc.).

There may be some of the at least one applied high energy photon and/or particle 120 that are being altered such as by ramping, reducing, modification, maintaining, in which the at least one applied high energy photon and/or particle 120 is applied to the matter of the individual can X-ray fluorescence within the at least one X-ray fluorescence range to the at least one prescribed substantial X-ray fluorescence visualizing, imaging, or information providing depth for that particular or instantaneous X-ray fluorescence visualizing, imaging, or information providing period. Certain embodiments of the X-ray fluorescence visualizer, imager, or information provider 100 can be configured to limit the effects of the at least one applied high energy photon and/or particle 120 that are returning from a depth greater than the within the at least one X-ray fluorescence range to the at least one prescribed substantial X-ray fluorescence depth. Additionally, the X-ray fluorescence depth visualizing, imaging, or information providing effects of these the at least one applied high energy photon and/or particle 120 can be included in the X-ray fluorescence visualization, imaging, or information providing, with any distortive effects during the ramping operation either ignored, filtered, and/or otherwise limited using signal processing techniques.

Such increase or ramping of the energy level of the at least one applied high energy photon and/or particle 120 can be performed by those embodiments of the X-ray fluorescence visualizer, imager, or information provider 100 that can be tuned. The rate of ramping (e.g., the rate of the photon energy level) can thereby be set or controlled either manually or by setting the X-ray fluorescence visualization, imaging, or information providing controller 97. Experimentation could be used to provide an indication of a suitable ramping rate for the particular matter(s) of the at least the portion of the individual.

With a ramping function, each increase in the energy of the at least one applied high energy photon and/or particle 120 such as would be expected to provide an increase in the at least one X-ray fluorescence range to the at least one prescribed substantial X-ray fluorescence depth which can be monitored by the X-ray fluorescence receiving assembly. For example, certain pulse signals can initially be applied, and time of flight calculations can be utilized to determine the within the at least one X-ray fluorescence range to the at least one prescribed substantial X-ray fluorescence depth.

3. Certain Embodiments of the X-Ray Fluorescence Visualization, Imaging, or Information Providing Controller This disclosure describes a number of embodiments of the X-ray fluorescence visualization, imaging, or information providing controller 97 as described with respect to FIG. 1 or 2, which is intended to control and/or adjust X-ray fluorescence visualization, imaging, or information providing by the X-ray fluorescence visualizer, imager, or information provider 100 of at least the portion of the individuals 82. Certain embodiments of the at least one X-ray fluorescence visualization, imaging, or information providing controller 97 can control and/or adjust a variety of aspects of X-ray fluorescence visualizing, imaging, or information providing by the X-ray fluorescence visualizer, imager, or information provider 100 within the at least some matter of the at least the portion of the individual and/or within at least one X-ray fluorescence range to the at least one prescribed substantial X-ray fluorescence depth as described in this disclosure. As such, certain embodiments of the X-ray fluorescence visualizer, imager, or information provider 100 can operate without, and/or with little interaction from, the X-ray fluorescence visualization, imaging, or information providing controller 97. By comparison, certain embodiments of the X-ray fluorescence visualizer, imager, or information provider 100 can utilize considerable input from, and/or entirely utilizing input from, the X-ray fluorescence visualization, imaging, or information providing controller 97.

Certain embodiments of the X-ray fluorescence visualizer, imager, or information provider 100 can thereby include the X-ray fluorescence visualization, imaging, or information providing controller 97 as described with respect to FIG. 1 or 2; while other embodiments of the X-ray fluorescence visualizer, imager, or information provider may not include utilizing the X-ray fluorescence visualization, imaging, or information providing controller. For example, certain scintillator-based and/or fluoroscope-based embodiments of the X-ray fluorescence visualizer, imager, or information provider may convert received X-ray based photons directly into viewable and/or visible photons (which may or may not be amplified using a photomultiplier or CCD) to allow direct X-ray fluorescence visualization, imaging, or information providing, which may limit the necessity of image processing that may largely rely on the X-ray fluorescence visualization, imaging, or information providing controller 97. By comparison, certain embodiments of the X-ray fluorescence visualizer, imager, or information provider 100 can utilize input from the user, such as to determine location, angle, position, resolution, X-ray frequency, energy level, time of X-ray fluorescence depth visualizing, imaging, or information providing, and other such X-ray fluorescence visualization, imaging, or information providing related factors or characteristics. Such X-ray fluorescence visualization, imaging, or information providing characteristics may be selected, controlled, and/or altered using certain embodiments of the X-ray fluorescence visualization, imaging, or information providing controller 97.

Some X-ray fluorescence depth visualizing, imaging, or information providing information, data, images, signals, etc. associated with certain embodiments of the X-ray fluorescence visualizer, imager, or information provider 100 and/or the X-ray fluorescence visualization, imaging, or information providing controller 97 may be digital based, while other embodiments may be analog based. For instance, certain embodiments of the X-ray fluorescence visualizer, imager, or information provider 100 including the X-ray fluorescence visualization, imaging, or information providing controller 97, which are largely digital and/or microprocessor-based, can provide for largely automated actuation of X-ray fluorescence visualization, imaging, or information providing and/or signals of the X-ray fluorescence visualizer, imager, or information provider 100 and/or the X-ray fluorescence visualizer, imager, or information provider(s) 104. A number of the components of the X-ray fluorescence visualizer, imager, or information provider(s) 104 may rely on analog and/or digital controllers and/or computers which may be capable of generating signals with considerable power. Other lower-powered signals from the X-ray fluorescence visualizer, imager, or information provider(s) 104 may be either analog and/or digitally controlled. Certain X-ray fluorescence visualization, imaging, or information providing controller 97 that are configured to turn particular circuits on or off, for example, may be particularly efficient and/or effective if digital based. Certain embodiments of the X-ray fluorescence visualization, imaging, or information providing controller 97 can be configured to, upon a normal operation, compensate for at least some distortion as can be provided by the X-ray fluorescence depth visualizing, imaging, or information providing region of the at least the portion of the individual. FIG. 1 or 2 can represent a block diagram of certain respective embodiments of the X-ray fluorescence visualizer, imager, or information provider 100 that can include the X-ray fluorescence visualization, imaging, or information providing controller 97 to either control and/or adjust the X-ray fluorescence visualization, imaging, or information providing within the X-ray fluorescence visualizer, imager, or information provider, or some other related operations.

Certain embodiments of the X-ray fluorescence visualizer, imager, or information provider 100 can be configured in which an energy level required to image using conventional transmissive X-ray technologies to the controllable or adjustable ones of the within the at least one X-ray fluorescence range to the at least one prescribed substantial X-ray fluorescence depth. In certain instances, the energy intrusion level can be less (and in certain instances, considerably less) than the energy intrusion level required to image using conventional transmissive X-ray technology through the entirety of the at least the portion of the individual 82. By using reduced to X-ray dosages, certain embodiments of the X-ray fluorescence visualizer, imager, or information provider 100 can image, utilize, or provide information while remaining within a safe emitted radiation level for the individual as well as though one or more users, which can result from application of smaller dosages. Certain embodiments of the X-ray fluorescence visualization, imaging, or information providing controller 97 can even be configured to monitor, change, adjust, or maintain X-ray exposure levels within the at least the portion of the individual. X-ray exposure levels by the individual and/or the user(s), and/or X-ray levels in the vicinity of the individual and/or the user, etc.

Certain embodiments of the X-ray fluorescence visualization, imaging, or information providing controller 97 are configured to provide control and/or adjustability of the X-ray fluorescence visualizer, imager, or information provider 100 based, at least in part, on the X-ray fluorescence visualization, imaging, or information providing operation and/or configuration of the X-ray fluorescence visualizer, imager, or information provider. For example, if a user wishes to control and/or adjust an angle, a position, an X-ray photon frequency or energy level, a resolution, the within the at least one X-ray fluorescence range to the at least one prescribed substantial X-ray fluorescence depth, or at least one other X-ray fluorescence visualization, imaging, or information providing parameter; then the user could provide suitable input to the X-ray fluorescence visualization, imaging, or information providing controller 97. Such input to the X-ray fluorescence visualization, imaging, or information providing controller 97 can be provided via the input/output interface, which in certain embodiments may be a graphical user interface (GUI), for example.

If the user wishes to X-ray fluorescence visualize, image, and/or provide information relating to a portion of the individual on a real time basis, a continuous basis, a sequential basis, or another repetitive basis, then the type of X-ray fluorescence depth visualizing, imaging, or information providing can also be selected using the input/output interface 811 of the X-ray fluorescence visualization, imaging, or information providing controller 97. Certain embodiments of the input/output interface 811 can additionally provide an indication to the user of some aspect of the X-ray fluorescence depth visualizations, images, and/or provided information, such as if the X-ray fluorescence visualizer, imager, or information provider is incapable of the depth imaging, X-ray fluorescence visualizing, or information providing; and will likely not expose the user and/or individual to unacceptable X-ray dosages, etc.

Certain embodiments of the X-ray fluorescence visualizer, imager, or information provider 100 can thereby include, but are not limited to, a variety of configurations of the X-ray fluorescence visualization, imaging, or information providing controller 97. Certain embodiments of the X-ray fluorescence visualization, imaging, or information providing controller 97 can also be at least partially computer based, controller based, mote based, cellular telephone-based, and/or electronics based. Certain embodiments of the X-ray fluorescence visualization, imaging, or information providing controller can be segmented into modules, and can utilize a variety of wireless communications and/or networking technologies to allow information, data, etc. to be transferred to the various distinct portions or embodiments of the X-ray fluorescence visualizer, imager, or information provider 100. Certain embodiments of the X-ray fluorescence visualization, imaging, or information providing controller 97 can be configured as a unitary device, a networked device, a stand alone device, and/or any combination of these and other known type devices.

Certain embodiments of the X-ray fluorescence visualization, imaging, or information providing controller 97 can vary as to their automation, complexity, and/or sophistication; and can be utilized to control, setup, establish, and/or maintain communications between a number of communicating devices during X-ray fluorescence visualization, imaging, or information providing operation(s). As described within this disclosure, multiple ones of the different embodiments of the X-ray fluorescence visualizer, imager, or information provider 100 can transfer information or data relating to the communication link to or from a remote location and/or some intermediate device as might be associated with communication, monitoring and/or other activities. Certain embodiments of the X-ray fluorescence visualizer, imager, or information provider 100 can vary as to the particular X-ray fluorescence visualization modality, imaging modality, and/or information providing modality.

Certain embodiments of the X-ray fluorescence visualization, imaging, or information providing controller 97, as well as certain embodiments of the X-ray fluorescence visualizer, imager, or information provider 100 (in general), can utilize distinct firmware, hardware, and/or software technology. For example, certain embodiments of the X-ray fluorescence visualizer, imager, or information provider 100 can at least partially utilize one or more of: mote-based technology, microprocessor-based technology, microcomputer-based technology, display technology, imaging technology, general-purpose computer technology, specific-purpose computer technology, Application-Specific Integrated Circuits (AASICs), and/or a variety of other computer, electronics, electromagnetic, imaging, X-ray fluorescence visualizing, and/or information providing technologies, such as can be utilized by certain embodiments of the X-ray fluorescence visualization, imaging, or information provider controller 97.

Certain embodiments of the X-ray fluorescence visualization, imaging, or information providing controller 97 can as described with respect to FIG. 1 or 2 can include depending on context a processor 803 such as a central processing unit (CPU), a memory 807, a circuit or circuit portion 809, and an input output interface (I/O) 811 that may include a bus (not shown). Certain embodiments of the X-ray fluorescence visualization, imaging, or information providing controller 97 of the X-ray fluorescence visualizer, imager, or information provider 100 can include and/or be a portion of a general-purpose computer, a specific-purpose computer, a microprocessor, a microcontroller, a personal display assistant (PDA), a cellular phone, a wireless communicating device, a hard-wired communication device, and/or any other known suitable type of communications device or phone, computer, and/or controller that can be implemented in hardware, software, electromechanical devices, and/or firmware. Certain embodiments of the processor 803, as described with respect to FIG. 1 or 2, can perform the processing and arithmetic operations for certain embodiments of the X-ray fluorescence visualization, imaging, or information providing controller 97 of the X-ray fluorescence visualizer, imager, or information provider 100. Certain embodiments of the X-ray fluorescence visualization, imaging, or information providing controller 97 of the X-ray fluorescence visualizer, imager, or information provider 100 can control the signal processing, database querying and response, computational, timing, data transfer, and other processes associated with X-ray fluorescence visualization, imaging, or information providing such as can be adjusted by and/or controlled by certain embodiments of the X-ray fluorescence visualization, imaging, or information providing controller 97 of the X-ray fluorescence visualizer, imager, or information provider 100.

Certain embodiments of the X-ray fluorescence visualization, imaging, or information providing controller 97 (depending in part of the X-ray fluorescence visualization, imaging, or information providing process being attempted or performed by the X-ray fluorescence visualizer, imager, or information provider 100), will undergo considerable image processing by the processor 803. Particularly, those embodiments of the X-ray fluorescence visualizer, imager, or information provider 100 that can X-ray fluorescence visualize, image, and/or provide information relating to a relatively large area, image to relatively high resolution, image continuously, sequentially, and/or repetitively will provide a large amount of images or image information. As such, certain embodiments of the components of the X-ray fluorescence visualization, imaging, or information providing controller 97 should be designed and configured to handle the type of X-ray fluorescence visualization, image, and/or provided information processing that the subsurface X-ray fluorescence image processing will be exposed. Certain types of image compression (e.g., lossy and/or lossless data compression techniques) may be utilized in the X-ray fluorescence visualization, imaging, or information providing controller 97 to limit production or storage of excessive volumes of redundant data.

Certain embodiments of the memory 807 of the X-ray fluorescence visualization, imaging, or information providing controller 97 can include a random access memory (RAM) and/or read only memory (ROM) that together can store the computer programs, operands, and other parameters that control the operation of certain embodiments of the X-ray fluorescence visualization, imaging, or information providing controller 97 of the X-ray fluorescence visualizer, imager, or information provider 100. The memory 807 can be configurable to contain data, information, images, X-ray fluorescence visualizations, image information, etc. that can be obtained, retained, or captured by that particular X-ray fluorescence visualization, imaging, or information providing controller 97, as described in this disclosure.

Certain embodiments of the bus can be configurable to provide for digital information transmissions between the processor 803, circuits 809, memory 807, I/O 811, the X-ray fluorescence visualization, image, and/or provided information memory or storage device (which may be integrated or removable), other portions within the X-ray fluorescence visualizer, imager, or information provider(s) 104, and/or other portions outside of the X-ray fluorescence visualizer, imager, or information provider(s) 104. In this disclosure, the memory 807 can be configurable as RAM, flash memory, semiconductor-based memory, of any other type of memory that can be configurable to store data pertaining to X-ray fluorescence depth visualizations, images, and/or provided information. Certain embodiments of the bus can also connects I/O 811 to the portions of certain embodiments of the X-ray fluorescence visualization, imaging, or information providing controller 97 of either the X-ray fluorescence visualizer, imager, or information provider 100 that can either receive digital information from, or transmit digital information to other portions of the X-ray fluorescence visualizer, imager, or information provider 100, or other systems and/or networking components associated therewith.

Certain embodiments of the X-ray fluorescence visualization, imaging, or information providing controller 97 of the X-ray fluorescence visualizer, imager, or information provider 100, as described with respect to FIG. 1 or 2, can include a separate, distinct, combined, and/or associated transmitter portion (not shown) that can be either included as a portion of certain embodiments of the X-ray fluorescence visualization, imaging, or information providing controller 97 of the X-ray fluorescence visualizer, imager, or information provider 100. Certain embodiments of the X-ray fluorescence visualization, imaging, or information providing controller 97 can alternately be provided as a separate and/or combined unit (e.g., certain embodiments might be processor-based and/or communication technology-based).

Certain embodiments of the X-ray fluorescence visualization, imaging, or information providing controller 97 of the X-ray fluorescence visualizer, imager, or information provider 100 as described with respect to FIG. 1 or 2 can include an operation altering or controlling portion (described with respect to FIG. 37) that can be either included as a portion of certain embodiments of the X-ray fluorescence visualization, imaging, or information providing controller 97 of the X-ray fluorescence visualizer, imager, or information provider 100, or alternately can be provided as a separate or combined unit.

Certain embodiments of the memory 807 can provide an example of a memory storage portion. In certain embodiments, the monitored value includes but is not limited to: a percentage of the memory 807, an indication of data that is or can be stored in the memory 807, or for data storage or recording interval. Such memory can include information about the individual, the treatment, the user, the treating or examining facility, etc.; and also may include one or more X-ray fluorescence visualization, image, or provided information as provided by certain embodiments of the X-ray fluorescence visualizer, imager, or information provider 100, or alternately as can be provided by another X-ray fluorescence visualization, image, or information source such as tomography X-ray fluorescence visualizations, images, or provided information, MRI, CT scan, PET scan, etc. such as can be used to provide a combined image, X-ray fluorescence visualization, or information. To provide for overflow ability for the memory 807 of certain embodiments of the X-ray fluorescence visualization, imaging, or information providing controller 97 of the X-ray fluorescence visualizer, imager, or information provider 100, a secondary storage device can be operably coupled to the memory 807 to allow a controllable transmitting of memory data from certain embodiments of the X-ray fluorescence visualization, imaging, or information providing controller 97 of the X-ray fluorescence visualizer, imager, or information provider 100 when the monitored value of data or other information within the memory 807 exceeds a prescribed value. The prescribed value can include, e.g., some percentage amount or some actual amount of the value.

In certain embodiments, a secondary communication link can be established between the certain embodiments of the X-ray fluorescence visualization, imaging, or information providing controller 97 of the X-ray fluorescence visualizer, imager, or information provider 100. The secondary communication link can be structured similar to as a communication link, or alternatively can utilize network-based computer connections, Internet connections, etc. to provide information and/or data transfer between certain embodiments of the X-ray fluorescence visualization, imaging, or information providing controller 97 of the X-ray fluorescence visualizer, imager, or information provider 100.

In certain embodiments of the X-ray fluorescence visualization, imaging, or information providing controller 97 of the X-ray fluorescence visualizer, imager, or information provider 100, the particular elements of certain embodiments of the X-ray fluorescence visualization, imaging, or information providing controller 97 of the X-ray fluorescence visualizer, imager, or information provider 100 (e.g., the processor 803, the memory 807, the circuits 809, and/or the I/O 811) can provide a monitoring function to convert raw data as displayed by an indicator. A monitoring function as provided by certain embodiments of the X-ray fluorescence visualization, imaging, or information providing controller 97 of the X-ray fluorescence visualizer, imager, or information provider 100 can be compared to a prescribed limit, such as whether the number of X-ray fluorescence depth visualizations, images, and/or provided information contained in the memory 807, the amount of data contained within the memory 807, or some other measure relating to the memory is approaching some value. The limits to the value can, in different embodiments, be controlled by the user or the manufacturer of certain embodiments of the X-ray fluorescence visualization, imaging, or information providing controller 97 of the X-ray fluorescence visualizer, imager, or information provider 100. In certain embodiments, the memory 807 can store such information as data, information, displayable information, readable text, motion X-ray fluorescence depth visualizations, images, and/or provided information, video X-ray fluorescence depth visualizations, images, and/or provided information, and/or audio X-ray fluorescence depth visualizations, images, and/or provided information, etc.

In certain embodiments, the I/O 811 provides an interface to control the transmissions of digital information between each of the components in certain embodiments of the X-ray fluorescence visualization, imaging, or information providing controller 97 of the X-ray fluorescence visualizer, imager, or information provider 100. The I/O 811 also provides an interface between the components of certain embodiments of the X-ray fluorescence visualization, imaging, or information providing controller 97 of the X-ray fluorescence visualizer, imager, or information provider 100. The circuits 809 can include such other user interface devices as a display and/or a keyboard. In other embodiments, the X-ray fluorescence visualization, imaging, or information providing controller 97 of the X-ray fluorescence visualizer, imager, or information provider 100 can be constructed as a specific-purpose computer such as an application-specific integrated circuit (ASIC), a microprocessor, a microcomputer, or other similar devices.

4. Certain Embodiments of the X-Ray Fluorescence Visualizer, Imager, or Information Provider With Relevant Flowcharts Within the disclosure, flow charts of the type described in this disclosure apply to method steps as performed by a computer or controller as could be contained within certain embodiments of the X-ray fluorescence visualizer, imager, or information provider 100, as described in this disclosure. Additionally, the flow charts as described in this disclosure apply operations or procedures that can be performed entirely and/or largely utilizing mechanical devices, systems, electromechanical devices, computerized devices, or the like, such as certain embodiments of the X-ray fluorescence visualizer, imager, or information provider 100 as described in this disclosure. The flow charts can also apply to apparatus devices, such as an antenna or a node associated therewith that can include, e.g., a general-purpose computer or specialized-purpose computer whose structure along with the software, firmware, electro-mechanical devices, and/or hardware, can perform the process or technique described in the flow chart.

An embodiment of the X-ray fluorescence visualizer, imager, or information provider 100 that can act to compensate for a distortion by the X-ray fluorescence depth visualizer has been described with respect to FIG. 1 or 2, and elsewhere in this disclosure. There can be a variety of embodiments of the X-ray fluorescence visualizer, imager, or information provider 100 that can be used to X-ray fluorescence visualize, image, or provide information etc. as described in this disclosure. There can be variety of embodiments of the X-ray fluorescence visualizer, imager, or information provider 100.

FIG. 51 shows certain embodiments of a X-ray fluorescence visualizing, imaging, of information providing technique 4600 such as described with respect to, but not limited to, the X-ray fluorescence visualizer, imager, or information provider 100 of FIG. 1 or 2, and elsewhere in this disclosure. Certain embodiments of a high-level flowchart of the X-ray fluorescence visualizing, imaging, of information providing technique 4600 is described with respect to FIG. 51 and can include, but is not limited to, operation 4602. Certain embodiments of operation 4602 can include, but is not limited to, determining a location of an at least one X-ray fluorescing event occurring within an at least some matter of at least a portion of an individual, wherein the determining the location of the at least one X-ray fluorescing event is based at least in part on determining a relative angle at which an at least one applied high energy photon and/or particle is being applied to the at least some matter of the at least the portion of the individual, a relative position from which an at least one applied high energy photon and/or particle is being applied to the at least some matter of the at least the portion of the individual, a detected location of an at least one induced fluorescing X-ray photon fluoresced during the at least one X-ray fluorescing event, and a received angle at which the at least one induced fluorescing X-ray photon is received. For example, certain embodiments of the X-ray fluorescence visualizer, imager, or information provider 100 can act responsive to X-ray fluorescence visualize, image, or provide information based at least partially on the following four "determining" factors including, but not limited to: determining a relative angle at which an at least one applied high energy photon and/or particle is being applied to the at least some matter of the at least the portion of the individual, determining a relative position from which an at least one applied high energy photon and/or particle is being applied to the at least some matter of the at least the portion of the individual, determining a detected location of an at least one induced fluorescing X-ray photon fluoresced during the at least one X-ray fluorescing event, and determining a received angle at which the at least one induced fluorescing X-ray photon is received. In certain instances, the determining the location of the at least one X-ray fluorescing event occurring within the at least some matter of the at least the portion of the individual is applied within at least one substantially fluoresced depth range to an at least one prescribed substantially fluoresced depth. Such X-ray optical devices as a lens, a mirror, an X-ray phase plate lens, a zone plate lens, a gradient device, angled holes, polarizers, etc. can be used. The order of the operations, methods, mechanisms, etc. as described with respect to FIG. 51 is intended to be illustrative in nature, and not limited in scope.

FIG. 52 shows certain embodiments of a X-ray fluorescence visualizing, imaging, of information providing technique 4800 such as described with respect to, but not limited to, the X-ray fluorescence visualizer, imager, or information provider 100 of FIG. 1 or 2, and elsewhere in this disclosure. Certain embodiments of a high-level flowchart of the X-ray fluorescence visualizing, imaging, of information providing technique 4800 is described with respect to FIG. 52 and can include, but is not limited to, operations 4802 and/or 4808. Certain embodiments of operation 4802 can include, but is not limited to, inducing at least one induced X-ray fluorescing photon within an at least some matter of an at least a portion of an at least one individual responsive to a single input energy event based at least partially on an at least some input energy being applied to the at least some matter of the at least the portion of the at least one individual. For example, certain embodiments of the X-ray fluorescence visualizer, imager, or information provider 100 can act responsive to such single input events as a substantially distinct location of emission of the at least some input energy, a substantially distinct direction of emission of the at least some input energy, and a substantially distinct time of emission of the at least some input energy, substantially distinct location of emission of the at least some input energy, and a substantially distinct direction of emission of the at least some input energy, etc. as described in this disclosure, particularly in the claims. Certain embodiments of operation 4808 can include, but is not limited to, X-ray fluorescence visualizing, imaging, or information providing within the at least some matter of the at least the portion of the at least one individual responsive to the inducing at least one induced X-ray fluorescing photon. For instance, a variety of embodiments of the X-ray fluorescence visualizing, imaging, or information providing can be provided, as described in this disclosure. The order of the operations, methods, mechanisms, etc. as described with respect to FIG. 52 is intended to be illustrative in nature, and not limited in scope.

In one or more various aspects, related systems include but are not limited to circuitry and/or programming for effecting the herein-referenced method aspects; the circuitry and/or programming can be virtually any combination of hardware, software, electro-mechanical system, and/or firmware configurable to effect the herein-referenced method aspects depending upon the design choices of the system designer.

5. Conclusion

This disclosure provides a number of embodiments of the X-ray fluorescence visualizer, imager, or information provider 100. The embodiments of the X-ray fluorescence visualizer, imager, or information provider as described with respect to this disclosure are intended to be illustrative in nature, and are not limiting its scope.

Those having skill in the art will recognize that the state of the art in computer, controller, communications, networking, and other similar technologies has progressed to the point where there is little distinction left between hardware, firmware, and/or software implementations of aspects of systems, such as may be utilized in the X-ray fluorescence visualizer, imager, or information provider. The use of hardware, firmware, and/or software can therefore generally represent (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle can vary with the context in which the processes and/or systems and/or other technologies are deployed. For example, if an implementer determines that speed and accuracy are paramount, the implementer and/or designer of the X-ray fluorescence visualizer, imager, or information provider may opt for mainly a hardware and/or firmware vehicle. In alternate embodiments, if flexibility is paramount, the implementer and/or designer may opt for mainly a software implementation. In yet other embodiments, the implementer and/or designer may opt for some combination of hardware, software, and/or firmware. Hence, there are several possible techniques by which the processes and/or devices and/or other technologies described herein may be effected, none of which is inherently superior to the other in that any vehicle to be utilized is a choice dependent upon the context in which the vehicle can be deployed and the specific concerns (e.g., speed, flexibility, or predictability) of the implementer, any of which may vary.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, target individual 82 and/or collectively, by a wide range of hardware, software, firmware, or virtually any combination thereof. In Certain embodiments, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, and computer memory; and transmission type media such as digital and analog communication links using TDM or IP based communication links (e.g., packet links).

All of the above U.S. patents, U.S. patent application publications, U.S. patent applications, foreign patents, foreign patent applications and non-patent publications referred to in this specification and/or listed in any Application Data Sheet, are incorporated herein by reference, in their entireties.

It is to be understood by those skilled in the art that, in general, that the terms used in the disclosure, including the drawings and the appended claims (and especially as used in the bodies of the appended claims), are generally intended as "open" terms. For example, the term "including" should be interpreted as "including but not limited to"; the term "having" should be interpreted as "having at least"; and the term "includes" should be interpreted as "includes, but is not limited to"; etc. In this disclosure and the appended claims, the terms "a", "the", and "at least one" positioned prior to one or more goods, items, and/or services are intended to apply inclusively to either one or a plurality of those goods, items, and/or services.

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that could have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that could have A alone, B alone, C alone, A and B together, A and C together, B and C together, and/or A, B, and C together, etc.).

Those skilled in the art will appreciate that the herein-described specific exemplary processes and/or devices and/or technologies are representative of more general processes and/or devices and/or technologies taught elsewhere herein, such as in the claims filed herewith and/or elsewhere in the present application.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A method, comprising:
   determining a location of an at least one X-ray fluorescing event occurring within an at least some matter of at least a portion of an individual, wherein the determining the location of the at least one X-ray fluorescing event is based at least in part on determining a relative angle at which an at least one applied high energy photon and/or particle is being applied to the at least some matter of the at least the portion of the individual, a relative position from which an at least one applied high energy photon and/or particle is being applied to the at least some matter of the at least the portion of the individual, a relative position at which an at least one induced fluorescing X-ray photon fluoresced during the at least one X-ray fluorescing event is received from the at least some matter of the at least the portion of the individual, and a relative angle at which the at least one induced fluorescing X-ray photon is received from the at least some matter of the at least the portion of the individual.

2. The method of claim 1, wherein the determining the location of the at least one X-ray fluorescing event occurring within the at least some matter of the at least the portion of the individual is applied within at least one substantially fluoresced depth range to an at least one prescribed substantially fluoresced depth.

3. The method of claim 1, wherein the determining the location of the at least one X-ray fluorescing event occurring within the at least some matter of the at least the portion of the individual is used within at least one fluorescence visualizing, imaging, or information providing depth range to an at least one prescribed visualization, imaging, or information providing depth.

4. The method of claim 1, further comprising fluorescence visualizing, imaging, or information providing of the at least some matter of the at least some matter of the at least the portion of the individual at least partially in response to the determining the location of the at least one X-ray fluorescing event.

5. The method of claim 1, further comprising fluorescence visualizing, imaging, or information providing, which at least partially includes:
   determining at least a portion of an elemental composition of the at least some matter of the at least the portion of the individual based at least partially on an energy of the at least one induced fluorescing X-ray photon.

6. The method of claim 1, further comprising fluorescence visualizing, imaging, or information providing, which at least partially includes:
   determining at least a portion of a chemical composition or compound composition of the at least some matter of the at least the portion of the individual based at least partially on an energy of the at least one induced fluorescing X-ray photon following an application of an at least some X-ray fluorescence enhancing additive or contrast agent to the at least some matter of the at least the portion of the individual.

7. The method of claim 1, wherein the relative angle at which the at least one applied high energy photon and/or particle is applied to the at least some matter of the at least the portion of the individual and the relative position from which the at least one applied high energy photon and/or particle is applied to the at least some matter of the at least the portion of the individual are determined in a mutually coordinated manner based upon operational characteristics of an X-ray optical device.

8. The method of claim 1, wherein the relative angle at which the at least one applied high energy photon and/or particle is applied to the at least some matter of the at least the portion of the individual and the relative position from which the at least one applied high energy photon and/or particle is applied to the at least some matter of the at least the portion of the individual are determined in a mutually coordinated manner based upon operational characteristics of an X-ray optical device, and wherein the X-ray optical device is a transmissive device.

9. The method of claim 1, wherein the relative angle at which the at least one applied high energy photon and/or particle is applied to the at least some matter of the at least the portion of the individual and the relative position from which the at least one applied high energy photon and/or particle is applied to the at least some matter of the at least the portion of the individual are determined in a mutually coordinated manner based upon operational characteristics of an X-ray optical device, and wherein the X-ray optical device is a reflective device.

10. The method of claim 1, wherein the relative angle at which the at least one applied high energy photon and/or particle is applied to the at least some matter of the at least the portion of the individual and the relative position from which the at least one applied high energy photon and/or particle is applied to the at least some matter of the at least the portion of the individual are determined in a mutually coordinated manner based upon operational characteristics of an X-ray optical device, and wherein the X-ray optical device is a diffractive device.

11. The method of claim 1, wherein the relative angle at which the at least one applied high energy photon and/or particle is applied to the at least some matter of the at least the portion of the individual and the relative position from which the at least one applied high energy photon and/or particle is applied to the at least some matter of the at least the portion of the individual are determined in a mutually coordinated manner based upon operational characteristics of an X-ray optical device, and wherein the X-ray optical device is an at least partially occlusive device.

12. The method of claim 1, wherein the relative angle at which the at least one induced fluorescing X-ray photon is received from the at least some matter of the at least the portion of the individual and the relative position at which the at least one induced fluorescing X-ray photon is received from the at least some matter of the at least the portion of the individual are determined in a mutually coordinated manner based upon operational characteristics of an X-ray optical device.

13. The method of claim 1, wherein the relative angle at which the at least one induced fluorescing X-ray photon is received from the at least some matter of the at least the portion of the individual and the relative position at which the at least one induced fluorescing X-ray photon is received from the at least some matter of the at least the portion of the individual are determined in a mutually coordinated manner based upon operational characteristics of an X-ray optical focusing device.

14. The method of claim 1, wherein the relative angle at which the at least one induced fluorescing X-ray photon is received from the at least some matter of the at least the portion of the individual and the relative position at which the at least one induced fluorescing X-ray photon is received from the at least some matter of the at least the portion of the individual are determined in a mutually coordinated manner based upon operational characteristics of an X-ray optical device, and wherein the X-ray optical device is a transmissive device.

15. The method of claim 1, wherein the relative angle at which the at least one induced fluorescing X-ray photon is received from the at least some matter of the at least the portion of the individual and the relative position at which the at least one induced fluorescing X-ray photon is received from the at least some matter of the at least the portion of the individual are determined in a mutually coordinated manner based upon operational characteristics of an X-ray optical device, and wherein the X-ray optical device is a reflective device.

16. The method of claim 1, wherein the relative angle at which the at least one induced fluorescing X-ray photon is received from the at least some matter of the at least the portion of the individual and the relative position at which the at least one induced fluorescing X-ray photon is received from the at least some matter of the at least the portion of the individual are determined in a mutually coordinated manner based upon operational characteristics of an X-ray optical device, and wherein the X-ray optical device is a diffractive device.

17. The method of claim 1, wherein the relative angle at which the at least one induced fluorescing X-ray photon is received from the at least some matter of the at least the portion of the individual and the relative position at which the at least one induced fluorescing X-ray photon is received from the at least some matter of the at least the portion of the individual are determined in a mutually coordinated manner based upon operational characteristics of an X-ray optical device, and wherein the X-ray optical device is an at least partially occlusive device.

18. The method of claim 1, wherein the determining the location of the at least one X-ray fluorescing event further comprises:
coapplying a first one of the at least one applied high energy photon and/or particle with a second one of the at least one applied high energy photon and/or particle within the at least some matter of the at least the portion of the individual to increase an intensity of the at least one X-ray fluorescing event.

19. The method of claim 1, wherein the determining the location of the at least one X-ray fluorescing event further comprises:
coapplying a first flux of a first one of the at least one applied high energy photon and/or particle with a second flux of a second one of the at least one applied high energy photon and/or particle within the at least some matter of the at least the portion of the individual to increase an intensity of the at least one X-ray fluorescing event.

20. The method of claim 1, wherein the determining the location of the at least one X-ray fluorescing event further comprises:
directing multiple ones of the at least one applied high energy photon and/or particle to a fluorescing region within the at least some matter of the at least the portion of the individual to increase a fluorescing intensity of the at least one X-ray fluorescing event.

21. The method of claim 1, wherein the determining the location of the at least one X-ray fluorescing event further comprises:
controlling the at least one applied high energy photon and/or particle.

22. The method of claim 1, wherein the determining the location of the at least one X-ray fluorescing event further comprises:
adjusting the at least one applied high energy photon and/or particle.

23. The method of claim 1, wherein the determining the location of the at least one X-ray fluorescing event further comprises:
directing the at least one applied high energy photon and/or particle towards the at least some matter of the at least the portion of the individual.

24. The method of claim 1, wherein the determining the location of the at least one X-ray fluorescing event further comprises:
directing the at least one applied high energy photon and/or particle towards the at least some matter of the at least the portion of the individual; and
correlating at least some matter at which the at least one applied high energy photon and/or particle is being directed with at least some matter which is undergoing fluorescence visualizing, imaging, or information providing.

25. The method of claim 1, further comprising fluorescence visualizing, imaging, or information providing of the at least some matter of the at least some matter of the at least the portion of the individual at least partially in response to the determining the location of the at least one X-ray fluorescing event, and wherein the fluorescence visualizing, imaging, or information providing of the at least some matter of the at least the portion of the individual is performed at a rate sufficient to substantially capture a physical motion that is consistent with an individual-based physiological process.

26. The method of claim 1, further comprising fluorescence visualizing, imaging, or information providing of the at least some matter of the at least some matter of the at least the portion of the individual at least partially in response to the determining the location of the at least one X-ray fluorescing event, and wherein the fluorescence visualizing, imaging, or information providing of the at least some matter of the at least the portion of the individual is performed at a rate sufficient to substantially capture a physical motion that is consistent with a user-observable physiological process.

27. The method of claim 1, further comprising:
fluorescence visualizing, imaging, or information providing of the at least some matter of the at least some matter of the at least the portion of the individual at least partially in response to the determining the location of the at least one X-ray fluorescing event, and wherein the fluorescence visualizing, imaging, or information providing is at least partially performed across a slice of the at least some matter of the at least the portion of the individual.

28. The method of claim 1, further comprising:
fluorescence visualizing, imaging, or information providing of the at least some matter of the at least some matter of the at least the portion of the individual at least partially in response to the determining the location of the at least one X-ray fluorescing event, and wherein the fluorescence visualizing, imaging, or information providing includes deconvoluting, transforming, filtering, or correlating information relating to the at least one induced fluorescing X-ray photon.

29. The method of claim 1, wherein the at least one applied high energy photon and/or particle is at least partially applied through an external surface at least partially defining the at least some matter of the at least the portion of the individual.

30. The method of claim 1, wherein the at least one applied high energy photon and/or particle is at least partially applied through at least a portion of an at least partially internal surface at least partially defining the at least some matter of the at least the portion of the individual.

31. The method of claim 1, wherein the at least some matter of the at least the portion of the individual includes at least some tissue, a bone, bone portion, bone fragment, or tooth, a fluid, a bodily fluid, or a man-made insert.

32. The method of claim 1, wherein the at least some matter of the at least the portion of the individual includes a metal, a chemical, a dielectric, or an element.

33. The method of claim 1, wherein the at least some matter of the at least the portion of the individual includes a mechanism configured for carrying, transporting, or maintaining a fluid.

34. The method of claim 4, further comprising combining the fluorescence visualizing, imaging, or information providing with at least one additional visualization, image, or provided information provided by an X-ray fluorescing based visualizing, imaging, or information providing modality.

35. The method of claim 4, further comprising combining the fluorescence visualizing, imaging, or information providing with at least one additional visualization, image, or provided information provided by a non X-ray-fluorescing based visualizing, imaging, or information providing modality.

36. The method of claim 4, wherein the fluorescence visualizing, imaging, or information providing involves a variety of input conditions for the at least one at least one applied high energy photon and/or particle.

37. The method of claim 4, wherein the fluorescence visualizing, imaging, or information providing involves a variety of input conditions for the at least one applied high energy photon and/or particle, wherein the variety of input conditions includes a variety of directions of the at least one applied high energy photon and/or particle.

38. The method of claim 4, wherein the fluorescence visualizing, imaging, or information providing involves a variety of input conditions for the at least one applied high energy photon and/or particle, wherein the variety of input conditions includes a variety of locations of the at least one applied high energy photon and/or particle.

39. The method of claim 4, wherein the fluorescence visualizing, imaging, or information providing involves a variety of input conditions for the at least one applied high energy photon and/or particle, wherein the variety of input conditions includes a variety of energy levels of the at least one applied high energy photon and/or particle.

40. The method of claim 4, further comprising mapping the at least some matter of the at least the portion of the individual at least partially in response to the fluorescence visualizing, imaging, or information providing.

41. The method of claim 4, wherein the fluorescence visualizing, imaging, or information providing of the at least some matter of the at least the portion of the individual comprises:
deriving a material characteristic distribution function that substantially fits at least some data obtained at least partially from the fluorescence visualizing, imaging, or information providing.

42. The method of claim 4, wherein the fluorescence visualizing, imaging, or information providing of the at least some matter of the at least the portion of the individual comprises:
tagging at least one visualization, image, or provided information to derive at least one characteristic of at least one element, chemical, or compound in the at least some matter of the at least the portion of the individual.

43. The method of claim 4, wherein at least some of the fluorescence visualizing, imaging, or information providing extends partially through the at least some matter of the at least the portion of the individual.

44. The method of claim 4, wherein at least some of the fluorescence visualizing, imaging, or information providing is limited to relatively near at least one surface of the at least some matter of the at least the portion of the individual.

45. The method of claim 1, wherein the individual includes at least one from a group, the group includes a person, an animal, a plant, or an organism.

46. An apparatus, comprising:
a high energy photon and/or particle emitter portion configured to induce at least one induced fluorescing X-ray photon at a fluorescence location within an at least some matter of an at least a portion of an at least one individual responsive to an at least one applied high energy photon and/or particle being applied to the at least some matter of the at least the portion of the at least one individual;
an X-ray fluorescence photon receiving portion configured to detect the at least one induced fluorescing X-ray photon; and
circuitry coupled to the high energy photon and/or particle emitter portion and to the X-ray fluorescence photon receiving portion and configured to determine fluorescence location information within the at least some matter of the at least the portion of the at least one individual based at least in part on determining a relative angle at which an at least one applied high energy photon and/or particle is being applied to the at least some matter of the at least the portion of the individual, a relative position from which an at least one at least one applied high energy photon and/or particle is being applied to the at least some matter of the at least the portion of the individual, a detected location of an at least one induced fluorescing X-ray photon fluoresced during the at least one X-ray fluorescing event, and a received angle at which the at least one induced fluorescing X-ray photon is received.

47. The apparatus of claim 46, wherein the at least one induced X-ray fluorescing photon has an energy of greater than or equal to 1 KeV, greater than or equal to 10 KeV, or greater than or equal to 100 KeV.

48. The apparatus of claim 46, wherein at least a portion of the high energy photon and/or particle emitter portion relies at least partially upon energy applied from an energy accumulator.

49. The apparatus of claim 46, wherein the high energy photon and/or particle emitter portion includes an X-ray based emissive structure.

50. The apparatus of claim 46, wherein the high energy photon and/or particle emitter portion includes an electron emissive structure.

51. The apparatus of claim 46, wherein the high energy photon and/or particle emitter portion includes an ion emissive structure.

52. The apparatus of claim 46, wherein at least one operative portion is translatable, tiltable, rotatable, or otherwise displaceable by a human user.

53. The apparatus of claim 46, wherein at least an operative portion is translatable, tiltable, rotatable, or otherwise displaceable by a machine-based user.

54. The apparatus of claim 46, wherein at least one operative characteristic of at least an operative portion is controllable.

55. The apparatus of claim 46, wherein at least one timing of at least an operative portion is controllable.

56. The apparatus of claim 46, wherein at least one energy of at least an operative portion is controllable.

57. The apparatus of claim 46, wherein the high energy photon and/or particle emitter portion is configured to apply the at least one applied high energy photon and/or particle with a controllable intensity.

58. The apparatus of claim 46, wherein the high energy photon and/or particle emitter portion is configured to apply the at least one applied high energy photon and/or particle with a controllable timing.

59. The apparatus of claim 46, wherein the high energy photon and/or particle emitter portion is configured to apply the at least one applied high energy photon and/or particle with a controllable energy.

60. The apparatus of claim 46, wherein the high energy photon and/or particle emitter portion is configured to apply the at least one applied high energy photon and/or particle from a controllable location.

61. The apparatus of claim 46, wherein the high energy photon and/or particle emitter portion is configured to apply the at least one applied high energy photon and/or particle with a controllable direction.

62. The apparatus of claim 46, wherein the X-ray fluorescence photon receiving portion comprises at least one energy level detector.

63. The apparatus of claim 46, wherein the X-ray fluorescence photon receiving portion comprises at least one photodetector.

64. The apparatus of claim 46, wherein the X-ray fluorescence photon receiving portion comprises at least one X-ray spectrometer.

65. A method, comprising:
X-ray fluorescence visualizing, imaging, or information providing within an at least some matter of at least a portion of an individual based at least in part on determining a relative angle at which an at least one applied high energy photon and/or particle is being applied to the at least some matter of the at least the portion of the individual, a relative position from which an at least one applied high energy photon and/or particle is being applied to the at least some matter of the at least the portion of the individual, a detected location of an at least one induced fluorescing X-ray photon fluoresced during the at least one X-ray fluorescing event, and a received angle at which the at least one induced fluorescing X-ray photon is received.

66. The method of claim 65, wherein the X-ray fluorescence visualizing, imaging, or information providing at least partially includes:
determining at least a portion of an elemental composition of the at least some matter of the at least the portion of the individual based at least partially on an energy of the at least one induced fluorescing X-ray photon.

67. The method of claim 65, wherein the X-ray fluorescence visualizing, imaging, or information providing at least partially includes:

determining at least a portion of a chemical composition or compound composition of the at least some matter of the at least the portion of the individual based at least partially on an energy of the at least one induced fluorescing X-ray photon following an application of an at least some X-ray fluorescence enhancing additive or contrast agent to the at least some matter of the at least the portion of the individual.

68. The method of claim 65, wherein the X-ray fluorescence visualizing, imaging, or information providing within the at least some matter of the at least the portion of the individual is applied within at least one substantially fluoresced depth range to an at least one prescribed substantially fluoresced depth.

69. The method of claim 65, wherein the X-ray fluorescence visualizing, imaging, or information providing within the at least some matter of the at least the portion of the individual is used within at least one fluorescence visualizing, imaging, or information providing depth range to an at least one prescribed visualization, imaging, or information providing depth.

* * * * *

UNITED STATES PATENT AND TRADEMARK OFFICE
CERTIFICATE OF CORRECTION

PATENT NO. : 7,738,627 B2  
APPLICATION NO. : 11/906156  
DATED : June 15, 2010  
INVENTOR(S) : Boyden et al.

Page 1 of 1

It is certified that error appears in the above-identified patent and that said Letters Patent is hereby corrected as shown below:

Claim 36, Col. 182, Line 36: Should Read,

"of input conditions for the at least one ~~at least one~~ applied high"

Claim 46, Col. 183, Line 39: Should Read,

"from which an at least one ~~at least one~~ applied high"

Signed and Sealed this

Twenty-seventh Day of July, 2010

David J. Kappos
*Director of the United States Patent and Trademark Office*